United States Patent
Punzak et al.

(10) Patent No.: US 7,865,373 B2
(45) Date of Patent: Jan. 4, 2011

(54) METHOD AND APPARATUS FOR SHARING HEALTHCARE DATA

(75) Inventors: Stephen Punzak, Dover, MA (US); Eric Akstin, Ellington, CT (US)

(73) Assignee: Medical Web Technologies, Inc., Dover, MA (US)

( * ) Notice: Subject to any disclaimer, the term of this patent is extended or adjusted under 35 U.S.C. 154(b) by 80 days.

(21) Appl. No.: 10/686,172

(22) Filed: Oct. 15, 2003

(65) Prior Publication Data

US 2005/0086074 A1 Apr. 21, 2005

(51) Int. Cl.
*G06Q 50/00* (2006.01)
(52) U.S. Cl. .................................. 705/2; 705/3; 705/4
(58) Field of Classification Search ............... 705/2, 705/3
See application file for complete search history.

(56) References Cited

U.S. PATENT DOCUMENTS

| | | | | |
|---|---|---|---|---|
| 6,381,029 B1 * | 4/2002 | Tipirneni | | 358/1.14 |
| 6,463,417 B1 * | 10/2002 | Schoenberg | | 705/2 |
| 6,523,009 B1 * | 2/2003 | Wilkins | | 705/3 |
| 2001/0041991 A1 * | 11/2001 | Segal et al. | | 705/3 |
| 2002/0026332 A1 * | 2/2002 | Snowden et al. | | 705/3 |
| 2002/0029157 A1 * | 3/2002 | Marchosky | | 705/3 |
| 2003/0040946 A1 * | 2/2003 | Sprenger et al. | | 705/6 |
| 2003/0130871 A1 * | 7/2003 | Rao et al. | | 705/2 |

* cited by examiner

*Primary Examiner*—R. D Rines
(74) *Attorney, Agent, or Firm*—DLA Piper LLP (US)

(57) ABSTRACT

A method for sharing medical information over a network is described. The method includes the steps of, allowing at least one medical patient to store medical history information in a computer database, and providing at least one medical professional the ability to view said medical history information. A computer system for implementing the method for sharing medical information is also described.

21 Claims, 103 Drawing Sheets

FIGURE 92

ONE MEDICAL PASSPORT
YOUR PASSPORT TO BETTER HEALTHCARE

- Home
- Contact Us
- Feedback
- Log Out

PATIENT ADMISSIONS

Welcome:
Art Test

Last logged in Aug 13 2003 11:03AM

- Send a copy of my Medical Passport to a physician and/or medical facility
  Update and submit your Medical Passport for new physician appointments or new scheduled surgery procedures

- Finish an incomplete copy of my Medical Passport

- Review / Edit a previously submitted copy of my Medical Passport
  You may only change information if your Medical Passport has not yet been downloaded by the medical facility or physician

- Personal Use Only
  Update the information in your Medical Passport without submitting it to a medical facility or physician

- View my Medical Passport usage history
- Print a copy of my Medical Passport
- Delete an existing copy of my Medical Passport
- Edit my name, address, insurance, or other personal information
- Change my password

| Change | Created | Contact Means | Type | Message |
|---|---|---|---|---|
| 🖼 | 7/15/2003 10:28:39 AM | staffstaff@staffstaff.com Reply | Technical Support | A password reminder request (from the hospital side, automated response) has been made for username staffstaff with codeword staffstaff. |
| 🖼 | 7/15/2003 10:38:22 AM | doctor10@doctor10.com Reply | Technical Support | A password reminder request (from the office side, automated response) has been made for username doctor10 with codeword test. |
| 🖼 | 7/15/2003 10:38:52 AM | doctor10@doctor10.com Reply | Technical Support | A password reminder request (from the office side, automated response) has been made for username doctor10 with codeword test. |
| 🖼 | 7/15/2003 10:43:02 AM | doctor10@doctor10.com Reply | Technical Support | A password reminder request (from the office side, automated response) has been made for username doctor10 with codeword test. |
| 🖼 | 7/15/2003 10:47:26 AM | test@test.com Reply | Technical Support | A password reminder request (from the office side, automated response) has been made for username staffone with codeword staffone. |
| 🖼 | 7/15/2003 10:57:24 AM | test@test.com Reply | Technical Support | A password reminder request (from the scheduling side, automated response) has been made for username zzztest with codeword test. |
| 🖼 | 8/13/2003 10:54:57 AM | akstin@snet.net Reply | Technical Support | A password reminder request (automated reply) has been made for username eakstin with codeword saben. |

To status: Reviewed

BACK   UPDATE

FIGURE 102

METHOD AND APPARATUS FOR SHARING HEALTHCARE DATA

FIELD OF THE INVENTION

This present invention relates to a method and apparatus for sharing healthcare information, and in particular, to a computer-based method and apparatus for entering and sharing healthcare information as between patients and various healthcare providers.

BACKGROUND OF THE INVENTION

Every time patients interact with the healthcare system, either at a physician's office, emergency room, or medical facility, they are required to repeat the same exhaustive list of demographic, insurance and medical information. In fact, patients are usually required to recite this information multiple times while being interviewed by different staff at the same medical facility. This is inefficient and costly: approximately $100 per patient per visit of wasted clerical, nursing and physician time. In addition, the omission and transcription errors that inevitably occur are a leading cause of morbidity and mortality (98,000 patients per year in the U.S., as reported in the 1998 Institute of Medicine Study).

Electronic Medical Records (EMRs) and Medical Information Systems (MIS) have held out the promise of improving the above situation. However, sizable up front costs for software and hardware, ongoing annual licensing fees, fear of choosing the "wrong" system and uncertain returns on investment (ROI) have made cash-strapped medical facilities and physician groups wary of adopting new technologies.

In addition, even when medical information is stored in electronic form, it is usually unavailable to actually help treat patients. This is because health information system vendors target distinct market segments: large medical centers, community hospitals, ambulatory surgery centers and individual physicians/physician groups, and the various systems don't "talk" to one another. Furthermore, even if two hospitals in the same city use the exact same medical information system, unless they are part of the same health system and the health system has an integrated information system, there is usually no way to transfer information from one facility to the other. The situation is further complicated by the fact that each transfer of information requires the documented consent of the patient.

The financial impact of the aforementioned inefficiencies is enormous: $100 per visit multiplied by 200,000,000 office visits and 80,000,000 surgeries and procedures in the U.S. per year represents a $28 billion dollar problem.

Because of the convergence of a number of factors: (a) reduced reimbursement to physicians and healthcare facilities, (b) a renewed interest in cost-cutting and efficiency, and (c) a critical number of patients, physicians and hospitals with Internet access, a web-based medical information solution is now feasible. Furthermore, two catalysts: the Health Insurance Portability and Accountability Act of 1996 (HIPAA), and a severe, world-wide, nursing shortage, have acted to speed the adoption of technologies that free physicians and nurses from time-consuming, inefficient, clerical work.

Thus, there is presently a need for web-based method for sharing healthcare information between patients and various healthcare providers.

SUMMARY OF THE INVENTION

An exemplary embodiment of the present invention comprises a method for sharing medical information over a network including the steps of, allowing at least one medical patient to store medical history information in a computer database, and providing at least one medical professional the ability to view said medical history information.

An exemplary embodiment of the present invention also comprises a computer system including at least one server computer, and at least one client computer coupled to the at least one server computer through a network, wherein the at least one server computer includes at least one program stored thereon, said at least one program performing the steps of allowing at least one medical patient stationed at the at least one client computer to store medical history information in a computer database, and providing at least one medical professional the ability to view said medical history information.

BRIEF DESCRIPTION OF THE DRAWINGS

FIG. 92 shows a patient admissions page.

FIG. 93 shows a patient admissions selection page.

FIG. 102 shows a mail page.

DETAILED DESCRIPTION

Figure 1:
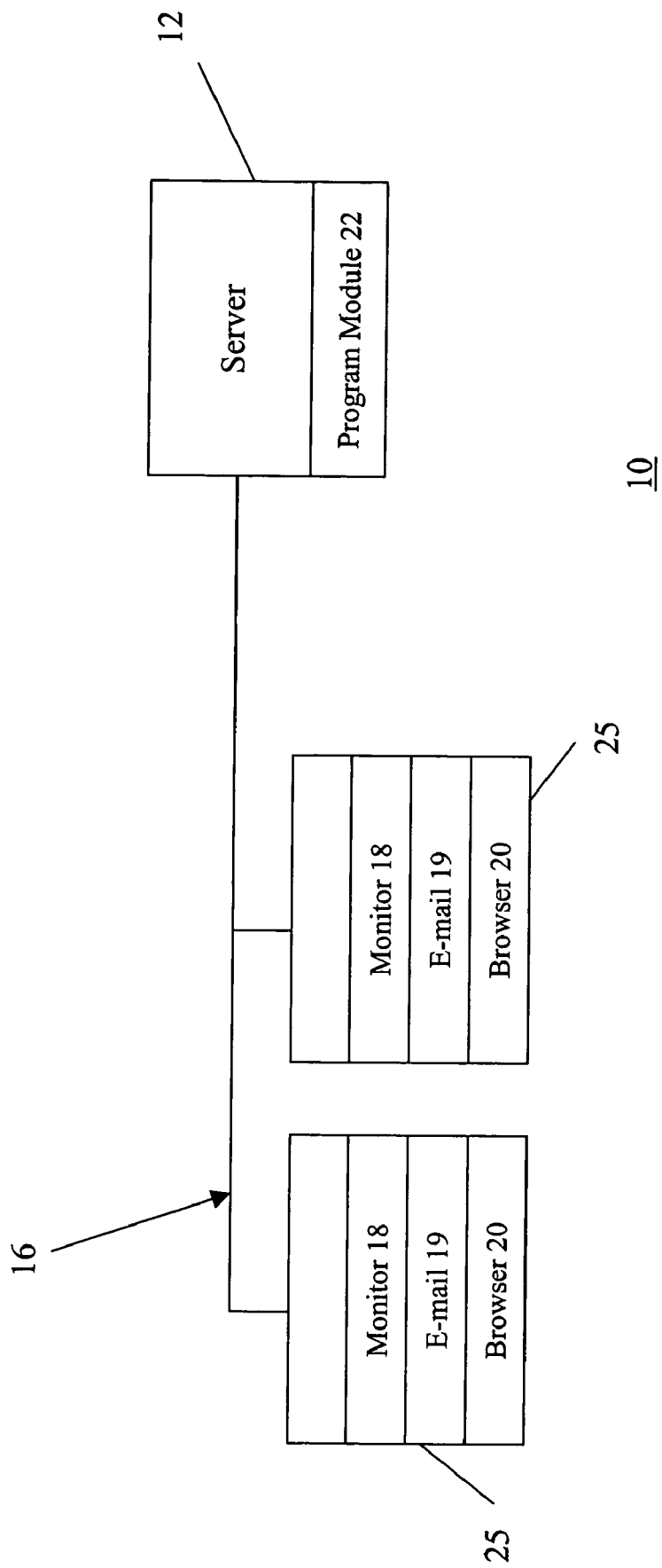
FIG. 1 is a block diagram showing a computer system according to an exemplary embodiment of the present invention.

An exemplary embodiment of the present invention comprises a computer-based, medical information system that captures, stores and distributes a patient's medical history, including comprehensive demographic and insurance information, to physicians and healthcare facilities.

Some exemplary aspects of the present invention include: (1) permitting patients to enter initial medical information themselves, thus saving significant labor costs for the physician/medical facility; (2) providing complete information in a uniform, legible format that is available to physicians, nurses and clerical workers before the patient is initially seen (the information is then simply reviewed with the patient rather than obtained at the time of visit, thus cutting interview times to a fraction of the usual time while simultaneously increasing patient satisfaction); (3) providing a universal, global system with no ties to any one hospital, health care system or physician group; (4) providing a low cost solution (the only costs being a small transaction fee and/or a monthly network access fee to medical facilities and certain physician groups per patient usage, thus ensuring immediate ROI); (5) providing a solution that only requires a personal computer (PC) with an Internet connection on the facility/physician side.

The medical history information that a patient provides is referred to herein as a "Medical Passport." All Medical Passports that patients create have at least three (3) major parts to them: (a) Registration (demographic information, insurance information, username, password, etc.), (b) Basic Medical History (height, weight, medications, medical problems, allergies, previous surgeries, etc.), and (c) Specialty History (infertility, pain management, pre-operative, internal medicine, etc.). The Basic Medical History section may be seven (7) to ten (10) computer screens long. Additionally, the Basic Medical History section may be customized based on certain patient criteria, such as whether the patient in registration indicates male or female gender, whether the patient indicates a certain age range, etc. The information requested from the patient in the Specialty History section are preferably unique to a specific medical specialty type. For example, if the patient is creating a Medical Passport for seeing an infertility specialist, the questions in the Specialty History section will relate directly to infertility of the patient. Similarly, if the patient is creating a Medical Passport for seeing a pain management specialist, the questions in the Specialty History section will relate to pain, and so on. The customization of the Basic Medical History and Specialty History sections based on the patient's prior responses (e.g., age, gender, etc.) makes the present method extremely easy to use from a patient's viewpoint.

Once an initial Medical Passport is created, subsequent Medical Passports may be more easily created by copying similar information. Accordingly, the patient does not need to re-enter the Registration section information every time the patient sees a different specialist. For example, if the patient creates an initial Medical Passport for his or her regular physician and subsequently needs to see a specialist, the Registration and Basic Medical History sections will be automatically populated (by the computer-implemented method 100 described below) when the subsequent Medical Passport is created.

The present invention has distinct advantages over present solutions. Medical facilities, physicians, nurses and administrative staff benefit from instant access to timely, accurate, comprehensive, legible information while greatly reducing the cost of caring for a patient. At the same time, the patient benefits from a far more efficient and convenient interaction with the healthcare system.

FIG. 1 shows a system 10 according to an exemplary embodiment of the present invention. The system includes at least one server computer 12, and a plurality of user computers (clients) 25. The server computer 12 and the user computers 25 may be connected by a network 16 (e.g., Internet, Intranet, etc.). The user computers 25 may be connected to the network 16 by a modem, Local Area Network (LAN), Wide Area Network (WAN), Digital Subscriber Line (DSL), or other equivalent connection means.

Each user computer 25 preferably includes a video monitor 18 for displaying information. Additionally, each user computer 25 preferably includes an electronic mail (e-mail) program 19 (e.g., Microsoft Outlook®) and a browser program 20 (e.g., Microsoft Internet Explorer®, Netscape Navigator®, etc.), as is well known in the art.

The server computer 12 preferably includes at least one program module 22 which allows the user computers 25 to communicate with the server computer over the network 16. The program module 22 may include program code, preferably written in Hypertext Mark-Up Language (HTML), JAVA™ (Sun Microsystems, Inc.), Active Server Pages (ASP) and/or Extensible Mark-Up Language (XML), which allows the user computers 25 to access the program module 22 through the respective browser programs 20 (i.e., by entering the Uniform Resource Locator (URL) associated with the server computer 12 and the program module 22. When a proper server computer 12 and program module 22 are specified by the user computer 25, the program module 22 will cause certain information to be displayed on the video monitor 18 of the user computer 25.

In an exemplary embodiment of the present invention, the network 16 comprises the Internet, and server computer 12 includes at least one program and data for implementing a method for sharing healthcare information in conjunction with the user computers 25. In the exemplary embodiment, the server computer 12 includes at least one program module 22 for performing various operations, as explained below.

Preferably, the program module 22 includes subroutines for performing the following procedures: (1) patient login, registration and update; (2) healthcare facility login, registration and update; (3) doctor's office login, registration and update; (4) scheduler login, registration and update; (5) admitting department login, registration and update; (6) administrator login, registration and update; (7) customer service representative login, registration and update; (8) anesthesiologist login, registration and update; and (9) patient post-operative login, registration and update. Each of these procedures will be addressed in detail below.

Figure 2:
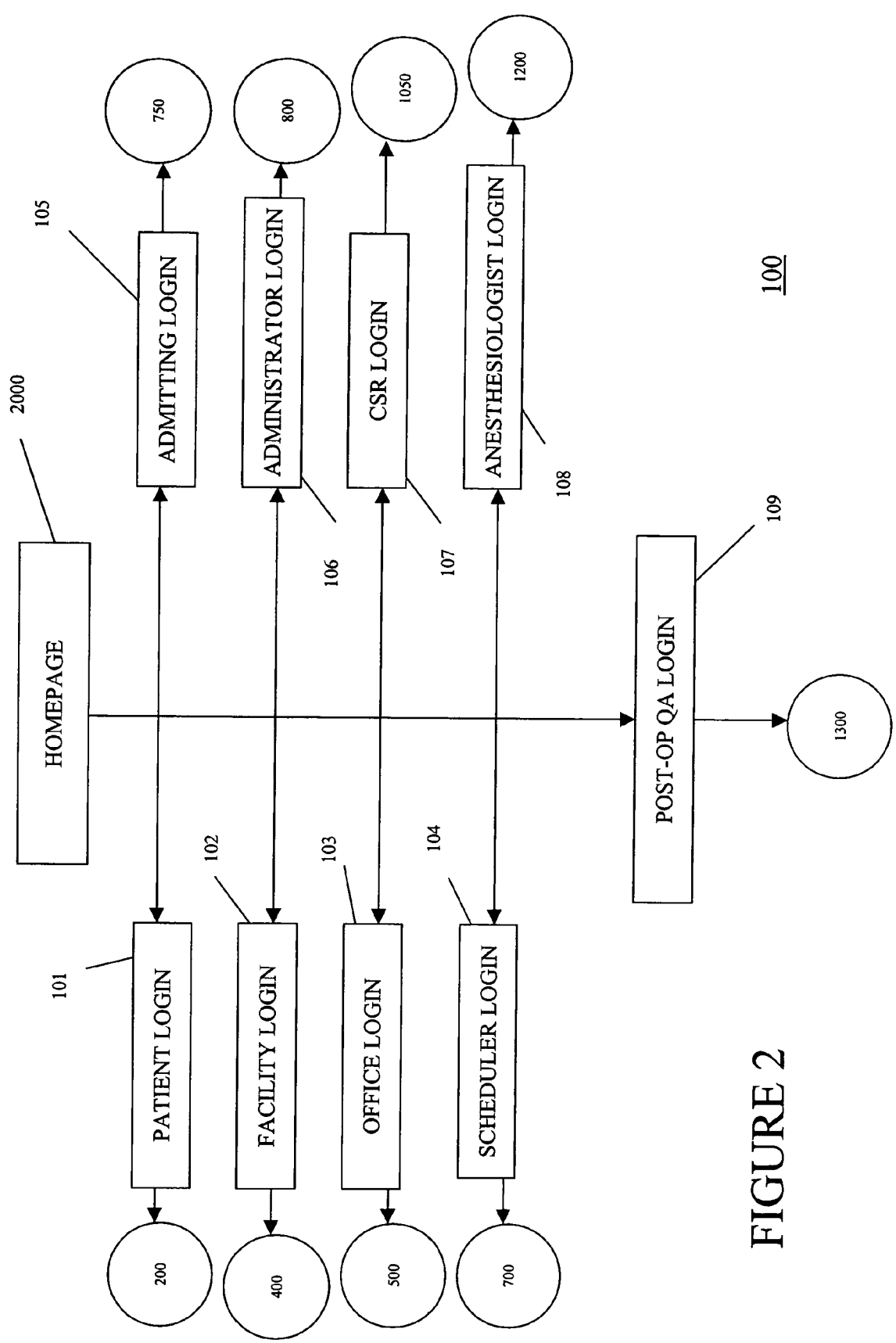
FIG. 2 is a flow diagram showing a method according to an exemplary embodiment of the present invention.

FIG. 2 is a flow chart showing a method 100 according to an exemplary embodiment of the present invention which is performed by the program module 22. The process method begins at the "homepage" 2000 of the server computer 12 and program module 22 (e.g., http://www.onemedicalpassport.com). For ease of reference, the website to which homepage 2000 corresponds is referred to herein as "One Medical Passport." As is well known, this homepage 2000 is specified by placing the address of the server computer in the main window of the browser program 20. From the homepage 2000, many different methods in accordance with the present invention may be selected. A user may select to login as a patient (step 101), as a healthcare facility (step 102), as a doctor's office (step 103), as a scheduler (step 104), as an admitting department employee (step 105), as a healthcare administrator (step 106), as a customer service representative (step 107), as an anesthesiologist (step 108), and as a post-operative patient (step 108).

Patient Login

Figure 3:
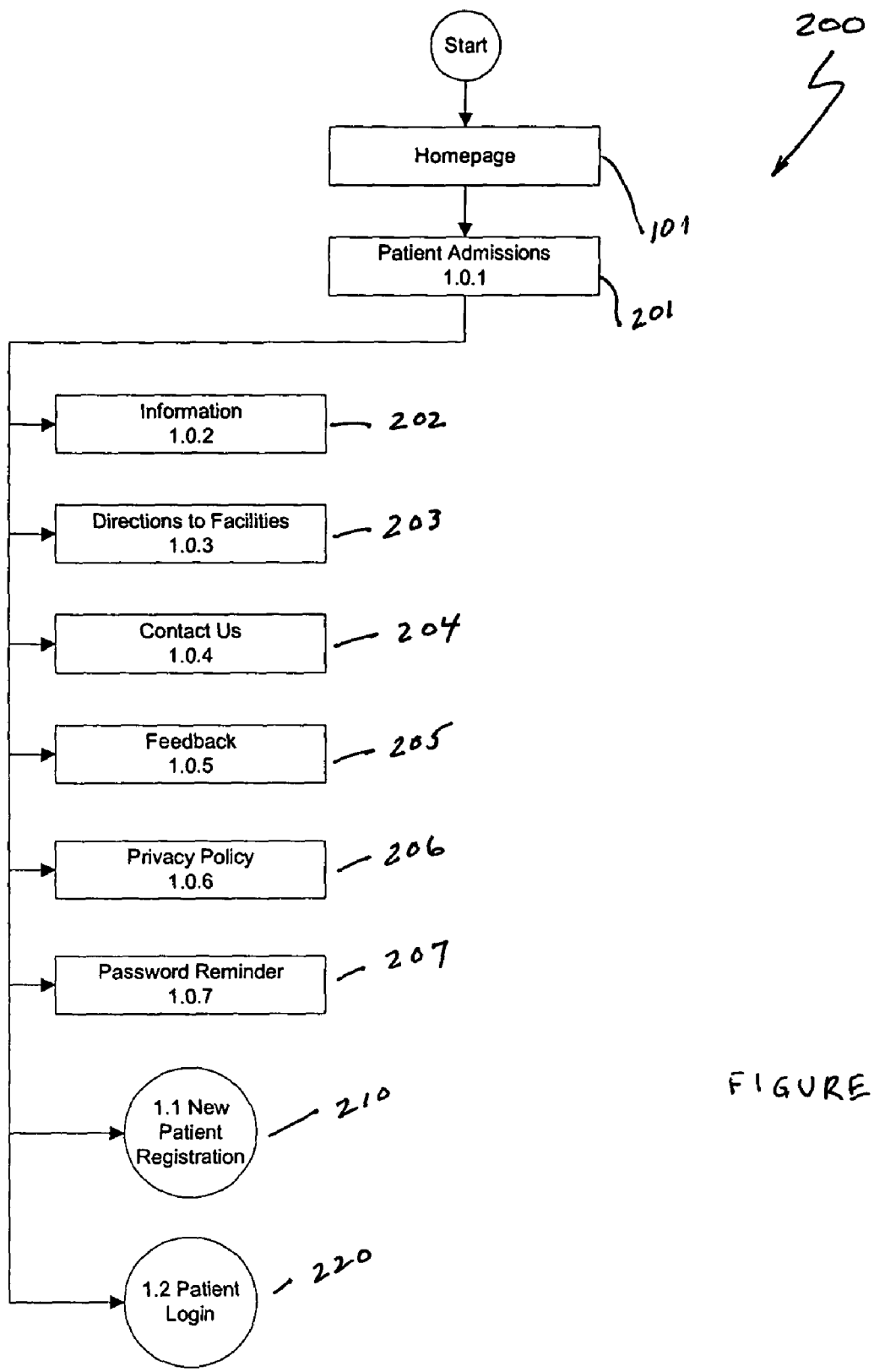
FIG. 3 is a flow diagram showing a patient login process.
Figure 91:
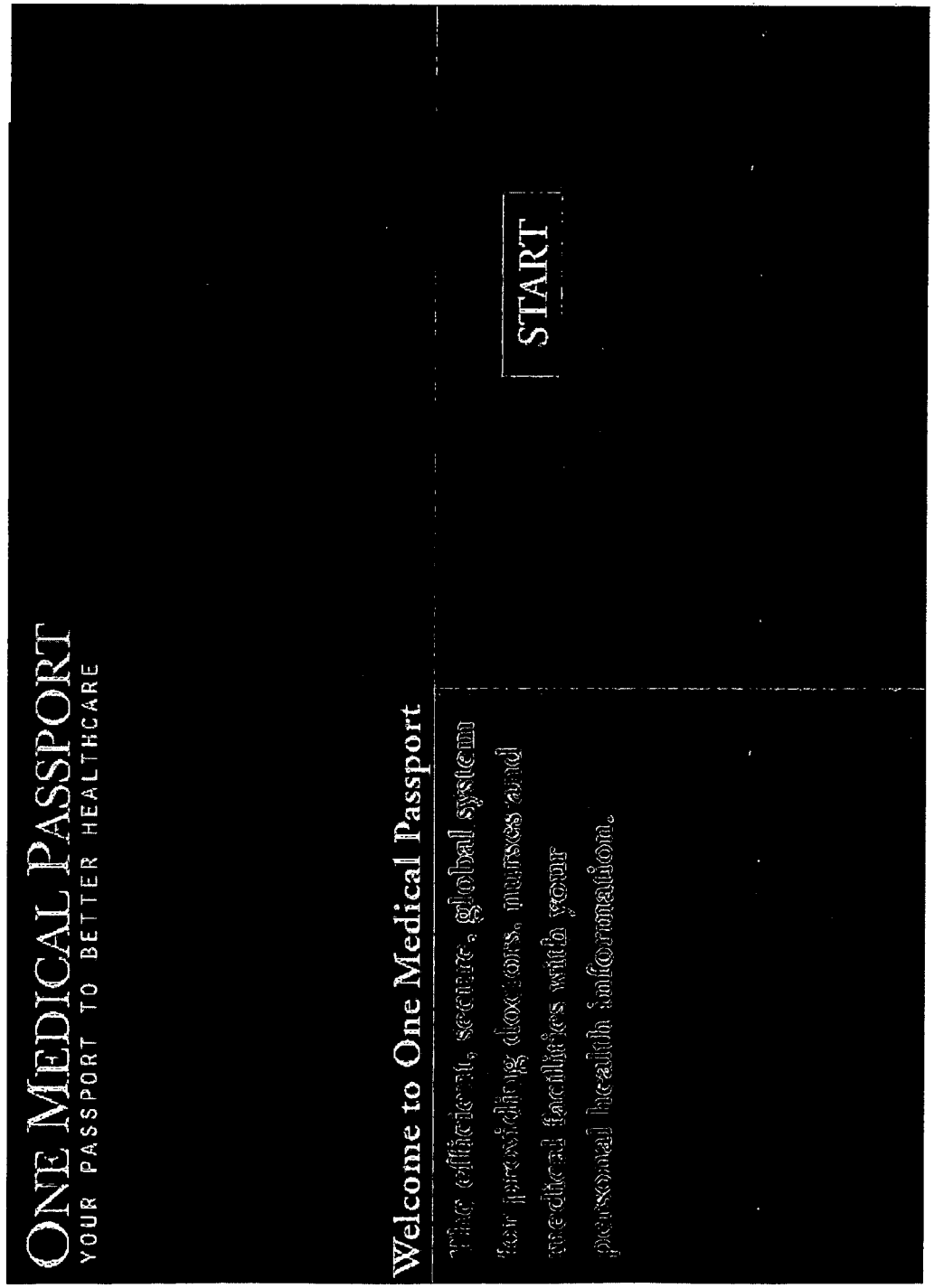
FIG. 91 shows a homepage for the method shown in FIG. 2.
Figure 92:
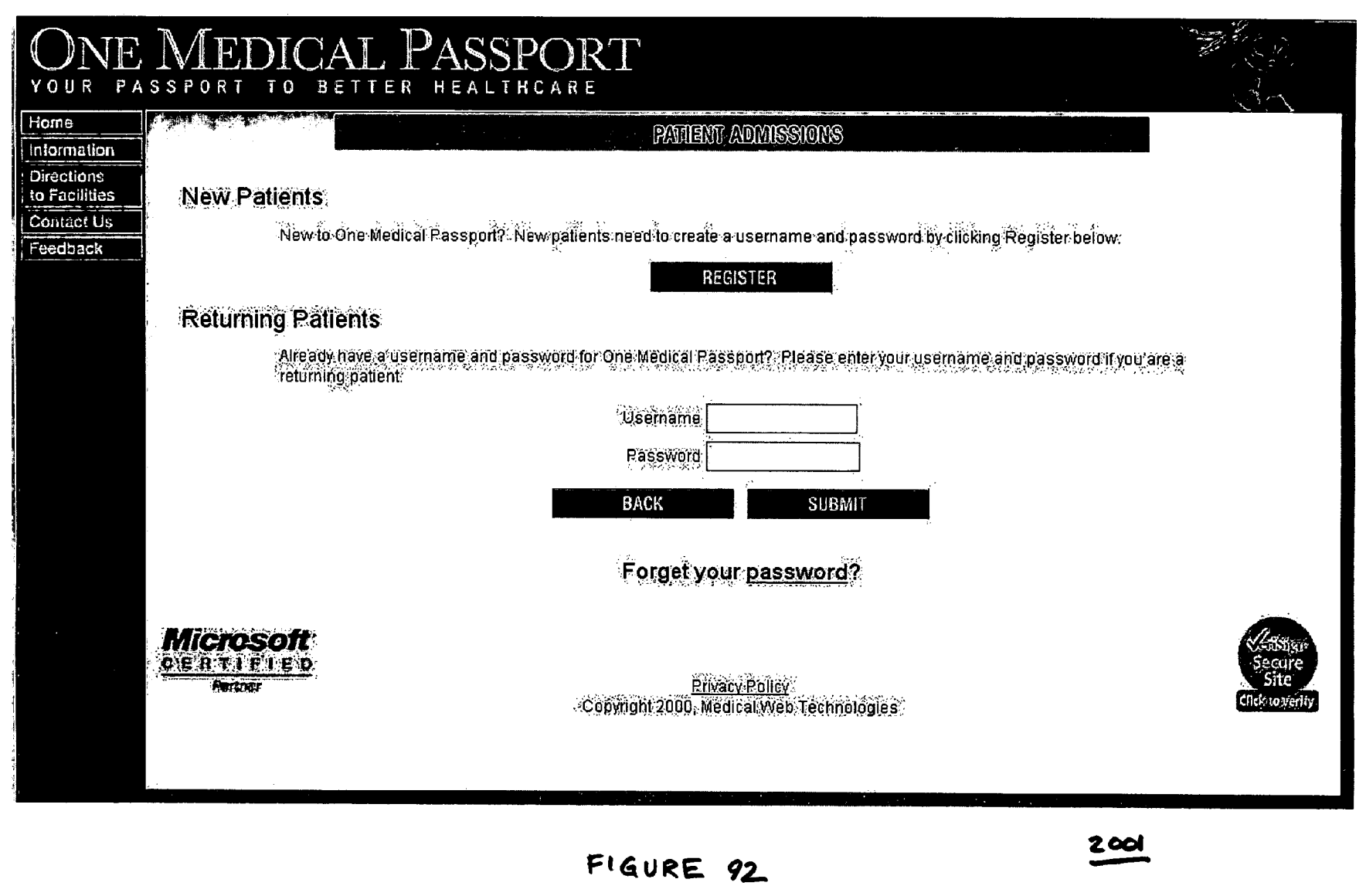

FIG. 3 is a flow chart showing the patient login process 200 which is initiated when the user selects to login as a 'patient' from the homepage 2000 (step 101 in FIG. 2; FIG. 91). The patient login process 200 begins with the patient selecting to login as either a "returning patient" or "new patient" from a patient admissions page 2001 (step 201; FIG. 92). The patient admissions page 2001 also provides access to an information page (step 202), a directions to healthcare facilities page (step 203), a contact information page (step 204), a feedback page (step 205), a privacy policy page (step 206) and a password reminder page (step 207). The password reminder page permits the user to be reminded of his or her password, if he or she has forgotten it. In one exemplary embodiment, the user provides his or her user name and a code word, or an answer to a challenge question. If the code word or challenge answer is correct, the password is transmitted to the user (e.g., via e-mail). If the patient selects to login as a "new patient", the process proceeds to a new patient registration process 210 (See FIG. 4). If the patient selects to login as a "returning patient", the process proceeds to a returning patient registration process 220 (See FIG. 5).

Figure 4:
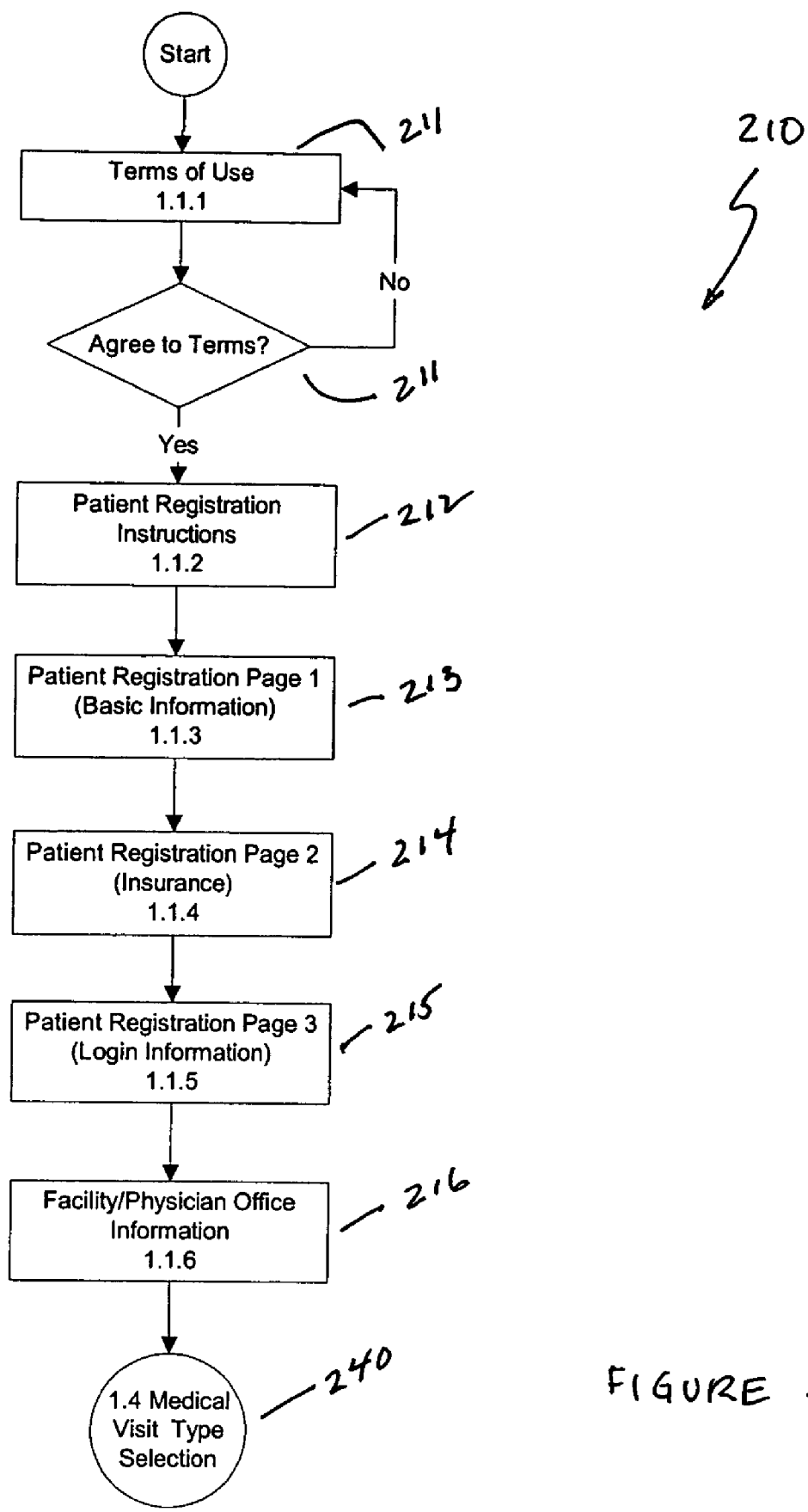
FIG. 4 is a flow diagram showing a new patient registration process.

FIG. 4 is a flow chart showing the new patient registration process 210. Initially, a user is presented with a page identifying the terms and conditions of use and asked to agree or disagree with such terms (step 211). If the user agrees with the terms, the patient is given registration instructions (step 212). The patient is then presented a "basic information" electronic form and asked to supply certain information (step 213). Once the user has provided all the "basic information", the user is presented a "insurance information" electronic form and asked to supply certain information (step 214). Once the user has provided all the "insurance information", the user is presented a "login information" electronic form and asked to supply certain information regarding a login for the next time the user accesses the homepage 2000 (step 215). Once the user has provided all the "login information", the user is presented a "facility/physician information" electronic form and asked to supply certain information (step 216). From this point, the user may enter the medical visit type process 240 (See FIG. 7).

Figure 5:
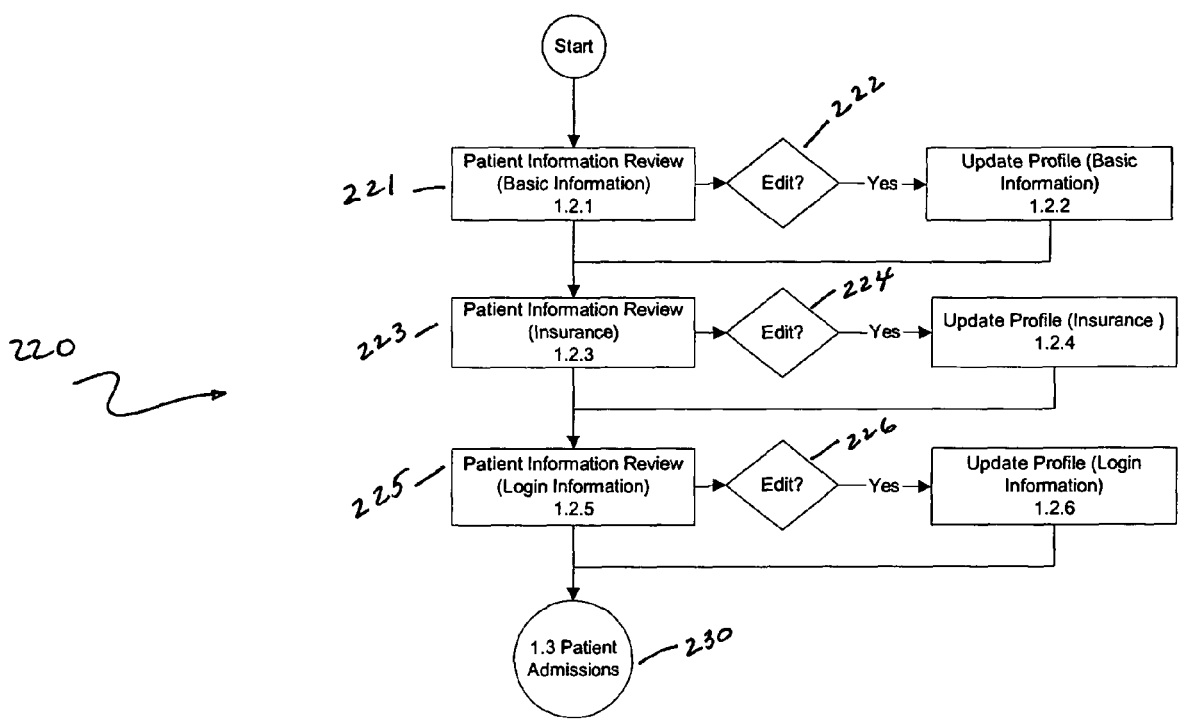
FIG. 5 is a flow diagram showing a returning patient registration process.

FIG. 5 is a flow chart showing the returning patient registration process 220. Initially, a user is presented with a page identifying the user's "basic information" (step 221). If the user wishes to edit this "basic information", such changes may be made (step 222). If no changes are necessary, the user is presented with a page identifying the user's "insurance information" (step 223). If the user wishes to edit this "insurance information", such changes may be made (step 224). If no changes are necessary, the user is presented with a page identifying the user's "login information" (step 225). If the user wishes to edit this "login information", such changes may be made (step 226). If no changes are necessary, the user is ready for the patient admission process 230.

Figure 6:
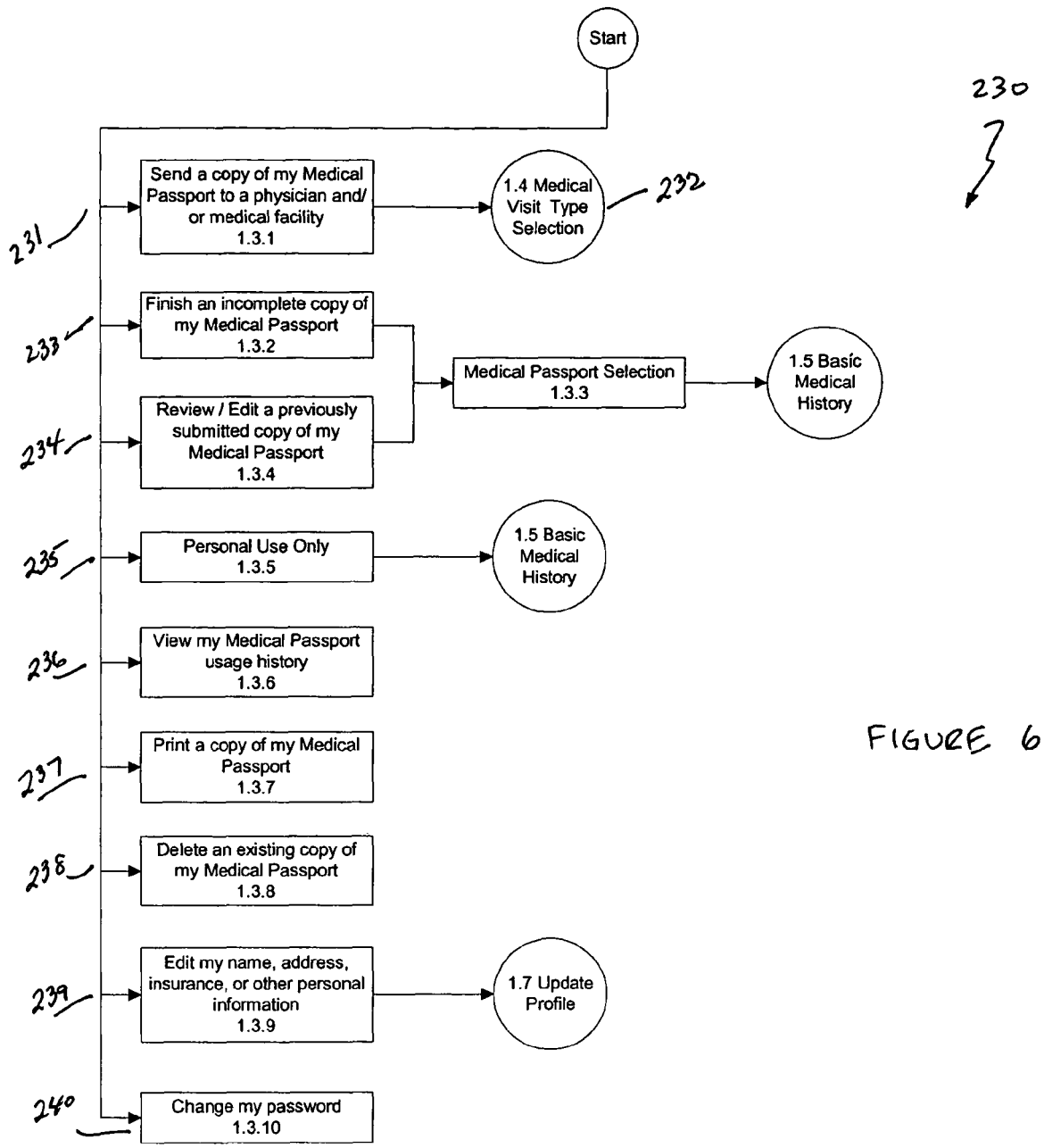
FIG. 6 is a flow diagram showing a patient admissions process.

FIG. 6 is a flow chart showing the patient admissions process 230. A patient admissions selection page 2005 is presented to the user when the patient admissions process 230 is initiated (See FIG. 93). The patient admission process 230, among other things, allows the patient to provide the entered medical information (referred to herein as a patient's "Medical Passport") to physicians and healthcare facilities (step 231). If the user decides to provide the Medical Passport to a physician or healthcare facility, the user must first complete the medical visit type process 240 (step 232). In addition to providing the Medical Passport to physicians and healthcare facilities, the user can also finish an incomplete Medical Passport (step 233), edit a previous Medical Passport (step 234), provide additional personal information to the physicians and healthcare facilities (step 235), view their Medical Passport usage history (step 236), print their Medical Passport (step 237), delete a Medical Passport (step 238), edit name, address, insurance, or other personal information (step 239), and change their password (step 240). If the user chooses to finish an incomplete Medical Passport (step 233), or edit a previous Medical Passport (step 234), the user must first select a Medical Passport (step 241) before proceeding to the basic medical history process 260 (See FIG. 8). When a user chooses to provide additional personal information to the physicians and healthcare facilities (step 235), they are provided immediately to the basic medical history process 260. If a user chooses to edit name, address, insurance, or other personal information (step 239), the user proceeds to the update profile process 280.

In order to allow patients to properly identify physicians when granting access to Medical Passports, each physician may be assigned a unique identifier. For example, each physician may be assigned a ten (10) digit number which specifically identifies the physician and physician's primary office. The first six (6) digits of the 10 digit number may be used to identify the physician, and the last four (4) digits may be used to identify the physician's office. Such a scheme permits a multi-physician group with multiple offices may have physicians assigned to the specific offices, and only those offices, where the physicians actually practice. When a patient elects to provide the entered medical information (Medical Passport) to physicians and/or healthcare facilities, the patient may enter the physician's unique 10 digit identifier.

Figure 7:
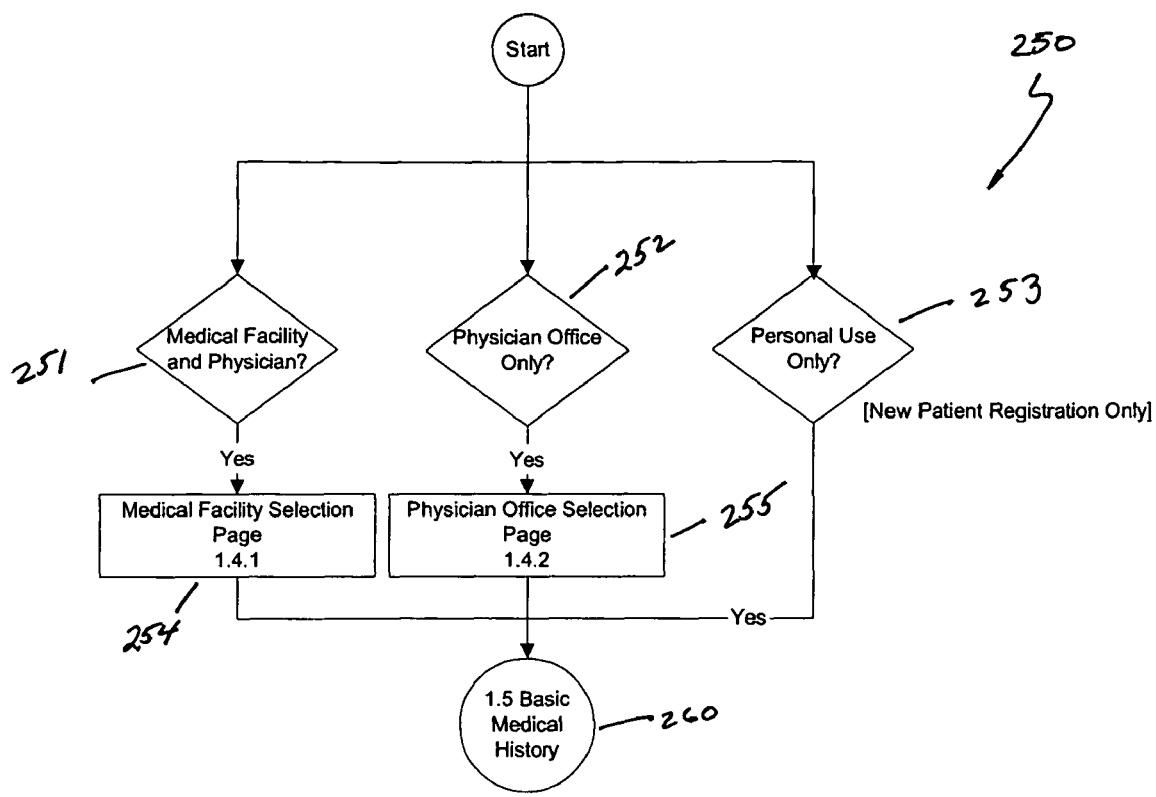
FIG. 7 is a flow diagram showing the medical visit type process.
Figure 94:
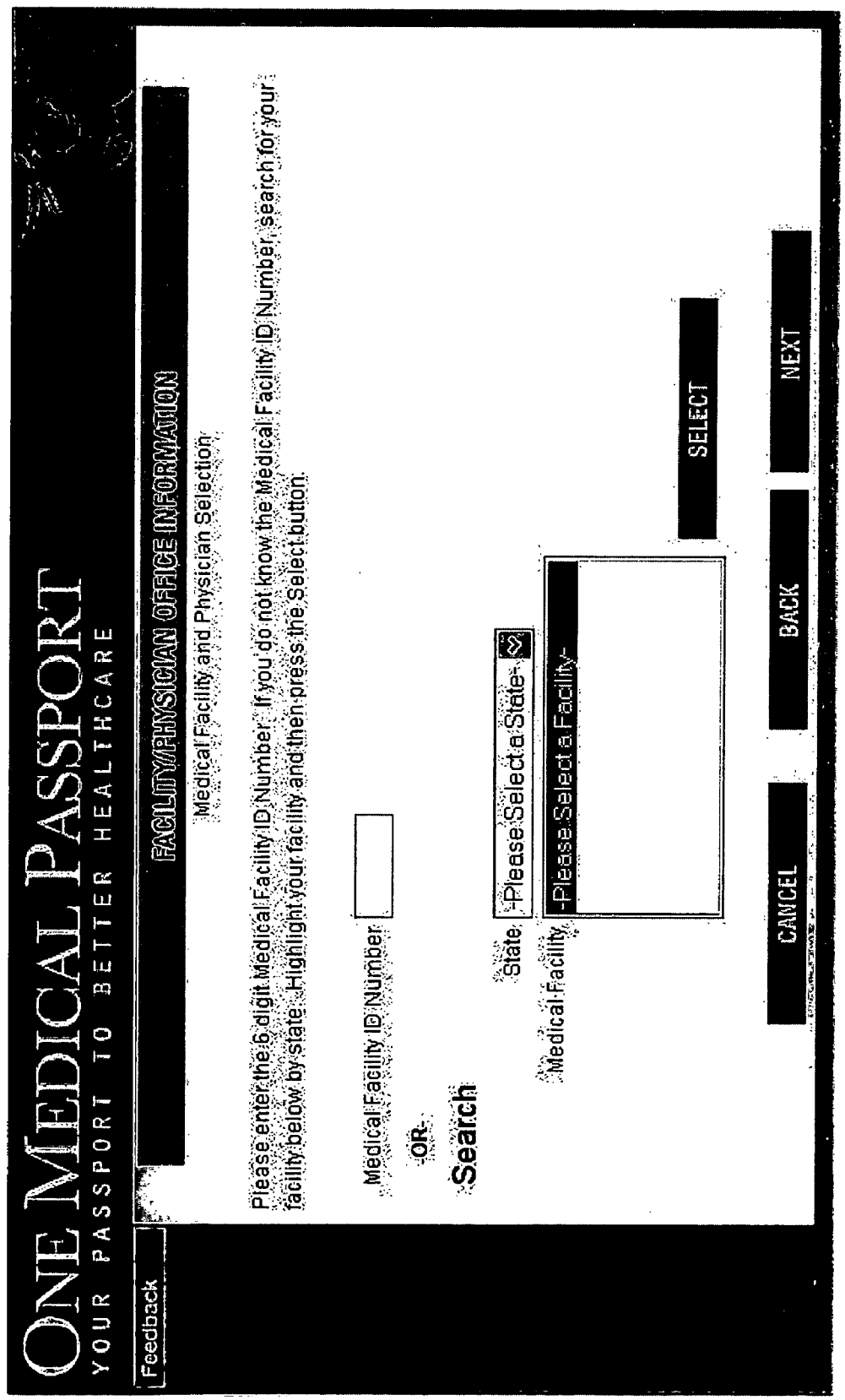
FIG. 94 shows a medical facility selection page.
Figure 95:
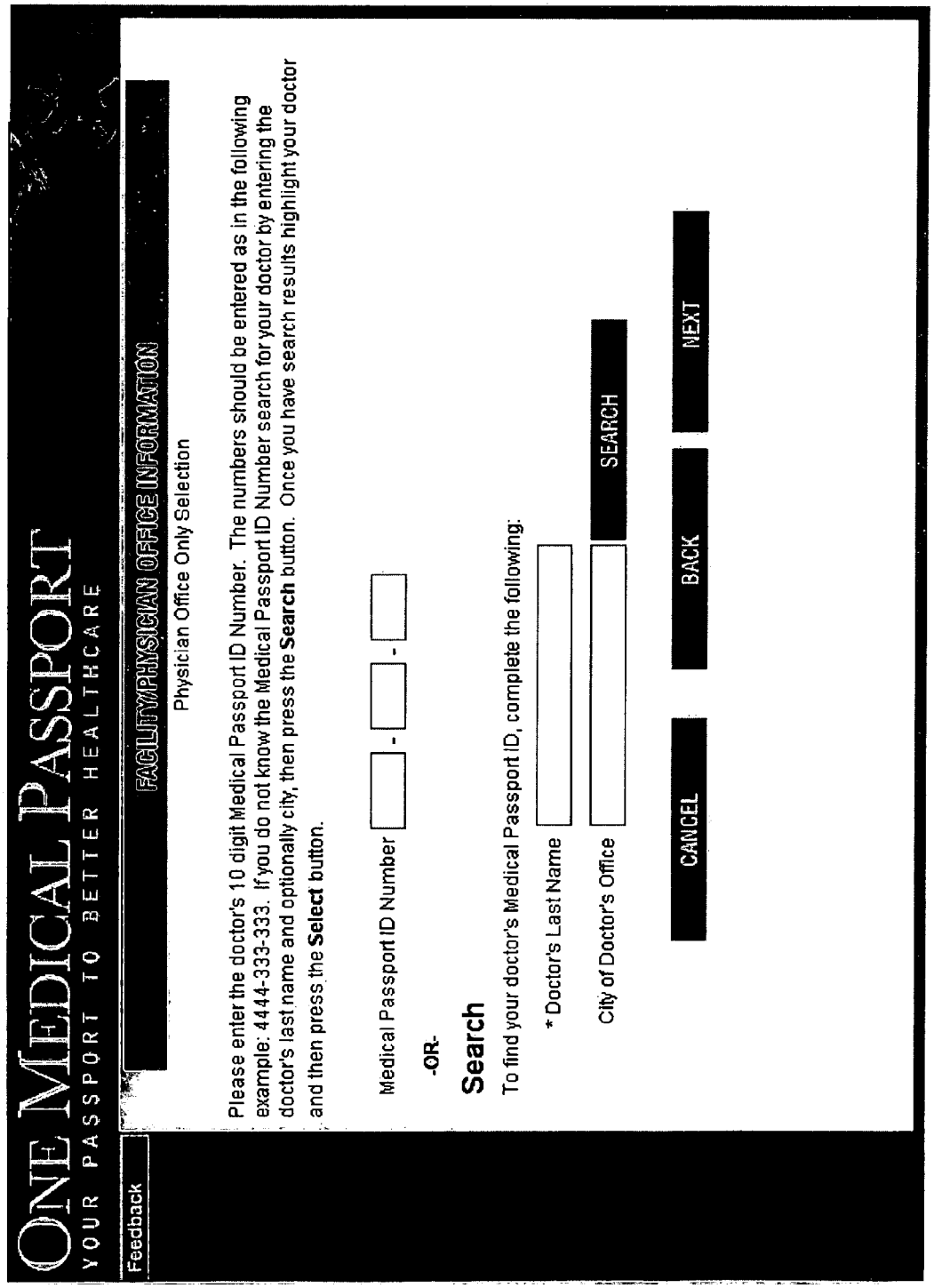
FIG. 95 shows a physician office selection page.

FIG. 7 is a flow chart showing the medical visit type process 250. The process begins with the user selecting the visit type: medical facility and physician (step 251), physician only (step 252), or personal use only (step 253). If the user selects 'medical facility and physician', the process proceeds to a medical facility selection page 2100 (step 254; FIG. 94). Once a medical facility has been selected, the process proceeds to the basic medical history process 260. Similarly, if the user selects 'physician only', the process proceeds to a physician office selection page 2200 (step 255; FIG. 95), and then to the basic medical history process 260. Finally, if the user selects 'personal use only', the process proceeds directly to the basic medical history process 260.

Figure 8:
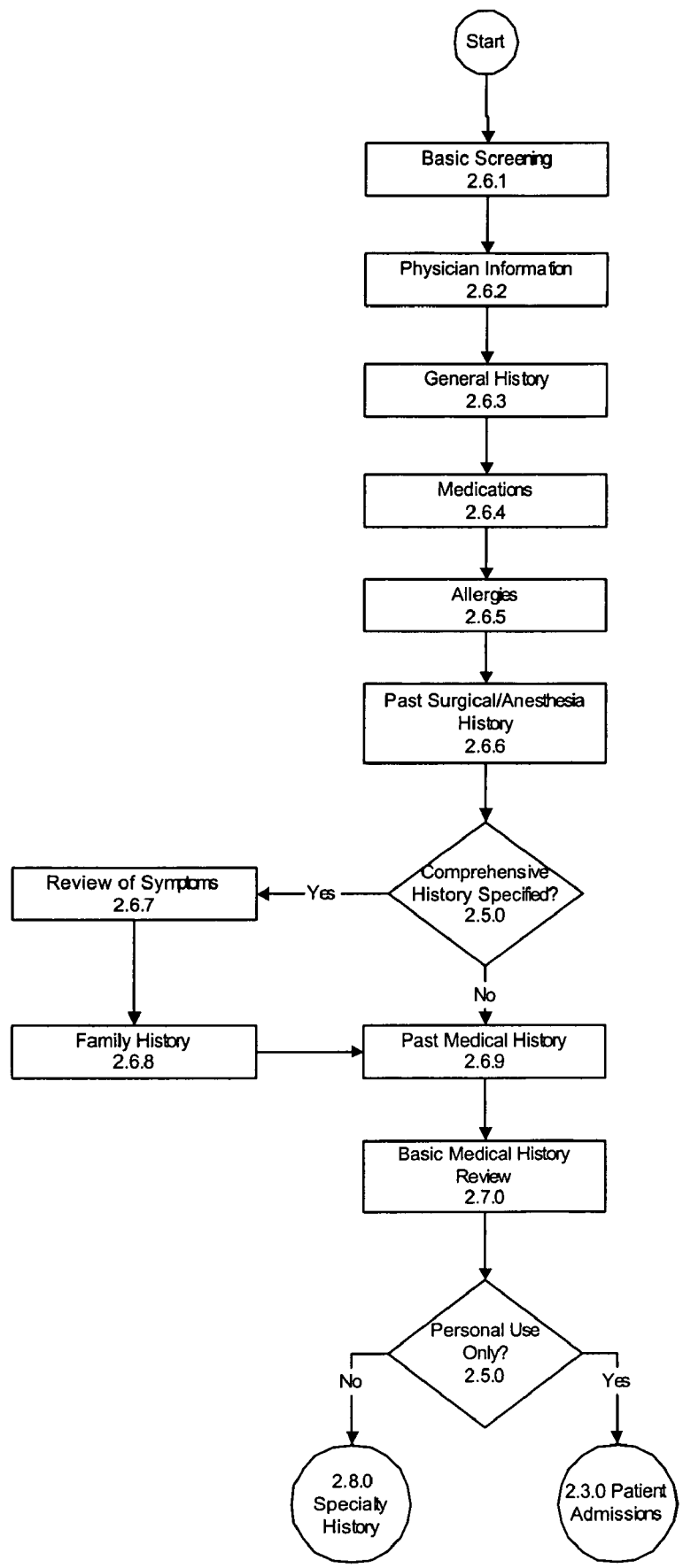
FIG. 8 is a flow diagram showing the basic medical history process.

FIG. 8 is a flow chart showing the basic medical history process 260. The process begins with a basic screening questionnaire including questions relating to height, weight, cigarette smoking, etc. (step 261). After the basic screening questionnaire has been completed, the process proceeds to a physician information questionnaire page (step 262). Additionally questionnaire pages are presented successively, including a general history questionnaire page (step 263), a medications questionnaire page (step 264), an allergies questionnaire page (step 265), a past surgical/anesthesia history questionnaire page (step 266), and a past medical history questionnaire page (step 269). If the medical facility or physician selected during the medical visit type process 250 requires a comprehensive medical history, a symptoms questionnaire page (step 267), and a family history questionnaire page (step 268) are also presented. Once all questionnaires have been answered, the user is permitted the opportunity to review the basic medical history information (step 270). If the information is acceptable to the user, the process proceeds to specialty selection process 280, unless the has previously selected 'personal use only' in the medical visit type process 250, in which case the process returns to the patient admissions process 230.

Figure 9:
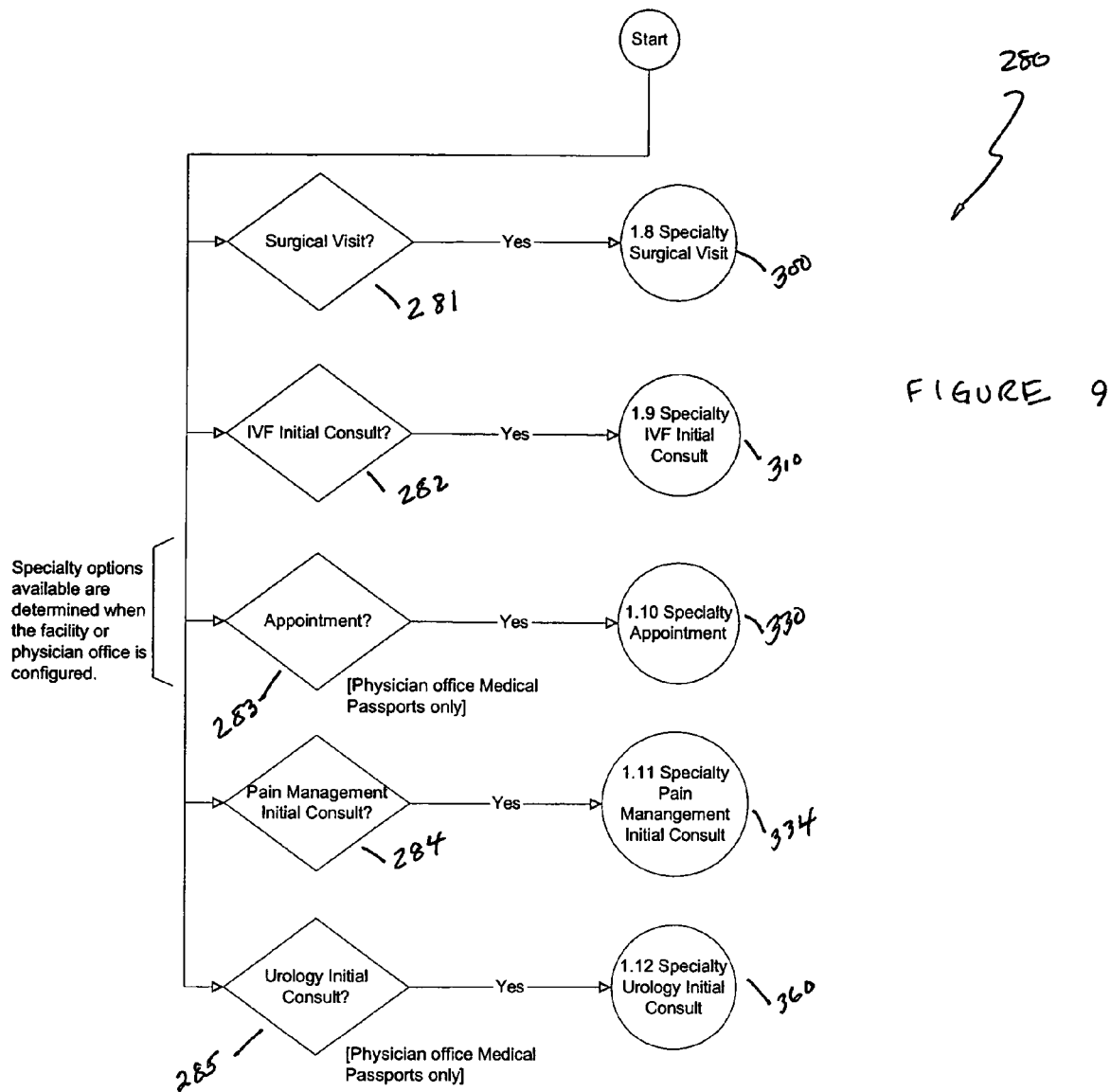
FIG. 9 is a flow diagram showing the specialty selection process.

FIG. 9 is a flow chart showing the specialty selection process 280. A specialty selection page presents various specialties from which the user may select one. In particular, the user may select a surgical visit (step 281), an In Vitro Fertilization (IVF) initial consult (step 282), an appointment (step 283), a pain management initial consult (step 284), or a urology initial consult (step 285). If the user selects a surgical visit, the process proceeds to the surgical visit process 300. If the user selects an IVF initial consult, the process proceeds to the IVF initial consult process 310. If the user selects an appointment, the process proceeds to the specialty appointment process 330. If the user selects a pain management initial consult, the process proceeds to the pain management initial consult process 340. Finally, if the user selects a urology initial consult, the process proceeds to the urology initial consult process 360.

Figure 10:
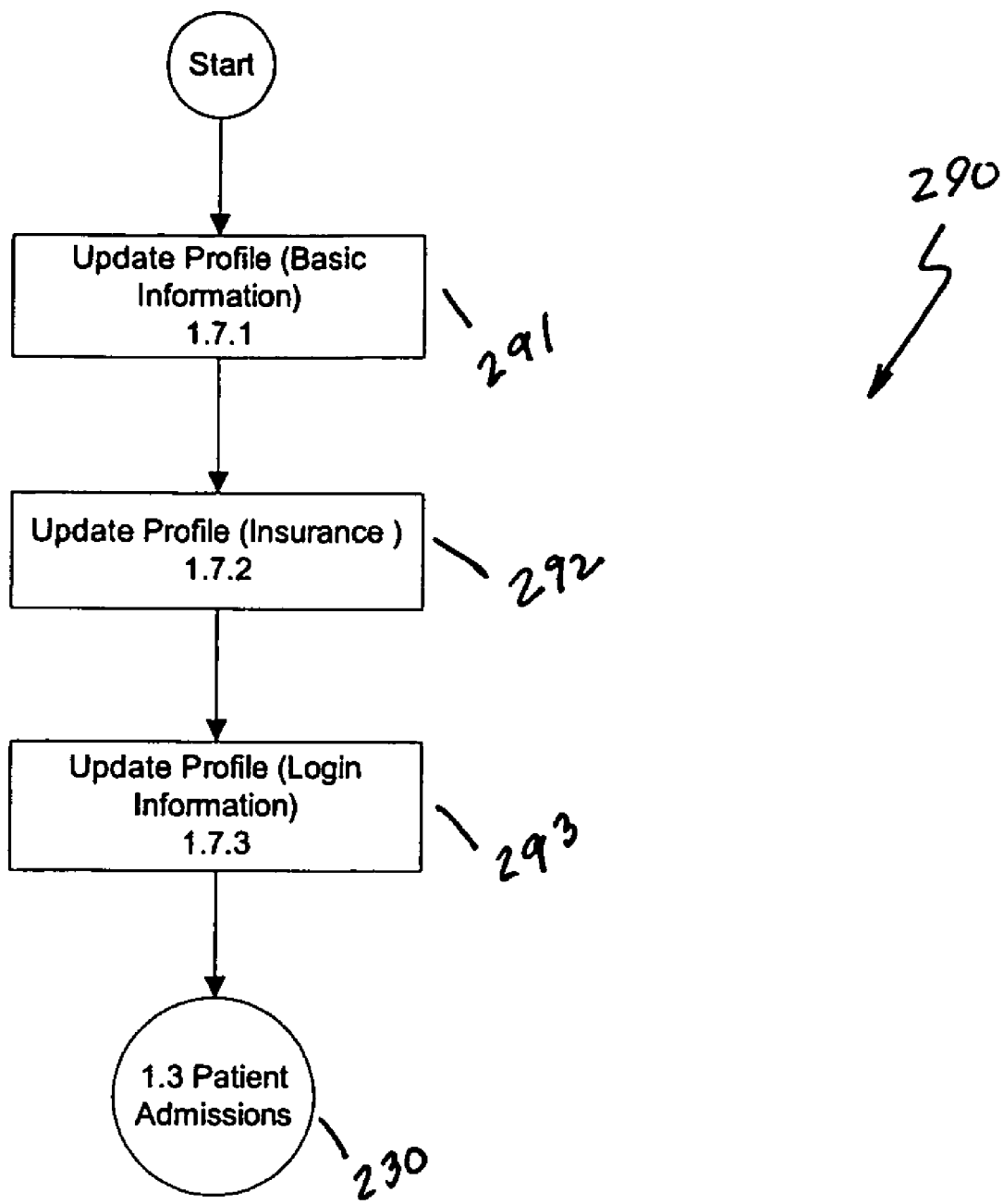
FIG. 10 is a flow diagram showing the update profile process.

FIG. 10 is a flow chart showing the update profile process 290. The user may enter this process from the patient admissions process 230, as explained above. The update profile process permits the user to edit "basic information" (step 291), "insurance information" (step 292), or "login information" (step 293) previously entered.

Figure 11:
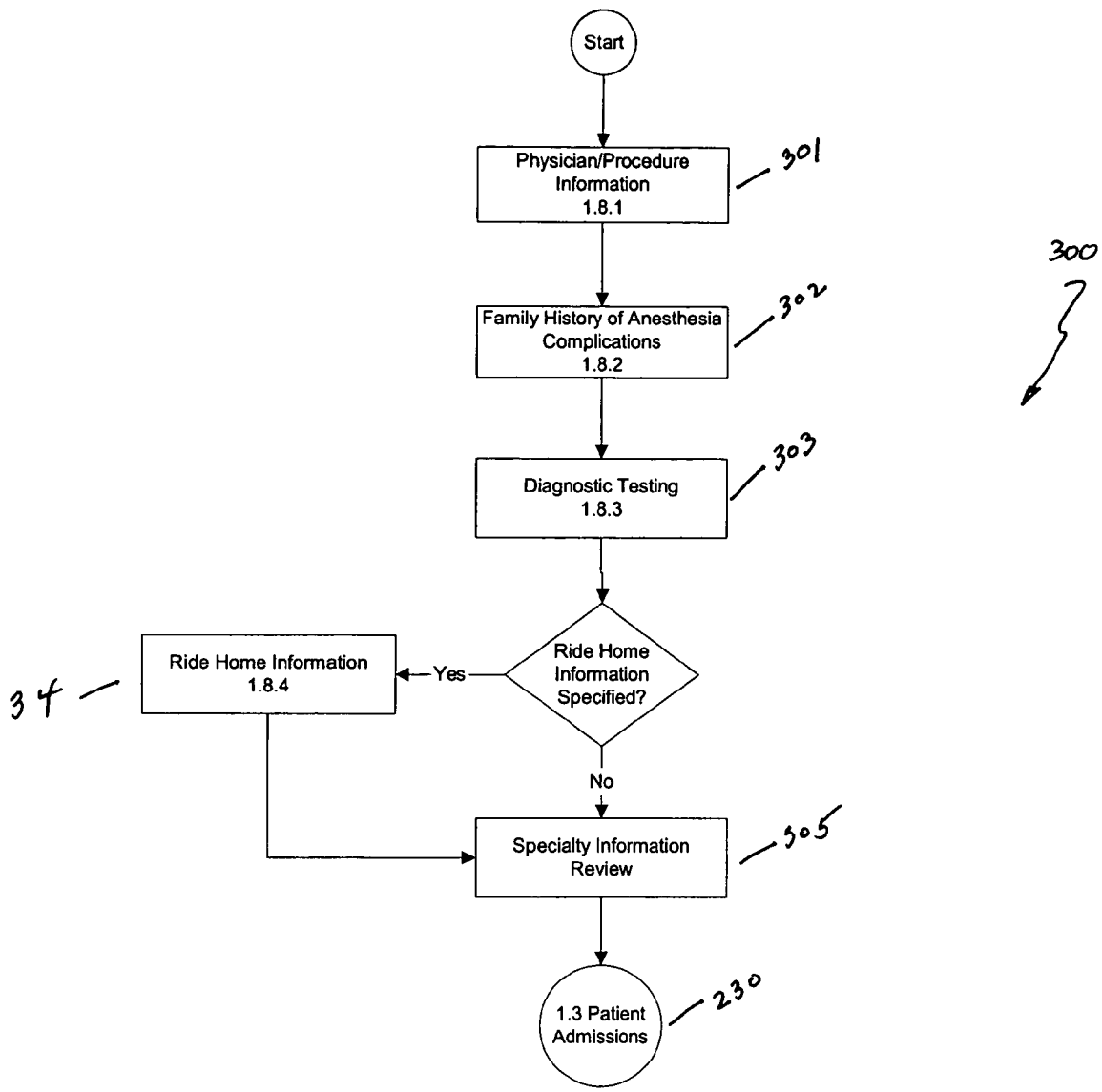
FIG. 11 is a flow diagram showing the surgical visit process.

FIG. 11 is a flow chart showing the surgical visit process 300. The surgical visit process comprises a series of successive questionnaires including a physician/procedure questionnaire (step 301), a family history of anesthesia complications questionnaire (step 302), a diagnostic testing questionnaire (step 303), and ride home information questionnaire (step 304). Once all questionnaires have been answered, the user is permitted the opportunity to review the surgical visit information (step 305). If the information is acceptable to the user, the process returns to the patient admissions process 230.

Figure 12:
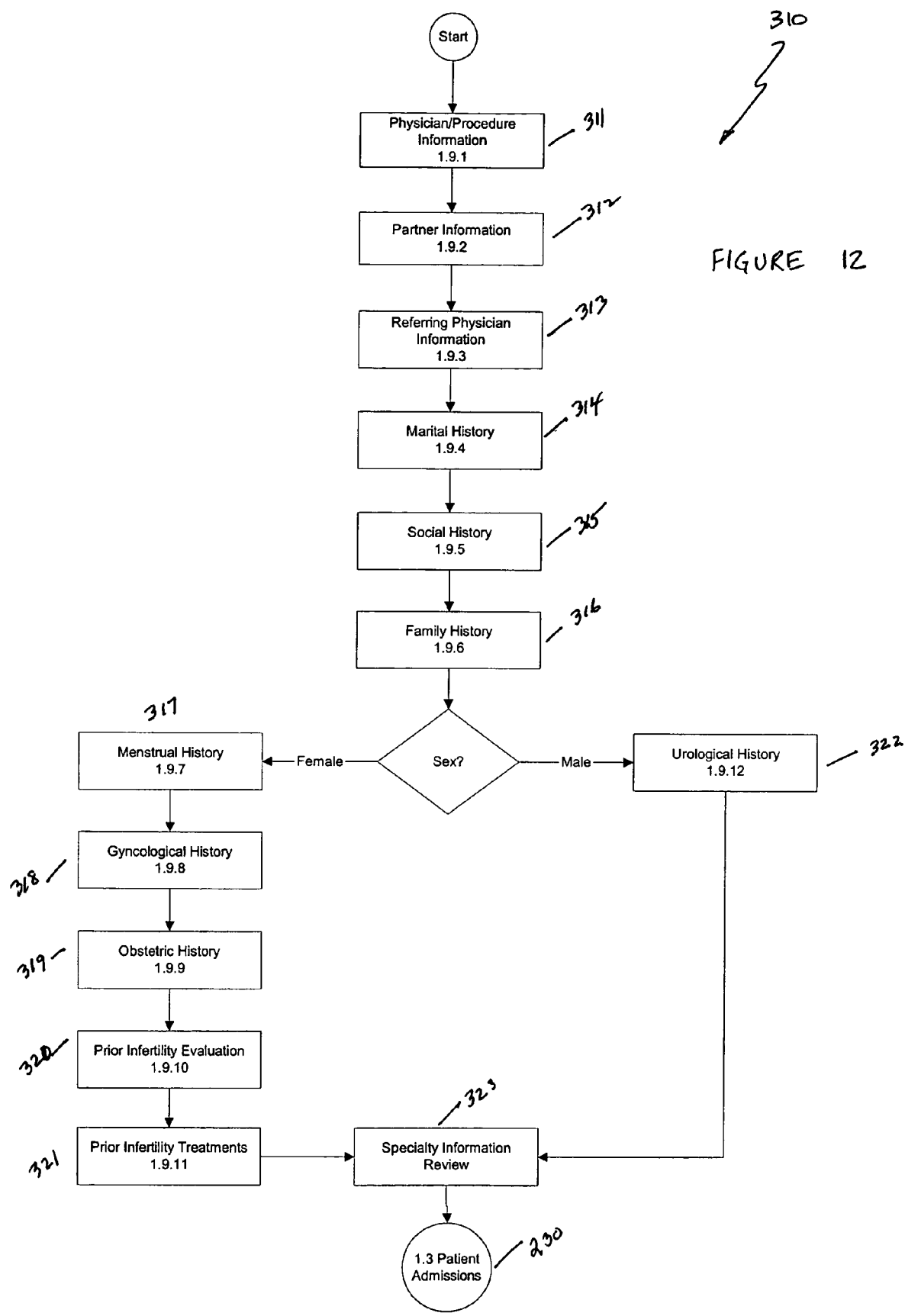
FIG. 12 is a flow diagram showing the IVF initial consult process.

FIG. 12 is a flow chart showing the IVF initial consult process 310. The IVF initial consult process 310 comprises a series of successive questionnaires including a physician/procedure questionnaire (step 311), a partner questionnaire (step 312), a referring physician questionnaire (step 313), a marital history questionnaire (step 314), a social history questionnaire (step 315), and a family history questionnaire (step 316). If the patient is female, additional questionnaires are presented, including a menstrual history questionnaire (step 317), a gynecological history questionnaire (step 318), a obstetric history questionnaire (step 319), a prior infertility questionnaire (step 320), and a prior infertility treatments questionnaire (step 321). If the patient is male, a urological history questionnaire is provided in place of the above-mentioned female questionnaires (step 322). Once all questionnaires have been answered, the user is permitted the opportunity to review the IVF initial consult information (step 323). If the information is acceptable to the user, the process returns to the patient admissions process 230.

Figure 13:
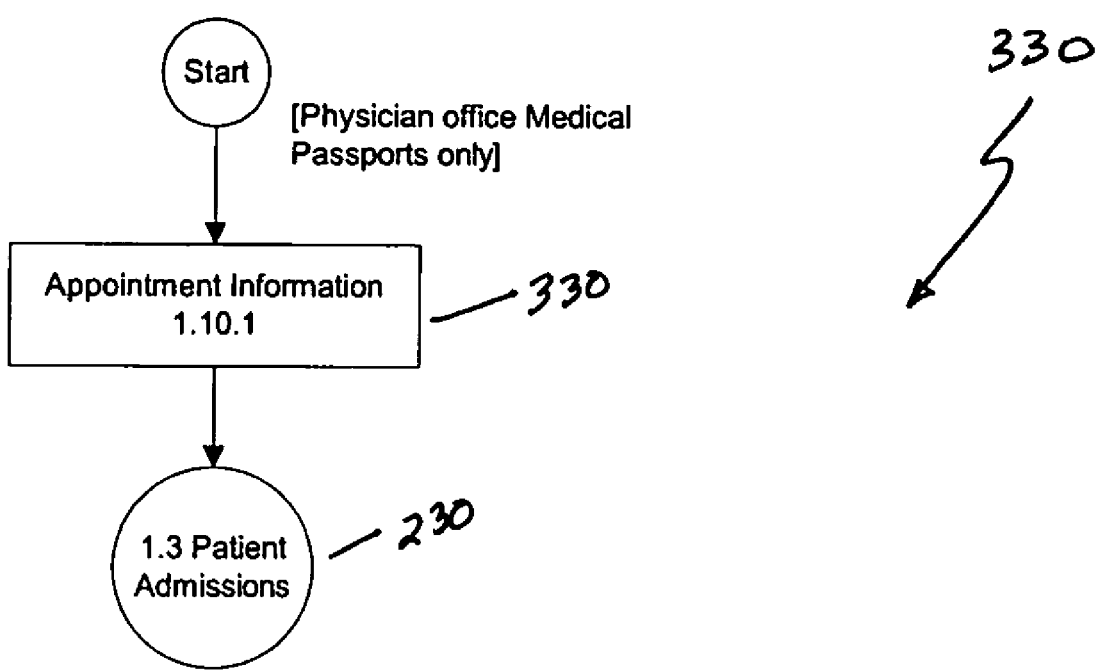
FIG. 13 is a flow diagram showing the specialty appointment process.

FIG. 13 is a flow chart showing the specialty appointment process 330. The specialty appointment process 330 permits the patient to specify the date, time, and other relevant information relating to the specialty appointment, and then the process returns to the patient admissions process 230.

Figure 14:
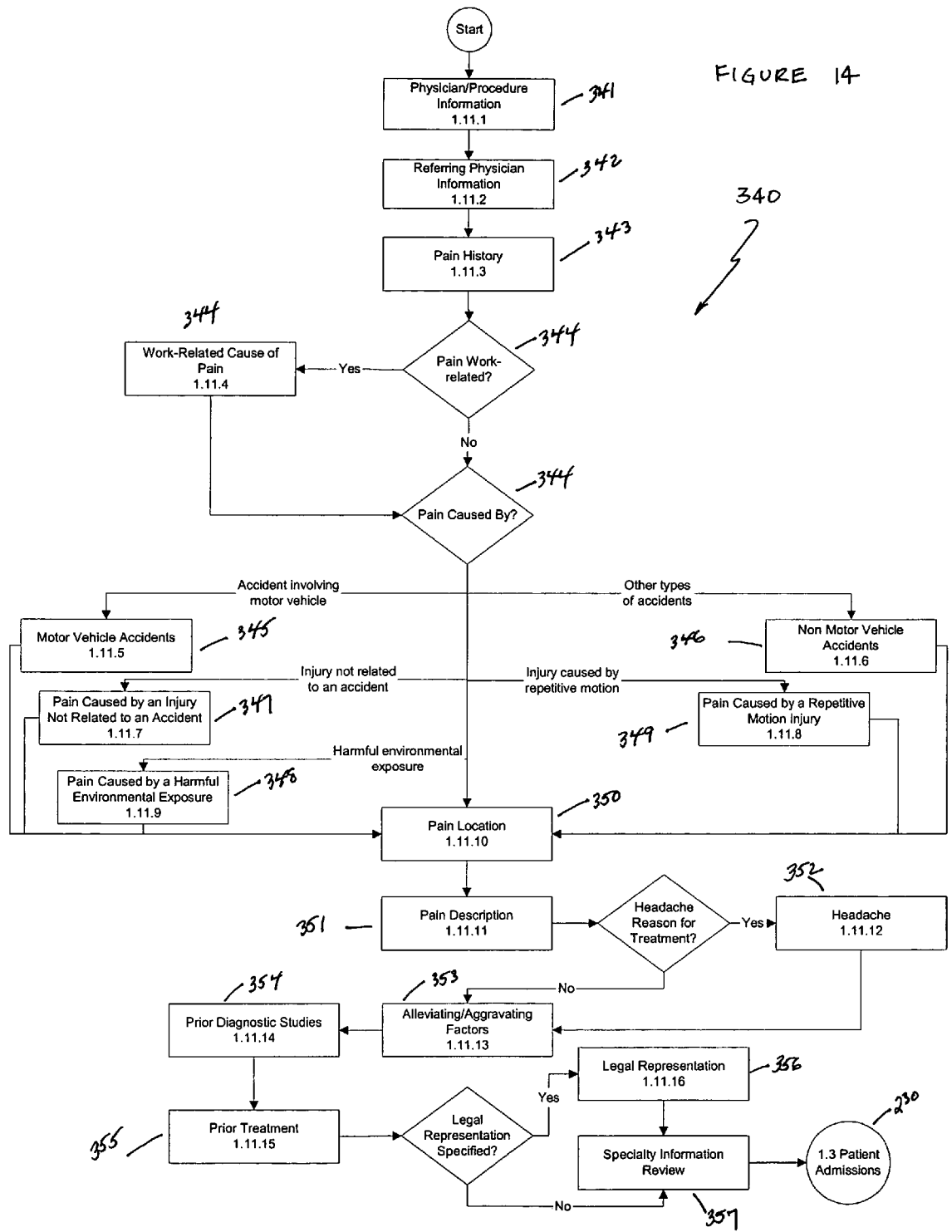
FIG. 14 is a flow diagram showing the pain management initial consult process.

FIG. 14 is a flow chart showing the pain management initial consult process 340. The pain management initial consult process 340 comprises a series of successive questionnaires including a physician/procedure questionnaire (step 341), a referring physician questionnaire (step 342), and a pain history questionnaire (step 343). If the pain is work-related, a work-related pain questionnaire is presented (step 344). If the pain is not work-related, the process proceeds to a either a motor vehicle accident questionnaire (step 345), a non-motor vehicle accident questionnaire (step 346), an injury not related to accident questionnaire (step 347), a harmful environmental exposure questionnaire (step 348), or a repetitive motion injury questionnaire (step 349), depending upon the user's choice. Once the particular questionnaire has been completed, the user is presented a pain location questionnaire (step 350), and a pain description questionnaire (step 351). If the pain description questionnaire identifies a 'headache' as a symptom, a headache questionnaire is also presented to the user (step 352). Additional questionnaires are successively provided, including a alleviating/aggravating factors questionnaire (step 353), a prior diagnostic studies questionnaire (step 354), and a prior treatment questionnaire (step 355). If the medical facility or physician's office requests information on the patient's legal representation, a legal representation questionnaire is also presented (step 356). Once all questionnaires have been answered, the user is permitted the opportunity to review the pain management initial consult information (step 357). If the information is acceptable to the user, the process returns to the patient admissions process 230.

Figure 15:
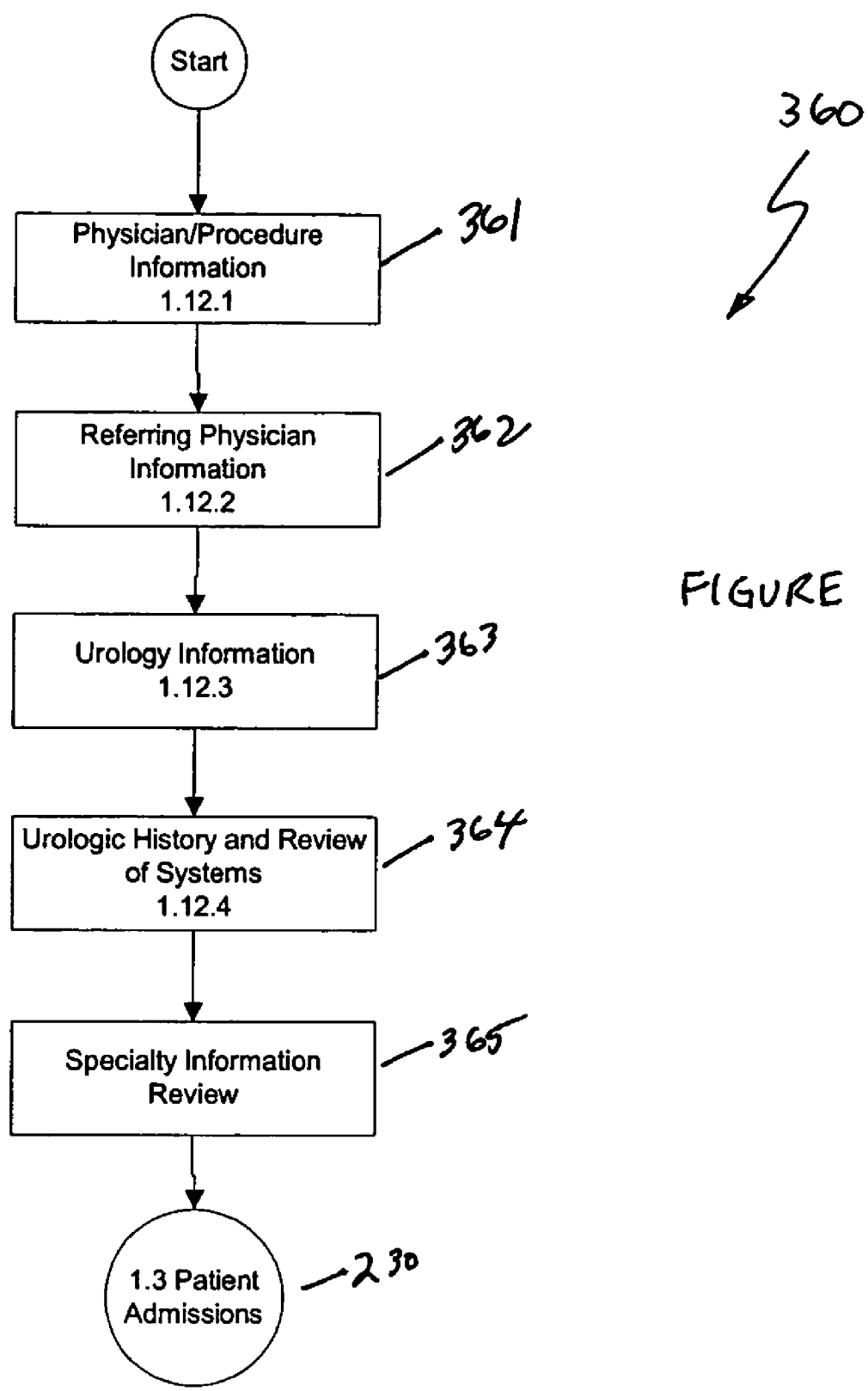
FIG. 15 is a flow diagram showing the urology initial consult process.

FIG. 15 is a flow chart showing the urology initial consult process 360. The urology initial consult process 360 comprises a series of successive questionnaires including a physician/procedure questionnaire (step 361), a referring physician questionnaire (step 362), a urology information questionnaire (step 363) and a urologic history questionnaire (step 364). Once all questionnaires have been answered, the user is permitted the opportunity to review the pain management initial consult information (step 365). If the information is acceptable to the user, the process returns to the patient admissions process 230.

The following listing further explains some of the items shown in FIGS. 3-15:

1.0.1 Patient Admissions—Main access point for returning patients to log in or new patients to register.
1.0.2 Information—Basic information about the One Medical Passport site for patients.
1.0.3 Directions to Facilities—Provides links to sites for medical facilities that utilize One Medical Passport (if available).
1.0.4 Contact Us—Allows patients to send an email to One Medical Passport support.
1.0.5 Feedback—Allows patients to provide feedback about the site to One Medical Passport staff.
1.0.6 Privacy Policy—Description of the terms and conditions surrounding the capture and use patient information.
1.0.7 Password Reminder—Automated password reminder for patients. Based on the email address, username, and a codeword the password is reset and emailed to the patient.
1.1 New Patient Registration
1.1.1 Terms of Use—Provides information about the terms of use for the patient. The user must agree with the terms of use to register.
1.1.2 Patient Registration Instructions—Lists information that the patient will need to register.
1.1.3 Basic Information—Questions pertaining to who is completing the registration, basic patient information, address, employment information, closest relative, and a contact person.
1.1.4 Insurance—Questions pertaining to the patient's primary and secondary insurance information.
1.1.5 Login Information—Allows the patient to create a username, password, and codeword reminder phrase. This permits the patient to reenter One Medical Passport.
1.1.6 Facility/Physician Office Information—Provides the options for the types of visits that are available. Patients scheduled for medical procedures or surgery at a medical facility selects the Medical Facility and Physician option. Patients scheduled for initial consultations or follow up visits with a physician select the Physician Office Only option. Patients that want to record their medical history, but not submit it, use the Personal Use Only option.
1.2 Patient Login
1.2.1 Basic Information Review—Review screen of questions pertaining to who is completing the registration, basic patient information, address, employment information, closest relative, and a contact person.

1.2.2 Basic Information Update—Questions pertaining to who is completing the registration, basic patient information, address, employment information, closest relative, and a contact person.

1.2.3 Insurance Review—Review screen of questions pertaining to the patient's primary and secondary insurance information.

1.2.4 Insurance Update—Questions pertaining to the patient's primary and secondary insurance information.

1.2.5 Login Information Review—Review screen of questions allowing the patient to create a username, password, and codeword reminder phrase.

1.2.6 Login Information Update. —Allows the patient to update username and codeword reminder phrase.

1.3 Patient Admissions 1.3.1 Send a copy of my Medical Passport to a physician and/or medical facility—Allows a patient to update any previously entered medical history and submit it to either a medical facility or physician office.

1.3.2 Finish an incomplete copy of my Medical Passport—Allows the patient to complete a partially entered Medical Passport.

1.3.3 Medical Passport Selection—Displays a listing of incomplete Medical Passports (for option 1.3.2) or pending/downloaded Medical Passports (for option 1.3.4).

1.3.4 Review/Edit a previously submitted copy of my Medical Passport—Allows a patient to edit a Medical Passport that has not been downloaded by a medical facility or physician office. If the Medical Passport has been downloaded the patient can only review the information submitted.

1.3.5 Personal Use Only—Allows the patient to enter their basic medical history without submitting it to a medical facility or physician office.

1.3.6 View my Medical Passport usage history—Displays a listing of all medical passports creating by a patient (by procedure date, completed date, procedure, physician, medical facility, Medical Passport type, and status).

1.3.7 Print a copy of my Medical Passport—Allows a patient to print their basic medical history for their personal use using Adobe Acrobat.

1.3.8 Delete an existing copy of my Medical Passport—Allows the patient to delete an incomplete or pending Medical Passport. A Medical Passport downloaded by a medical facility or physician office may not be deleted.

1.3.9 Edit my name, address, insurance, or other personal information—Allows the patient to change their basic demographic information.

1.3.10 Change my password—Allows the patient to change their login password.

1.4 Medical Visit Type Selection 1.4.1 Medical Facility Selection Page—Allows a patient to select the medical facility for the Medical Passport. This is for patients scheduled for medical procedures or surgery at a medical facility.

1.4.2 Physician Office Selection Page—Allows a patient to select the doctor's Medical Passport ID for the Medical Passport. This is for patients scheduled for initial consultations or follow up visits with a physician.

1.5 Basic Medical History 1.5.1. Basic Screening—Questions pertaining to height, weight, cigarette smoking, alcoholic beverages, and recreational drug use.

1.5.2. Physician Information—Questions pertaining to primary care physician and specialists.

1.5.3. General History—Questions pertaining to wearing, use, or implanting of glasses, contact lenses, dentures or partials, hearing aids, cardiac pacemaker, artificial joints, medical plates, screws, pins, and body piercing.

1.5.4. Medications—Questions pertaining to prescription medications, nonprescription medications, complementary alternative medications, and herbals.

1.5.5. Allergies—Questions pertaining to allergies or adverse reactions to medications or medical products, food allergies, latex product allergies, adhesive tape allergies, and iodine or x-ray dye allergies.

1.5.6. Past Surgical/Anesthesia History—Questions pertaining to medical procedures that required anesthesia.

1.5.7. Review of Symptoms—Questions pertaining to overall health and physical activity. This is an optional page that is only displayed if the medical facility or physician office has specified to collect a comprehensive medical history.

1.5.8. Family History—Questions pertaining to the family history of immediate relatives. This is an optional page that is only displayed if the medical facility or physician office has specified to collect a comprehensive medical history.

1.5.9. Past Medical History—Questions pertaining to past medical history by system. Systems include cardiac, pulmonary, renal (questions based on sex), hepatic, neurologic, GI, endocrine/oncologic, hematologic, musculoskeletal, psychiatric, obstetrical (for females).

1.7 Update Profile 1.7.1 Basic Information Update—Questions pertaining to who is completing the registration, basic patient information, address, employment information, closest relative, and a contact person.

1.7.2 Insurance Update—Questions pertaining to the patient's primary and secondary insurance information.

1.7.3 Login Information Update—Allows the patient to update username and codeword reminder phrase.

1.8 Specialty Surgical Visit 1.8.1 Physician/Procedure Information—Questions pertaining to surgical site, type of procedure, physician, and scheduled date of procedure.

1.8.2 Family History of Anesthesia Complications—Questions pertaining to malignant hyperthermia, pseudocholinesterase deficiency, and motion sickness.

1.8.3 Diagnostic Testing—Questions pertaining to the EKG, chest XRAY, cardiac stress test, and cardiac echo diagnostic tests.

1.8.4 Ride Home Information—Questions pertaining to fulfilling the requirement by some medical facilities that the patient have a ride home from their procedure.

1.9 Specialty IVF Initial Consult 1.9.1 Physician/Procedure Information—Questions pertaining to physician and scheduled date of procedure.

1.9.2 Partner Information—Questions pertaining to the patient's partner (name, address, and date of birth) and reason for the consult appointment.

1.9.3 Referring Physician Information—Questions pertaining to who the physician was that referred the patient to the practice.

1.9.4 Marital History—Questions pertaining to current marital status, years with current partner, number of pregnancies, prior marriages, and children.

1.9.5 Social History—Questions pertaining to occupation, caffeine intake, heat exposure, radiation exposure, chemical exposure, and ancestral background.

1.9.6 Family History—Questions pertaining to the patient's family history (such as birth defects, stillbirth, etc).

1.9.7 Menstrual History—Questions pertaining to periods and frequency of intercourse.

1.9.8 Gynecological History—Questions pertaining to gynecological history (such as pelvic infection, birth control pills, etc.).

1.9.9 Obstetric History—Questions pertaining to obstetric history (date and outcome).

1.9.10 Prior Infertility Evaluation—Questions pertaining to urine ovulation kits, endometrial biopsy, semen analysis, hysterosalpingogram, laparoscopy, hysteroscopy, and FSH blood tests.

1.9.11 Prior Infertility Treatments—Questions pertaining to clomid or serophene, FSH injectable medications, intrauterine insemination, and WVF or GIFT.

1.9.12 Urological History—Questions pertaining to urological history (such as mumps, vasectomy, etc).

1.10 Specialty Appointment 1.10.1 Appointment Information—Allows the patient to specify the date of the appointment at the physician's office.

1.11 Specialty Urology Initial Consult 1.11.1 Physician/Procedure Information—Question pertaining to the doctor's Medical Passport ID and scheduled date of procedure.

1.11.2 Referring Physician Information—Questions pertaining to the physician who referred the patient to the practice.

1.11.3 Pain History—Questions pertaining to the primary reason for seeking treatment, when the pain first started, how the pain started, what the pain was a result of, if the pain was work related, and dominant hand.

1.11.4 Work-Related Cause of Pain—Questions about the employer during the work-related cause of pain and if workers' compensation was involved.

1.11.5 Motor Vehicle Accidents—Questions pertaining to type of vehicle involved, speed of accident, details of accident, loss of consciousness, time to seek medical treatment, time after that pain started, and broken bones from accident.

1.11.6 Non Motor Vehicle Accidents—Questions pertaining to type of accident, details of accident, loss of consciousness, time to seek medical treatment, time after the pain started, and broken bones from accident.

1.11.7 Pain Caused by an Injury Unrelated to an Accident—Question about the details involved in the cause of pain.

1.11.8 Pain Caused by a Repetitive Motion Injury—Question about the details involved in the cause of pain.

1.11.9 Pain Caused by a Harmful Environmental Exposure—Question about the details involved in the cause of pain.

1.11.10 Pain Location—Questions pertaining to the location of the primary area of pain and where the pain radiates to (if it radiates).

1.11.11 Pain Description—Questions pertaining to the quality of pain, frequency, any numbness, temperature changes in area, color changes in area, previous episodes of pain, time when pain is better, time when pain is worse, a pain score, ability to work, ability to sleep, interference with relationships, depression caused by pain, and suicidal feelings caused by pain.

1.11.12 Headache—Questions pertaining to age headaches started, head trauma, frequency, symptoms, length, last eye exam date, caffeine intake, and relationship to menstrual cycle (if patient is female).

1.11.13 Alleviating/Aggravating Factors—Questions pertaining to what makes your pain worse or better.

1.11.14 Prior Diagnostic Studies—Questions pertaining to the patient having X-Rays, CT scans, MRI scans, Bone scans, and EMG.

1.11.15 Prior Treatment—Questions pertaining to visiting a chiropractor, physical therapy, pain medications, and injection/nerve blocks.

1.11.16 Legal Representation—Questions pertaining to if the patient is being represented by a lawyer and involvement in litigation. This screen is only displayed if it is specified when the medical facility or physician office is setup.

1.12 Specialty Urology Initial Consult 1.12.1 Physician/Procedure Information—Question pertaining to the scheduled date of procedure.

1.12.2 Referring Physician Information—Questions pertaining to who the physician was that referred the patient to the practice.

1.12.3 Urology Information—Questions pertaining to if the patient has visited a urologist before, the main reason for the appointment, and the number of children.

1.12.4 Urologic History and Review of Systems—Questions pertaining to sexual dysfunction, kidney or bladder infections, kidney stones, blood in urine, urinating too frequently, difficulty starting urination, slow urinary stream, awakening at night to urinate, bedwetting, and vaginal discharge (for females).

Facility Login

Figure 16:
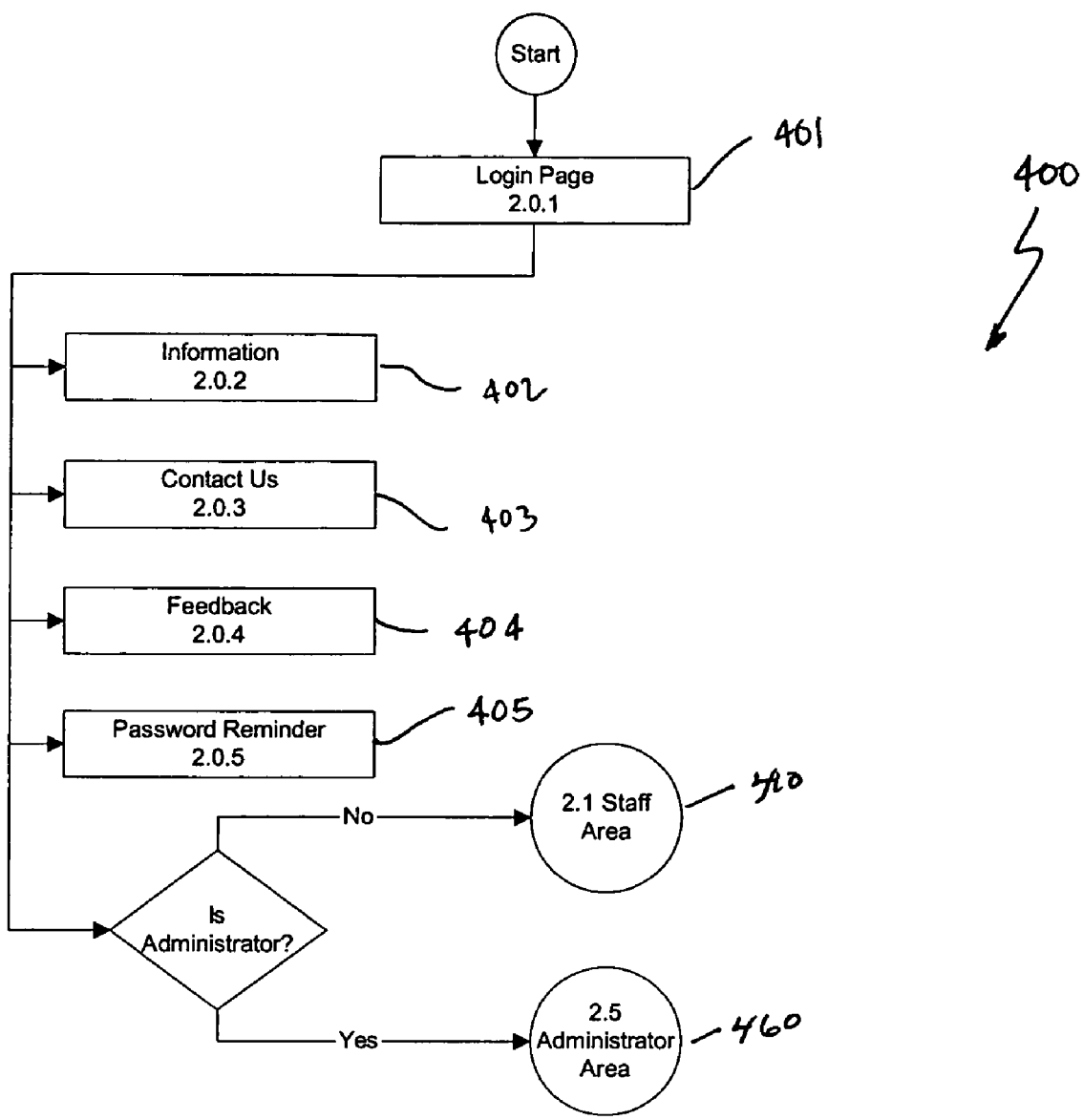
FIG. 16 is a flow diagram showing the facility login process

FIG. 16 is a flow chart showing the facility login process 400 which is initiated when the user selects to login as a 'facility' from the homepage 2000 (step 102 in FIG. 2). The facility login process 400 begins with the facility user selecting to login as either a "staff" or "administrator" from a facility login page 2300 (step 401). The facility login page 2300 (not shown) also provides access to an information page (step 402), a contact information page (step 403), a feedback page (step 404), and a password reminder page (step 405). If the user selects to login as "staff", the process proceeds to the staff administration process 410 (See FIG. 17). If the user selects to login as an "administrator", the process proceeds to administrator administration process 460 (See FIG. 21).

Figure 17:
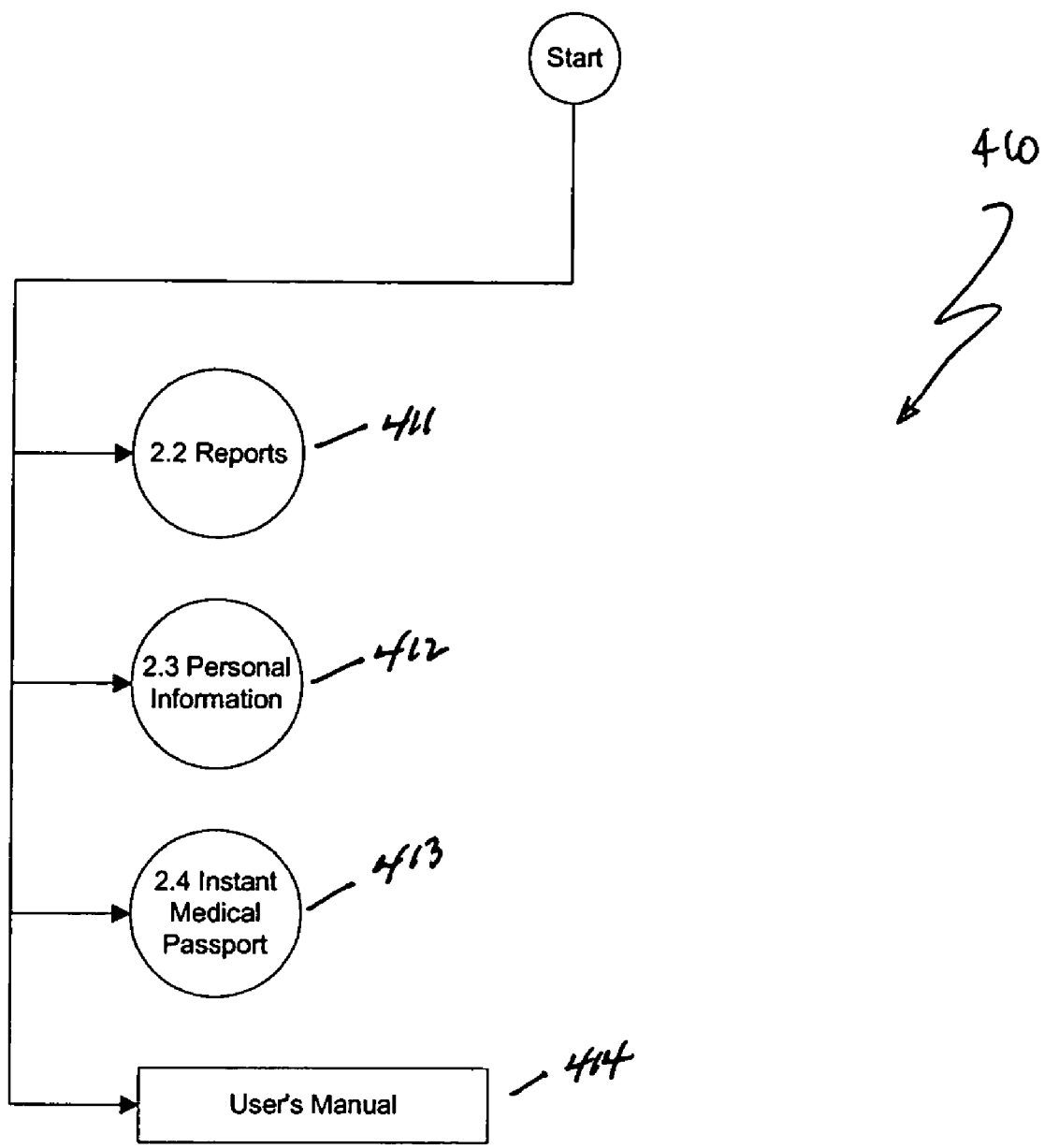
FIG. 17 is a flow diagram showing the staff administration process.
Figure 96:
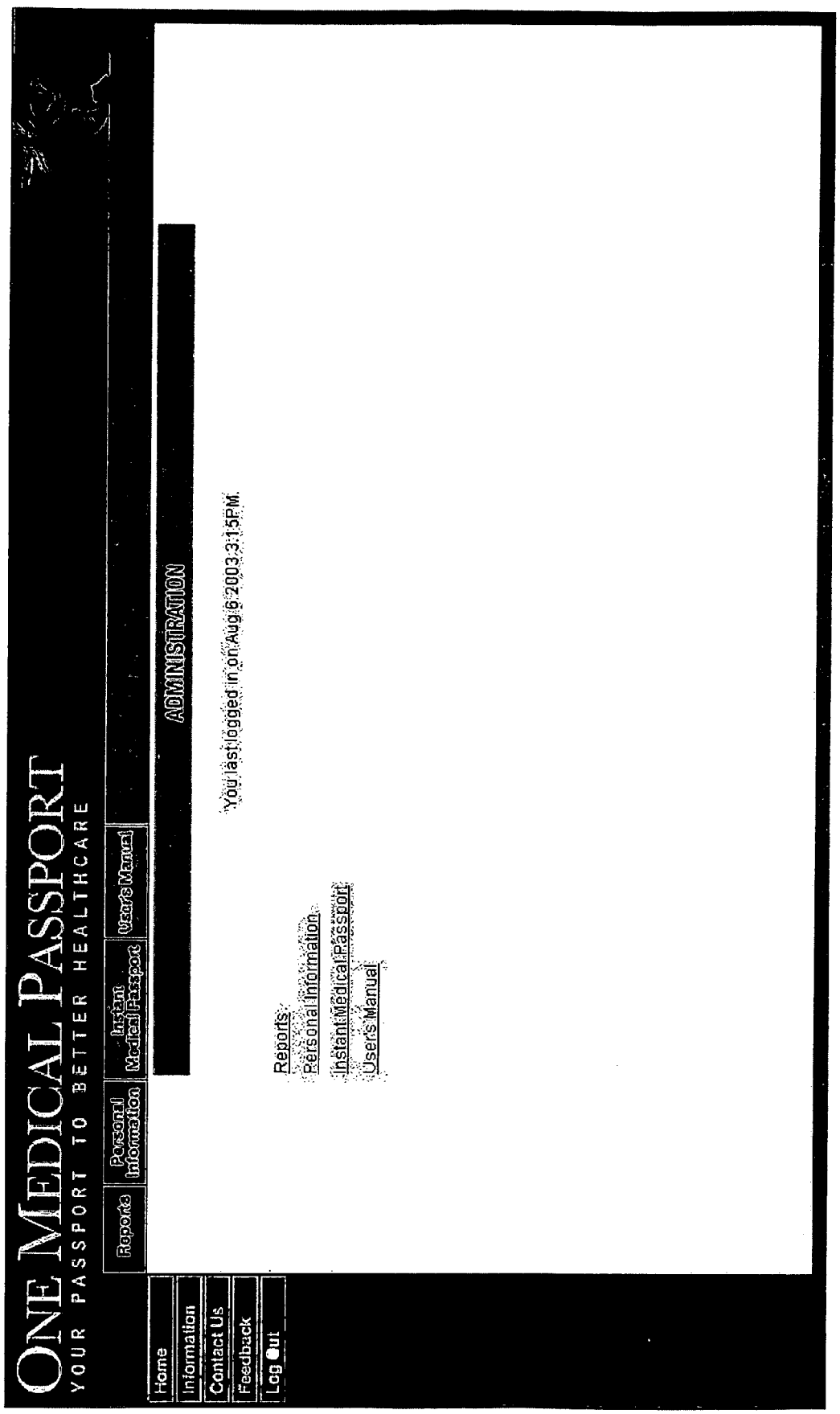
FIG. 96 shows a staff administration page.

FIG. 17 is a flow chart showing the staff administration process 410. Upon initiation of the staff administration process 410 the user is presented a staff administration page 2310 (see FIG. 96) which provides links to other processes, such as a reports process 420 (step 411), a personal information process 430 (step 412), and a instant medical passport process 440 (step 413). The staff user may also access a user's manual from the staff administration page 2310 (step 414).

Figure 18:
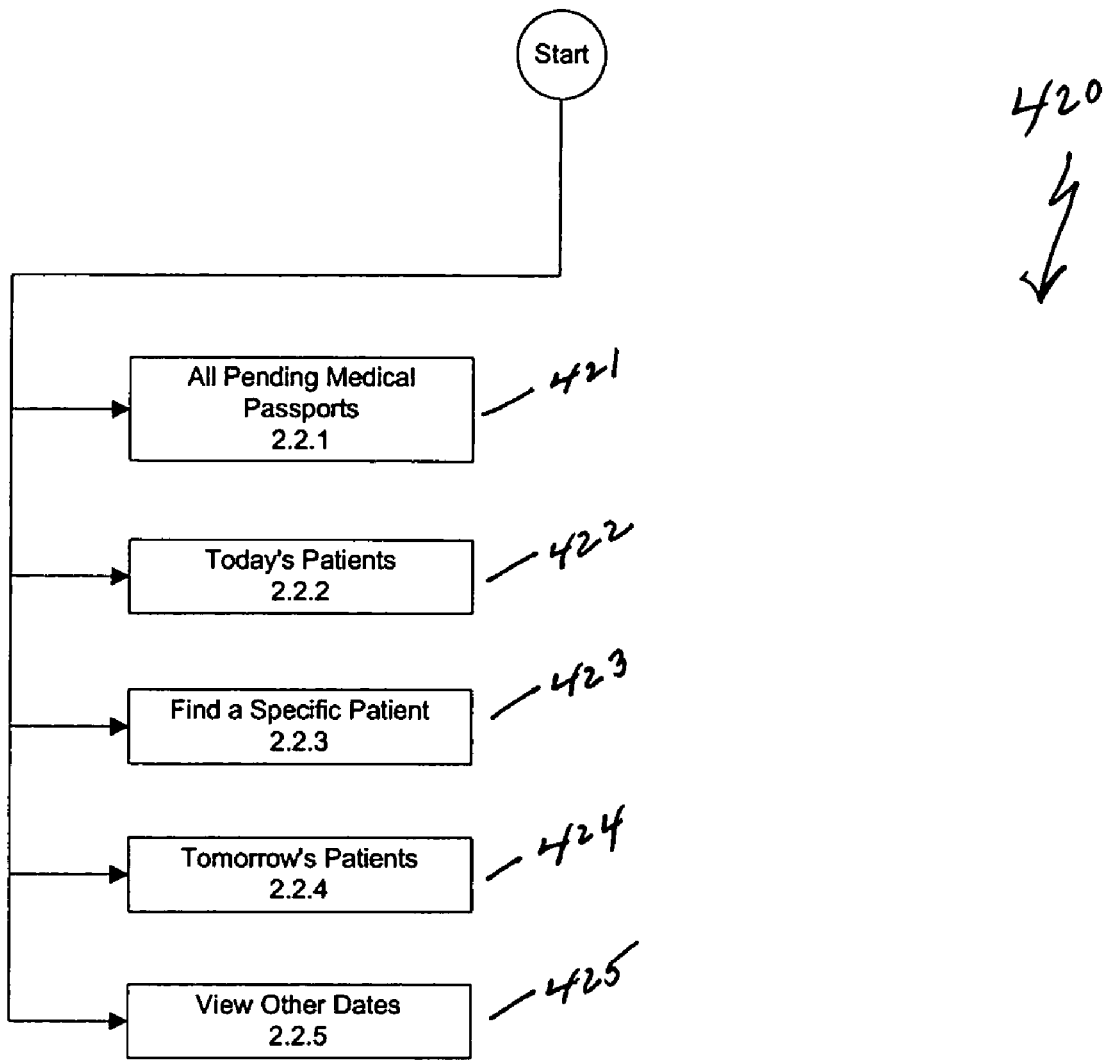
FIG. 18 is a flow diagram showing the reports process.

FIG. 18 is a flow chart showing the reports process 420. Using this process, the staff user may generate reports of Medical Passports in several different ways. The staff user may display all pending Medical Passports (step 421), Medical Passports for the day's patients (step 422), Medical Passport for a specific patient (step 423), Medical Passports for tomorrow's patients (step 424), and/or Medical Passports for any selected date or date range (step 425).

Figure 19:
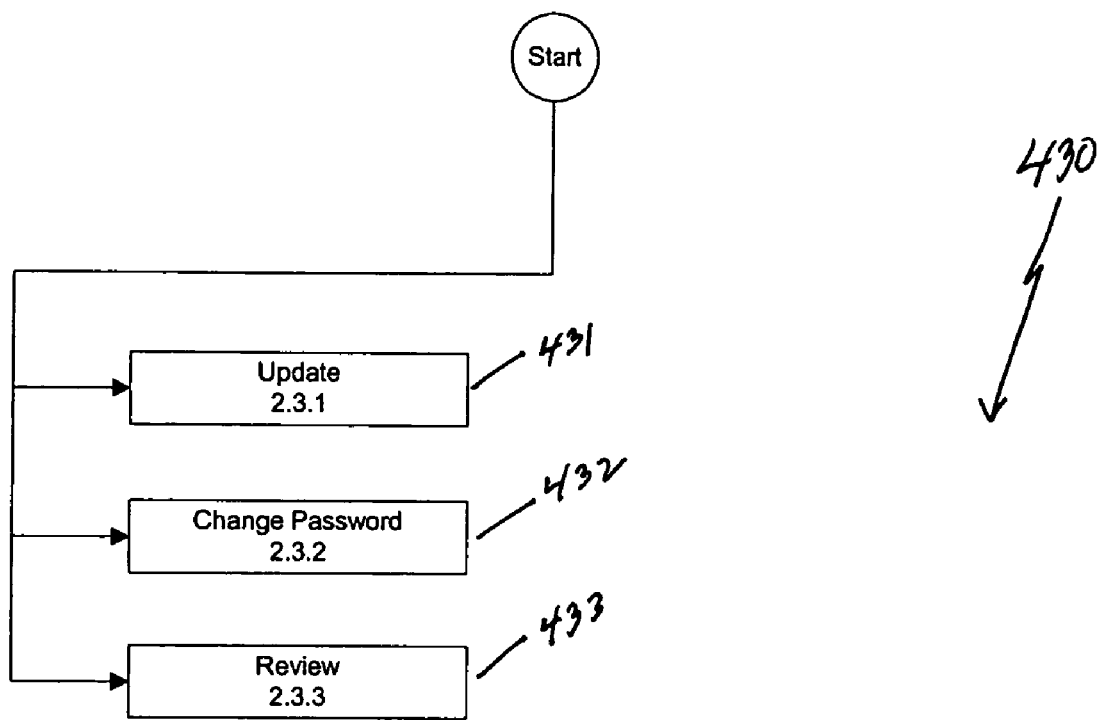
FIG. 19 is a flow diagram showing the personal information process.

FIG. 19 is a flow chart showing the personal information process 430. Using this process, the staff user may update his or her personal information, such as by updating his or her name, phone etc. (step 431), and/or his or her password (step 432). Once all information had been updated, the staff member is given the opportunity to review the information before finalizing (step 433).

Figure 20:
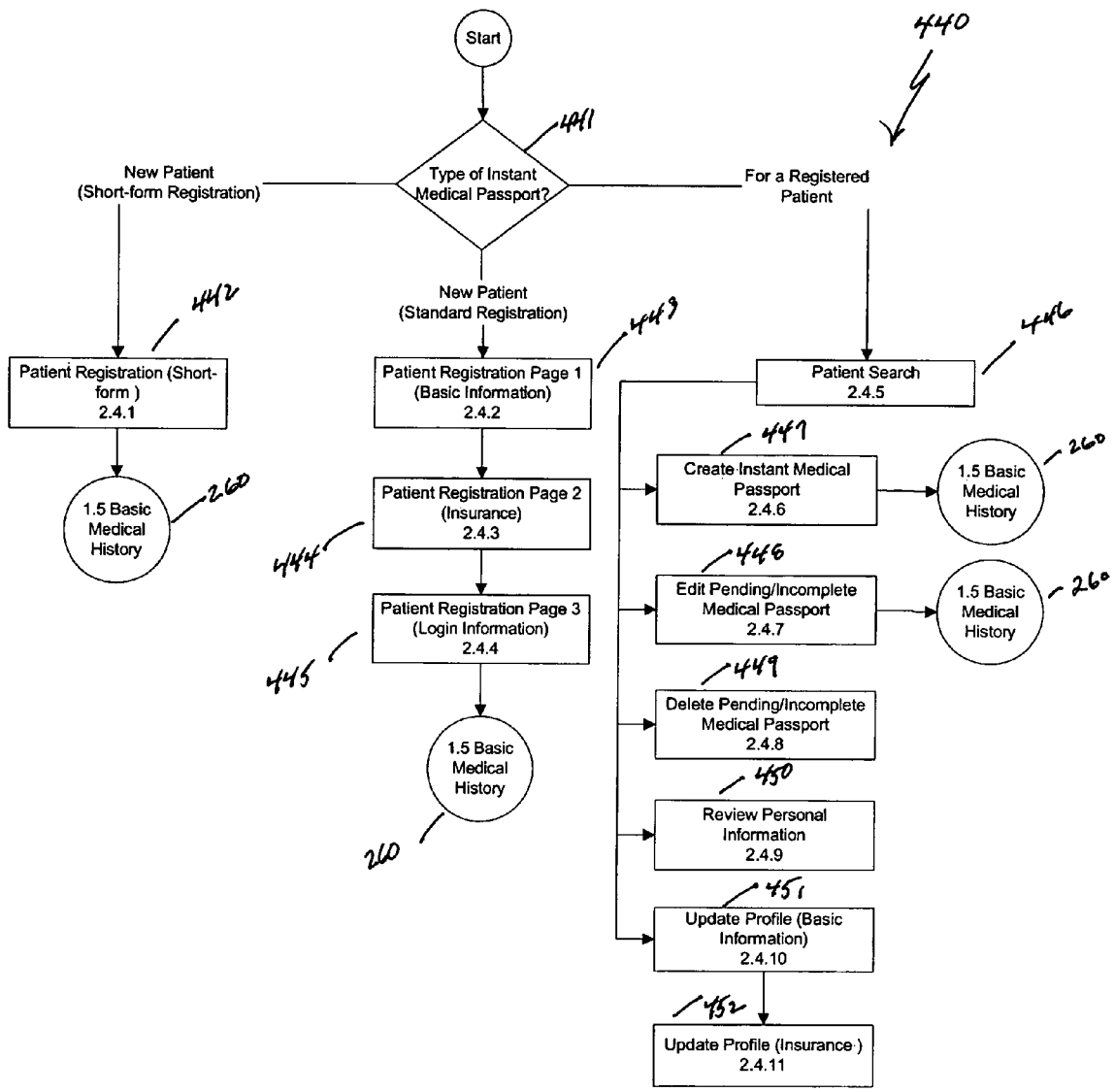
FIG. 20 is a flow diagram showing the instant medical passport process.

FIG. 20 is a flow chart showing the instant medical passport process 440. Using this process, the staff user may generate a Medical Passport for a patient who does not yet have one, or update or complete the Medical Passport of a patient. The staff member must first select "new patient (short form)", "new patient (standard)" or "registered patient" to initiate the instant medical passport process 440 (step 441). If the staff member selects "new patient (short form)", the process proceeds to a patient registration short form (step 442), and then to the basic medical history process 260 described above with reference to FIG. 8. If the staff member selects "new patient (standard)", the process proceeds successively through a basic information questionnaire (step 443), an insurance information questionnaire (step 444), and a login information questionnaire (step 445), before the basic medical history process 260 described above with reference to FIG. 8. If the staff member selects "registered patient", the process proceeds to a patient search (step 446). The patient search will produce any registration information associated with the patient (e.g., name, address, etc.). If a full or partial Medical Passport is associated with the patient, such will be also displayed to the staff member. At this point the staff member may create a new Medical Passport (step 447), edit a pending Medical Passport (step 448), delete a Medical Passport (step 449), review the registration information (step 450), and/or update patient "basic" and "insurance" information (steps 451, 452).

Figure 21:
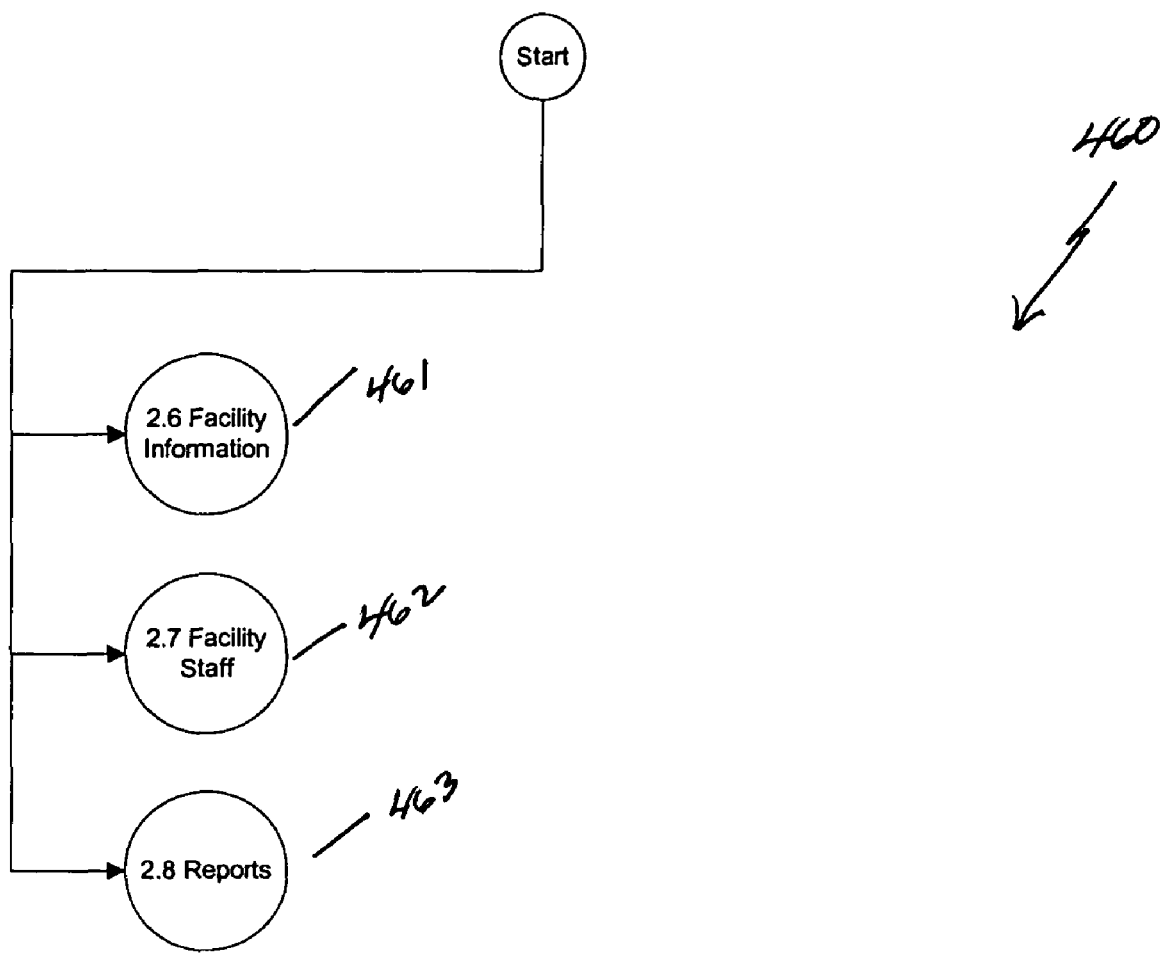
FIG. 21 is a flow diagram showing the administrator administration process.

FIG. 21 is a flow chart showing the administrator administration process 460. Upon initiation of the administrator administration process 460 the user is presented a administrator administration page 2320 (not shown) which provides links to other processes, such as a facility information process 470 (step 461), a facility staff process 480 (step 462), and an administrator reports process 490 (step 463).

Figure 22:
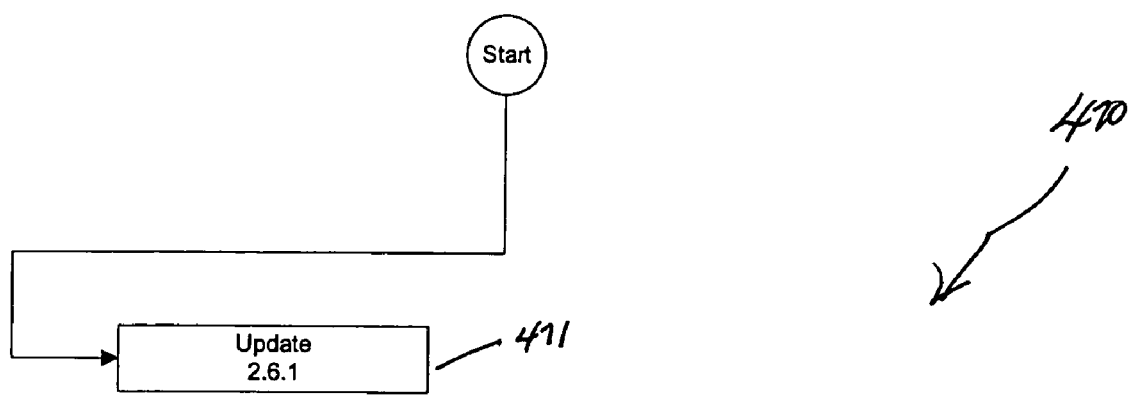
FIG. 22 is a flow diagram showing the facility information process.

FIG. 22 is a flow chart showing the facility information process 470. This process allows the administrator to update the facility information, such as name, address, etc. (step 471).

Figure 23:
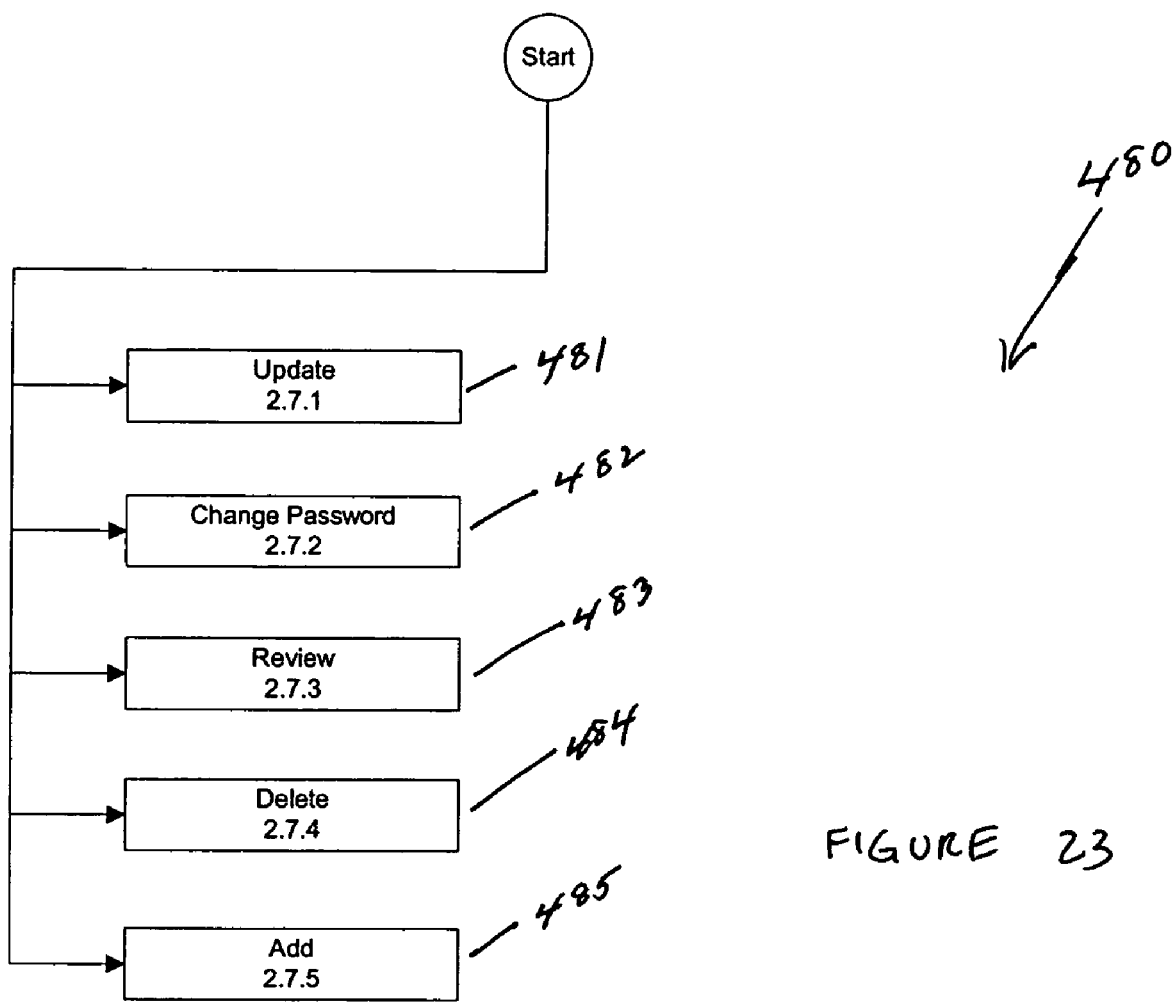
FIG. 23 is a flow diagram showing the facility staff process.

FIG. 23 is a flow chart showing the facility staff process 480. This process allows the administrator to update staff information (step 481), change his or her password (step 482), review staff information (step 483), delete staff members (step 484), and/or add staff members (step 485).

Figure 24:
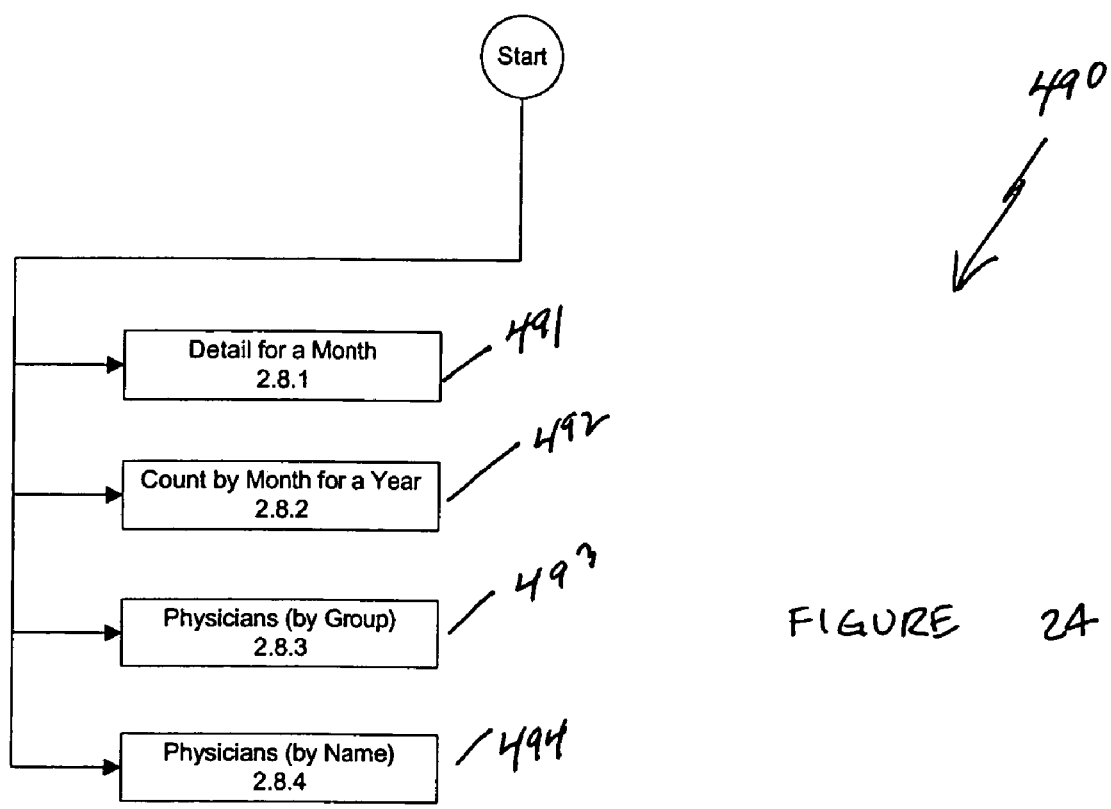
FIG. 24 is a flow diagram showing the administrator reports process.

FIG. 24 is a flow chart showing the administrator reports process 490. This process allows the administrator to create reports of Medical Passports by month (step 491), by year (step 492), and/or reports listing physicians by medical facility or name (steps 493, 494).

The following listing further explains some of the items shown in FIGS. 16-24:

2.0 Facility Login
2.0.1 Login Page—Main access point for medical facility staff or medical facility administrators to log in.
2.0.2 Information—A link to the Medical Web Technologies' corporate Web site.
2.0.3 Contact Us—Allows personnel to send an email to One Medical Passport support.
2.0.4 Feedback—Allows personnel to provide feedback about the site to One Medical Passport staff.
2.0.5 Password Reminder—Automated password reminder for personnel. Based on the email address, username, and a codeword the password is reset and emailed to the personnel.
2.2 Reports
2.2.1 All Pending Medical Passports—Displays a list of patients with a Medical Passport that has not been downloaded yet by the medical facility. A medical facility may only see and download reports for their specific facility. Reports are in Adobe Acrobat format.
2.2.2 Today's Patients—Displays a list of patients with a Medical Passport scheduled for today's date. A medical facility may only see and download reports for their specific facility. Reports are in Adobe Acrobat format.
2.2.3 Find a Specific Patient—Displays a list of patients with a Medical Passport based on name and date of birth. A medical facility may only see and download reports for their specific facility. Reports are in Adobe Acrobat format.
2.2.4 Tomorrow's Patients—Displays a list of patients with a Medical Passport scheduled for tomorrow's date. A medical facility may only see and download reports for their specific facility. Reports are in Adobe Acrobat format.
2.2.5 View Other Dates—Displays a list of patients with a Medical Passport scheduled for a specified date range. A medical facility may only see and download reports for their specific facility. Reports are in Adobe Acrobat format.
2.3 Personal Information
2.3.1 Update—Allows the staff member to update their name, position, phone, email, username, and codeword information.
2.3.2 Change Password—Permits staff members to change their password.
2.3.3 Review—Allows staff members to review their name, position, phone, email, username, and codeword information.
2.4 Instant Medical Passport
2.4.1 Patient Registration (Short-form)—Questions pertaining to basic patient information, address, and the option to enter login information (username, password, and codeword).
2.4.2 Basic Information—Questions pertaining to basic patient information, address, employment information, closest relative, and a contact person.
2.4.3 Insurance—Questions pertaining to the patient's primary and secondary insurance information.
2.4.4 Login Information—Allows the patient to create a username, password, and codeword reminder phrase. This permits the patient to reenter One Medical Passport.
2.4.5 Patient Search—Allows the staff member to find a previously registered patient that has previously had a Medical Passport submitted to that facility.
2.4.6 Create Instant Medical Passport—Allows the staff member to create a new Medical Passport for the selected patient.
2.4.7 Edit Pending/Incomplete Medical Passport—Permits the staff member modify a pending Medical Passport or to complete an incomplete Medical Passport for the selected patient and the staff member's medical facility.
2.4.8 Delete Pending/Incomplete Medical Passport—Allows the staff member to delete a Medical Passport for that facility that is either pending or incomplete.
2.4.9 Review Personal Information—Displays registration information for the selected patient.
2.4.10 Basic Information Update—Questions pertaining to basic patient information, address, employment information, closest relative, and a contact person.
2.4.11 Insurance Update—Questions pertaining to the patient's primary and secondary insurance information.
2.6 Facility Information
2.6.1 Update—Allows the administrator to update the medical facility name, address, phone, and email.
2.7 Facility Staff
2.7.1 Update—Allows the administrator to update a staff member's name, position, phone, email, username, and codeword information for that medical facility.
2.7.2 Change Password—Permits an administrator to change staff member's passwords for that medical facility.
2.7.3 Review—Allows administrators to review staff members' name, position, phone, email, username, and codeword information for that medical facility.

2.7.4 Delete—Allows the administrator to remove a staff member from One Medical Passport for that medical facility.

2.7.5 Add—Allows the administrator to add a new staff member to their facility for One Medical Passport.

2.8 Reports 2.8.1 Detail for a Month—For a specified month and year the date, patient name, type of Medical Passport, procedure, doctor, and doctor's Medical Passport ID are displayed for the medical facility.

2.8.2 Count by a Month for a Year—Count for a specified year by month of Medical Passports that have been entered for the medical facility.

2.8.3 Physicians (by Group)—Physician listing by group for the medical facility.

2.8.4 Physicians (by Name)—Physician listing by name for the medical facility.

Physician's Office Login

Figure 25:
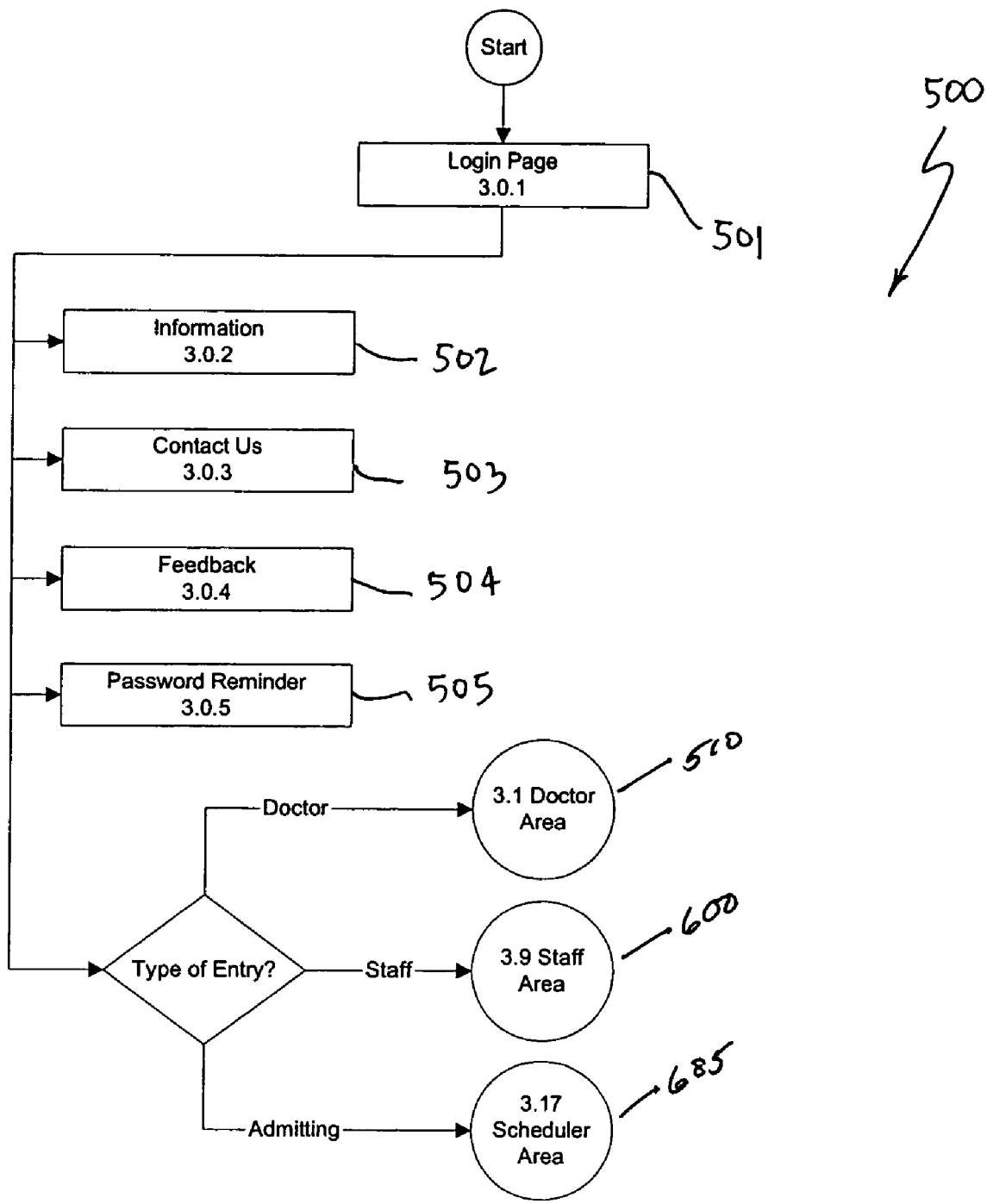
FIG. 25 is a flow diagram showing the physician's office login process.
Figure 97:
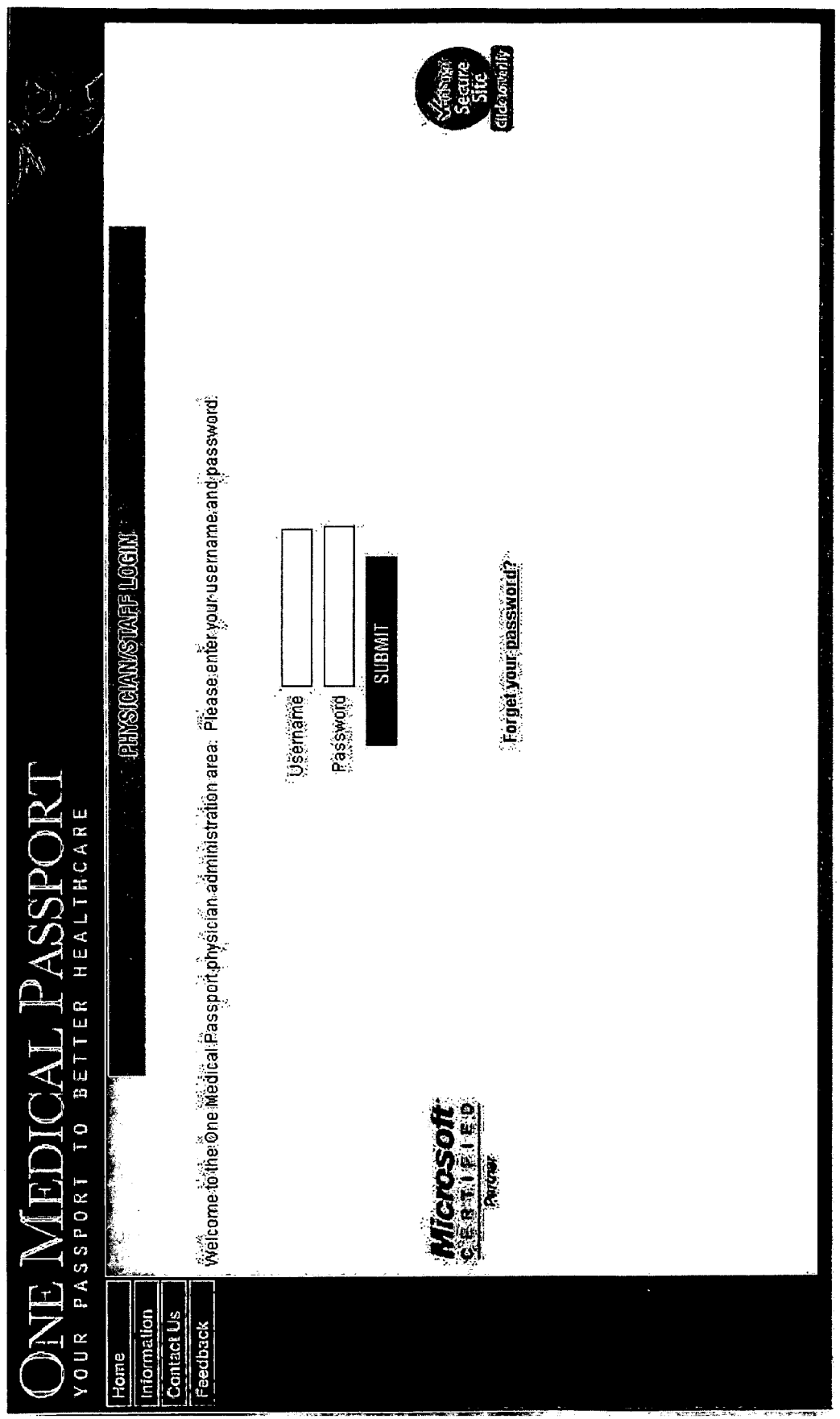
FIG. 97 shows a office login page.

FIG. 25 is a flow chart showing the physician's office login process 500 which is initiated when the user selects to login as a 'office' from the homepage 2000 (step 103 in FIG. 2). The office login process 500 begins with the office user selecting to login as either a "doctor", "staff" or "scheduler" from a office login page 2340 (step 501; FIG. 97). The office login page 2340 also provides access to an information page (step 502), a contact information page (step 503), a feedback page (step 504), and a password reminder page (step 505). If the user selects to login as "doctor", the process proceeds to the doctor area process 510 (See FIG. 26). If the user selects to login as "staff", the process proceeds to the staff area process 600 (See FIG. 34). If the user selects to login as a "scheduler", the process proceeds to scheduler area process 685 (See FIG. 42).

Figure 26:
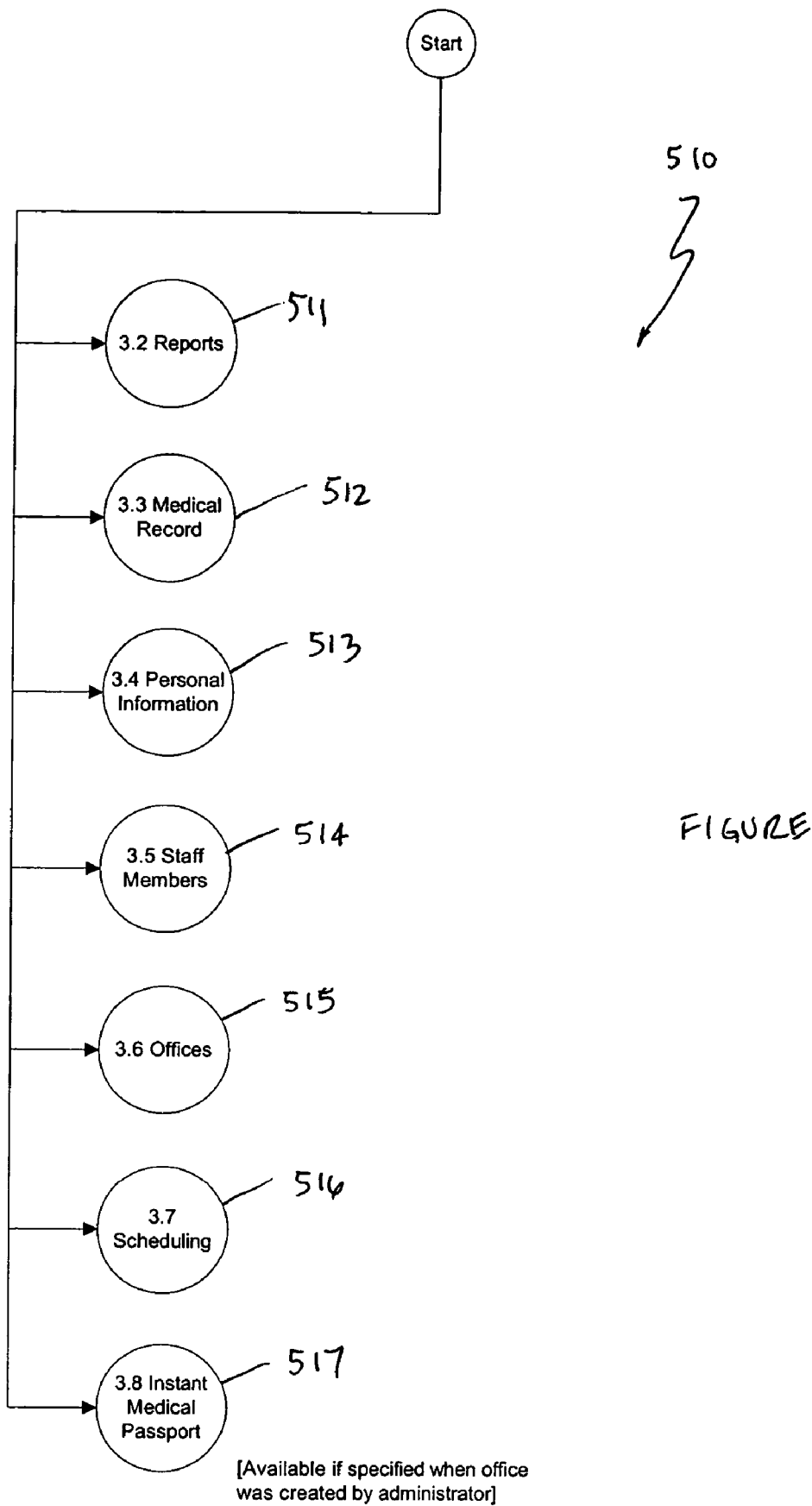
FIG. 26 is a flow diagram showing the doctor area process.
Figure 98:
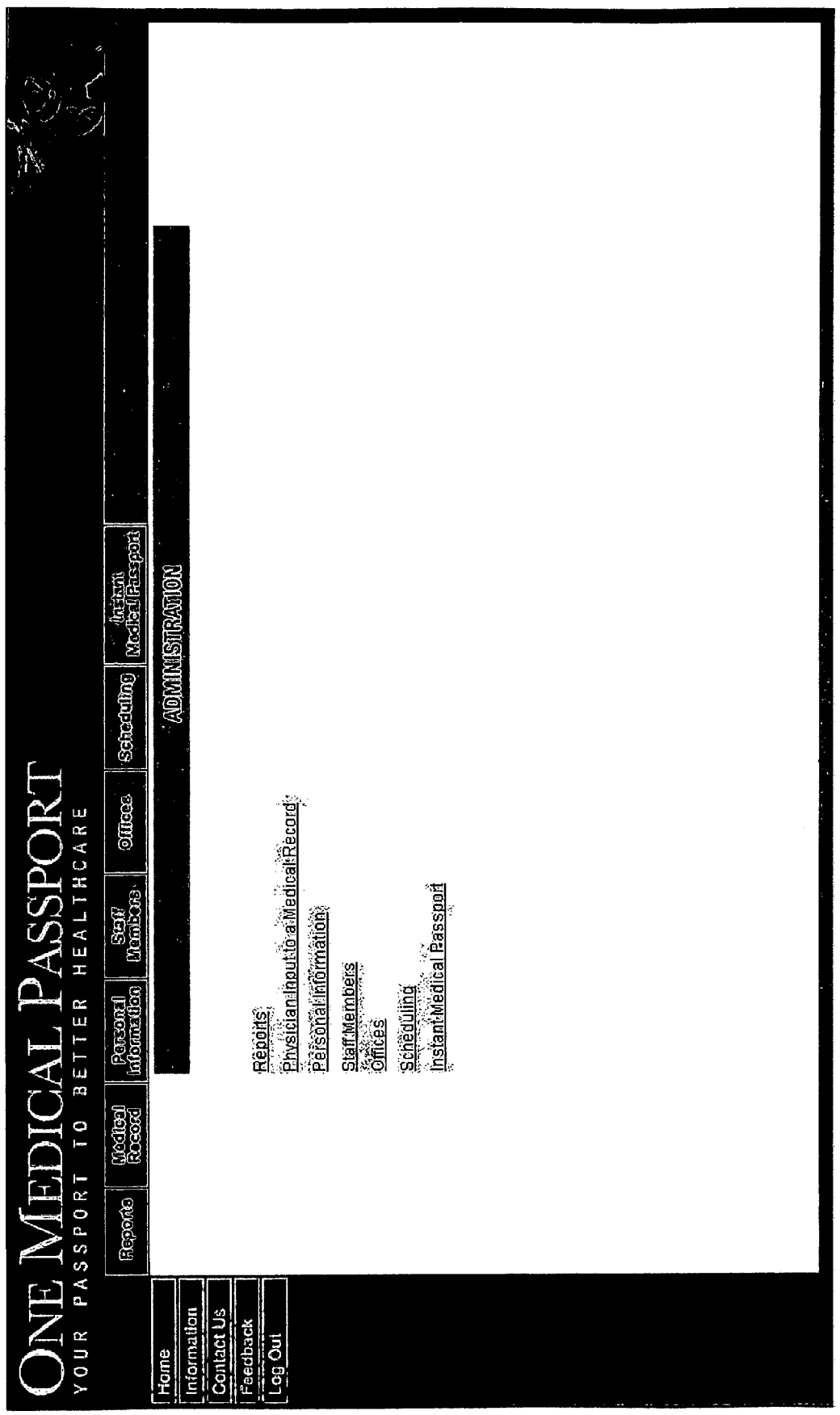
FIG. 98 shows a doctor area page.

FIG. 26 is a flow chart showing the doctor area process 510. Upon initiation of the doctor area process 510 the user is presented a doctor area page 2350 (see FIG. 98) which provides links to other processes, such as a doctor's reports process 520 (step 511), a medical record process 530 (step 512), a personal information process 540 (step 513), a staff members process 550 (step 514), an offices process 560 (step 515), a scheduling process 570 (step 516), and an Instant Medical Passport process 580 (step 517). The Instant Medical Passport process 580 is optional, and is only made available in the doctor area process 510 if enabled by the administrator who sets the parameters for the doctor's office in the system.

Figure 27:
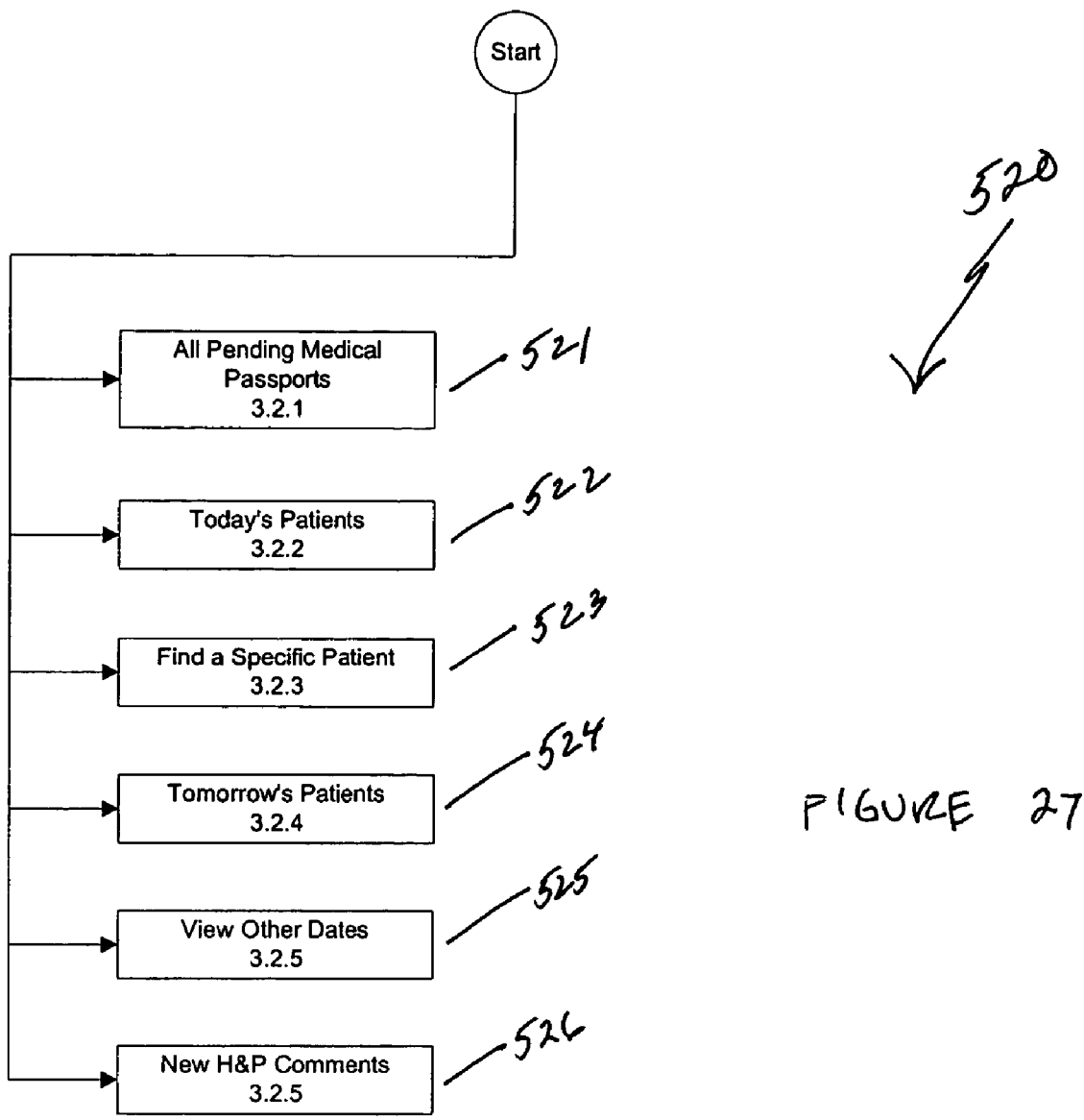
FIG. 27 is a flow diagram showing the doctor's reports process.

FIG. 27 is a flow chart showing the doctor's reports process 520. Using this process, the doctor user may generate reports of Medical Passports in several different ways. The doctor user may display all pending Medical Passports (step 521), Medical Passports for the day's patients (step 522), Medical Passport for a specific patient (step 523), Medical Passports for tomorrow's patients (step 524), Medical Passports for any selected date or date range (step 525) and/or completed Medical Passports for patients with new history and comments (step 526).

Figure 28:
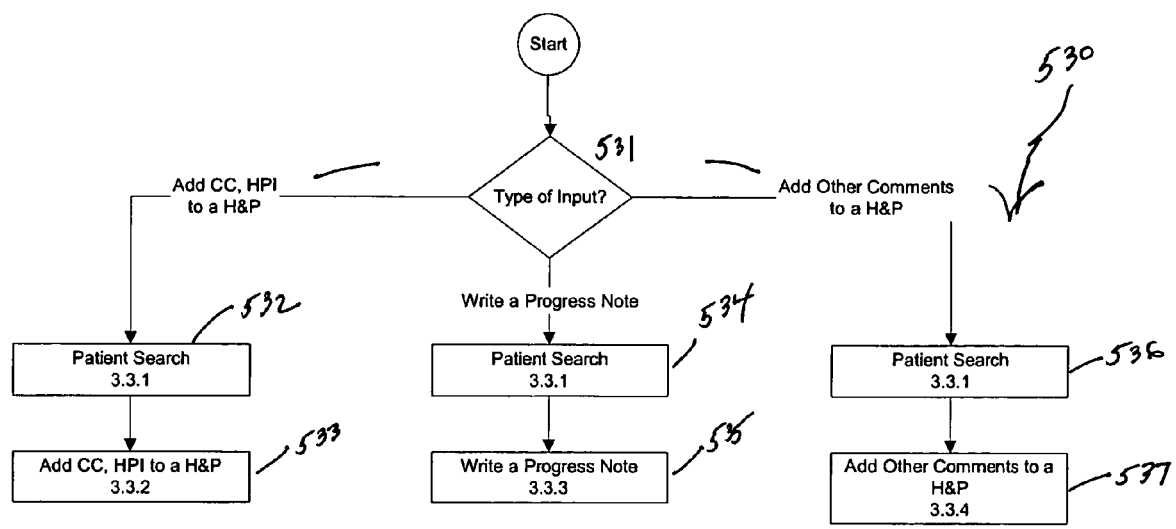
FIG. 28 is a flow diagram showing the medical record process.

FIG. 28 is a flow chart showing the medical record process 530. The medical record process 530 allows the doctor user to enter comments to a patient's medical record (referred to herein as History & Physical or "H&P"). The doctor may either enter Chief Complaint (CC) and/or History of Present Illness (HPI), a Progress Note, or Other Comments (step 531). If the doctor chooses to enter CC or HPI, the process proceeds to a patient search where the doctor can select a specific patient (step 532). Once the patient has been selected, the doctor can enter a CC or HPI on the H&P (step 533). If the doctor chooses to enter a Progress Note in the H&P, the process proceeds to a patient search where the doctor can select a specific patient (step 534). Once the patient has been selected, the doctor can enter a Progress Note on the H&P (step 535). If the doctor chooses to enter Other Comments in the H&P, the process proceeds to a patient search where the doctor can select a specific patient (step 536). Once the patient has been selected, the doctor can enter a Other Comments on the H&P (step 537).

Figure 29:
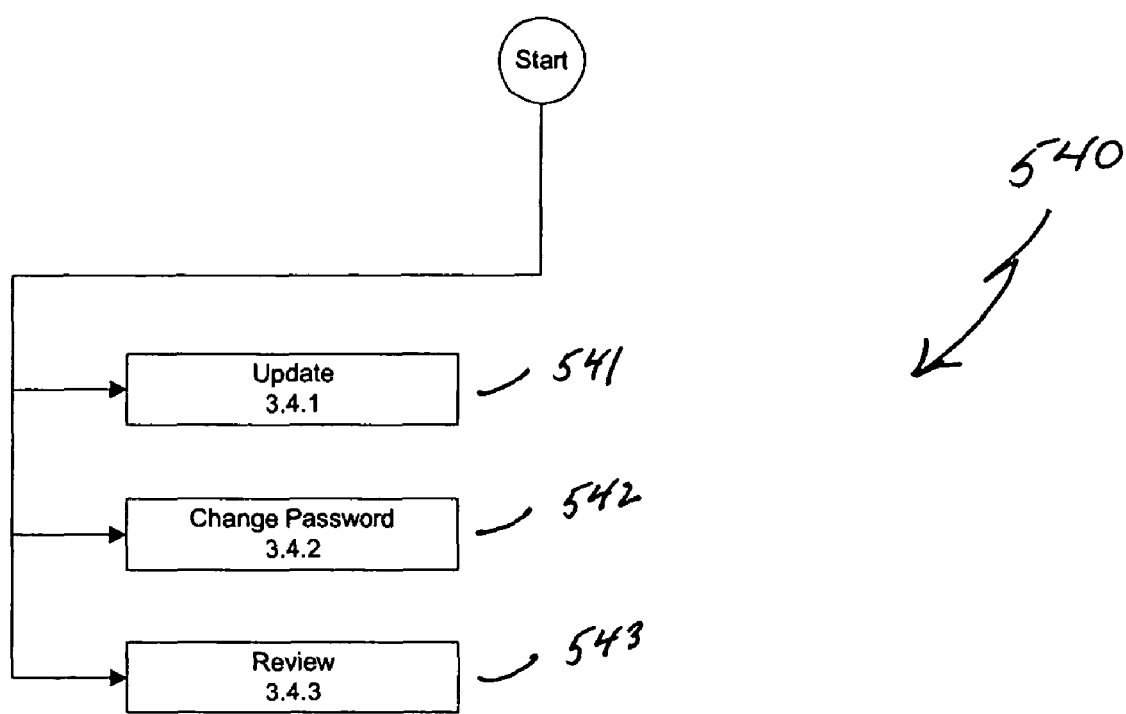
FIG. 29 is a flow diagram showing the personal information process.

FIG. 29 is a flow chart showing the personal information process 540. The personal information process 540 allows the doctor user to update his or her personal information, such as by updating his or her name, phone etc. (step 541), and/or his or her password (step 542). Once all information had been updated, the doctor is given the opportunity to review the information before finalizing (step 543).

Figure 30:
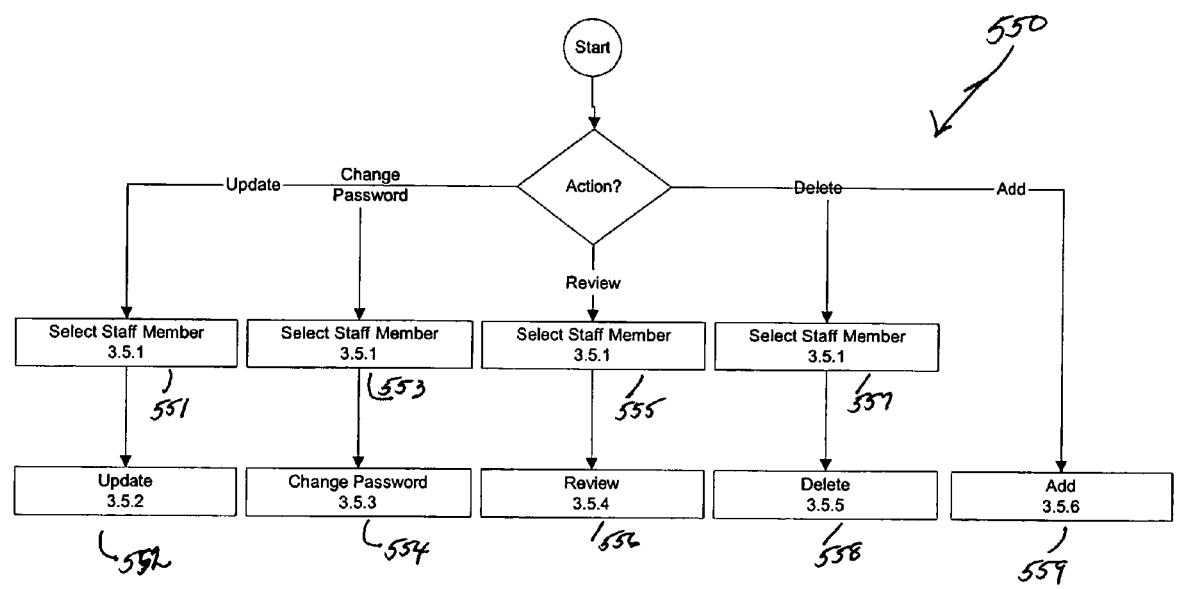
FIG. 30 is a flow diagram showing the staff members process.

FIG. 30 is a flow chart showing the staff members process 550. The staff members process 550 allows the doctor user to update a staff member's information (steps 551, 552), change a staff member's password (steps 553, 554), review a staff member's information (steps 555, 556), delete a staff member (steps 557, 558), and/or add a staff member (step 559).

Figure 31:
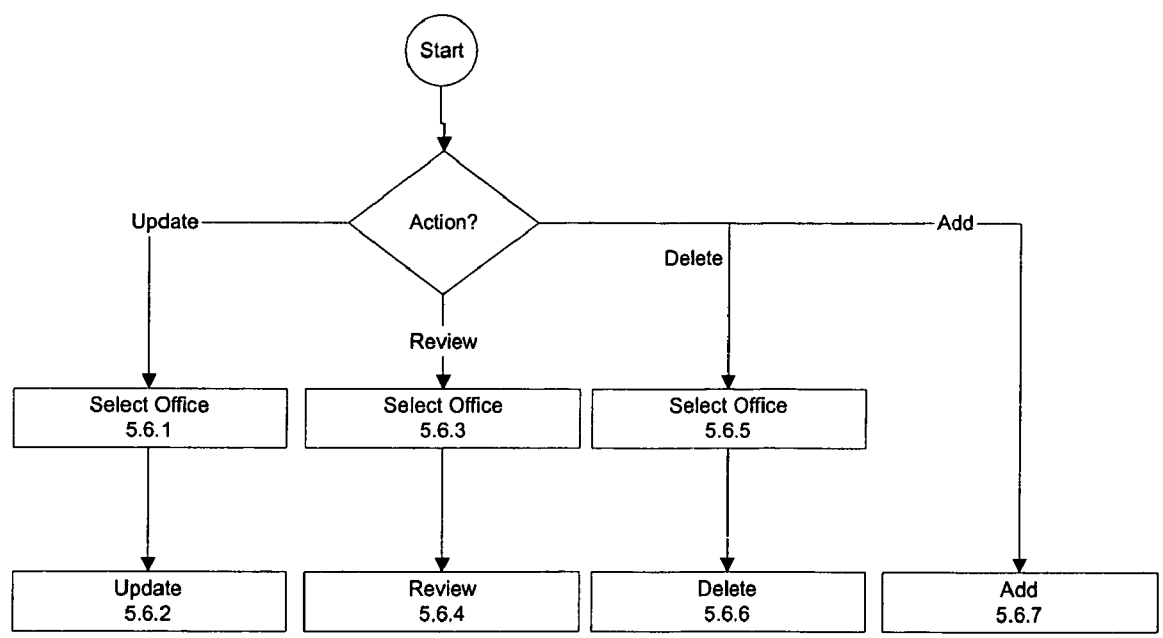
FIG. 31 is a flow diagram showing the offices process.

FIG. 31 is a flow chart showing the offices process 560. The offices process 560 allows the doctor user to update a physician's office information (steps 561, 562), review a physician's office information (steps 563, 564), delete a physician's office (steps 565, 566), and/or add a physician's office (step 567).

Figure 32:
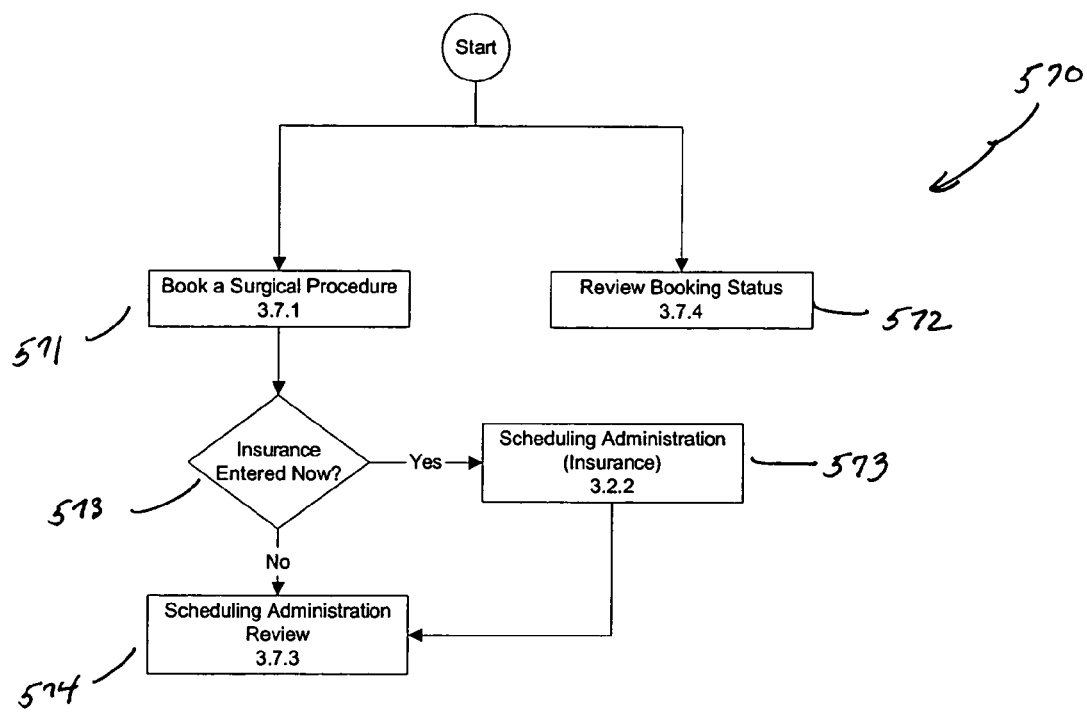
FIG. 32 is a flow diagram showing the scheduling process.

FIG. 32 is a flow chart showing the scheduling process 570. The scheduling process 570 allows the doctor user to book a surgical procedure (step 571), and/or review booking status (step 572). If the doctor chooses to book a procedure, the doctor may also enter insurance information (step 573), and/or reviewing the booking before submission (step 574).

Figure 33:
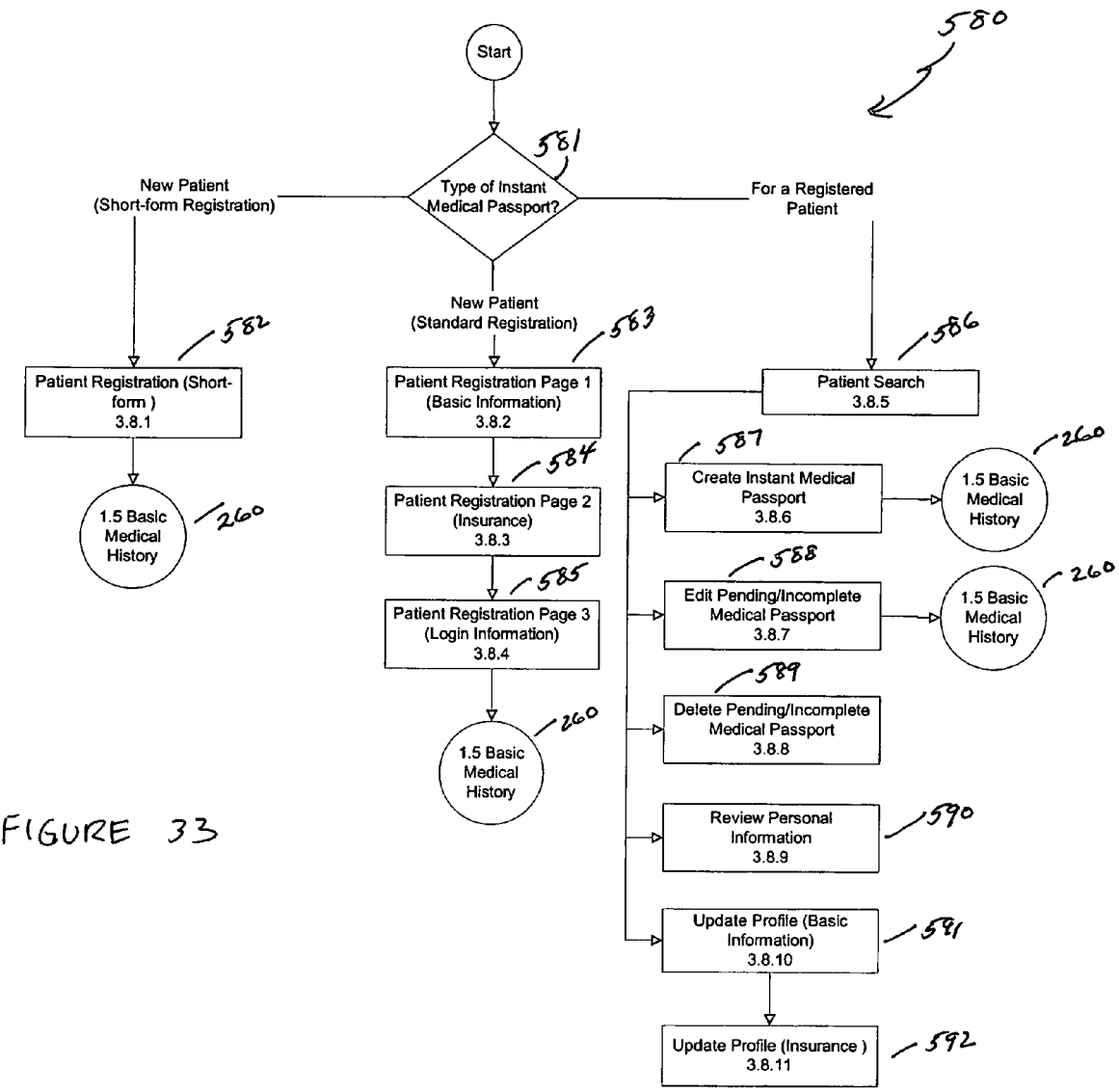
FIG. 33 is a flow diagram showing the Instant Medical Passport process.

FIG. 33 is a flow chart showing the Instant Medical Passport process 580. Using this process, the doctor user may generate a Medical Passport for a patient who does not yet have one, or update or complete the Medical Passport of a patient. The doctor must first select "new patient (short form)", "new patient (standard)" or "registered patient" to initiate the Instant Medical Passport process 580 (step 581). If the doctor selects "new patient (short form)", the process proceeds to a patient registration short form (step 582), and then to the basic medical history process 260 described above with reference to FIG. 8. If the doctor selects "new patient (standard)", the process proceeds successively through a basic information questionnaire (step 583), an insurance information questionnaire (step 584), and a login information questionnaire (step 585), before the basic medical history process 260 described above with reference to FIG. 8. If the doctor selects "registered patient", the process proceeds to a patient search (step 586). The patient search will produce any registration information associated with the patient (e.g., name, address, etc.). If a full or partial Medical Passport is associated with the patient, such will be also displayed to the doctor. At this point the doctor may create a new Medical Passport (step 587), edit a pending Medical Passport (step 588), delete a Medical Passport (step 589), review the registration information (step 590), and/or update patient "basic" and "insurance" information (steps 591, 592).

Figure 34:
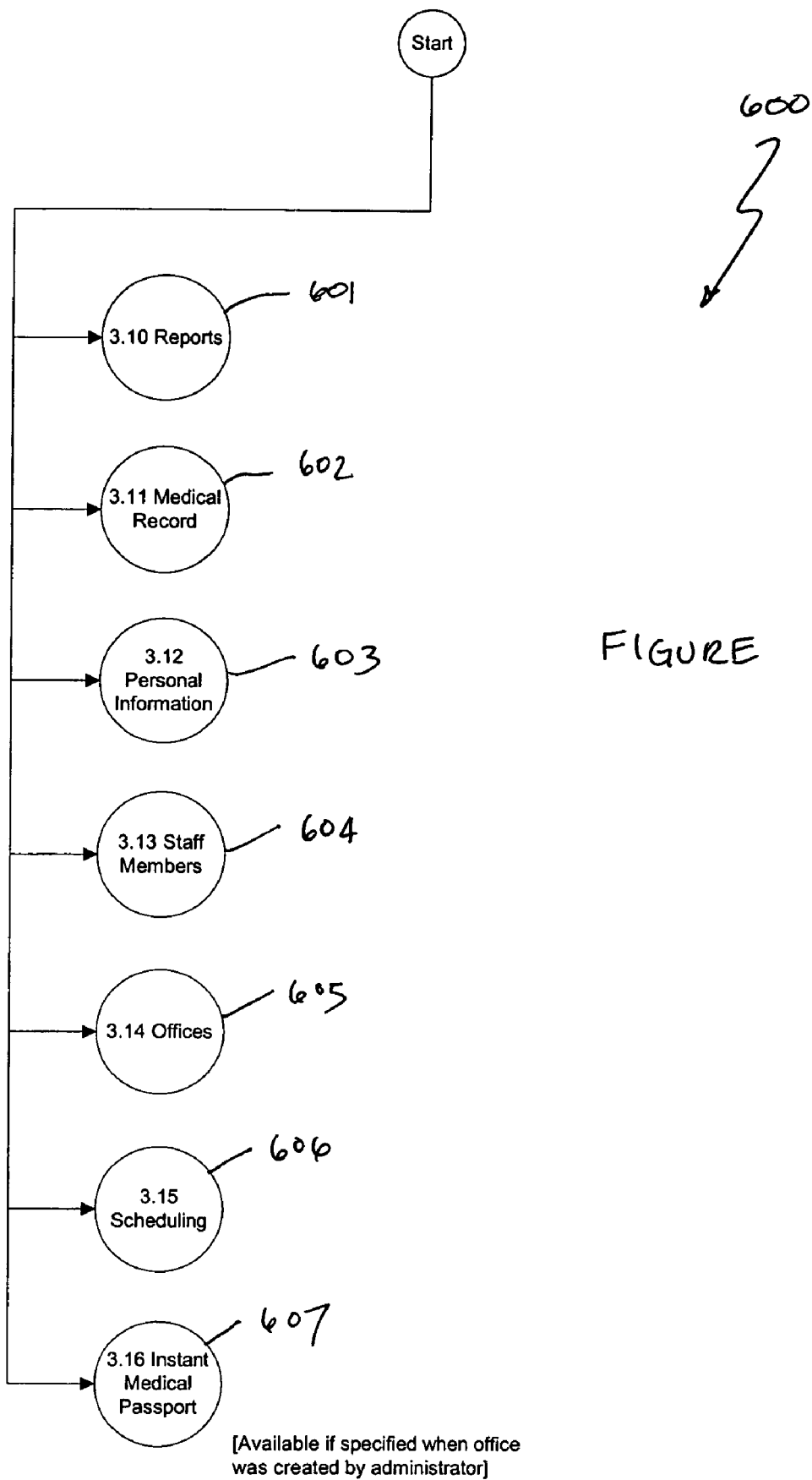
FIG. 34 is a flow diagram showing the staff area process.

FIG. 34 is a flow chart showing the staff area process 600. Upon initiation of the staff area process 600 the user is presented a staff area page 2360 (not shown) which provides links to other processes, such as a staff's reports process 610 (step 601), a medical record process 620 (step 602), a personal information process 630 (step 603), a staff members process 640 (step 604), an offices process 650 (step 605), a scheduling process 660 (step 606), and an Instant Medical Passport process 670 (step 607). The Instant Medical Passport process 670 is optional, and is only made available in the staff area process 600 if enabled by the administrator who sets the parameters for the doctor's office in the system.

Figure 35:
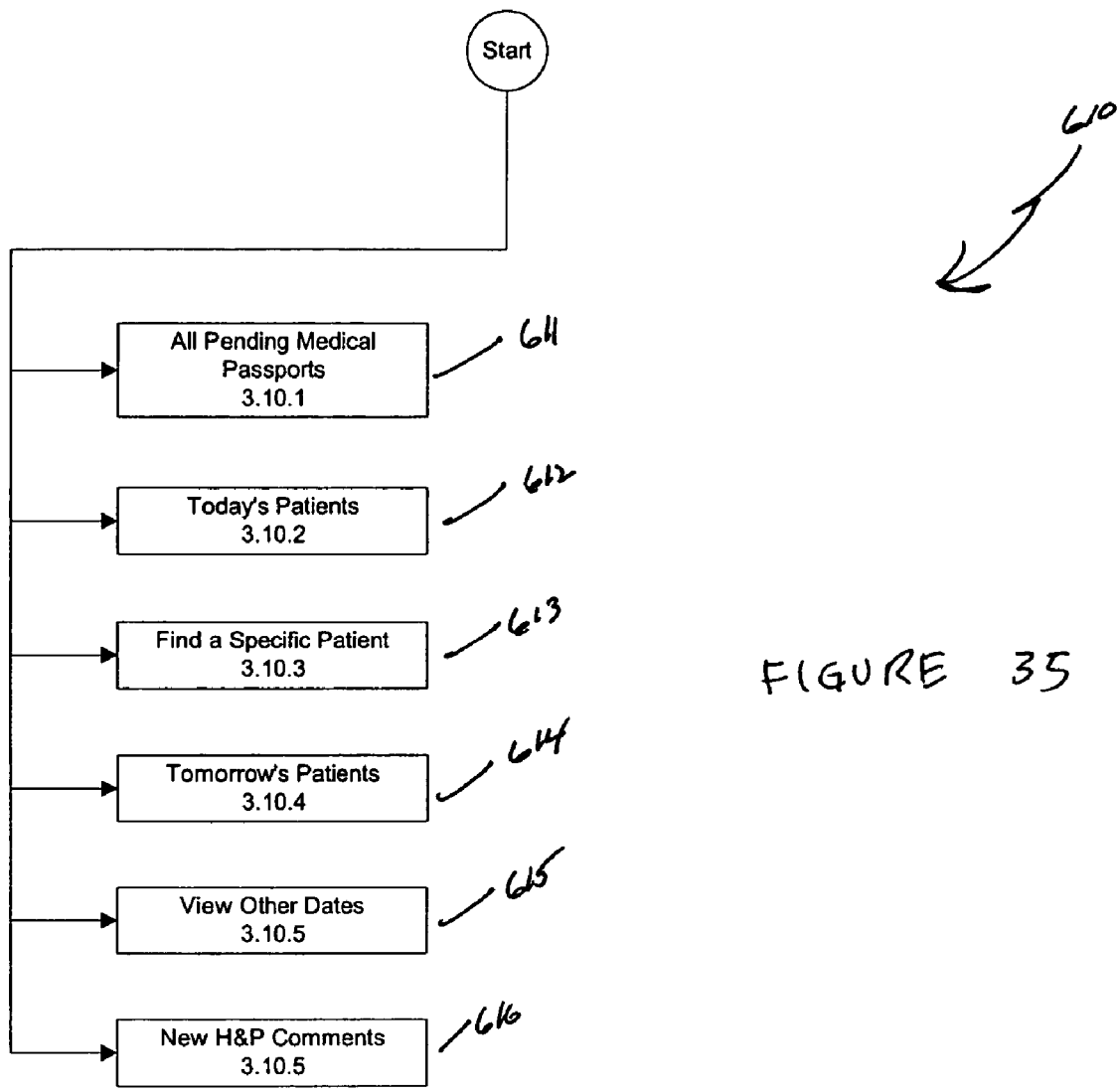
FIG. 35 is a flow diagram showing the staff's reports process.

FIG. 35 is a flow chart showing the staff's reports process 610. Using this process, the staff user may generate reports of Medical Passports in several different ways. The staff member may display all pending Medical Passports (step 611), Medical Passports for the day's patients (step 612), Medical Passport for a specific patient (step 613), Medical Passports for tomorrow's patients (step 614), Medical Passports for any selected date or date range (step 615) and/or completed Medical Passports for patients with new history and comments (step 616).

Figure 36:
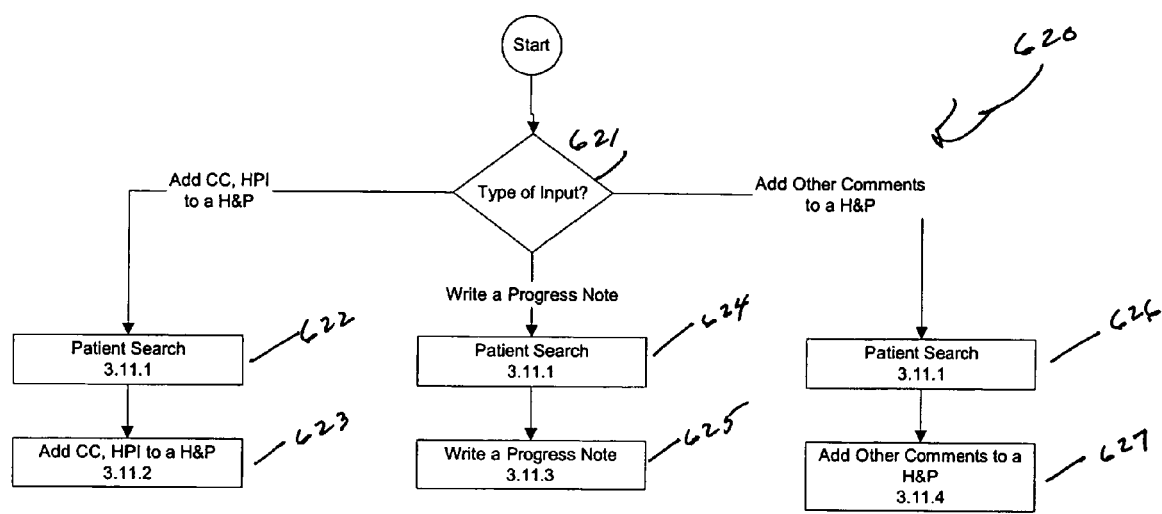
FIG. 36 is a flow diagram showing the medical record process.

FIG. 36 is a flow chart showing the medical record process 620. The medical record process 620 allows the staff user to enter comments to a patient's medical record (referred to herein as History & Physical or "H&P"). The staff member may either enter Chief Complaint (CC) and/or History of Present Illness (HPI), a Progress Note, or Other Comments (step 621). If the staff member chooses to enter CC or HPI, the process proceeds to a patient search where the staff member can select a specific patient (step 622). Once the patient has been selected, the staff member can enter a CC or HPI on the H&P (step 623). If the staff member chooses to enter a Progress Note in the H&P, the process proceeds to a patient search where the staff member can select a specific patient (step 624). Once the patient has been selected, the staff member can enter a Progress Note on the H&P (step 625). If the staff member chooses to enter Other Comments in the H&P, the process proceeds to a patient search where the staff member can select a specific patient (step 626). Once the patient has been selected, the staff member can enter a Other Comments on the H&P (step 627).

Figure 37:
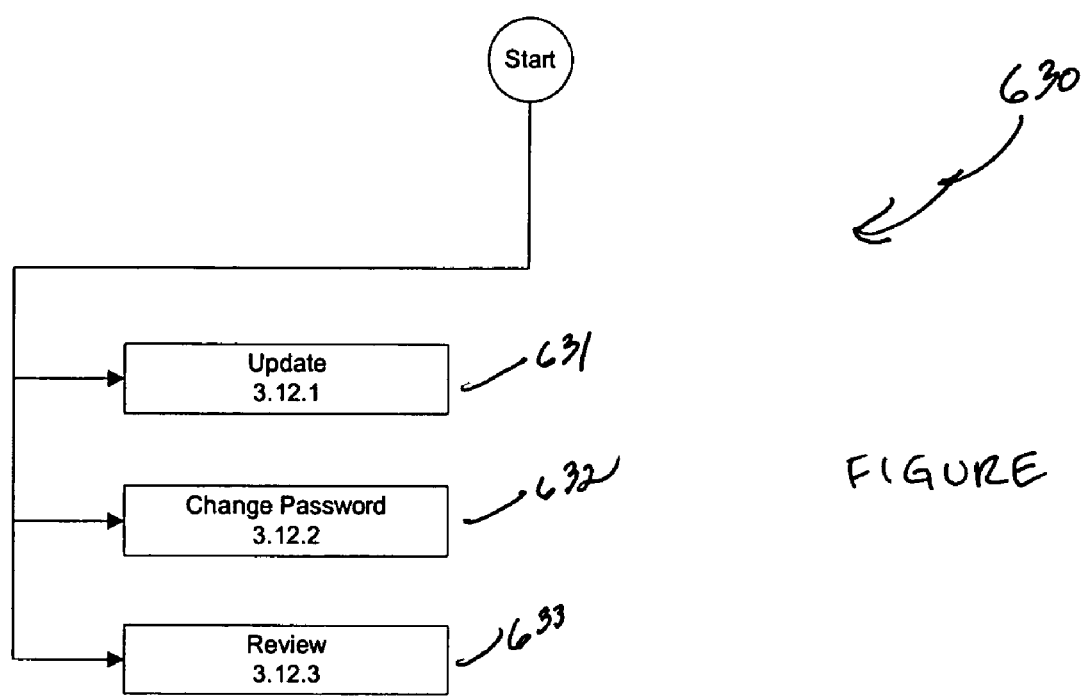
FIG. 37 is a flow diagram showing the personal information process.

FIG. 37 is a flow chart showing the personal information process 630. The personal information process 630 allows the staff member to update his or her personal information, such as by updating his or her name, phone etc. (step 631), and/or his or her password (step 632). Once all information had been updated, the staff member is given the opportunity to review the information before finalizing (step 633).

Figure 38:
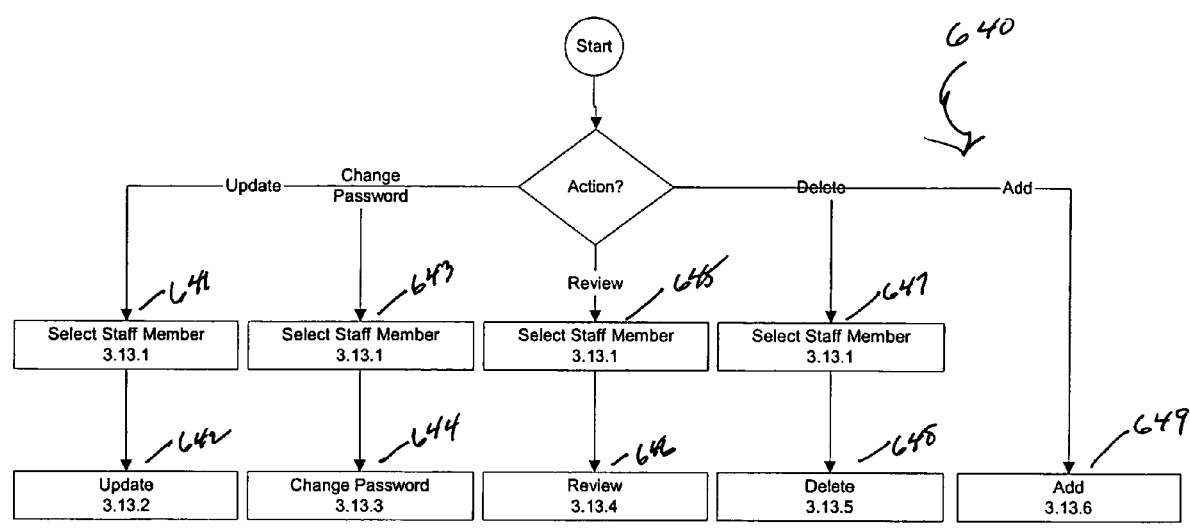
FIG. 38 is a flow diagram showing the staff members process.

FIG. 38 is a flow chart showing the staff members process 640. The staff members process 640 allows the staff member to update a staff member's information (steps 641, 642), change a staff member's password (steps 643, 644), review a staff member's information (steps 645, 646), delete a staff member (steps 647, 648), and/or add a staff member (step 649).

Figure 39:
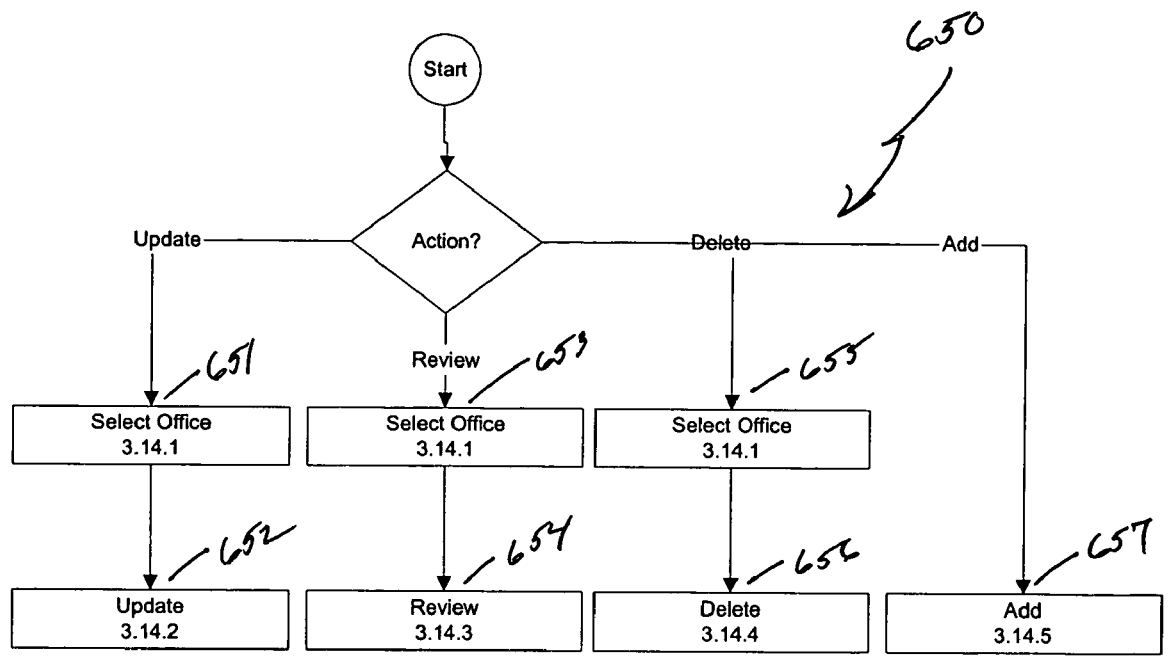
FIG. 39 is a flow diagram showing the offices process.

FIG. 39 is a flow chart showing the offices process 650. The offices process 650 allows the staff member to update a physician's office information (steps 651, 652), review a physician's office information (steps 653, 654), delete a physician's office (steps 655, 656), and/or add a physician's office (step 657).

Figure 40:
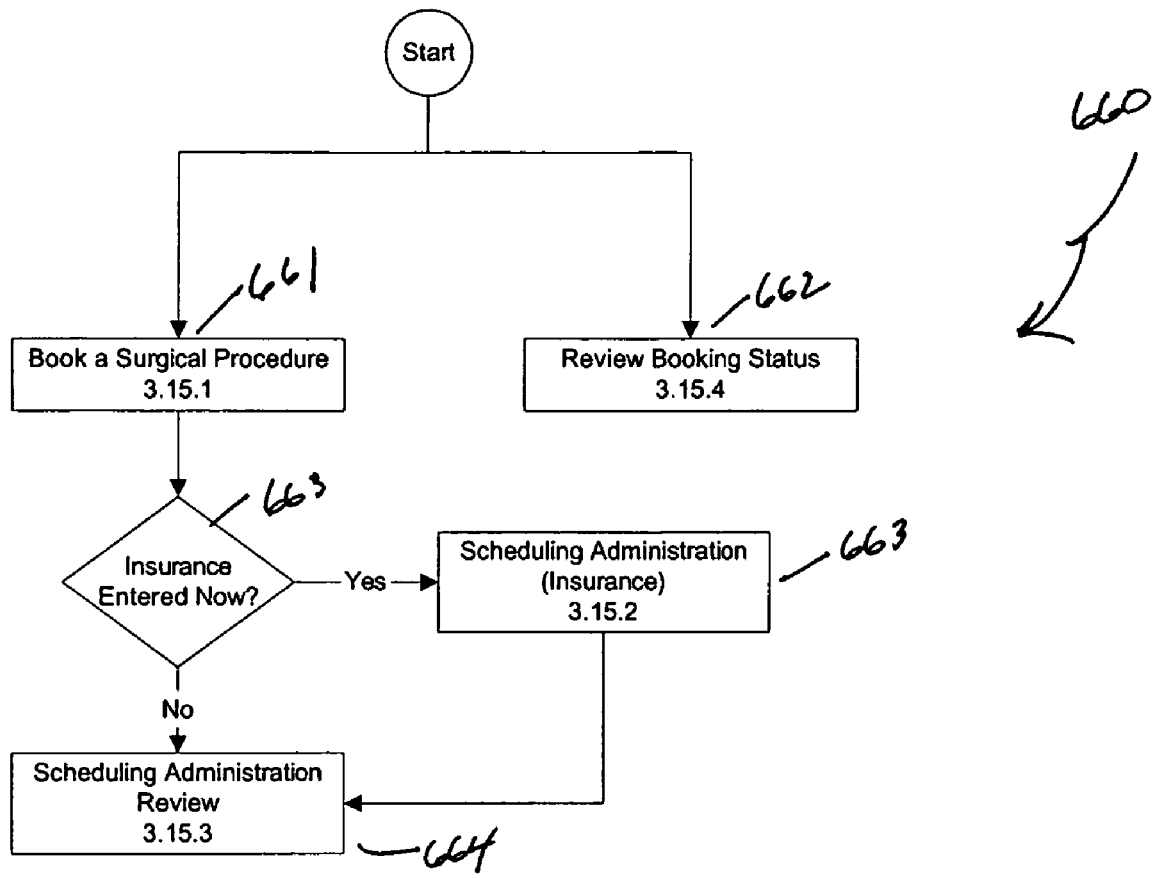
FIG. 40 is a flow diagram showing the scheduling process.

FIG. 40 is a flow chart showing the scheduling process 660. The scheduling process 660 allows the staff member to book a surgical procedure (step 661), and/or review booking status (step 662). If the staff member chooses to book a procedure, the staff member may also enter insurance information (step 663), and/or reviewing the booking before submission (step 664).

Figure 41:
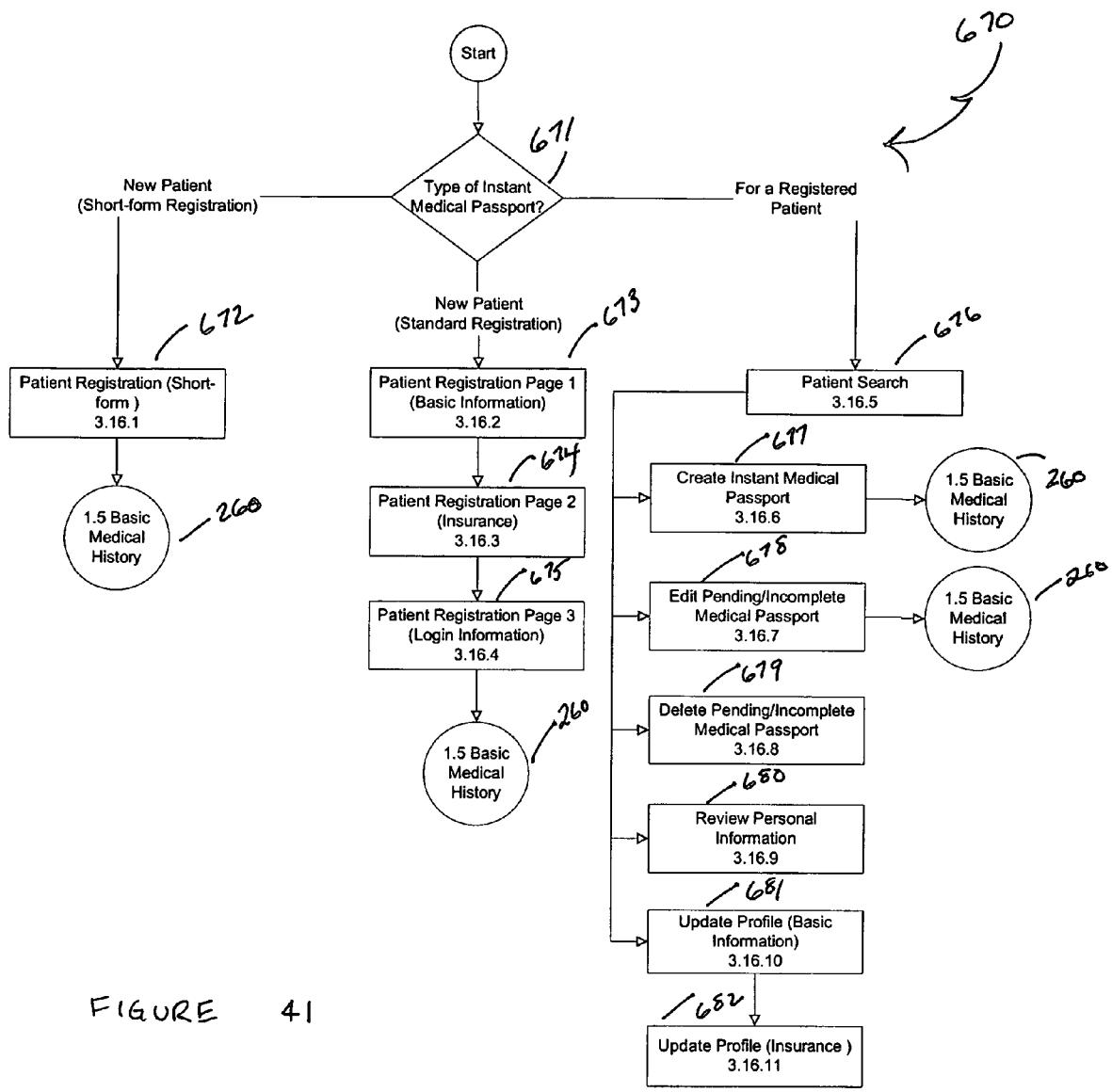
FIG. 41 is a flow diagram showing the Instant Medical Passport.

FIG. 41 is a flow chart showing the Instant Medical Passport process 670. Using this process, the staff member may generate a Medical Passport for a patient who does not yet have one, or update or complete the Medical Passport of a patient. The staff member must first select "new patient (short form)", "new patient (standard)" or "registered patient" to initiate the Instant Medical Passport process 670 (step 671). If the staff member selects "new patient (short form)", the process proceeds to a patient registration short form (step 672), and then to the basic medical history process 260 described above with reference to FIG. 8. If the staff member selects "new patient (standard)", the process proceeds successively through a basic information questionnaire (step 673), an insurance information questionnaire (step 674), and a login information questionnaire (step 675), before the basic medical history process 260 described above with reference to FIG. 8. If the staff member selects "registered patient", the process proceeds to a patient search (step 676). The patient search will produce any registration information associated with the patient (e.g., name, address, etc.). If a full or partial Medical Passport is associated with the patient, such will be also displayed to the staff member. At this point the doctor may create a new Medical Passport (step 677), edit a pending Medical Passport (step 678), delete a Medical Passport (step 679), review the registration information (step 680), and/or update patient "basic" and "insurance" information (steps 681, 682).

Figure 42:
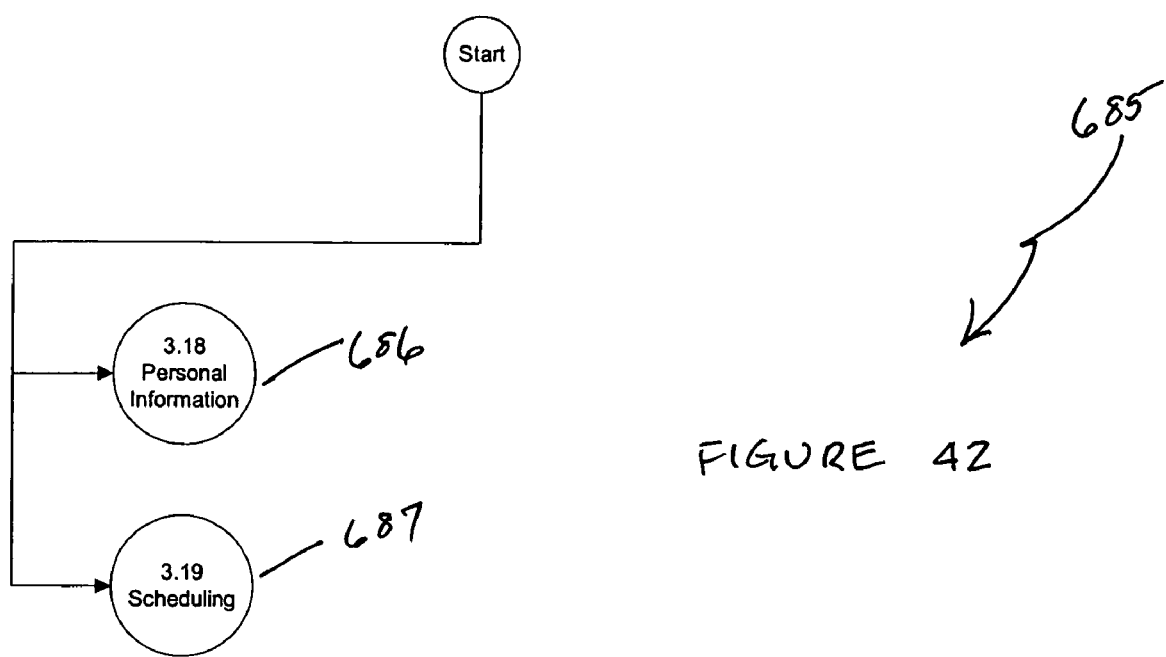
FIG. 42 is a flow diagram showing the schedule area process.

FIG. 42 is a flow chart showing the scheduler area process 685. Upon initiation of the scheduler area process 685 the user is presented a scheduler area page 2370 (not shown) which provides links to other processes, such as a personal information process 690 (step 686), and a scheduling process 695 (step 687).

Figure 43:
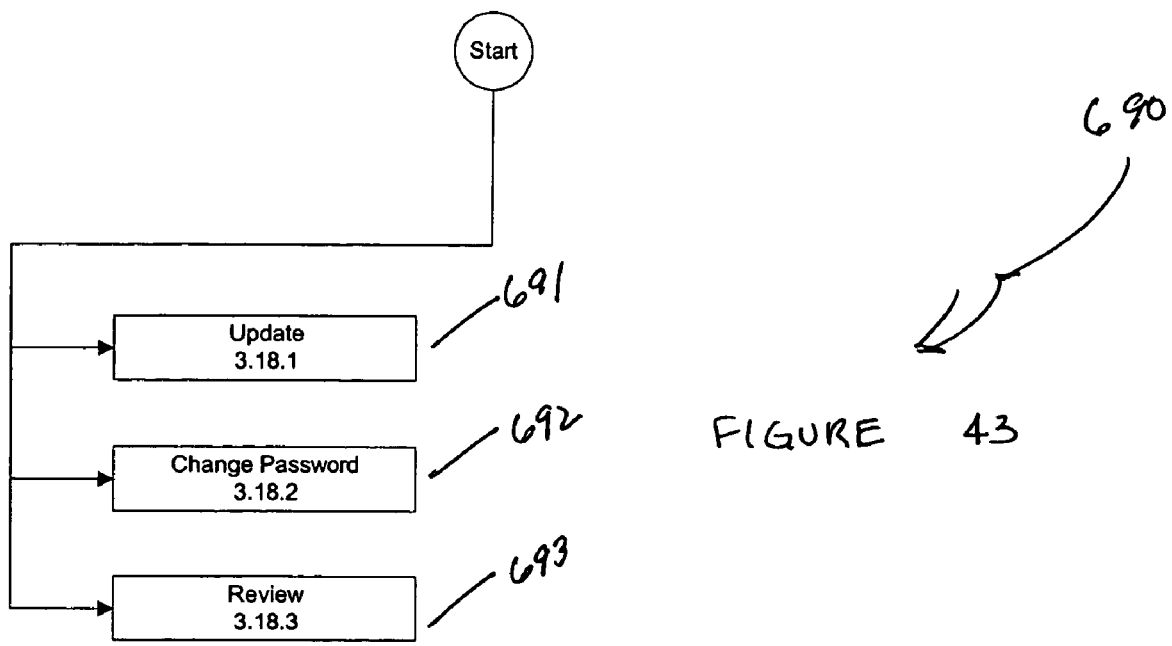
FIG. 43 is a flow diagram showing the personal information process.

FIG. 43 is a flow chart showing the personal information process 690. The personal information process 690 allows the scheduler to update his or her personal information, such as by updating his or her name, phone etc. (step 691), and/or his or her password (step 692). Once all information had been updated, the scheduler is given the opportunity to review the information before finalizing (step 693).

Figure 44:
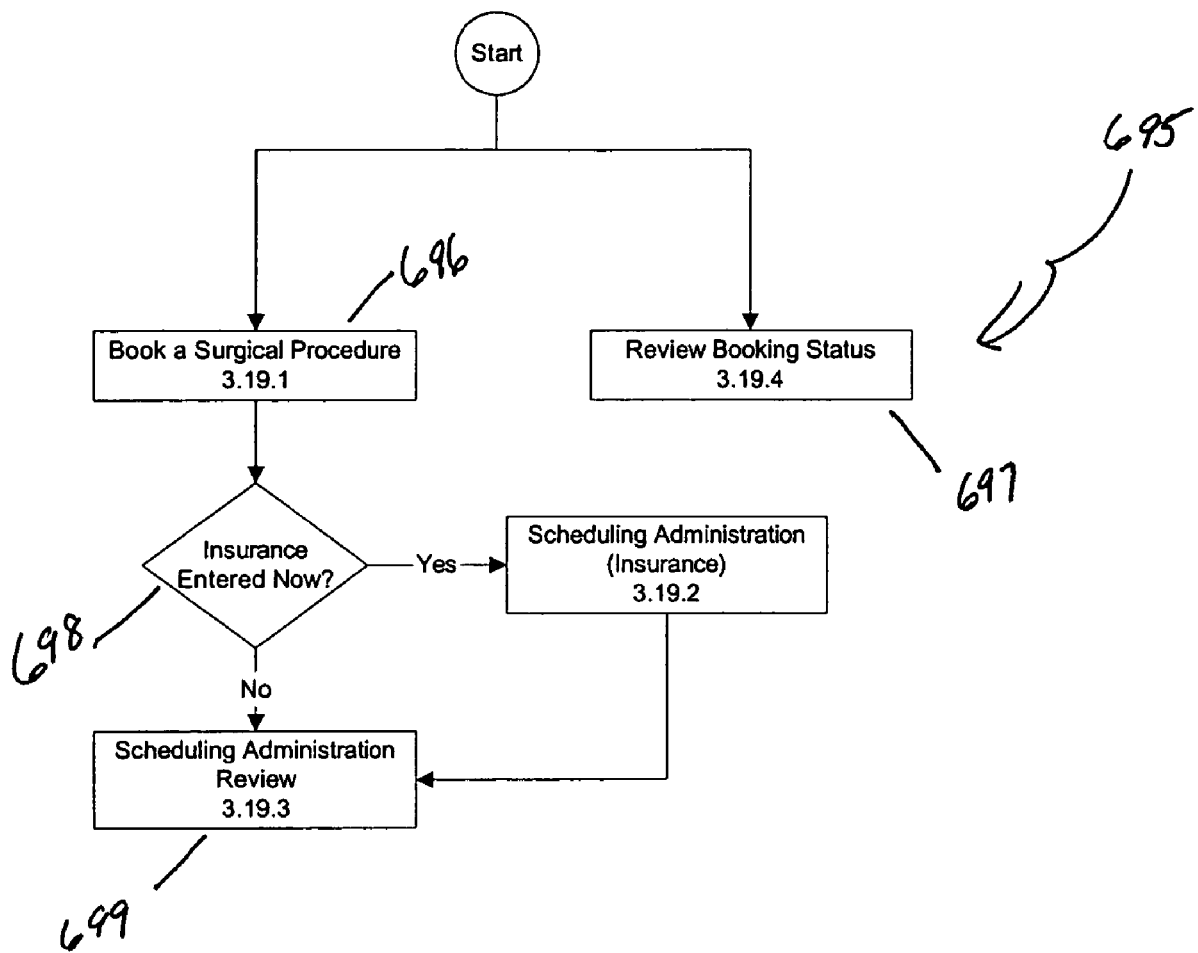
FIG. 44 is a flow diagram showing the scheduling process.

FIG. 44 is a flow chart showing the scheduling process 695. The scheduling process 695 allows the scheduler to book a surgical procedure (step 696), and/or review booking status (step 697). If the scheduler chooses to book a procedure, the scheduler may also enter insurance information (step 698), and/or reviewing the booking before submission (step 699).

The following listing further explains some of the items shown in FIGS. 25-44:

3.0 Office Login 3.0.1 Login Page—Main access point for physician office staff (physician, staff, and admitting personnel) to log in.

3.0.2 Information—A link to the Medical Web Technologies' corporate Web site.

3.0.3 Contact Us—Allows personnel to send an email to One Medical Passport support.

3.0.4 Feedback—Allows personnel to provide feedback about the site to One Medical Passport staff.

3.0.5 Password Reminder—Automated password reminder for personnel. Based on the email address, username, and a codeword the password is reset and emailed to the personnel.

3.2 Reports 3.2.1 All Pending Medical Passports—Displays a list of patients with a Medical Passport that has not been downloaded yet by the medical facility for the doctor. A doctor may only see and download reports specified for them. Reports are in Adobe Acrobat format.

3.2.2 Today's Patients—Displays a list of patients with a Medical Passport scheduled for today's date. A doctor may only see and download reports specified for them. Reports are in Adobe Acrobat format.

3.2.3 Find a Specific Patient—Displays a list of patients with a Medical Passport based on name and date of birth. A doctor may only see and download reports specified for them. Reports are in Adobe Acrobat format.

3.2.4 Tomorrow's Patients—Displays a list of patients with a Medical Passport scheduled for tomorrow's date. A doctor may only see and download reports specified for them. Reports are in Adobe Acrobat format.

3.2.5 View Other Dates—Displays a list of patients with a Medical Passport scheduled for a specified date range. A doctor may only see and download reports specified for them. Reports are in Adobe Acrobat format.

3.2.6 New H&P Comments—Displays a list of completed Medical Passports for patients with new history and physical comments added. A doctor may only see and download reports specified for them. Reports are in Adobe Acrobat format.

3.3 Medical Record 3.3.1 Patient Search—Displays a list of patients with a Medical Passport for the doctor based on the specified last name and date of birth.

3.3.2 Add CC, HPI to a H&P—For the specified patient allows entry of a chief complaint, history of present illness, and on the comments to the history and physical.

3.3.3 Write a Progress Note—For the specified patient allows entry of a progress note to the history and physical.

3.3.4 Add Other Comments to a H&P—For the specified patient allows entry of comments to the history and physical.

3.4 Personal Information 3.4.1 Update—Allows the doctor to update their name, specialty, primary medical facility, secondary medical facility, offices associated with, email, username, and codeword information.

3.4.2 Change Password—Permits the doctor to change their password.

3.4.3 Review—Allows the doctor to review their name, specialty, primary medical facility, secondary medical facility, offices associated with, email, username, and codeword information.

3.5 Staff Members 3.5.1 Select Staff Member—Allows the doctor to select a staff member for the physician office to perform the selected action on.

3.5.2 Update—Allows the doctor to update a staff member's name, position, doctors associated with, email, username, and codeword information.

3.5.3 Change Password—Pen-nits the doctor to change a staff member's password.

3.5.4 Review—Allows the doctor to review a staff member's name, position, doctors associated with, email, username, and codeword information.

3.5.5 Delete—Allows the doctor to remove a staff member from having access to One Medical Passport.

3.5.6 Add—Allows the doctor to add a new staff member to their physician office by specifying name, position, doctors associated with, email, username, and codeword information.

3.6 Offices 3.6.1 Select Office—Allows the doctor to select a particular physician office to perform the selected action on.

3.6.2 Update—Allows the doctor to update a physician office's address, phone, fax, doctors associated with, and email.

3.6.3 Review—Allows the doctor to review a physician office's address, phone, fax, doctors associated with, and email.

3.6.4 Delete—Allows the doctor to remove a physician office.

3.6.5 Add—Allows the doctor to add a new physician office by specifying address, phone, fax, doctors associated with, and email.

3.7 Scheduling 3.7.1 Book a Surgical Procedure—Allows a doctor to book a surgical procedure by specifying the patient information, procedure, anesthesia, scheduling preference, pre-op testing, and insurance.

3.7.2 Book a Surgical Procedure (Insurance)—Allows a doctor to add primary and secondary insurance information to a schedule request.

3.7.3 Scheduling Administration Review—Allows a doctor to review the schedule request before submitting it.

3.7.4 Review a Booking Request—Allows a doctor to check the status of a booking request for a patient by specifying a patient's social security number and last name.

3.8 Instant Medical Passport 3.8.1 Patient Registration (Short-form)—Questions pertaining to basic patient information, address, and the option to enter login information (username, password, and codeword).

3.8.2 Basic Information—Questions pertaining to basic patient information, address, employment information, closest relative, and a contact person.

3.8.3 Insurance—Questions pertaining to the patient's primary and secondary insurance information.

3.8.4 Login Information—Allows the patient to create a username, password, and codeword reminder phrase. This permits the patient to re-enter One Medical Passport.

3.8.5 Patient Search—Allows the doctor to find a previously registered patient that has previously had a Medical Passport submitted to that physician office.

3.8.6 Create Instant Medical Passport—Allows the doctor to create a new Medical Passport for the selected patient.

3.8.7 Edit Pending/Incomplete Medical Passport—Permits the doctor modify a pending Medical Passport or to complete an incomplete Medical Passport for the selected patient and the doctor's physician office.

3.8.8 Delete Pending/Incomplete Medical Passport—Allows the doctor to delete a Medical Passport for that doctor that is either pending or incomplete.

3.8.9 Review Personal Information—Displays registration information for the selected patient.

3.8.10 Basic Information Update—Questions pertaining to basic patient information, address, employment information, closest relative, and a contact person.

3.8.11 Insurance Update—Questions pertaining to the patient's primary and secondary insurance information.

3.10 Reports 3.10.1 All Pending Medical Passports—Displays a list of patients with a Medical Passport that has not been downloaded yet by the medical facility for the physician office. A staff member may only see and download reports specified for doctors they are associated with. Reports are in Adobe Acrobat format.

3.10.2 Today's Patients—Displays a list of patients with a Medical Passport scheduled for today's date. A staff member may only see and download reports specified for doctors they are associated with. Reports are in Adobe Acrobat format.

3.10.3 Find a Specific Patient—Displays a list of patients with a Medical Passport based on name and date of birth. A staff member may only see and download reports specified for doctors they are associated with. Reports are in Adobe Acrobat format.

3.10.4 Tomorrow's Patients—Displays a list of patients with a Medical Passport scheduled for tomorrow's date. A staff member may only see and download reports specified for doctors they are associated with. Reports are in Adobe Acrobat format.

3.10.5 View Other Dates—Displays a list of patients with a Medical Passport scheduled for a specified date range. A staff member may only see and download reports specified for doctors they are associated with. Reports are in Adobe Acrobat format.

3.10.6 New H&P Comments—Displays a list of completed Medical Passports for patients with new history and physical comments added. A staff member may only see and download reports specified for doctors they are associated with. Reports are in Adobe Acrobat format.

3.11 Medical Record 3.11.1 Patient Search—Displays a list of patients with a Medical Passport for the doctor(s) the staff member is associated with based on the specified last name and date of birth.

3.11.2 Add CC, HPI to a H&P—For the specified patient allows entry of a chief complaint, history of present illness, and other comments to the history and physical.

3.11.3 Write a Progress Note—For the specified patient allows entry of a progress note to the history and physical.

3.11.4 Add Other Comments to a H&P—For the specified patient allows entry of comments to the history and physical.

3.12 Personal Information 3.12.1 Update—Allows the doctor to update their name, position, offices associated with, email, username, and codeword information.

3.12.2 Change Password—Permits the doctor to change their password.

3.12.3 Review—Allows the doctor to review their name, position, offices associated with, email, username, and codeword information.

3.13 Staff Members 3.13.1 Select Staff Member—Allows the staff member to select a staff member for the physician office to perform the selected action on.

3.13.2 Update—Allows the staff member to update a staff member's name, position, doctors associated with, email, username, and codeword information.

3.13.3 Change Password—Permits the staff member to change a staff member's password.

3.13.4 Review—Allows the staff member to review a staff member's name, position, doctors associated with, email, username, and codeword information.

3.13.5 Delete—Allows the staff member to remove a staff member from having access to One Medical Passport.

3.13.6 Add—Allows the staff member to add a new staff member to their physician office by specifying name, position, doctors associated with, email, username, and codeword information.

3.14 Offices 3.14.1 Select Office—Allows the staff member to select a particular physician office to perform the selected action on.

3.14.2 Update—Allows the staff member to update a physician office's address, phone, fax, doctors associated with, and email.

3.14.3 Review—Allows the staff member to review a physician office's address, phone, fax, doctors associated with, and email.

3.14.4 Delete—Allows the staff member to remove a physician office.

3.14.5 Add—Allows the staff member to add a new physician office by specifying address, phone, fax, doctors associated with, and email.

3.15 Scheduling 3.15.1 Book a Surgical Procedure—Allows a staff member to book a surgical procedure by specifying the patient information, procedure, anesthesia, scheduling preference, pre-op testing, and insurance.

3.15.2 Book a Surgical Procedure (Insurance)—Allows a staff member to add primary and secondary insurance information to a schedule request.

3.15.3 Scheduling Administration Review—Allows a staff member to review the schedule request before submitting it.

3.15.4 Review a Booking Request—Allows a staff member to check the status of a booking request for a patient by specifying a patient's social security number and last name.

3.16 Instant Medical Passport 3.16.1 Patient Registration (Short-form)—Questions pertaining to basic patient information, address, and the option to enter login information (username, password, and codeword).

3.16.2 Basic Information—Questions pertaining to basic patient information, address, employment information, closest relative, and a contact person.

3.16.3 Insurance—Questions pertaining to the patient's primary and secondary insurance information.

3.16.4 Login Information—Allows the patient to create a username, password, and codeword reminder phrase. This permits the patient to reenter One Medical Passport.

3.16.5 Patient Search—Allows the doctor to find a previously registered patient that has previously had a Medical Passport submitted to that physician office.

3.16.6 Create Instant Medical Passport—Allows the doctor to create a new Medical Passport for the selected patient.

3.16.7 Edit Pending/Incomplete Medical Passport—Permits the doctor modify a pending Medical Passport or to complete an incomplete Medical Passport for the selected patient and the doctor's physician office.

3.16.8 Delete Pending/Incomplete Medical Passport—Allows the doctor to delete a Medical Passport for that doctor that is either pending or incomplete.

3.16.9 Review Personal Information—Displays registration information for the selected patient.

3.16.10 Basic Information Update—Questions pertaining to basic patient information, address, employment information, closest relative, and a contact person.

3.16.11 Insurance Update—Questions pertaining to the patient's primary and secondary insurance information.

3.18 Personal Information 3.18.1 Update—Allows the scheduler to update their name, doctors associated with, position, email, username, and codeword information.

3.18.2 Change Password—Pen-nits the scheduler to change their password.

3.18.3 Review—Allows the scheduler to review their name, doctors associated with, position, email, username, and codeword information.

3.19 Scheduling 3.19.1 Book a Surgical Procedure—Allows a scheduler to book a surgical procedure by specifying the patient information, procedure, anesthesia, scheduling preference, pre-op testing, and insurance.

3.19.2 Book a Surgical Procedure (Insurance)—Allows a scheduler to add primary and secondary insurance information to a schedule request.

3.19.3 Scheduling Administration Review—Allows a scheduler to review the schedule request before submitting it.

3.19.4 Review a Booking Request—Allows a scheduler to check the status of a booking request for a patient by specifying a patient's social security number and last name.

Scheduling Login

Figure 45:
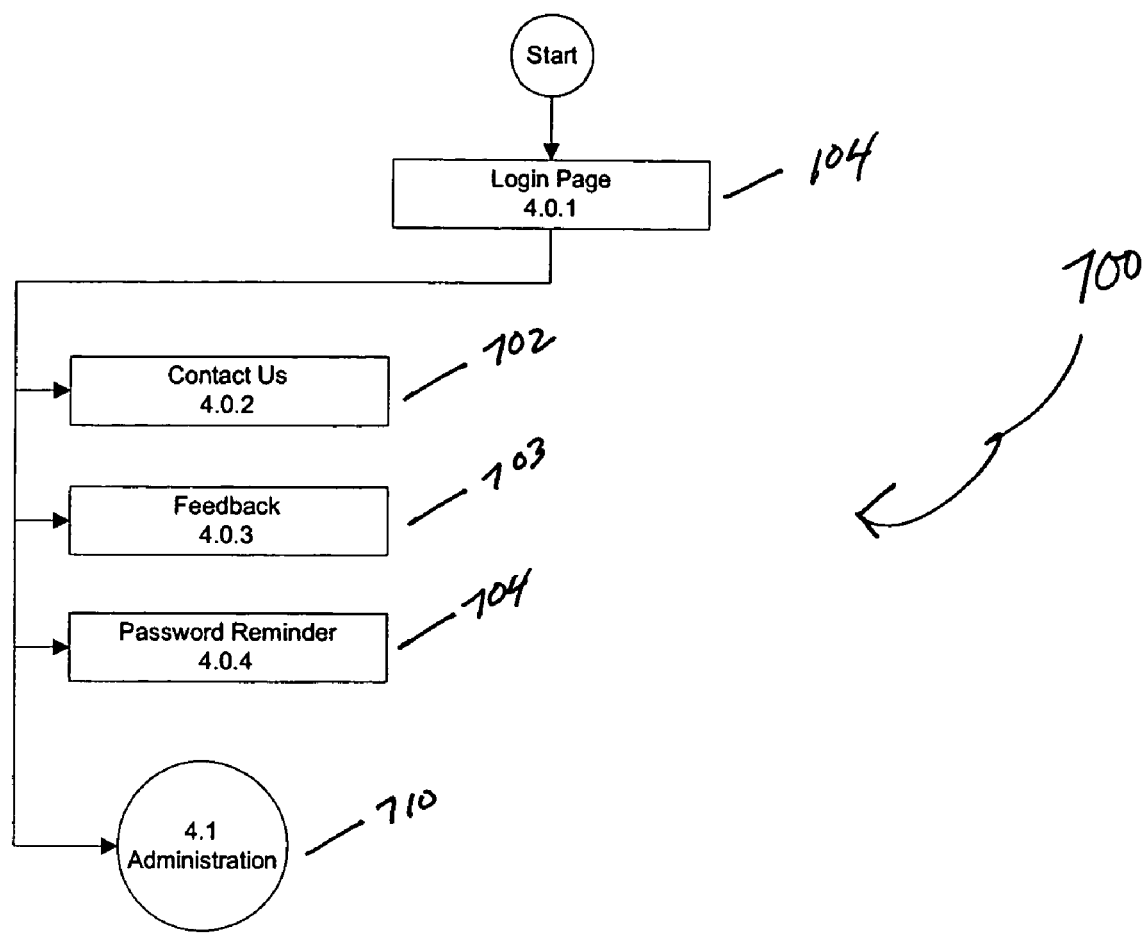
FIG. 45 is a flow diagram showing the scheduling login process.

FIG. 45 is a flow chart showing the scheduling login process 700 which is initiated when the user selects to login as a 'scheduler' from the homepage 2000 (step 104 in FIG. 2). The scheduling login process 700 begins with the scheduler selecting to login from a scheduler login page 2380 (step 701; not shown). The scheduler login page 2380 also provides access to a contact information page (step 702), a feedback page (step 703), and a password reminder page (step 704). If the user selects to login as a "scheduler", the process proceeds to the scheduler administration process 710 (See FIG. 46).

Figure 46:
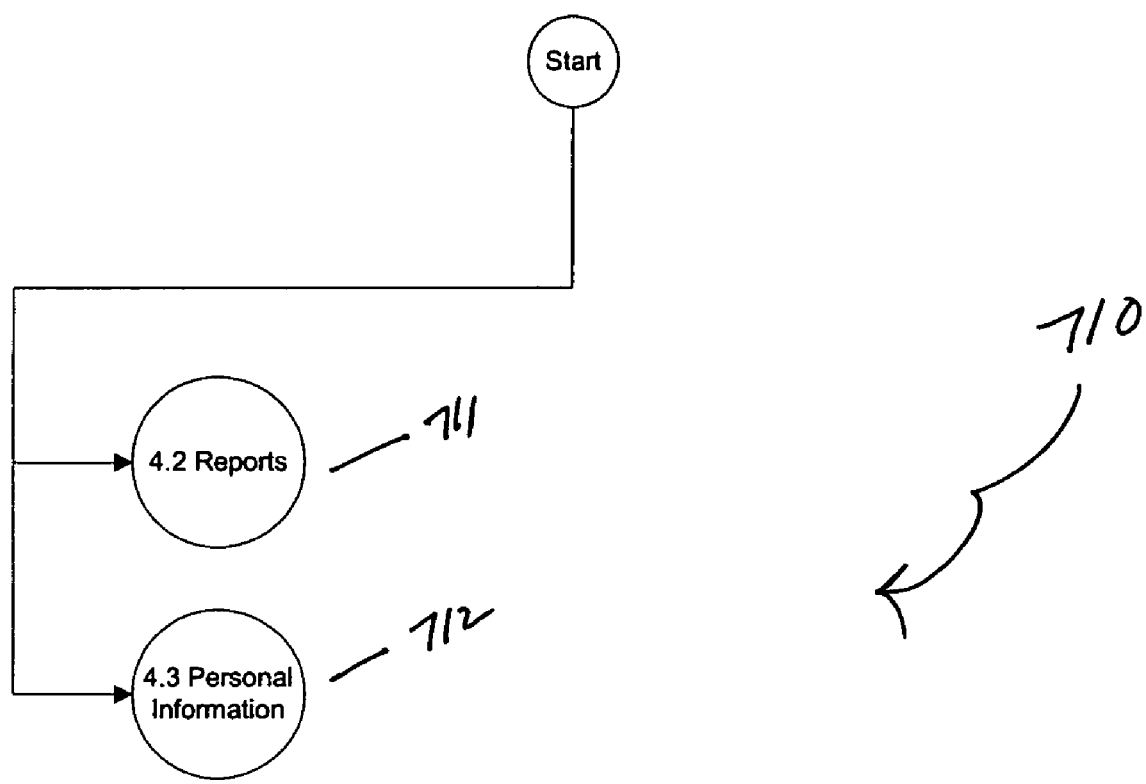
FIG. 46 is a flow diagram showing the scheduler administration process.
Figure 99:
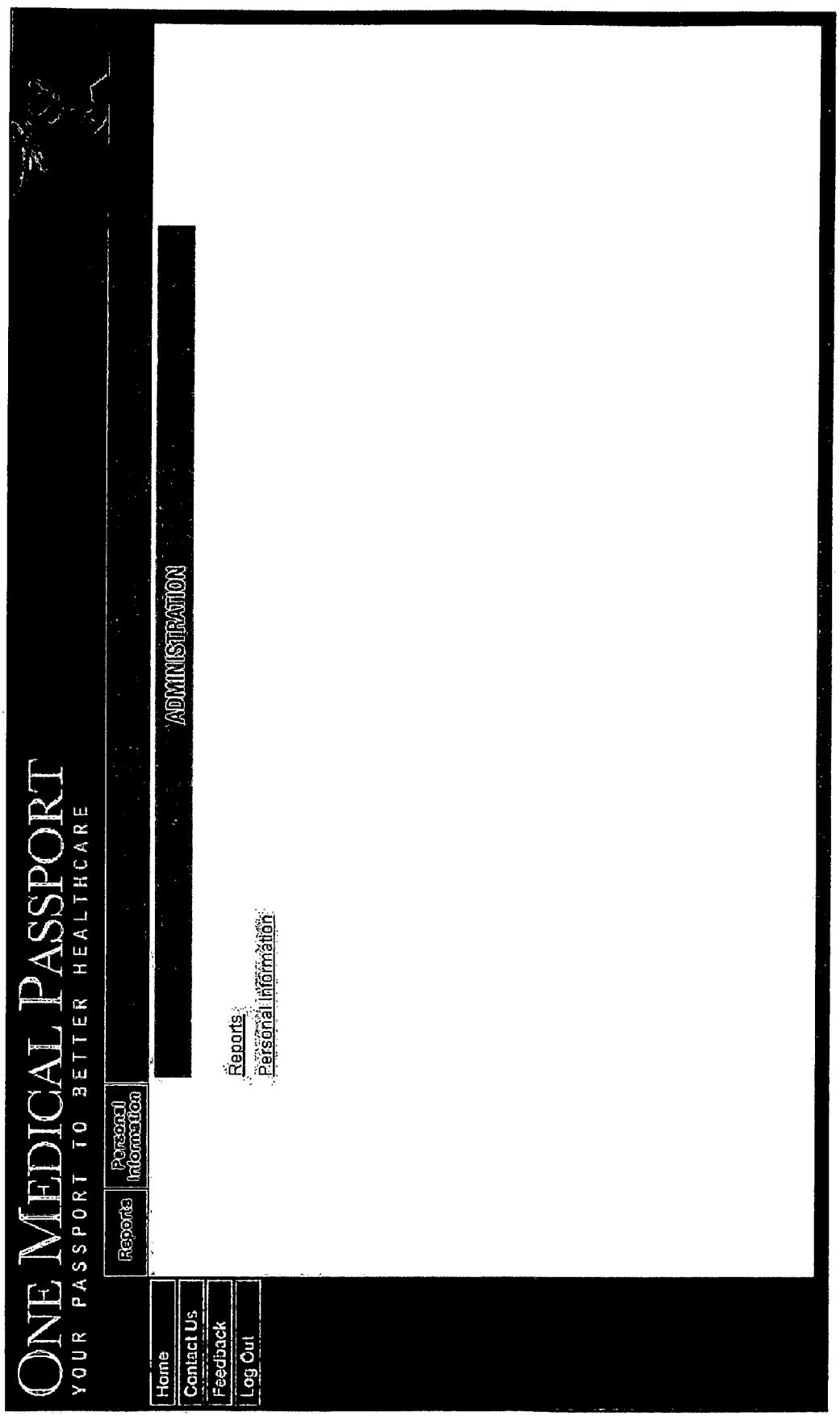
FIG. 99 shows a scheduler administration page.

FIG. 46 is a flow chart showing the scheduler administration process 710. Upon initiation of the scheduler administration process 710 the user is presented a scheduler administration page 2390 (see FIG. 99) which provides links to other processes, such as a scheduler reports process 720 (step 711), and a personal information process 730 (step 712).

Figure 47:
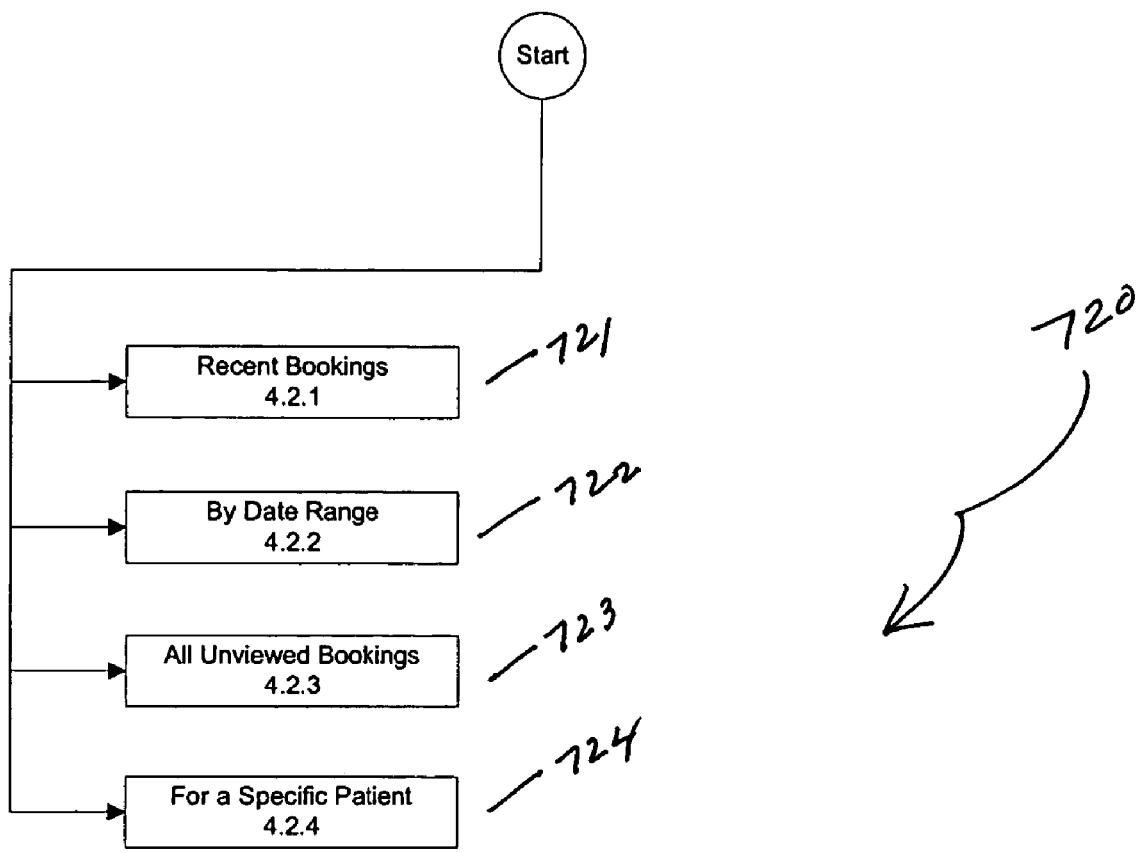
FIG. 47 is a flow diagram showing the scheduler reports process.

FIG. 47 is a flow chart showing the scheduler reports process 720. Using this process, the scheduler for a particular physician's office or medical facility may generate scheduling reports of in several different ways. The scheduler may display all recent bookings (step 721), bookings by date range (step 722), all unviewed bookings (step 723), and/or bookings for a specific patient (step 724).

Figure 48:
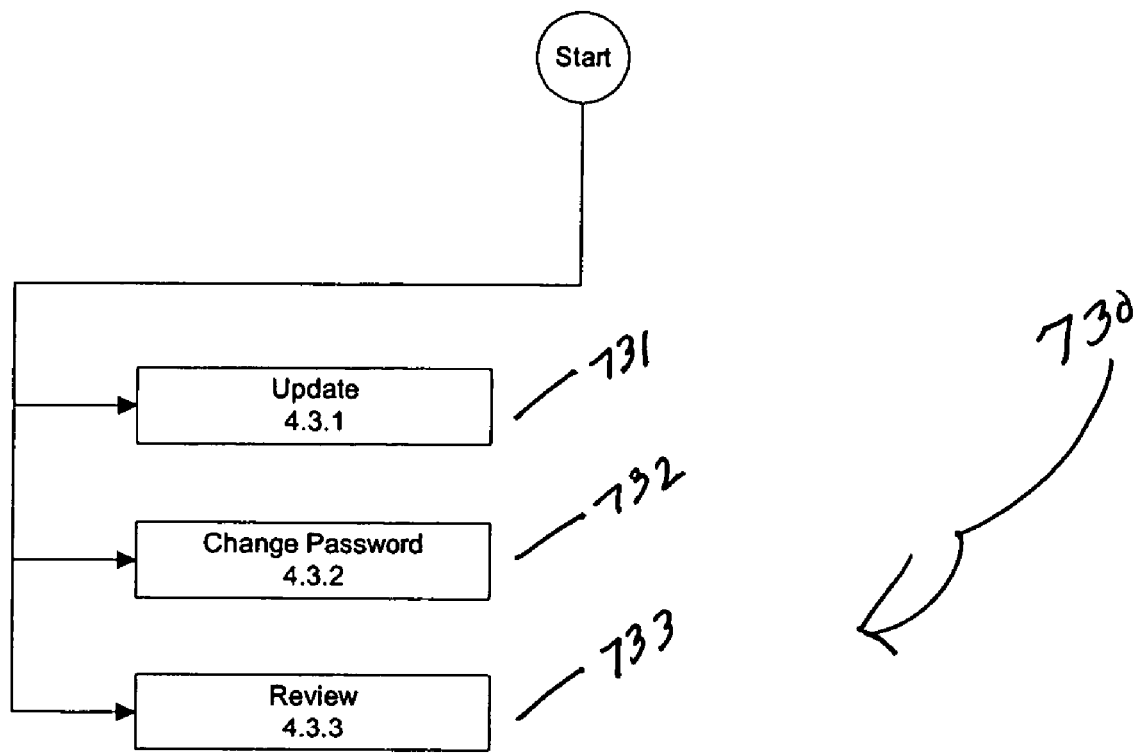
FIG. 48 is a flow chart showing the personal information process.

FIG. 48 is a flow chart showing the personal information process 730. The personal information process 730 allows the scheduler to update his or her personal information, such as by updating his or her name, phone etc. (step 731), and/or his or her password (step 732). Once all information had been updated, the scheduler is given the opportunity to review the information before finalizing (step 733). This is similar to the personal information process 690 which takes place during the office login process 500.

The following listing further explains some of the items shown in FIGS. 45-48:

4.0 Scheduling Login 4.0.1 Login Page—Main access point for medical facility schedulers to log in.

4.0.2 Contact Us—Allows schedulers to send an email to One Medical Passport support.

4.0.3 Feedback—Allows schedulers to provide feedback about the site to One Medical Passport staff.

4.0.4 Password Reminder—Automated password reminder for schedulers. Based on the email address, username, and a codeword the password is reset and emailed to the scheduler.

4.2 Reports 4.2.1 Recent Bookings—Displays a list of bookings for the medical facility for the upcoming week.

4.2.2 By Date Range—Displays a list of bookings for the medical facility by a specified date range.

4.2.3 All Unviewed Bookings—Displays a list of unviewed bookings for the medical facility.

4.2.4 For a Specific Patient—Displays a list of bookings for the medical facility for a patient by specifying the patient's social security number and last name.

4.3 Personal Information 4.3.1 Update—Allows the scheduler to update their name, phone, email, username, and codeword information.

4.3.2 Change Password—Permits the scheduler to change their password.

4.3.3 Review—Allows the scheduler to review their name, phone, email, username, and codeword information.

Admitting Login

Figure 49:
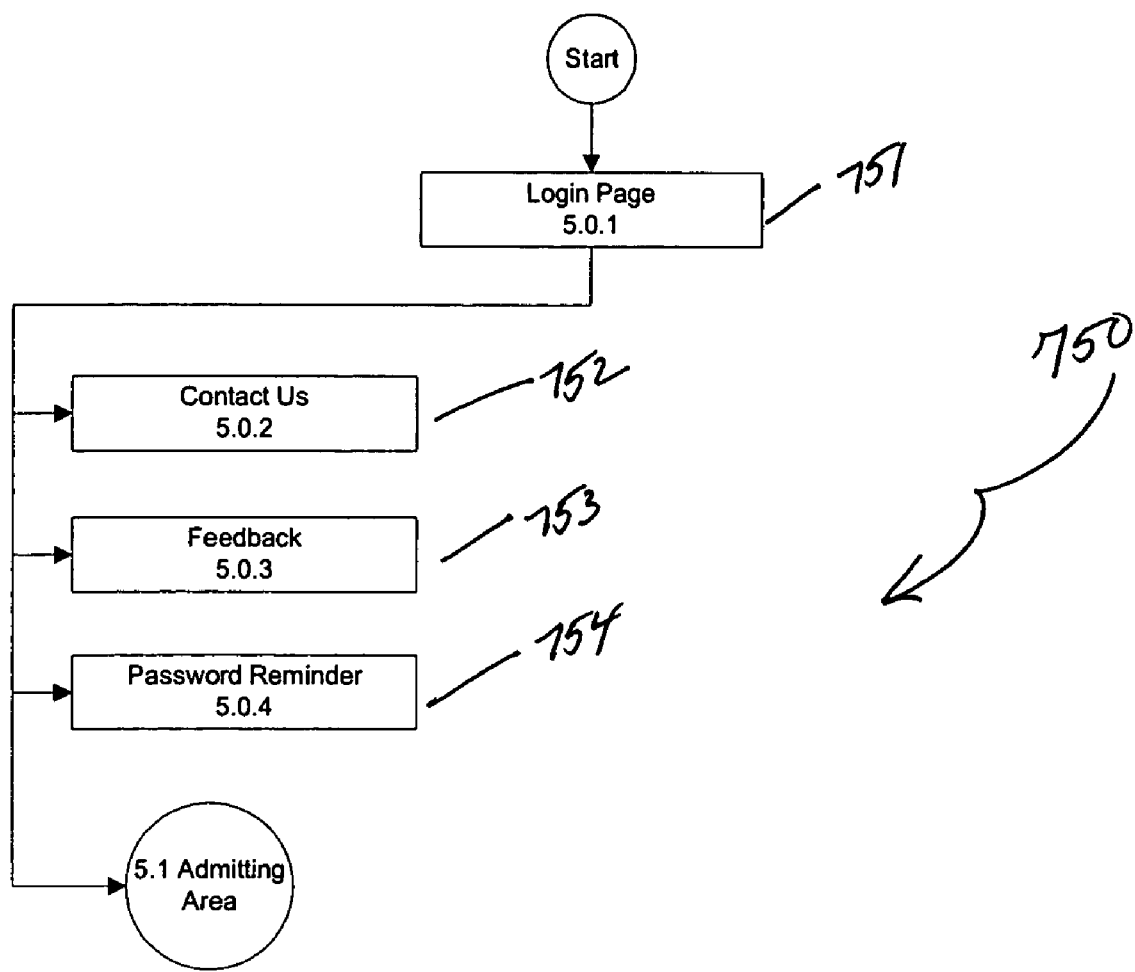
FIG. 49 is a flow diagram showing the admitting login process.
Figure 100:
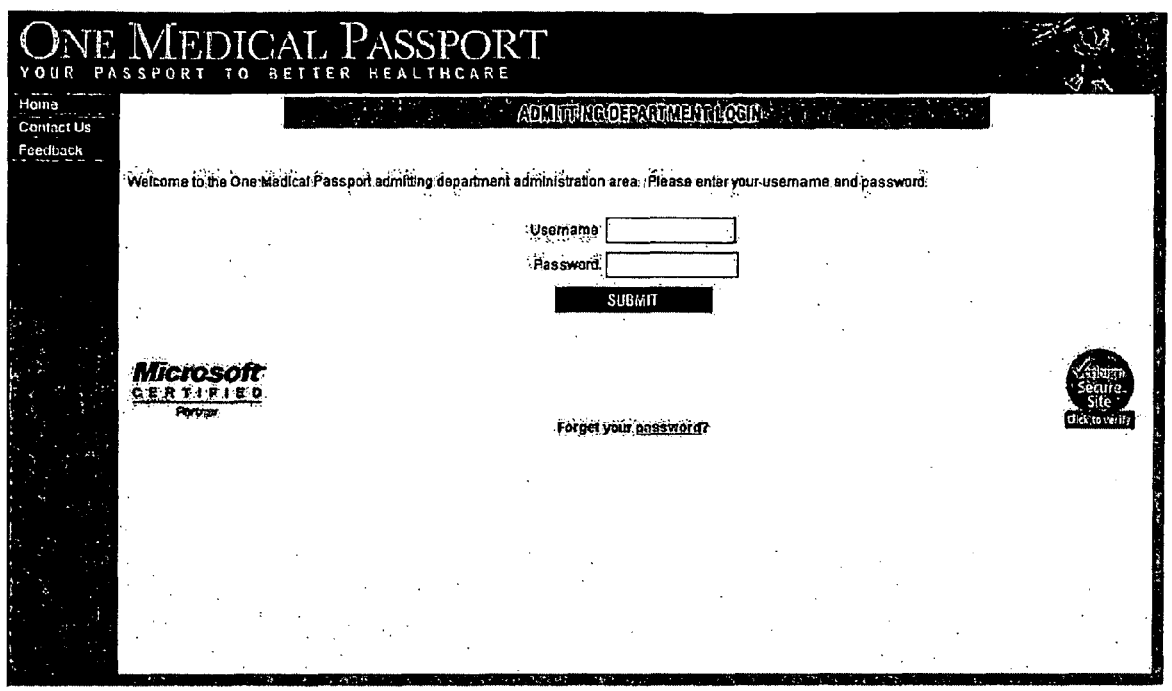
FIG. 100 shows an admitting login page.

FIG. 49 is a flow chart showing the admitting login process 750 which is initiated when the user selects to login as an 'admitting' from the homepage 2000 (step 105 in FIG. 2). The admitting login process 700 begins with the admitting user selecting to login from an admitting login page 2400 (step 751; FIG. 100). The admitting login page 2400 also provides access to a contact information page (step 752), a feedback page (step 753), and a password reminder page (step 754). If the user selects to login as an "admitting", the process proceeds to the admitting area process 760 (See FIG. 50).

Figure 50:
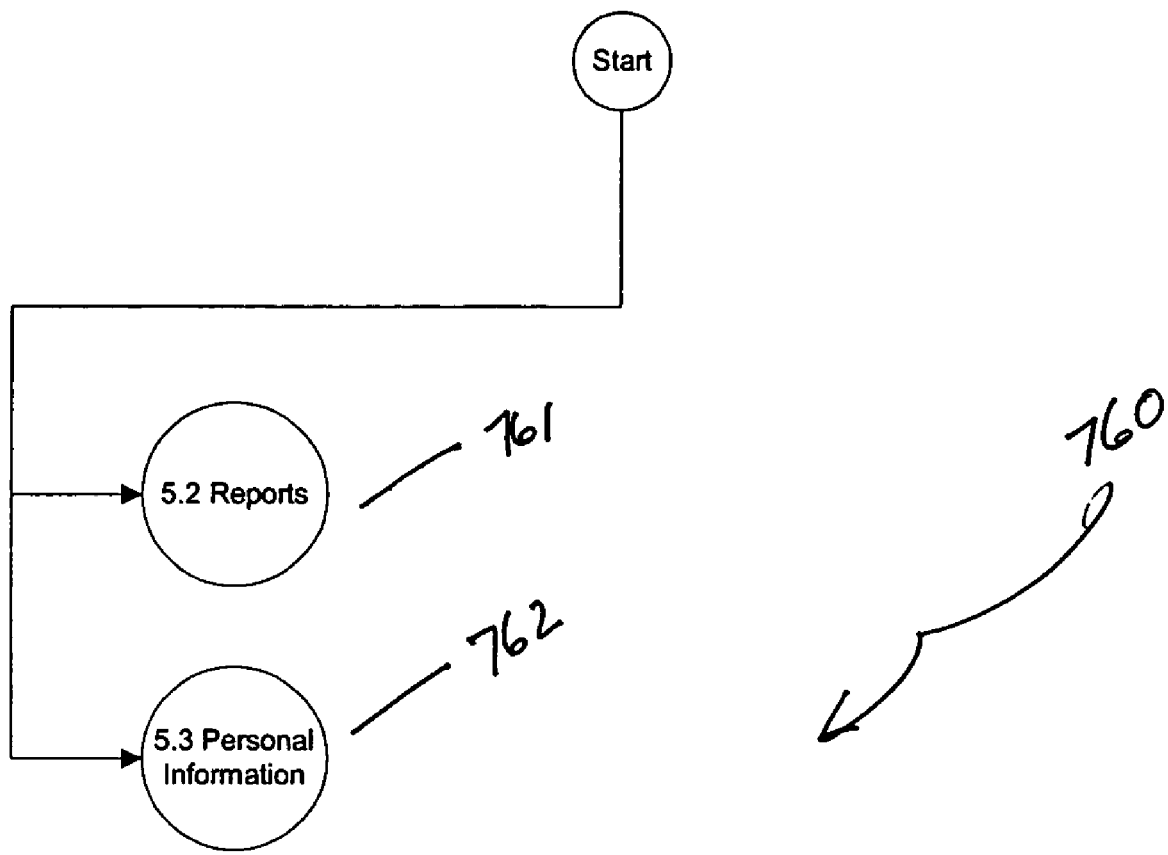
FIG. 50 is a flow diagram showing the admitting area process.

FIG. 50 is a flow chart showing the admitting area process 760. Upon initiation of the admitting area process 760 the user is presented an admitting page 2410 (not shown) which provides links to other processes, such as a admitting reports process 770 (step 761), and a personal information process 780 (step 762).

Figure 51:
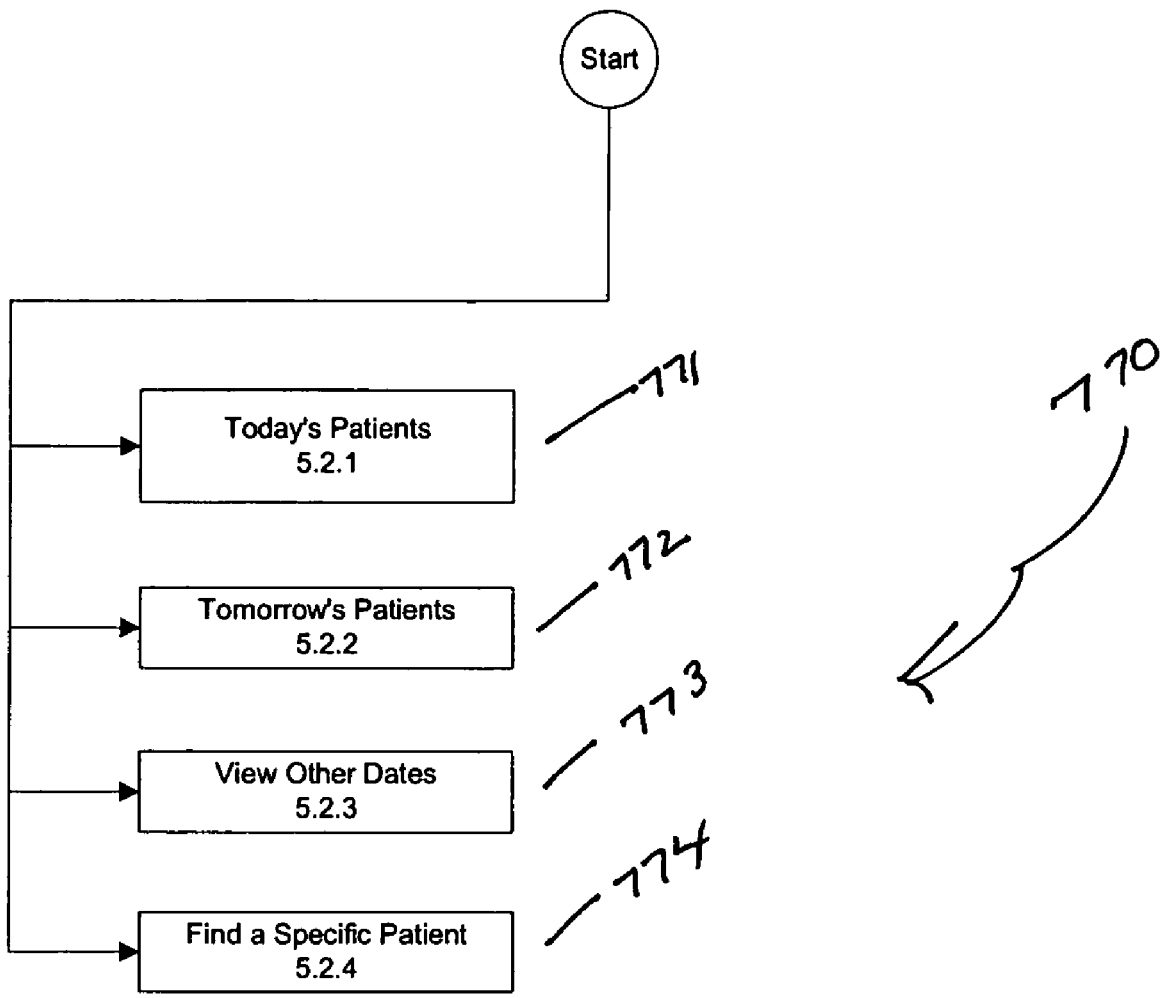
FIG. 51 is a flow diagram showing the admitting reports process.

FIG. 51 is a flow chart showing the admitting reports process 770. Using this process, the admitting user may generate reports of Medical Passports in several different ways. The admitting user may display all Medical Passports for today's patients (step 771), Medical Passports for tomorrow's patients (step 772), Medical Passports for any selected date or date range (step 773) and/or Medical Passports for specific patients (step 774).

Figure 52:
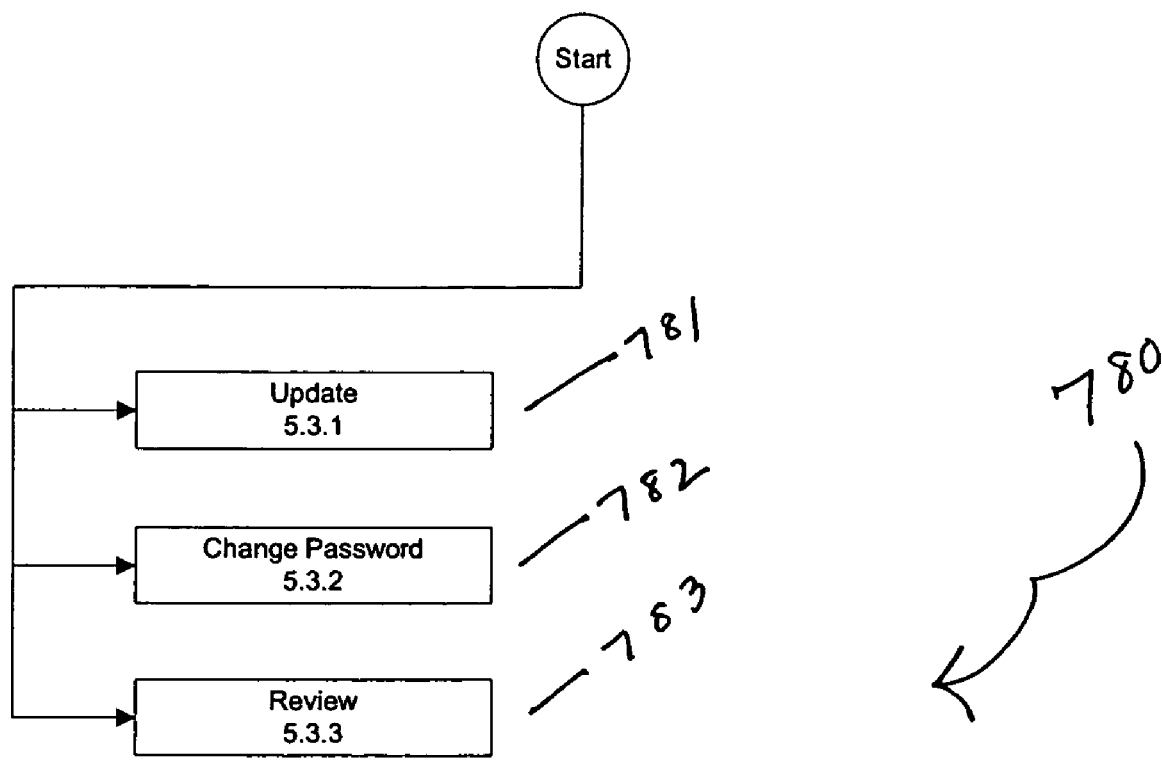
FIG. 52 is a flow diagram showing the personal information process.

FIG. 52 is a flow chart showing the personal information process 780. The personal information process 780 allows the admitting user to update his or her personal information, such as by updating his or her name, phone etc. (step 781), and/or his or her password (step 782). Once all information had been updated, the admitting user is given the opportunity to review the information before finalizing (step 733). This is similar to the personal information process 690 which takes place during the office login process 500, and the personal information process 730 which takes place during the scheduling login process 700.

The following listing further explains some of the items shown in FIGS. 49-52:

5.0 Admitting Login 5.0.1 Login Page—Main access point for admitting department staff to log in.

5.0.2 Contact Us—Allows admitting department staff to send an email to One Medical Passport support.

5.0.3 Feedback—Allows admitting department staff to provide feedback about the site to One Medical Passport staff.

5.0.4 Password Reminder—Automated password reminder for admitting department staff. Based on the email address, username, and a codeword the password is reset and emailed to the admitting department staff member.

5.2 Reports 5.2.1 Today's Patients—Displays a list of patients with a Medical Passport scheduled for today's date. An admitting department staff member may only see and download reports specified for the facility they are associated with. Reports are in Adobe Acrobat format.

5.2.2 Tomorrow's Patients—Displays a list of patients with a Medical Passport scheduled for tomorrow's date. An admitting department staff member may only see and download reports specified for the facility they are associated with. Reports are in Adobe Acrobat format.

5.2.3 View Other Dates—Displays a list of patients with a Medical Passport scheduled for a specified date range. An admitting department staff member may only see and download reports specified for the facility. Reports are in Adobe Acrobat format.

5.2.4 Find a Specific Patient—Displays a list of patients with a Medical Passport based on name and date of birth. An admitting department staff member may only see and download reports specified for the facility. Reports are in Adobe Acrobat format.

5.3 Personal Information 5.3.1 Update—Allows the admitting department staff member to update their name, phone, email, username, and codeword information.

5.3.2 Change Password—Permits the admitting department staff member to change their password.

5.3.3 Review—Allows the admitting department staff member to review their update their name, phone, email, username, and codeword information.

Administration Login

Figure 53:
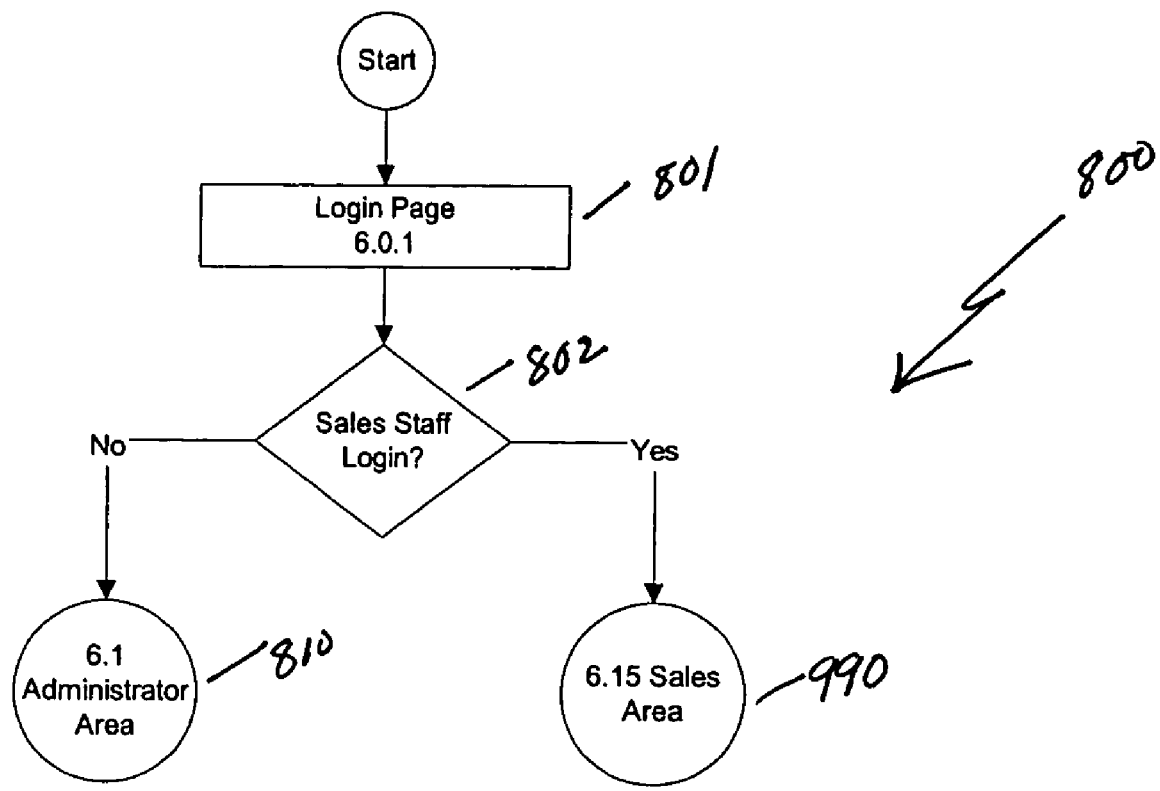
FIG. 53 is a flow diagram showing the administrator login process.

FIG. 53 is a flow chart showing the administrator login process 800 which is initiated when the user selects to login as an 'administrator' from the homepage 2000 (step 106 in FIG. 2). The administrator login process 800 begins with the administrator user selecting to login from an administrator login page 2500 (step 801; not shown). The administrator user then selects whether to login as an "administrator" or "sales staff" (step 802). If the administrator user selects to login as an "administrator", the process proceeds to the administrator area process 810 (See FIG. 54). Alternatively, if the administrator user selects to login as "sales staff", the process proceeds to the sales area process 990 (See FIG. 70)

Figure 54:
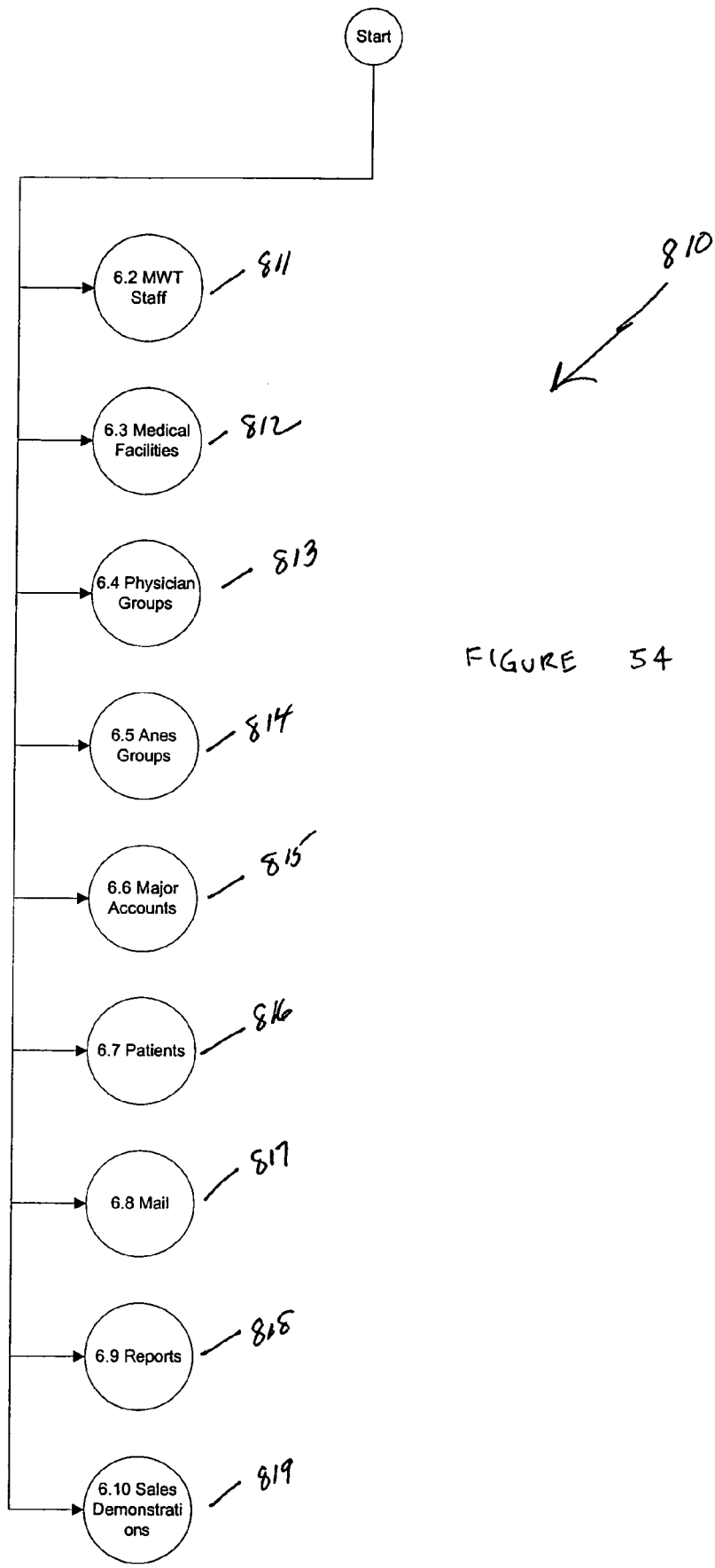
FIG. 54 is a flow diagram showing the administrator area process.
Figure 101:
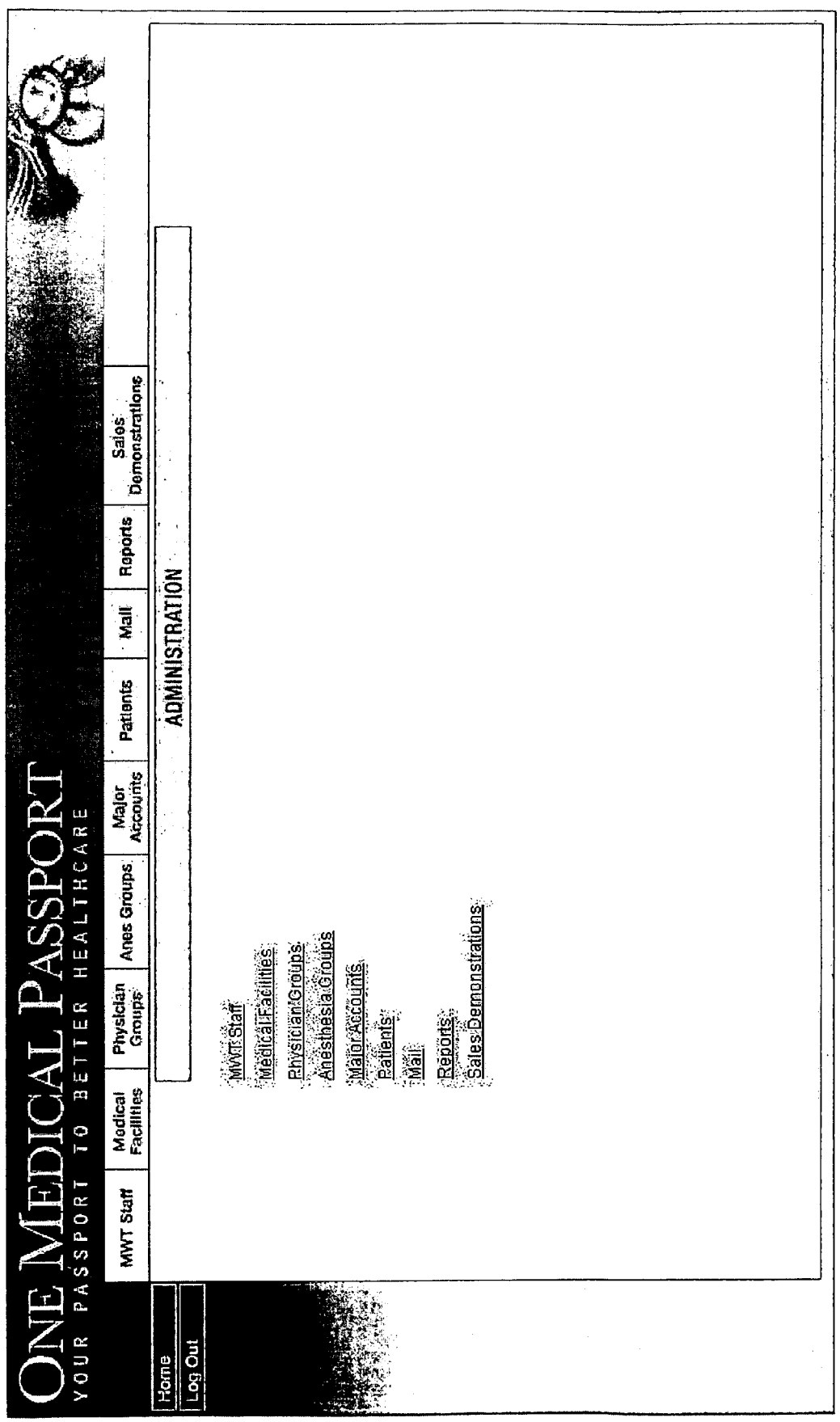
FIG. 101 shows an administrator area page.

FIG. 54 is a flow chart showing the administrator area process 810. Upon initiation of the administrator area process 810 the user is presented an administrator area page 2510 (see FIG. 101) which provides links to other processes, such as a staff process 820 (step 811), a medical facilities process 840 (step 812), a physician groups process 850 (step 813), a anesthesiologists groups process 860 (step 814), a major accounts process 870 (step 815), a patients process 880 (step 816), a mail process 890 (step 817), a reports process 900 (step 818), and a sales demonstrations process 920 (step 819).

Figure 55:
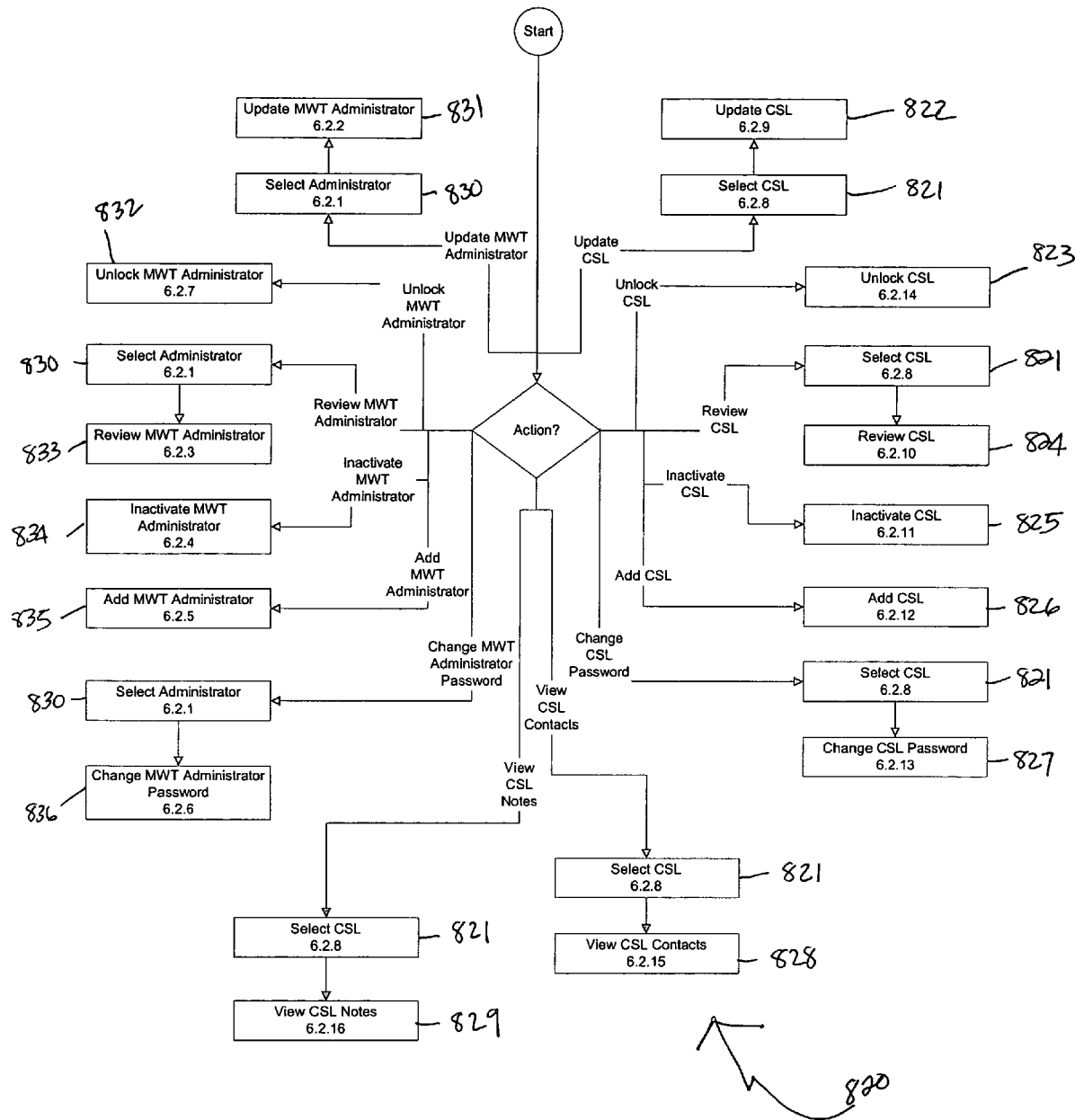
FIG. 55 is a flow diagram showing the staff process.

FIG. 55 is a flow chart showing the staff process 820. The administrator user has various choices of actions relating to staff (e.g., administrators, customer service representatives, etc.), for example, the user may update Customer Service Liaison (CSL) personnel (steps 821, 822), unlock a CSL's access to the system (step 823), review a CSL's information (steps 821, 824), inactivate a CSL (step 825), add a CSL (step 826), change a CSL's password (steps 821, 827), view a CSL's contacts (steps 821, 828), and view a CSL's notes (steps 821, 829). The administrator user may also choose to update system administrator personnel (steps 830, 831), unlock a system administrator's access to the system (step 832), review a system administrator's information (steps 830, 833), inactivate a system administrator (step 834), add a system administrator (step 835), and change a system administrator's password (steps 830, 836).

Figure 56:
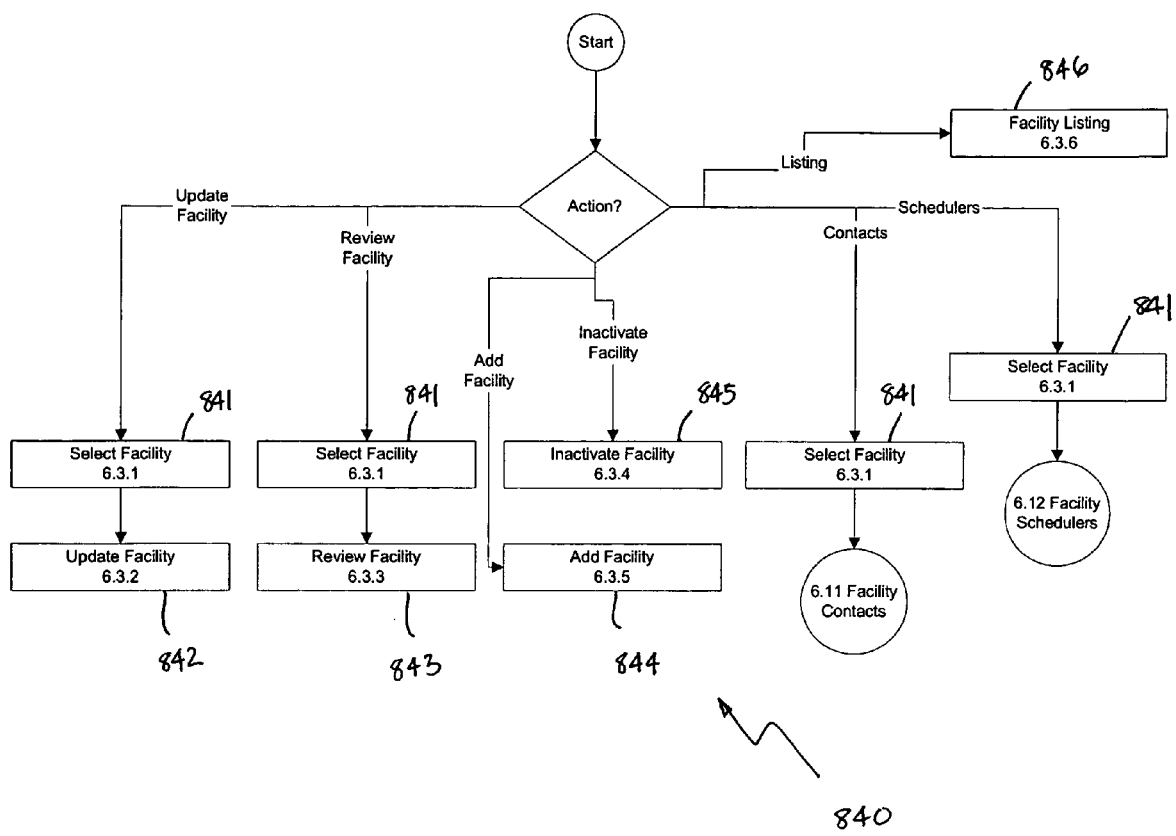
FIG. 56 is a flow diagram showing the medical facilities process.

FIG. 56 is a flow chart showing the medical facilities process 840. Using this process, the administrator user may take various actions with regard to the medical facilities, such as update a facility (steps 841, 842), review a facility (steps 841, 843), add a facility (step 844), inactivate a facility (step 845), and display a facility listing (step 846). The administrator user may also choose to review facility contacts and facility schedulers, in which case the process proceeds to the facility contacts process 930 (FIG. 64) or the facility schedulers process 940 (FIG. 65), respectively.

Figure 57:
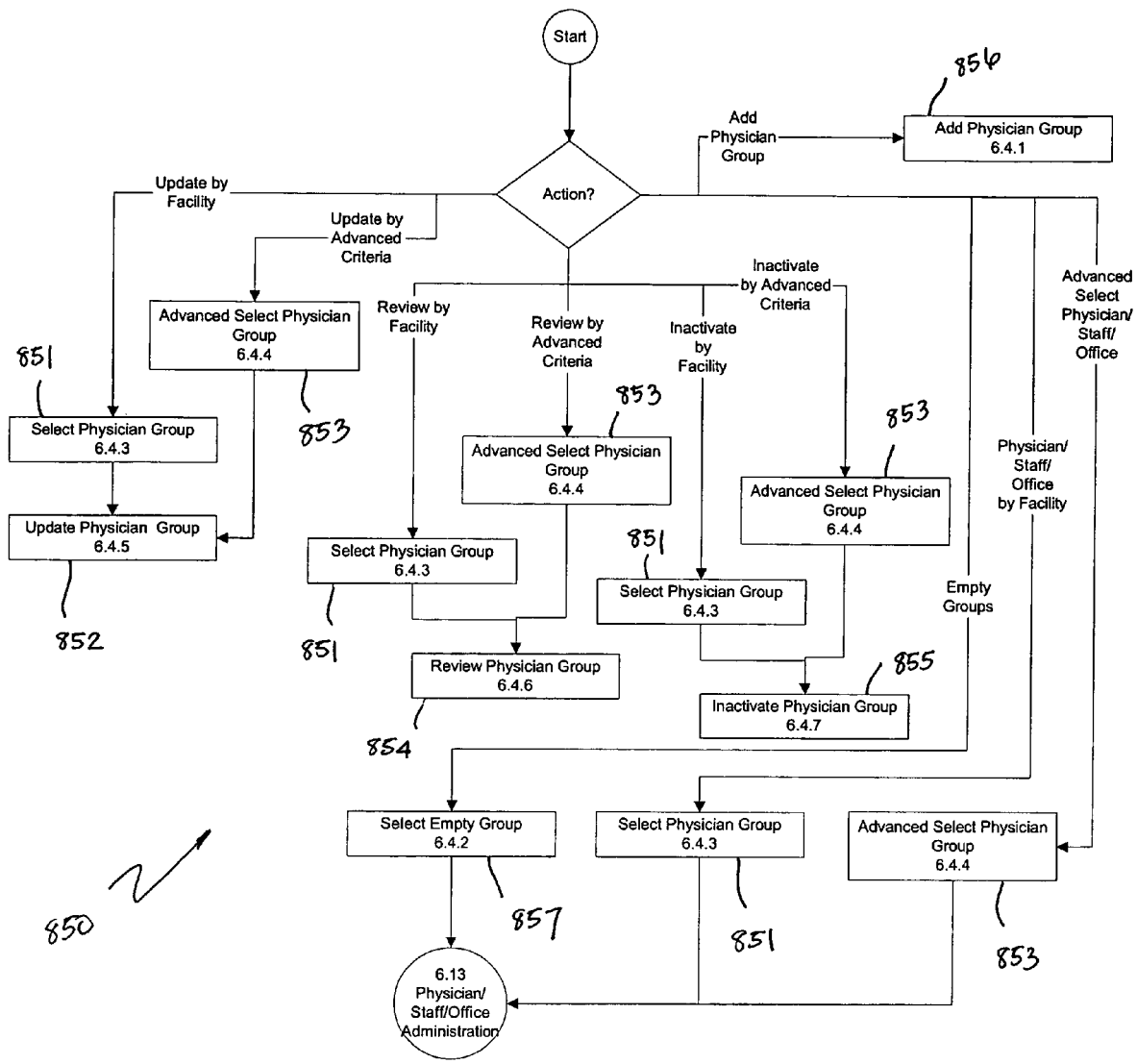
FIG. 57 is a flow diagram showing the physician groups process.

FIG. 57 is a flow chart showing the physician groups process 850. Using this process, the administrator user may take various actions with regard to the physicians and physician's groups, such as update a physician group by facility (steps 851, 852), update a physician group by advanced criteria (steps 853, 852), review physician group by facility (steps 851, 854), review physician group by advanced criteria (steps 853, 854), inactivate physician group by facility (steps 851, 855), inactivate physician group by advanced criteria (steps 853, 855), add a physician group (step 856), and/or select an empty physician group (step 857). Upon selecting a physician group (e.g., empty, standard, advanced), the administrator user may also proceed to: (1) the physician administration process 950 (FIG. 66), where the user can update information relating to the physicians in the particular physician group, (2) the staff administration process 960 (FIG. 67), where the user can update staff information relating to the physicians in the particular physician group, and/or (3) the office administration process 970 (FIG. 68), where the user can update office information relating to the physicians in the particular physician group.

Figure 58:
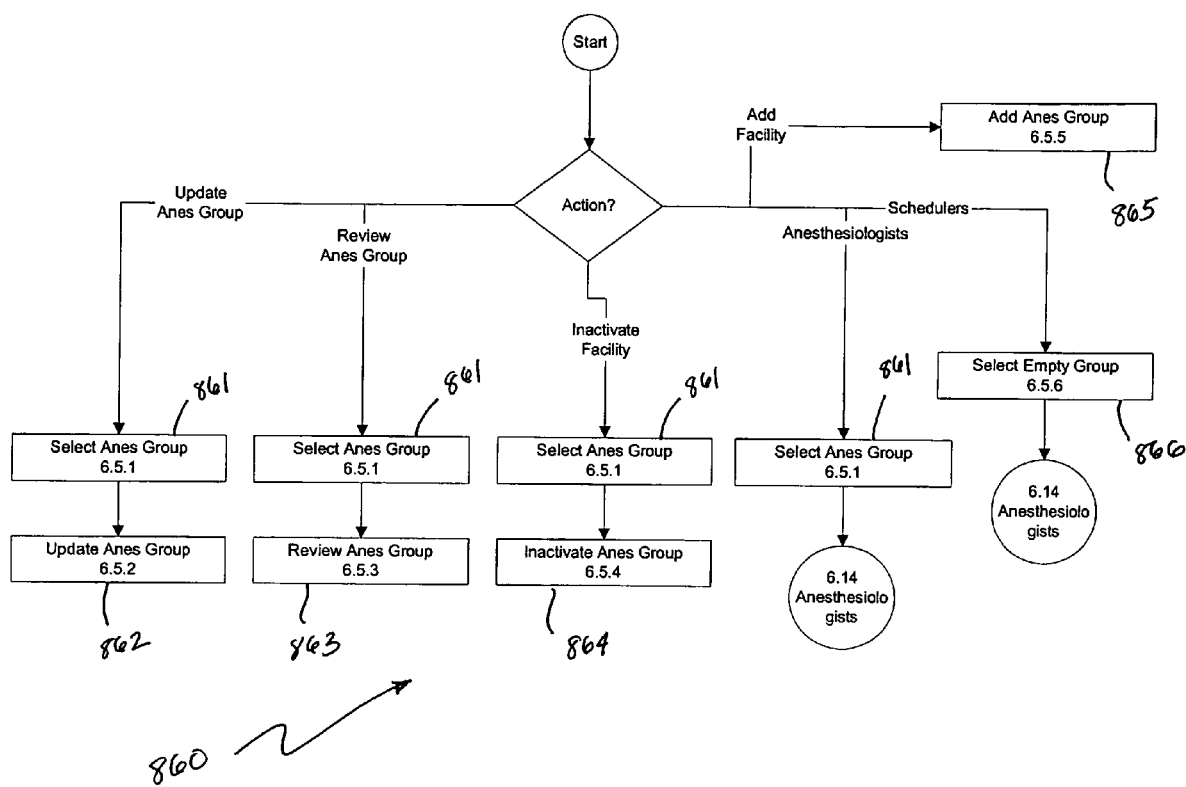
FIG. 58 is a flow diagram showing the anesthesiologists groups process.

FIG. 58 is a flow chart showing the anesthesiologists groups process 860. Using this process, the administrator user may take various actions with regard to the anesthesiologists and anesthesiologists' groups, such as update an anesthesiologist group (steps 861, 862), review an anesthesiologists group (steps 861, 863), inactivate an anesthesiologist (steps 861, 864), add an anesthesiologist (step 865), and/or select an empty anesthesiologist group (step 866). Upon selecting an anesthesiologists group (e.g., empty or standard), the administrator user may also proceed to the anesthesiologist administration process 980 (FIG. 69), where the user can update information relating to the anesthesiologists.

Figure 59:
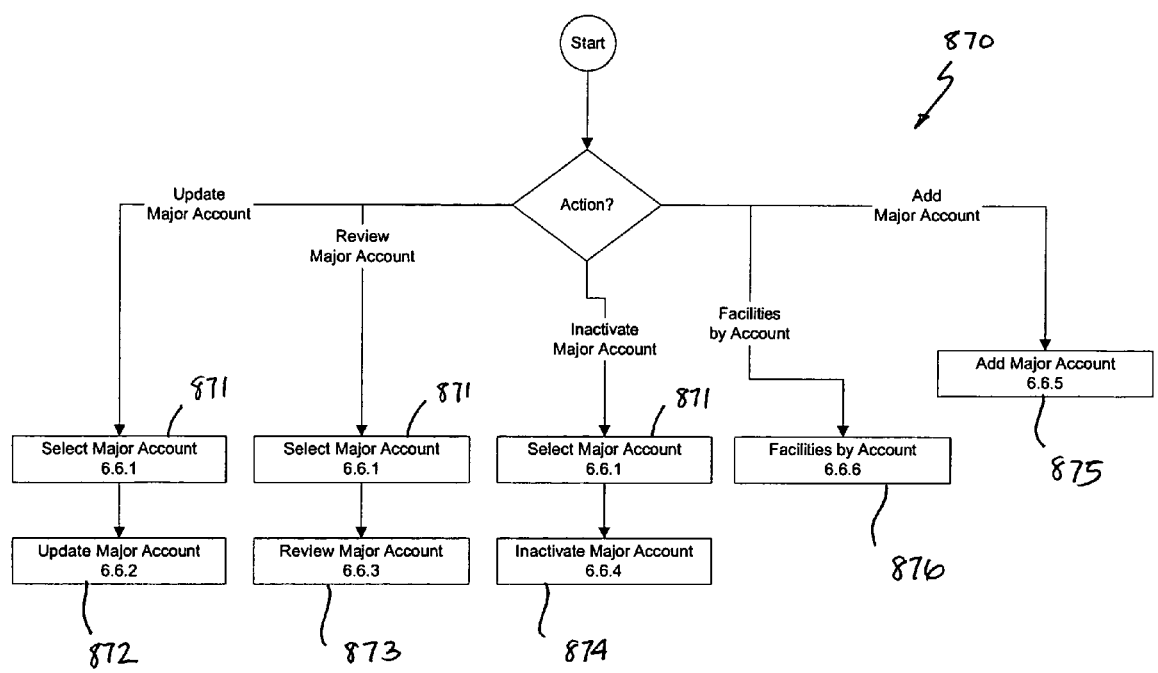
FIG. 59 is a flow diagram showing the major accounts process.

FIG. 59 is a flow chart showing the major accounts process 870. Using this process, the administrator user may take various actions with regard to 'major accounts' (e.g., physicians, hospitals, etc.), such as, update major account (steps 871, 872), review major account (steps 871, 873), inactivate a major account (steps 871, 874), add a major account (step 875), and/or display a listing of facilities by major account (step 876).

Figure 60:
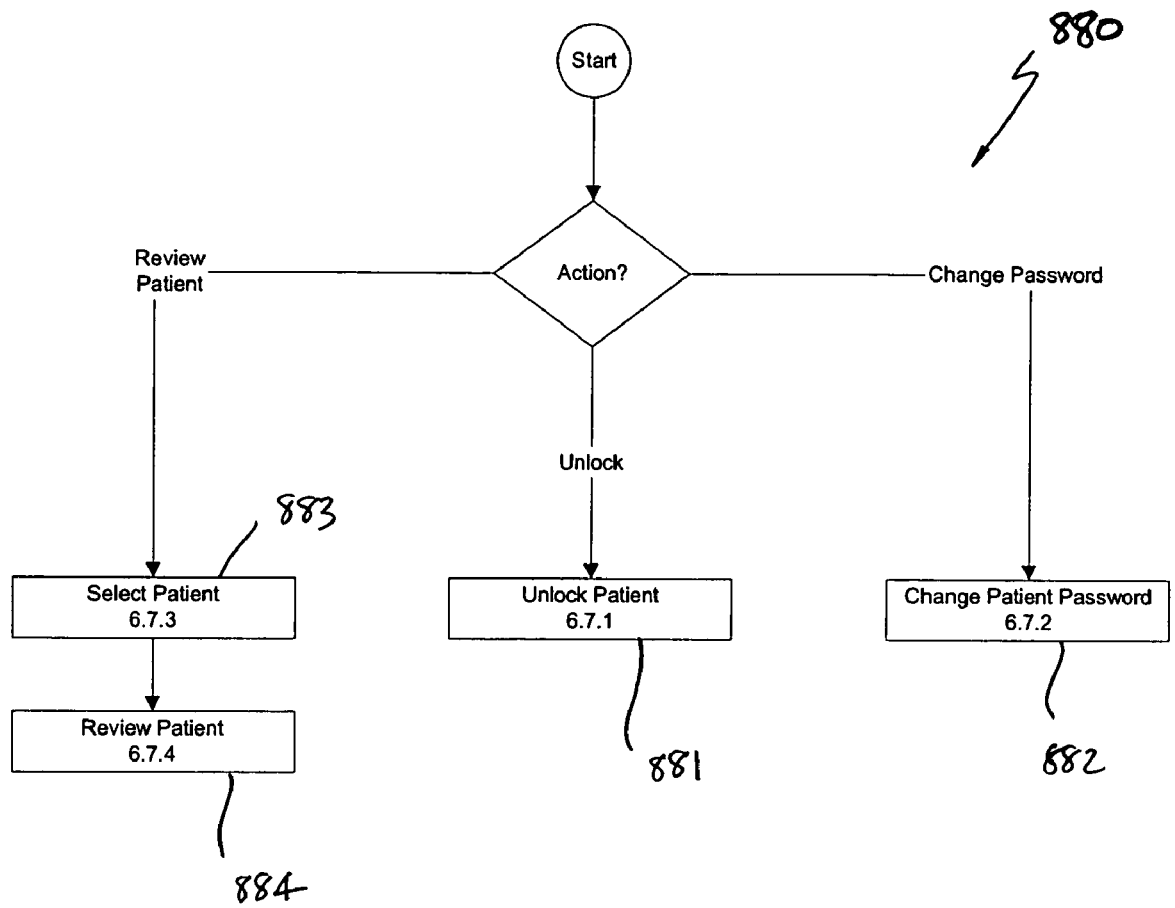
FIG. 60 is a flow diagram showing the patients process.

FIG. 60 is a flow chart showing the patients process 880. Using this process, the administrator user may take various actions with regard to patients, such as, unlock a patient who has locked themselves out of the system, by for example, attempting to login a certain number of times unsuccessfully (step 881), change a patient's password (step 882), and/or review patient information (steps 883, 884).

Figure 61:
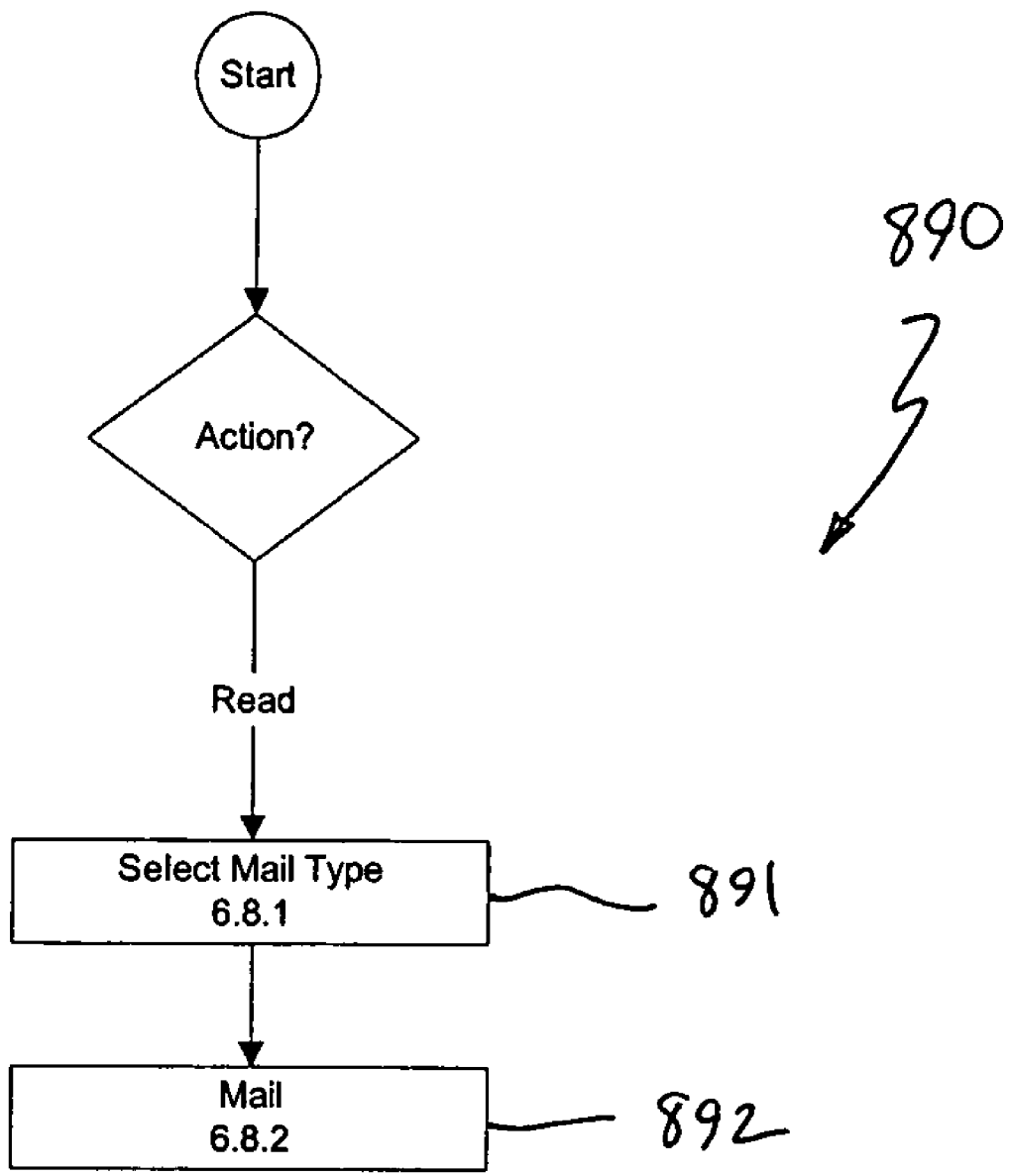
FIG. 61 is a flow diagram showing the mail process.

FIG. 61 is a flow chart showing the mail process 890. Using this process, the administrator user may view electronic mail messages (steps 891, 892). When the user initiates the mail process 890, they are presented with a mail page 2515 (See FIG. 102).

Figure 62:
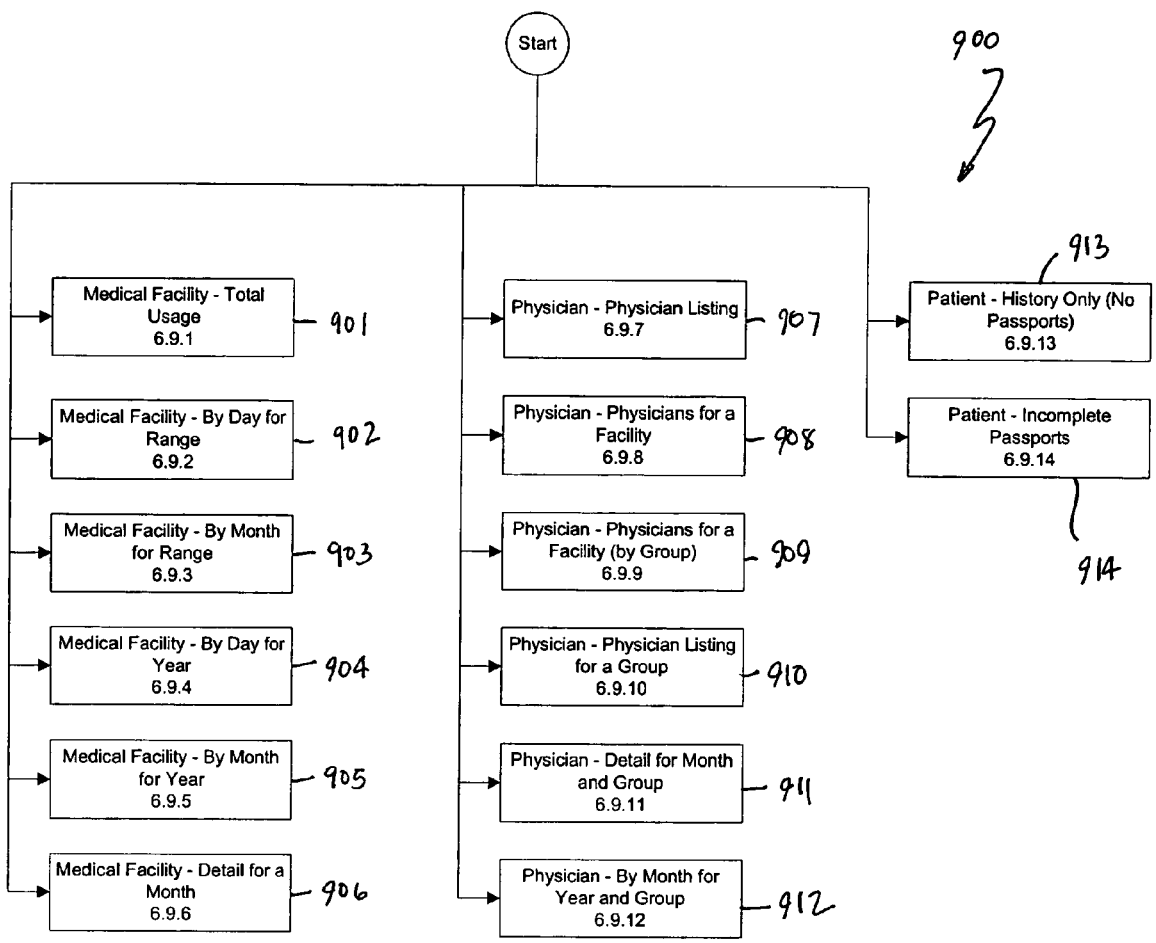
FIG. 62 is a flow diagram showing the reports process.

FIG. 62 is a flow chart showing the reports process 900. Using this process, the administrator user can generate various reports, such as, a medical facility total usage report (step 901), a medical facility "by day for range" report (step 902), a medical facility "by month for range" report (step 903), a medical facility "by day for year" report (step 904), a medical facility "by month for year" report (step 905), a medical facility "detail for month" report (step 906), a "physician-physician" report (step 907), a "physician-physician for facility" report (step 908), a "physician-physician for facility by group" report (step 909), a "physician-physician for group"

report (step 910), a "physician-detail for month and group" report (step 911), a "physician-by month for year and group" report (step 912), a "patient-history only" report (step 913), and/or a "patient-incomplete passports" report (step 914).

Figure 63:
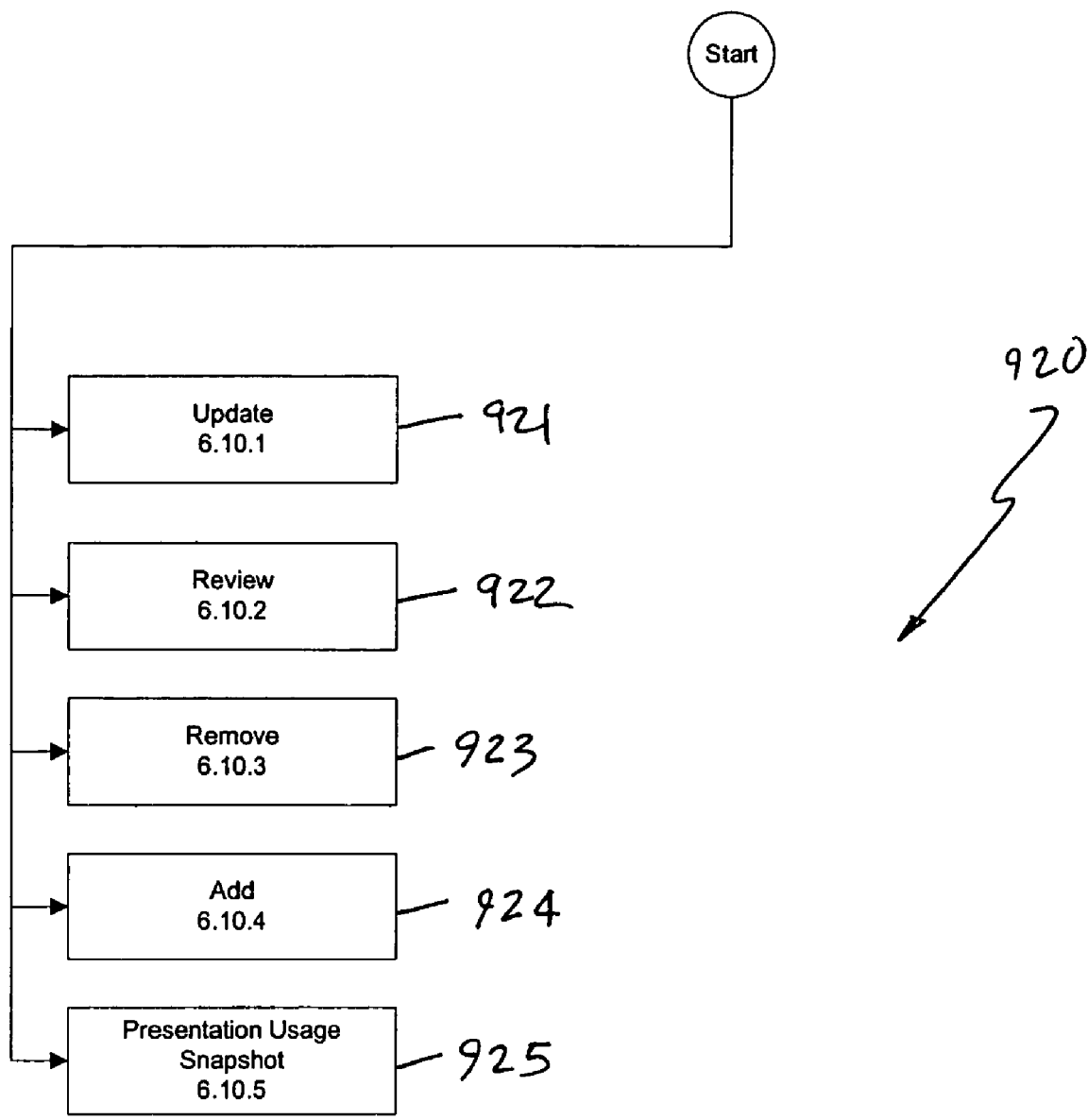
FIG. 63 is a flow diagram showing the sales demonstrations process.

FIG. 63 is a flow chart showing the sales demonstrations process 920. Using this process, the administrator user may take various actions with regard to sales demonstrators, such as, update a sales demonstrator's information (e.g., name, phone, etc.) (step 921), review a sales demonstrator's information (step 922), remove a sales demonstrator's information (step 923), add a sales demonstrator's information (step 924), and/or view a sales demonstrator's contacts (step 925).

Figure 64:
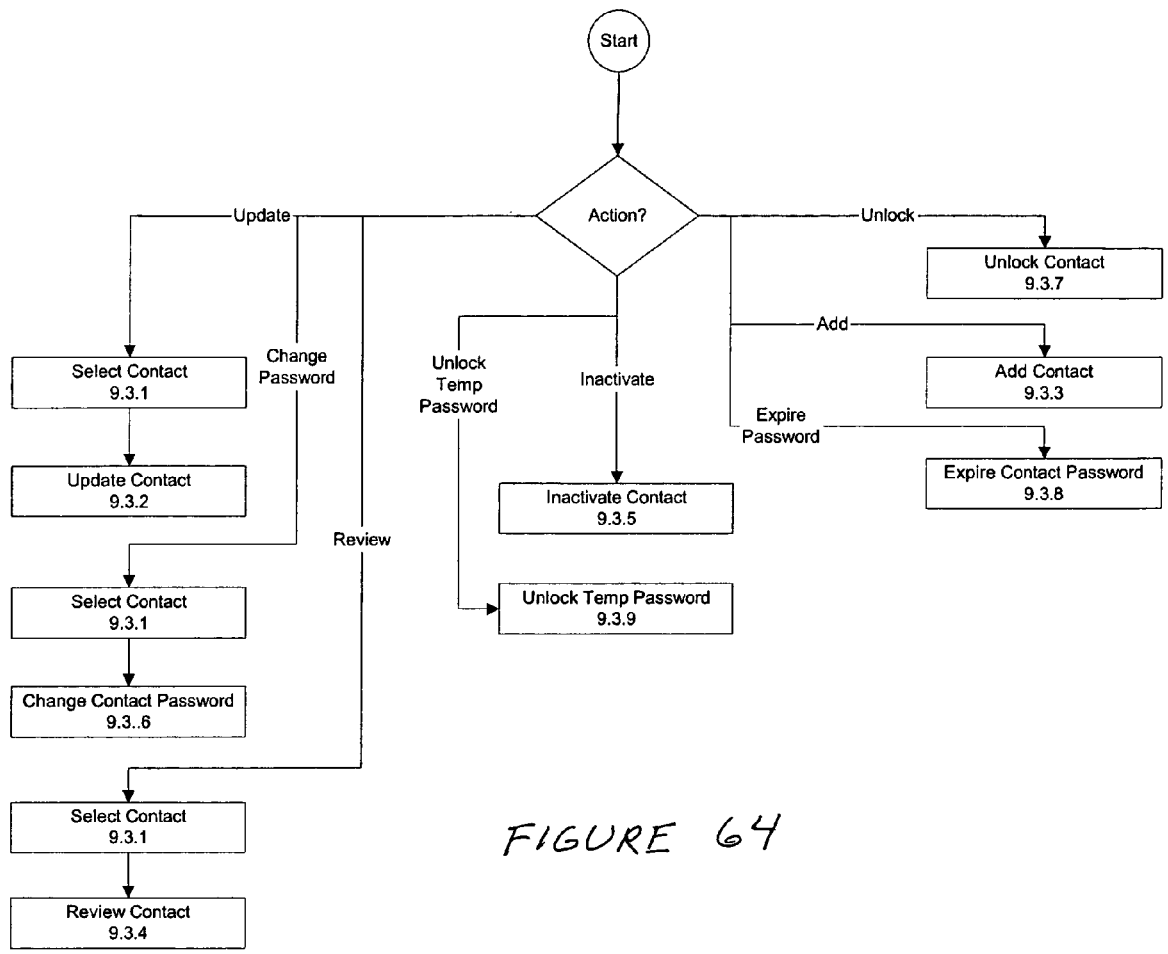
FIG. 64 is a flow diagram showing the facility contacts process.

FIG. 64 is a flow chart showing the facility contacts process 930. As noted above, this process is initiated when the administrator user selects a facility during the medical facilities process 840 (See FIG. 56). Using this process, the administrator user may take various actions with regard to the 'contacts' information for the various facilities, such as update a facility contact (steps 931, 932), add a facility contact (step 933), review facility contact (steps 931, 934), inactivate a facility contact (step 935), change a facility contact password (steps 931, 936), unlock a facility contact who has been locked out of the system (step 937), make a facility contact's password expire (step 938), and/or unlock a temporary password for a facility contact (step 939).

Figure 65:
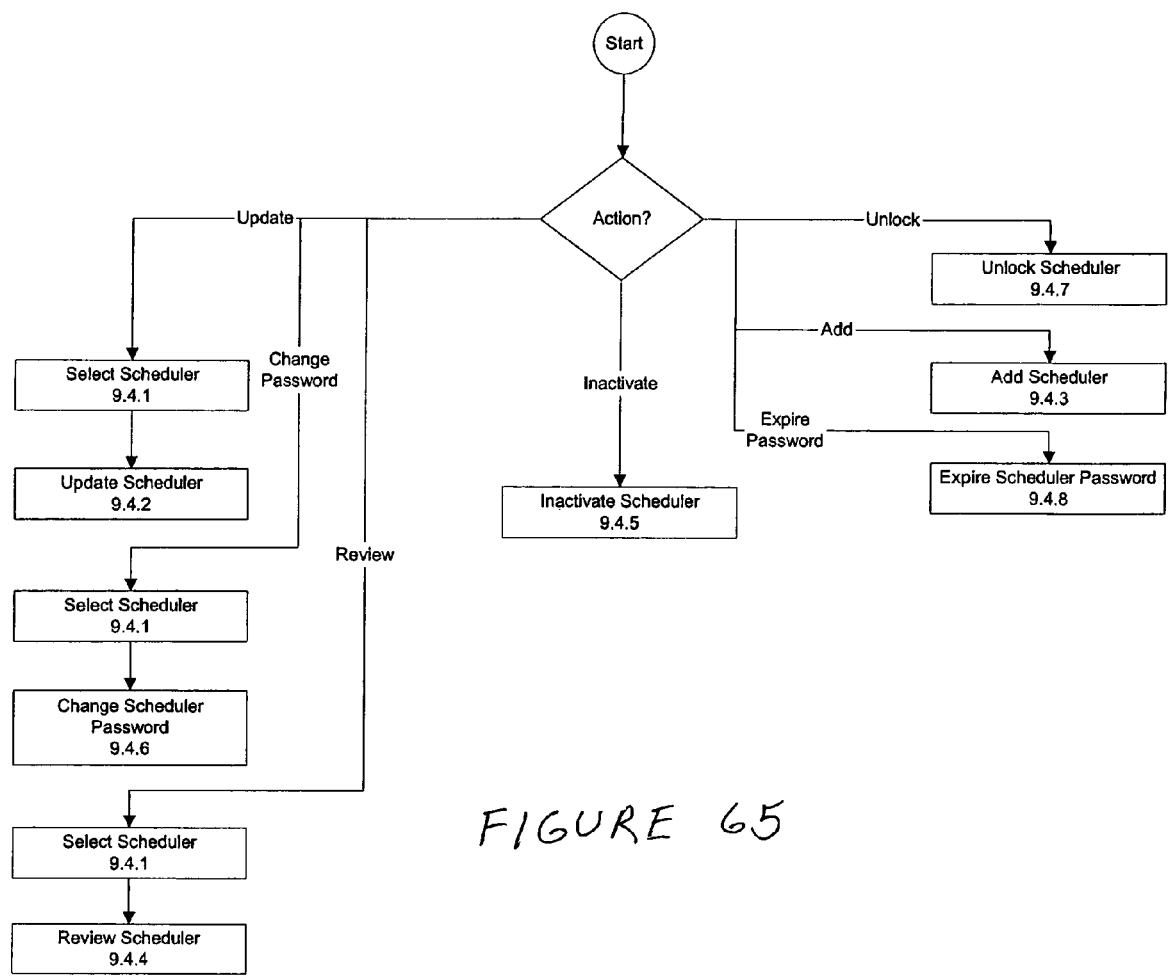
FIG. 65 is a flow diagram showing the facility schedulers process.

FIG. 65 is a flow chart showing the facility schedulers process 940. As noted above, this process is initiated when the administrator user selects a facility during the medical facilities process 840 (See FIG. 56). Using this process, the administrator user may take various actions with regard to the 'schedulers' information for the various facilities, such as update a scheduler contact (steps 941, 942), add a scheduler contact (step 943), review a scheduler contact (steps 941, 944), inactivate a scheduler contact (step 945), change a scheduler contact password (steps 941, 946), unlock a scheduler contact who has been locked out of the system (step 947), and/or make a scheduler contact's password expire (step 948).

Figure 66:
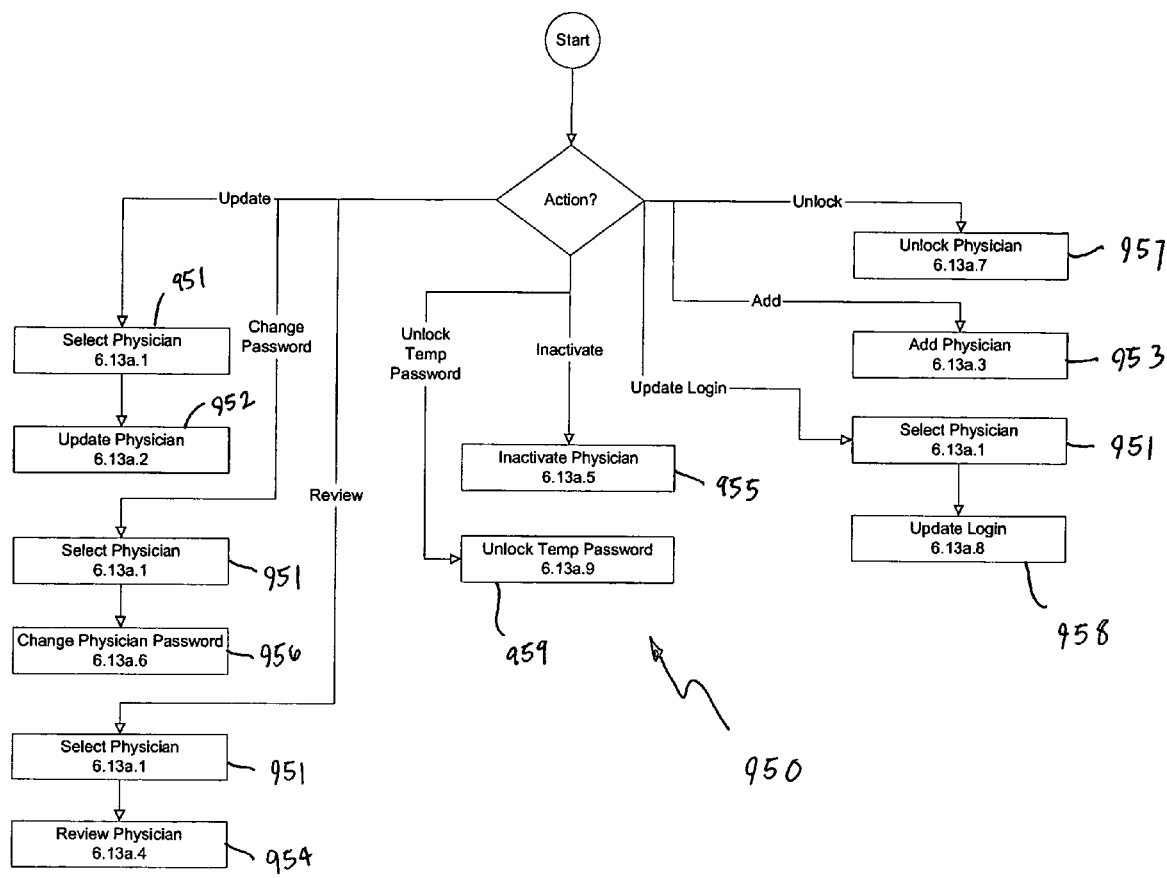
FIG. 66 is a flow diagram showing the physician administration process.

FIG. 66 is a flow chart showing the physician administration process 950. As noted above, this process is initiated when the administrator user selects a physician group during the physician groups process 850 (See FIG. 57). Using this process, the administrator user may take various actions with regard to the 'physician' information for the various facilities, such as update a physician's information (steps 951, 952), add a physician (step 953), review a physician's information (steps 951, 954), inactivate a physician (step 955), change a physician's password (steps 951, 956), unlock a physician who has been locked out of the system (step 957), make a physician's password expire (step 958), and/or unlock a temporary password for a physician (step 959).

Figure 67:
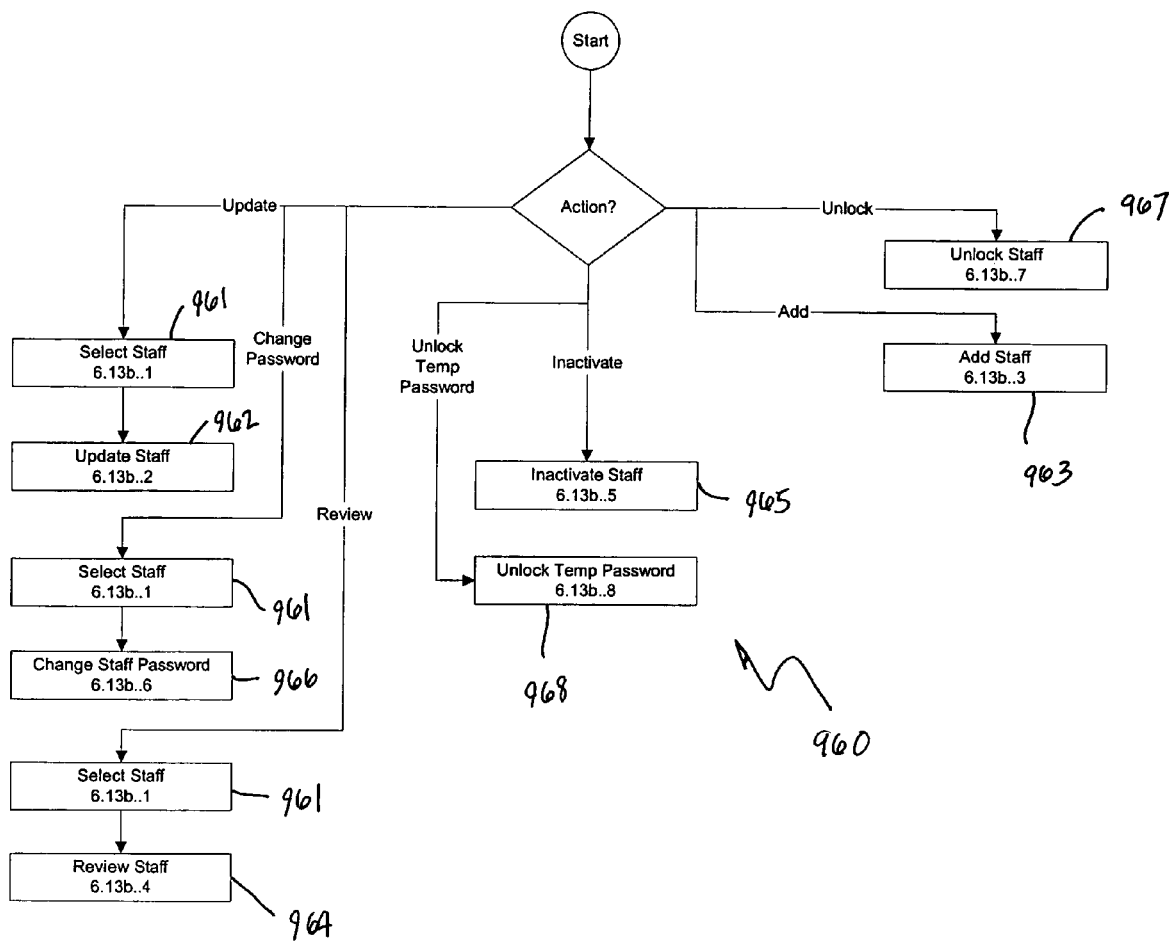
FIG. 67 is a flow diagram showing the staff administration process.

FIG. 67 is a flow chart showing the staff administration process 960. As noted above, this process is initiated when the administrator user selects a physician group during the physician groups process 850 (See FIG. 57). Using this process, the administrator user may take various actions with regard to the 'staff' information for the various facilities, such as update a staff member's information (steps 961, 962), add a staff member (step 963), review a staff member's information (steps 961, 964), inactivate a staff member (step 965), change a staff member's password (steps 961, 966), unlock a staff member who has been locked out of the system (step 967), and/or unlock a temporary password for a staff member (step 968).

Figure 68:
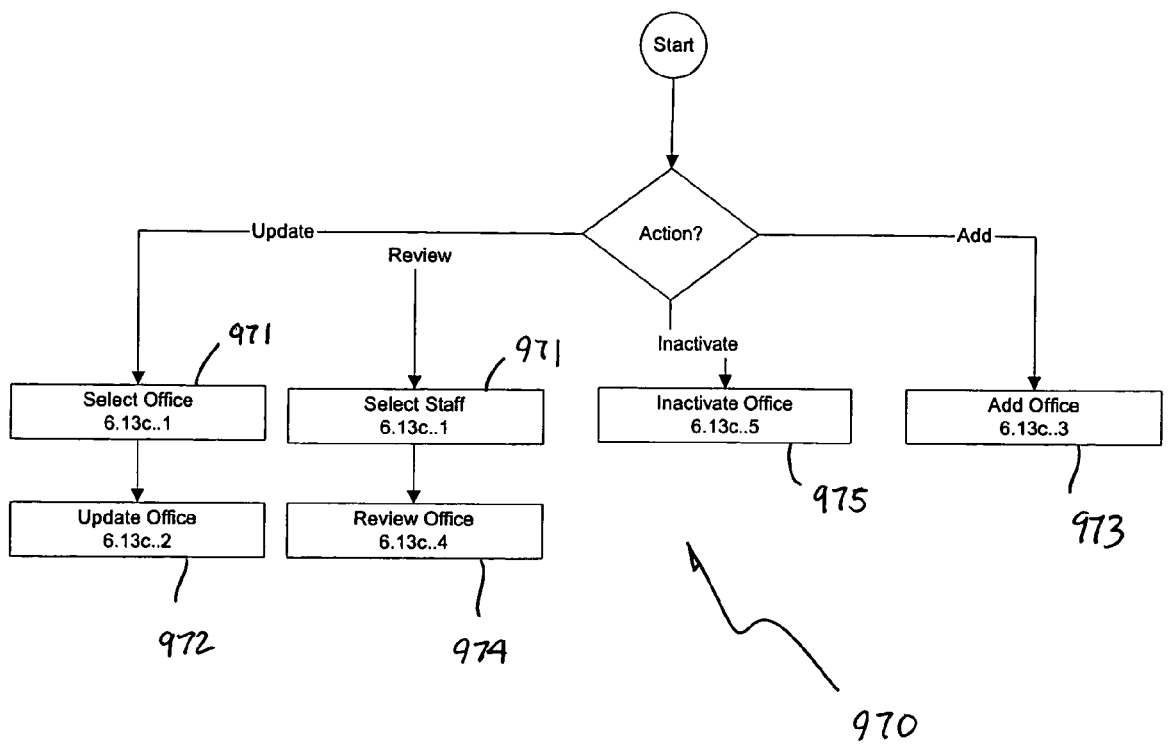
FIG. 68 is a flow diagram showing the staff administration process.

FIG. 68 is a flow chart showing the staff administration process 970. As noted above, this process is initiated when the administrator user selects a physician group during the physician groups process 850 (See FIG. 57). Using this process, the administrator user may take various actions with regard to the 'office' information for the various facilities, such as update a office's information (steps 971, 972), add an office (step 973), review office's information (steps 971, 974), and/or inactivate an office (step 975).

Figure 69:
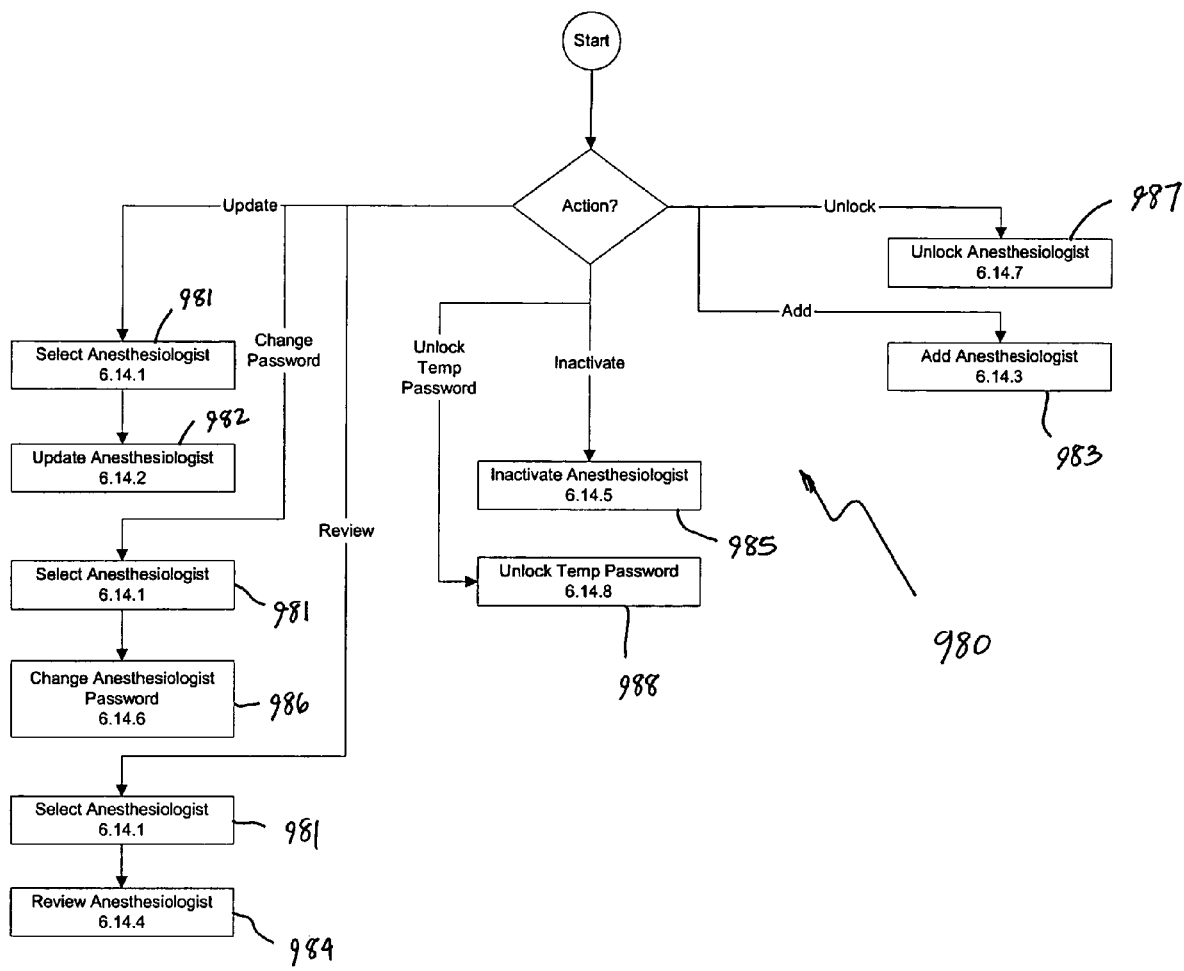
FIG. 69 is a flow diagram showing the anesthesiologist administration process.

FIG. 69 is a flow chart showing the anesthesiologist administration process 980. As noted above, this process is initiated when the administrator user selects a anesthesiologist group during the anesthesiologists groups process 860 (See FIG. 69). Using this process, the administrator user may take various actions with regard to the 'anesthesiologist' information for the various facilities, such as update a anesthesiologist's information (steps 981, 982), add an anesthesiologist (step 983), review an anesthesiologist's information (steps 981, 984), inactivate an anesthesiologist (step 985), change an anesthesiologist's password (steps 981, 986), unlock an anesthesiologist who has been locked out of the system (step 987), and/or unlock a temporary password for an anesthesiologist (step 988).

Figure 70:
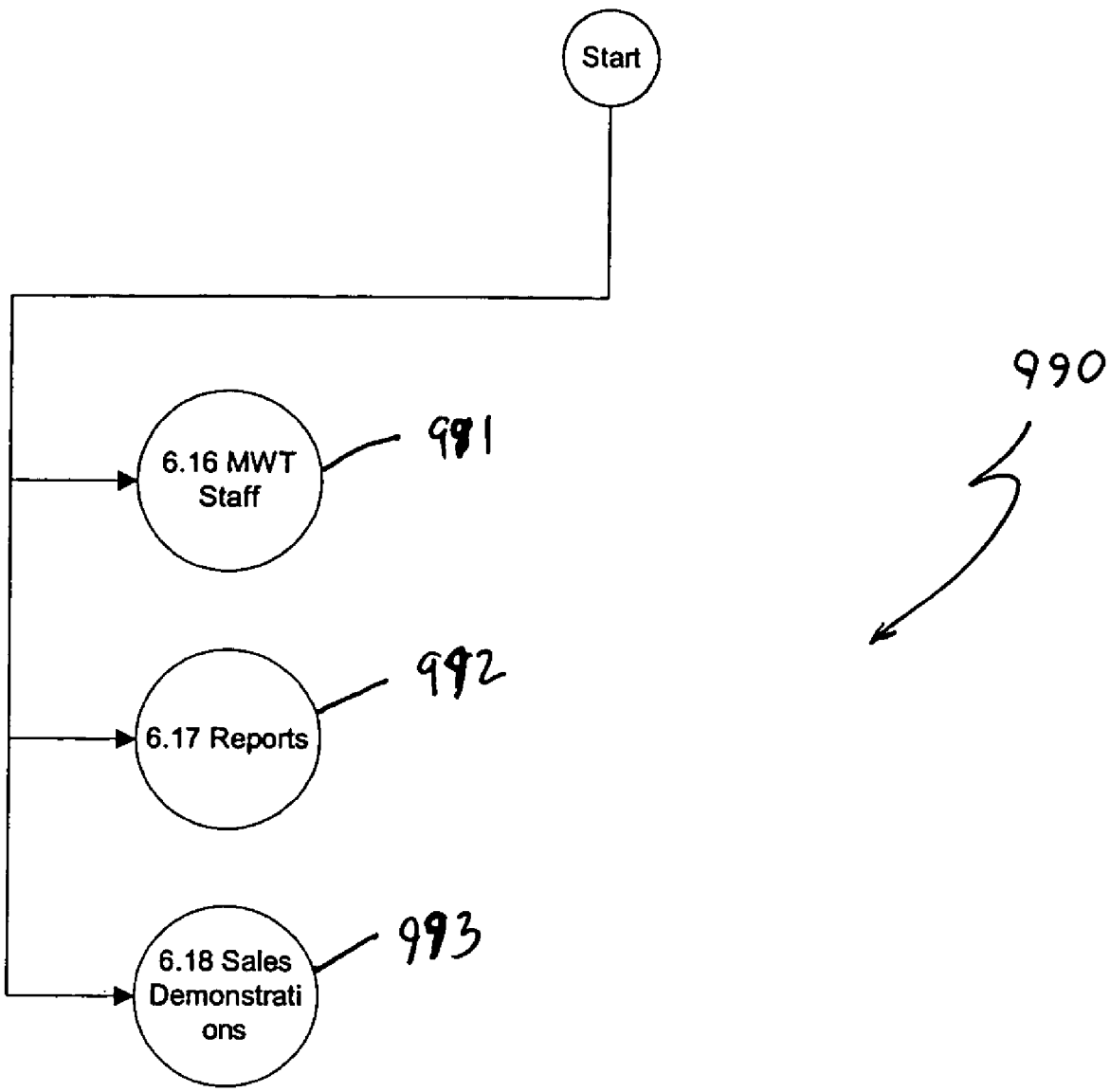
FIG. 70 is a flow diagram showing the sales area process.

FIG. 70 is a flow chart showing the sales area process 990. As noted above, this process is initiated when the administrator (sales) user selects to login as "sales staff" from the administrator login page 2500, during the administrator login process 800. At this point the administrator user is presented with a sales area page 2520 (not shown) which provides links to other processes, such as a staff process 1000 (step 991), a reports process 1010 (step 992), and a sales demonstrations process 1030 (step 993).

Figure 71:
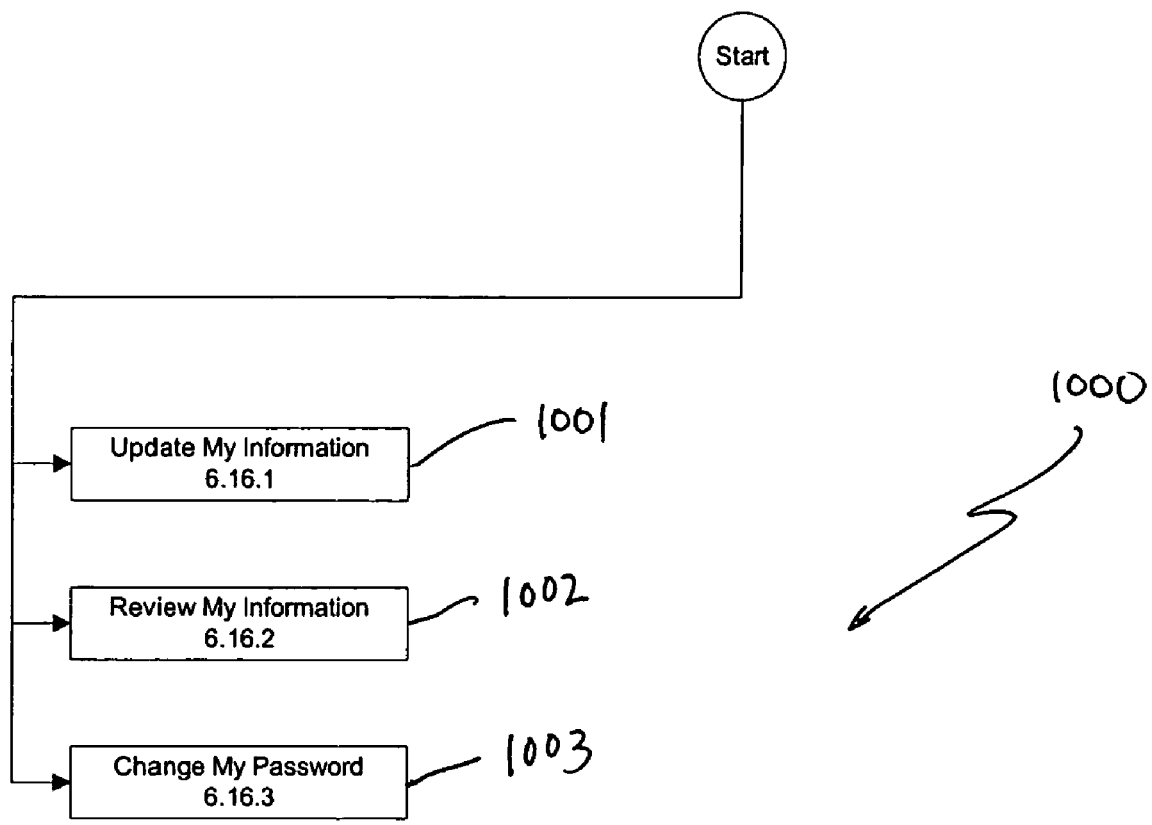
FIG. 71 is a flow diagram showing the staff process.

FIG. 71 is a flow chart showing the staff process 1000. Using this process, the sales staff user can update his or her personal information (step 1001), review his or her personal information (step 1002), or change his or her password (step 1003).

Figure 72:
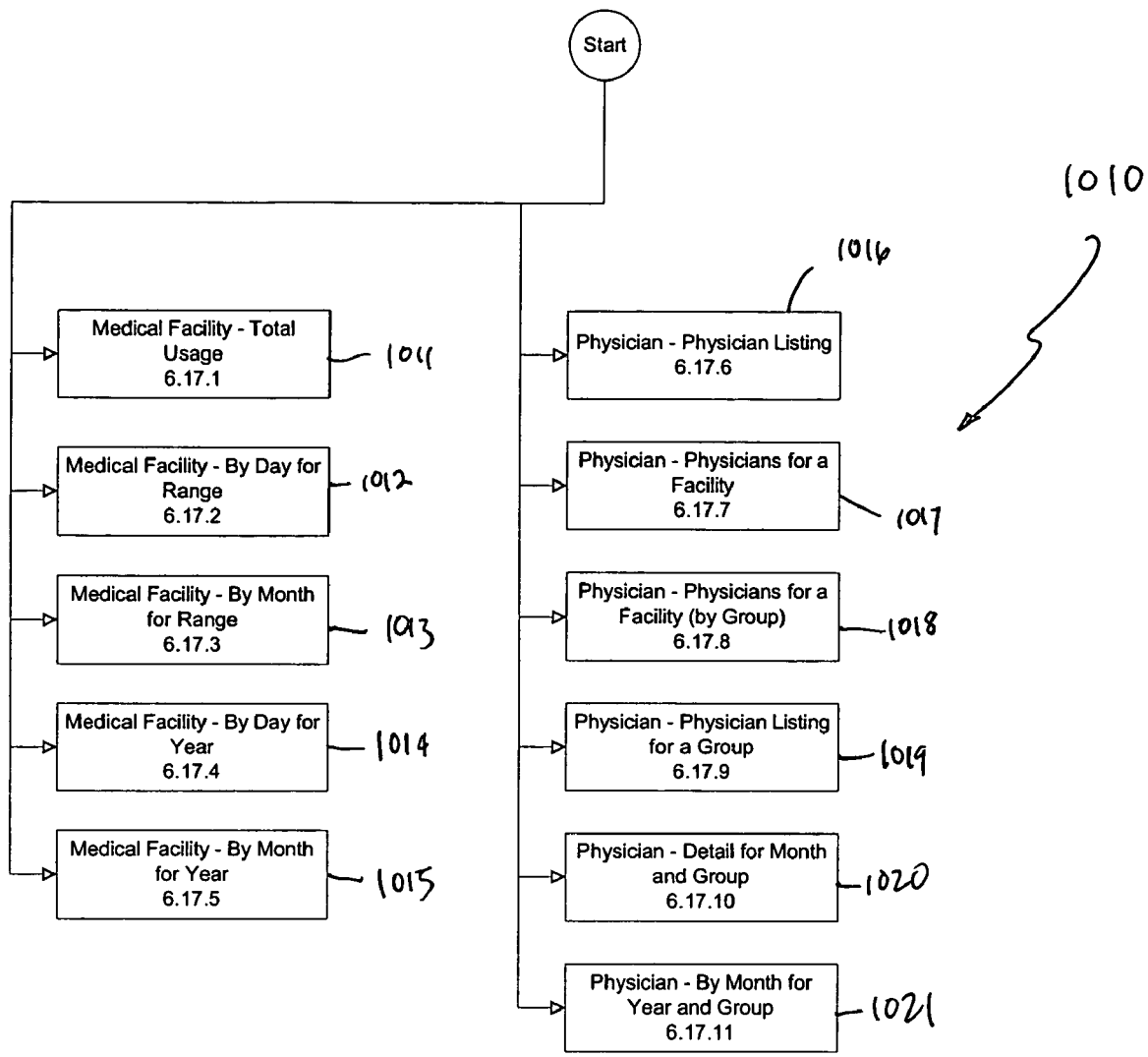
FIG. 72 is a flow diagram showing the reports process.

FIG. 72 is a flow chart showing the reports process 1010. Using this process, the administrator (sales) user can generate various reports, such as, a medical facility total usage report (step 1011), a medical facility "by day for range" report (step 1012), a medical facility "by month for range" report (step 1013), a medical facility "by day for year" report (step 1014), a medical facility "by month for year" report (step 1015), a "physician-physician" report (step 1016), a "physician-physician for facility" report (step 1017), a "physician-physician for facility by group" report (step 1018), a "physician-physician for group" report (step 1019), a "physician-detail for month and group" report (step 1020), a "physician-by month for year and group" report (step 1021).

Figure 73:
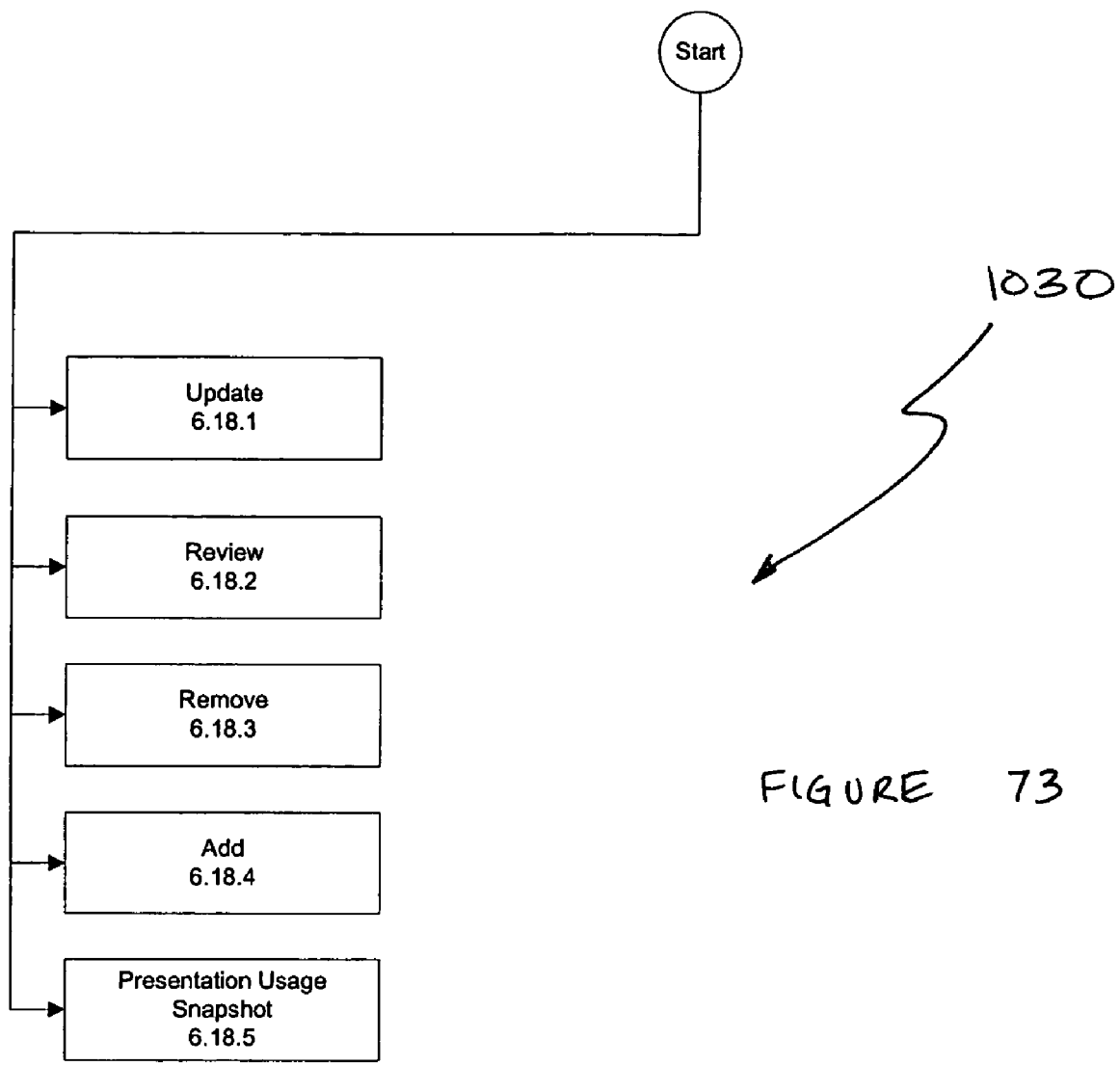
FIG. 73 is a flow diagram showing the sales demonstrations process.

FIG. 73 is a flow chart showing the sales demonstrations process 1030. Using this process, the administrator (sales) user may take various actions with regard to sales demonstrators, such as, update a sales demonstrator's information (e.g., name, phone, etc.) (step 1031), review a sales demonstrator's information (step 1032), remove a sales demonstrator's information (step 1033), add a sales demonstrator's information (step 1034), and/or view a sales demonstrator's contacts (step 1035).

The following listing further explains some of the items shown in FIGS. 53-73:

6.0.1 Login Page—Main access point for One Medical Passport administrators and sales staff to log in.

6.2.1 Select Administrator—Allows selection of a MWT administrator or sales staff member.

6.2.2 Update MWT Administrator—Allows the administrator to update name, position, email, and username for a selected MWT administrator or sales staff member.

6.2.3 Review MWT Administrator—Allows the administrator to review the name, email, username, and password last changed password date for a selected MWT administrator or sales staff member.

6.2.4 Inactivate MWT Administrator—Permits the administrator to remove access for a MWT administrator or sales staff member.

6.2.5 Add MWT Administrator—Allows the administrator to add a MWT administrator or sales staff member by entering their name, email, username, and password.

6.2.6 Change MWT Administrator Password—Permits the administrator to change the password for a selected MWT administrator or sales staff member.

6.2.7 Unlock MWT Administrator—Allows the administrator to unlock a MWT administrator or sales staff member (would be locked by 5 invalid login attempts).

6.2.8 Select CSL—Allows selection of a CSL member.

6.2.9 Update CSL—Allows the administrator to update name, position, phone, email, if has CSL administration rights, username, and facilities associated with for a selected CSL member.

6.2.10 Review CSL—Allows the administrator to review the name, position, phone, email, if has CSL administration rights, username, and facilities associated with for a selected CSL member.

6.2.11 Inactivate CSL—Permits the administrator to remove access for a CSL member.

6.2.12 Add CSL—Allows the administrator to add a CSL member by entered their name, position, phone, email, if has CSL administration rights, username, password, and facilities associated with.

6.2.13 Change CSL Password—Permits the administrator to change the password for a selected CSI, member.

6.2.14 Unlock CSI, —Allows the administrator to unlock a CSL member (would be locked by 5 invalid login attempts).

6.2.15 View CSL Contacts—Allows the administrator to view the contacts for a selected CSL member. The contact information displayed is the name, position, phone, email address, and medical facility/physician group.

6.2.16 View CSL Notes—Allows the administrator to view the notes for a selected CSL member sorted by date.

6.3.1 Select Facility—Allows selection of a medical facility.

6.3.2 Update Facility—Allows the administrator to update the selected facility's name, address, phone, email, medical facility type, configuration options, and report options.

6.3.3 Review Facility—Allows the administrator to review a selected facility's name, address, phone, email, medical facility type, configuration options, and report options.

6.3.4 Add Facility—Allows the administrator to add a facility's name, address, phone, email, medical facility type, configuration options, and report options.

6.3.5 Facility Listing—Displays a listing of facilities with their ID numbers.

6.4.1 Add Physician Group—Allows the administrator to add a physician group's name, specialty, primary medical facility, secondary medical facility, physician group type, configuration options, and report options.

6.4.2 Select Empty Group—Allows the administrator to select a physician group without any physicians, staff, or offices assigned to it.

6.4.3 Select Physician Group—Allows the administrator to select a physician group based on selection of state and primary medical facility.

6.4.4 Advanced Select Physician Group—Allows the administrator to select a physician group based on entering a group name, physician's last name, city, and/or state.

6.4.5 Update Physician Group—Allows the administrator to update a physician group's name, specialty, primary medical facility, secondary medical facility, physician group type, configuration options, and report options.

6.4.6 Review Physician Group—Allows the administrator to review a physician group's name, specialty, primary medical facility, secondary medical facility, physician group type, configuration options, and report options.

6.4.7 Inactivate Physician Group—Allows the administrator to remove a physician group from One Medical Passport.

6.5 Anesthesiologist Groups 6.5.1 Select Anesthesia Group—Allows selection of an anesthesia group. The selection criteria are the group name, anesthesiologist's last name, city, and/or state.

6.5.2 Update Anesthesia Group—Allows the administrator to update the selected anesthesia group's name, address, phone, and email.

6.5.3 Review Anesthesia Group—Allows the administrator to review the anesthesiologists associated with a selected group 6.5.4 Inactivate Anesthesia Group—Allows the administrator to remove the selected anesthesiologist group from One Medical Passport.

6.5.5 Add Anesthesia Group—Allows the administrator to add an anesthesia group's name, address, phone and email.

6.5.6 Select Empty Group—Displays a listing of anesthesiologist groups that do not have any anesthesiologist assigned to it. Clicking on a group allows the administrator to add anesthesiologists.

6.6.1 Select Major Account—Allows selection of a major account.

6.6.2 Update Major Account—Allows the administrator to update the selected major account's name, address, phone, and email, Web site, and comments.

6.6.3 Review Major Account—Allows the administrator to review the selected major account's name, address, phone, and email, Web site, and comments.

6.6.4 Inactivate Major Account—Allows the administrator to remove the selected major account from One Medical Passport.

6.6.5 Add Major Account—Allows the administrator to add a major account's name, address, phone, and email, Web site, and comments.

6.6.6 Facilities by Account—Displays a listing of facilities by major account. Information displayed includes major account, facility, and facility type (type of Medical Passports the facility is configured for).

6.7.1 Unlock Patient—Displays a list of locked patients that the administrator may unlock. A patient account is locked after 5 invalid login attempts.

6.7.2 Change Patient Password—Allows the administrator to change the patient's password by entering the username and new password for the patient.

6.7.3 Select Patient—Allows the administrator to select a patient to review. Selection criteria are username, last name, and/or email.

6.7.4 Review Patient—Displays a list of matching patients for the criteria selected. The information displayed is name, username, date of birth, address, phone, email, codeword information, and Medical Passport usage history.

6.8 Mail 6.8.1 Select Mail Type—Allows the administrator to view unread, on hold, or reviewed mail messages.

6.8.2 Mail—Displays messages for the specified mail type.

6.9 Reports 6.9.1 Medical Facility—Total Usage—Report displays listing of usage for a specified year. Data displayed is number of visits by physician office, by medical facility, total visits, running total by day, average daily usage, and run rate by date for each month.

6.9.2 Medical Facility—By Day for Range—Report displays a count of Medical Passports by day created by specified date range and medical facility.

6.9.3 Medical Facility—By Month for Range—Report displays a count of Medical Passports by month created by specified date range and medical facility.

6.9.4 Medical Facility—By Day for Year—Report displays a count of Medical Passports by day created by specified year and medical facility.

6.9.5 Medical Facility—By Month for Year—Report displays a count of Medical Passports by month created by specified year and medical facility.

6.9.6 Medical Facility—Detail for a Month—Report displays a listing of Medical Passports by date, patient name, type of Medical Passport, procedure, physician, Medical Passport ID, and scheduled date created by specified year, month, and medical facility.

6.9.7 Physician—Physician Listing—Report listing Medical Passport IUD, physician name, office, and physician group for each physician in One Medical Passport.

6.9.8 Physician—Physicians for a Facility—Report listing Medical Passport ID, physician name, office, and physician group for each physician for a specified medical facility.

6.9.9 Physician—Physicians for a Facility (By Group)—Report listing Medical Passport ID, physician name, office, and physician group for each physician for a specified medical facility and sorted by physician group name.

6.9.10 Physician—Physician Listing for a Group—Report listing Medical Passport ID, physician name, and office for each physician for a specified physician group.

6.9.11 Physician—Detail for Month and Group—Report listing patient name, type of Medical Passport, procedure, physician, Medical Passport ID, and Scheduled Date for a specified physician group and date.

6.9.12 Physician—By Month for Year and Group—Report listing count of Medical Passports by month for a specified physician group and year.

6.9.13 Patient—History Only (No Passports)—Report listing patients who have registered but not created a Medical Passport.

6.9.14 Patient—Incomplete Passports—Report listing patients who have incomplete passports for the specified date range.

6.10 Sales Demonstrations 6.10.1 Update—Allows the administrator to update the username, password, name, position, department, medical facility, address, phone, email, contact method, and access level for a specified sales demonstration user.

6.10.2 Review—Allows the administrator to review the username, password, name, position, department, medical facility, address, phone, email, contact method, access level, times used, and date created for a specified sales demonstration user.

6.10.3 Remove—Allows the administrator to remove a sales demonstration user based on their username.

6.10.4 Add—Allows the administrator to add a sales demonstration user by specifying the username, password, name, position, department, medical facility, address, phone, email, contact method, and access level for the specified sales demonstration user.

6.10.5 Presentation Usage Snapshot—Allows the administrator to view sales demonstration contacts by name, facility, date last used, total hits, and date created.

6.11 Facility Contacts 6.11.1 Select Contact—Allows the administrator to select a contact to perform the selected action on.

6.11.2 Update Contact—Allows the administrator to update a specified contact's name, position, phone, email, username, and codeword information.

6.11.3 Add Contact—Allows the administrator to add a new contact by specifying name, position, phone, email, username, and codeword information.

6.11.4 Review Contact—Allows the administrator to review a specified contact's name, position, phone, email, username, and codeword information.

6.11.5 Inactivate Contact—Allows the administrator to remove a contact from One Medical Passport 6.11.6 Change Contact Password—Allows the administrator to change a contact's password.

6.11.7 Unlock Contact—Allows the administrator to unlock a contact whose account has been locked because of 5 invalid login attempts.

6.11.8 Expire Contact Password—Allows the administrator to force a contact to change their password the next time they log into One Medical Passport.

6.11.9 Unlock Temporary Password—Allows the administrator to reset the password for a contact that was created but hasn't entered One Medical Passport within 30 days.

6.12 Facility Schedulers 6.12.1 Select Scheduler—Allows the administrator to select a scheduler to perform the selected action on.

6.12.2 Update Scheduler—Allows the administrator to update a specified scheduler's name, phone, email, username, and codeword information.

6.12.3 Add Scheduler—Allows the administrator to add a new scheduled by specifying name, phone, email, username, and codeword information.

6.12.4 Review Scheduler—Allows the administrator to review a specified scheduler's name, phone, email, username, and codeword information.

6.12.5 Inactivate Scheduler—Allows the administrator to remove a scheduler from One Medical Passport.

6.12.6 Change Scheduler Password—Allows the administrator to change a scheduler's password.

6.12.7 Unlock Scheduler—Allows the administrator to unlock a scheduler whose account has been locked because of 5 invalid login attempts.

6.12.8 Expire Scheduler Password—Allows the administrator to force a scheduler to change their password the next time they log into One Medical Passport.

6.13a Physician Administration 6.13.1 Select Physician—Allows the administrator to select a physician to perform the selected action on.

6.13.2 Update Physician—Allows the administrator to update a specified physician's name, specialty, suffix, primary medical facility, secondary medical facility, offices associated with, and email.

6.13.3 Add Physician—Allows the administrator to add a new physician by specifying name, specialty, suffix, primary medical facility, secondary medical facility, offices associated with, email, username, password, and codeword information.

6.13.4 Review Physician—Allows the administrator to review a specified physician's physician ID, name, specialty, suffix, primary medical facility, secondary medical facility, offices associated with, email, username, password, and codeword information.

6.13.5 Inactivate Physician—Allows the administrator to remove a physician from One Medical Passport 6.13.6 Change Physician Password—Allows the administrator to change a physician's password.

6.13.7 Unlock Physician—Allows the administrator to unlock a physician whose account has been locked because of 5 invalid login attempts.

6.13.8 Update Login—Allows the administrator to update the specified physician's username and codeword information 6.13.9 Unlock Temporary Password—Allows the administrator to reset the password for a physician that was created but hasn't entered One Medical Passport within 30 days.

6.13b Staff Administration 6.13.1 Select Staff—Allows the administrator to select a physician office staff member to perform the selected action on.

6.13.2 Update Staff—Allows the administrator to update a specified physician office staff member's name, specialty, suffix, primary medical facility, secondary medical facility, offices associated with, and email.

6.13.3 Add Staff—Allows the administrator to add a new physician office staff member by specifying name, specialty, suffix, primary medical facility, secondary medical facility, offices associated with, email, username, password, and codeword information.

6.13.4 Review Staff—Allows the administrator to review a specified physician office staff member's Physician ID, name, specialty, suffix, primary medical facility, secondary medical facility, offices associated with, email, username, password, and codeword information.

6.13.5 Inactivate Staff—Allows the administrator to remove a physician office staff member from One Medical Passport 6.13.6 Change Staff Password—Allows the administrator to change a physician office staff member's password.

6.13.7 Unlock Staff—Allows the administrator to unlock a physician office staff member whose account has been locked because of 5 invalid login attempts.

6.13.8 Unlock Temporary Password—Allows the administrator to reset the password for a physician office staff member that was created but hasn't entered One Medical Passport within 30 days.

6.13c Office Administration 6.13.1 Select Office—Allows the administrator to select an office to perform the selected action on.

6.13.2 Update Office—Allows the administrator to update a specified office's address, phone, fax, physicians to associate with, and email.

6.13.3 Add Office—Allows the administrator to add a specified office's address, phone, fax, physicians to associate with, and email.

6.13.4 Review Office—Allows the administrator to review a specified office's Office ID, address, phone, fax, physicians to associate with, and email.

6.13.5 Inactivate Office—Allows the administrator to remove an office from One Medical Passport.

6.14 Anesthesiologists 6.14.1 Select Anesthesiologist—Allows the administrator to select an anesthesiologist to perform the selected action on.

6.14.2 Update Anesthesiologist—Allows the administrator to update a specified anesthesiologist's name, phone, email, facilities associated with, username, and codeword information.

6.14.3 Add Anesthesiologist—Allows the administrator to add a new anesthesiologist by specifying name, phone, email, facilities associated with, username, password, and codeword information.

6.14.4 Review Anesthesiologist—Allows the administrator to review a specified anesthesiologist's name, phone, email, facilities associated with, username, and codeword information.

6.14.5 Inactivate Anesthesiologist—Allows the administrator to remove an anesthesiologist from One Medical Passport 6.14.6 Change Anesthesiologist Password—Allows the administrator to change an anesthesiologist's password.

6.14.7 Unlock Anesthesiologist—Allows the administrator to unlock an anesthesiologist whose account has been locked because of 5 invalid login attempts.

6.14.8 Unlock Temporary Password—Allows the administrator to reset the password for an anesthesiologist that was created but hasn't entered One Medical Passport within 30 days.

6.15 MWT Staff 6.15.1 Update My Information—Allows the One Medical Passport sales staff member to update their name, email, and username.

6.15.2 Review My Information—Allows the One Medical Passport sales staff member to review their name, email, username, and password last changed date.

6.15.3 Change My Password—Allows the One Medical Passport sales staff member to change their password.

6.16 MWT Staff 6.16.1 Update My Information—Allows the One Medical Passport sales staff member to update their name, email, and username.

6.16.2 Review My Information—Allows the One Medical Passport sales staff member to review their name, email, username, and password last changed date.

6.16.3 Change My Password—Allows the One Medical Passport sales staff member to change their password.

6.17.1 Medical Facility—Total Usage—Report displays listing of usage for a specified year. Data displayed is number of visits by physician office, by medical facility, total visits, running total by day, average daily usage, and run rate by date for each month.

6.17.2 Medical Facility—By Day for Range—Report displays a count of Medical Passports by day created by specified date range and medical facility.

6.17.3 Medical Facility—By Month for Range—Report displays a count of Medical Passports by month created by specified date range and medical facility.

6.17.4 Medical Facility—By Day for Year—Report displays a count of Medical Passports by day created by specified year and medical facility.

6.17.5 Medical Facility—By Month for Year—Report displays a count of Medical Passports by month created by specified year and medical facility.

6.17.6 Physician—Physician Listing—Report listing Medical Passport ID, physician name, office, and physician group for each physician in One Medical Passport.

6.17.7 Physician—Physicians for a Facility—Report listing Medical Passport ID, physician name, office, and physician group for each physician for a specified medical facility.

6.17.8 Physician—Physicians for a Facility (By Group)—Report listing Medical Passport ID, physician name, office, and physician group for each physician for a specified medical facility and sorted by physician group name.

6.17.9 Physician—Physician Listing for a Group—Report listing Medical Passport ID, physician name, and office for each physician for a specified physician group.

6.17.10 Physician—Detail for Month and Group—Report listing patient name, type of Medical Passport, procedure, physician, Medical Passport ID, and Scheduled Date for a specified physician group and date.

6.17.11 Physician—By Month for Year and Group—Report listing count of Medical Passports by month for a specified physician group and year.

6.18.1 Update—Allows the administrator to update the username, password, name, position, department, medical facility, address, phone, email, contact method, and access level for a specified sales demonstration user.

6.18.2 Review—Allows the administrator to review the username, password, name, position, department, medical facility, address, phone, email, contact method, access level, times used, and date created for a specified sales demonstration user.

6.18.3 Remove—Allows the administrator to remove a sales demonstration user based on their username.

6.18.4 Add—Allows the administrator to add a sales demonstration user by specifying the username, password, name, position, department, medical facility, address, phone, email, contact method, and access level for the specified sales demonstration user.

6.18.5 Presentation Usage Snapshot—Allows the administrator to view sales demonstration contacts by name, facility, date last used, total hits, and date created.

Customer Service Liasion Login

Figure 74:
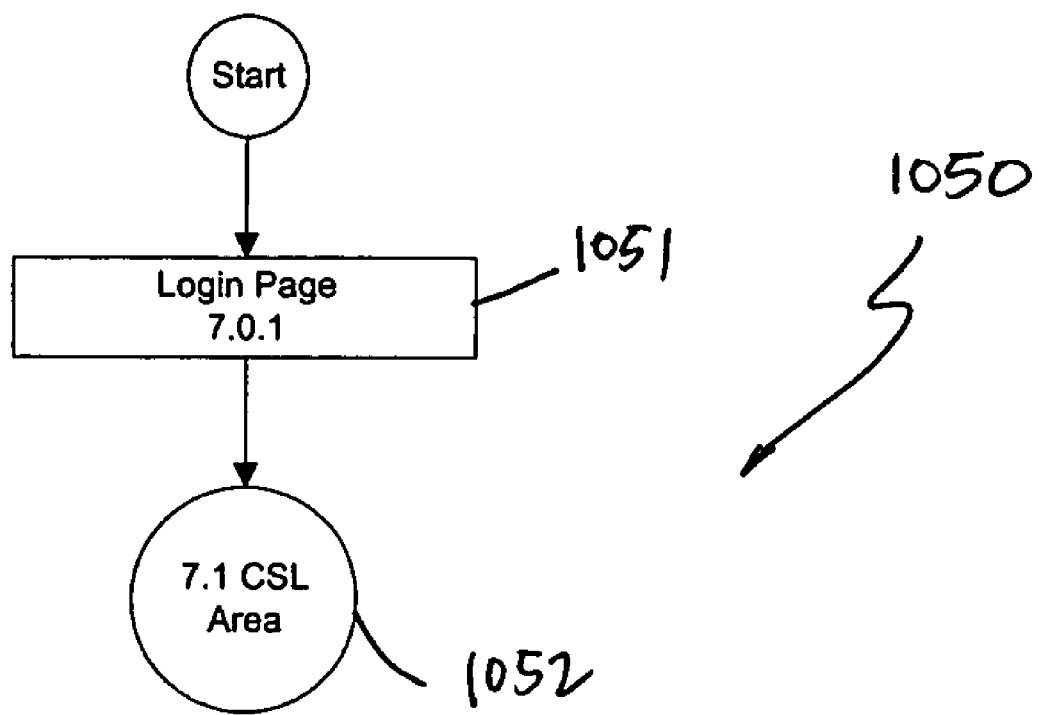
FIG. 74 is a flow diagram showing the customer service liaison (CSL) login process.

FIG. 74 is a flow chart showing the customer service liaison (CSL) login process 1050 which is initiated when the user selects to login as an 'customer service liaison' from the homepage 2000 (step 107 in FIG. 2). The customer service liaison login process 1050 begins with the CSL user selecting to login from a CSL login page 2600 (step 1051; not shown). When the CSL user logs in, the process proceeds to a CSL area process 1055 (step 1052).

Figure 75:
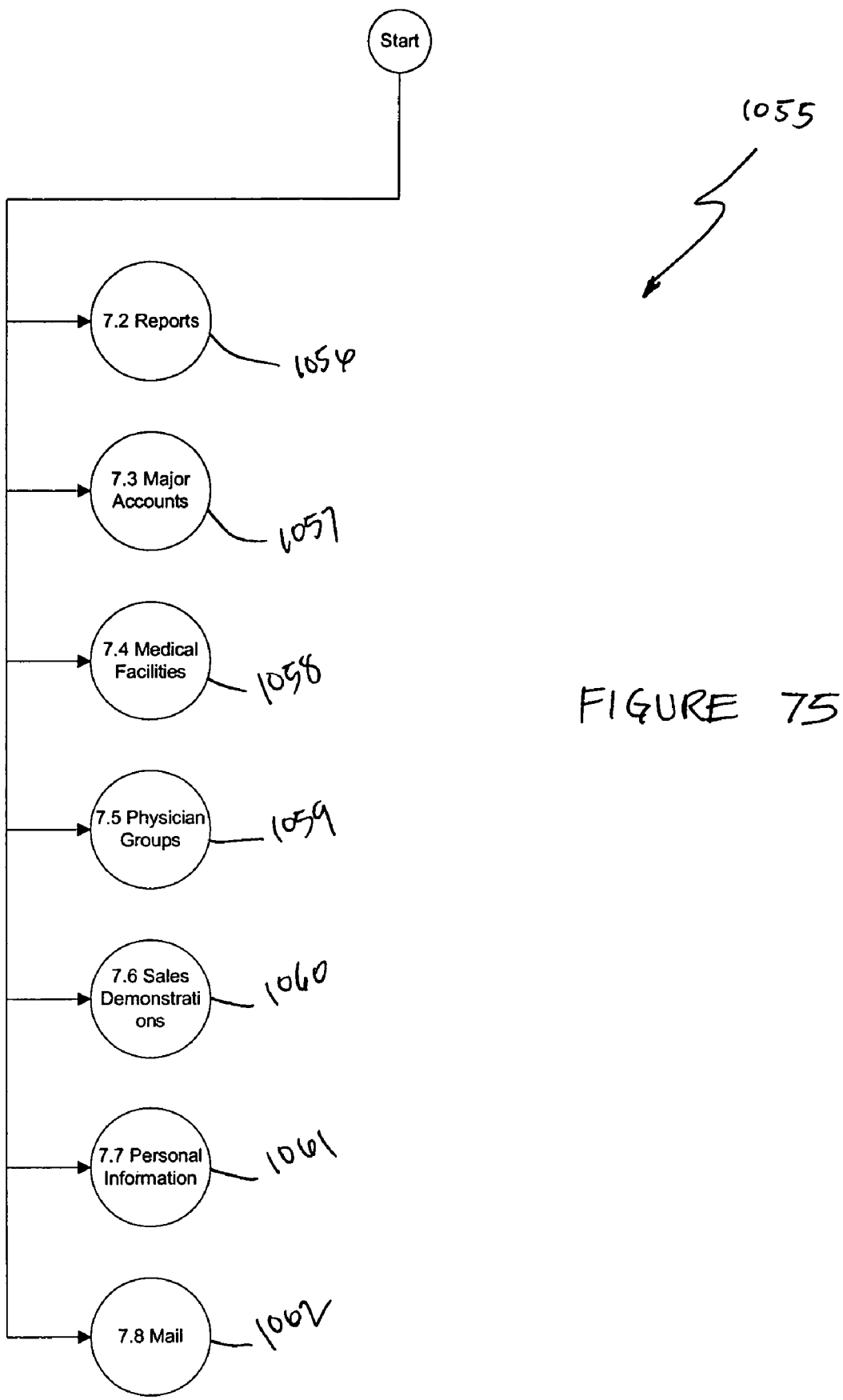
FIG. 75 is a flow diagram showing the CSL area process.

FIG. 75 is a flow chart showing the CSL area process 1055. Upon initiation of the CSL area process 1055 the user is presented a CSL area page 2610 (not shown) which provides links to other processes, such as a reports process 1065 (step 1056), a major accounts process 1070 (step 1057), a medical facilities process 1080 (step 1058), a physician groups process 1115 (step 1059), a sales demonstrations process 1150 (step 1060), a personal information process 1160 (step 1061), and a mail process 1170 (step 1062).

Figure 76:
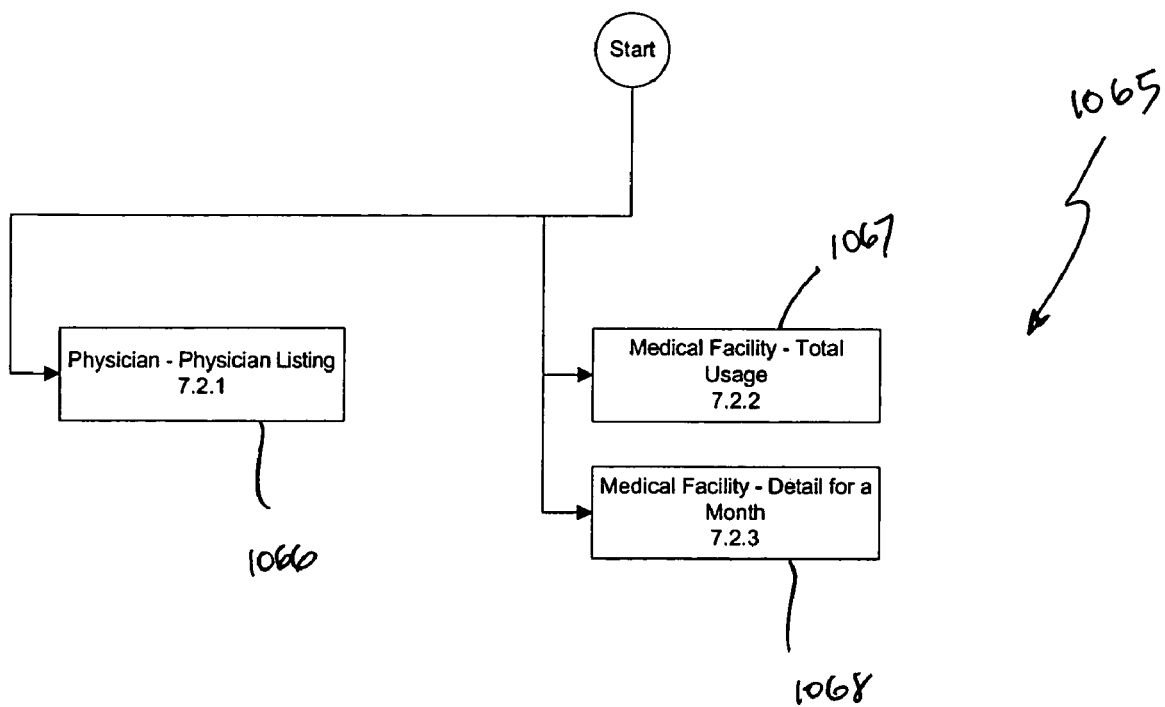
FIG. 76 is a flow diagram showing the reports process.

FIG. 76 is a flow chart showing the reports process 1065. Using this process, the CSL user can generate various reports, such as, a "physician-physician" report (step 1066), medical facility total usage report (step 1067), and/or a medical facility "detail for month" report (step 1068).

Figure 77:
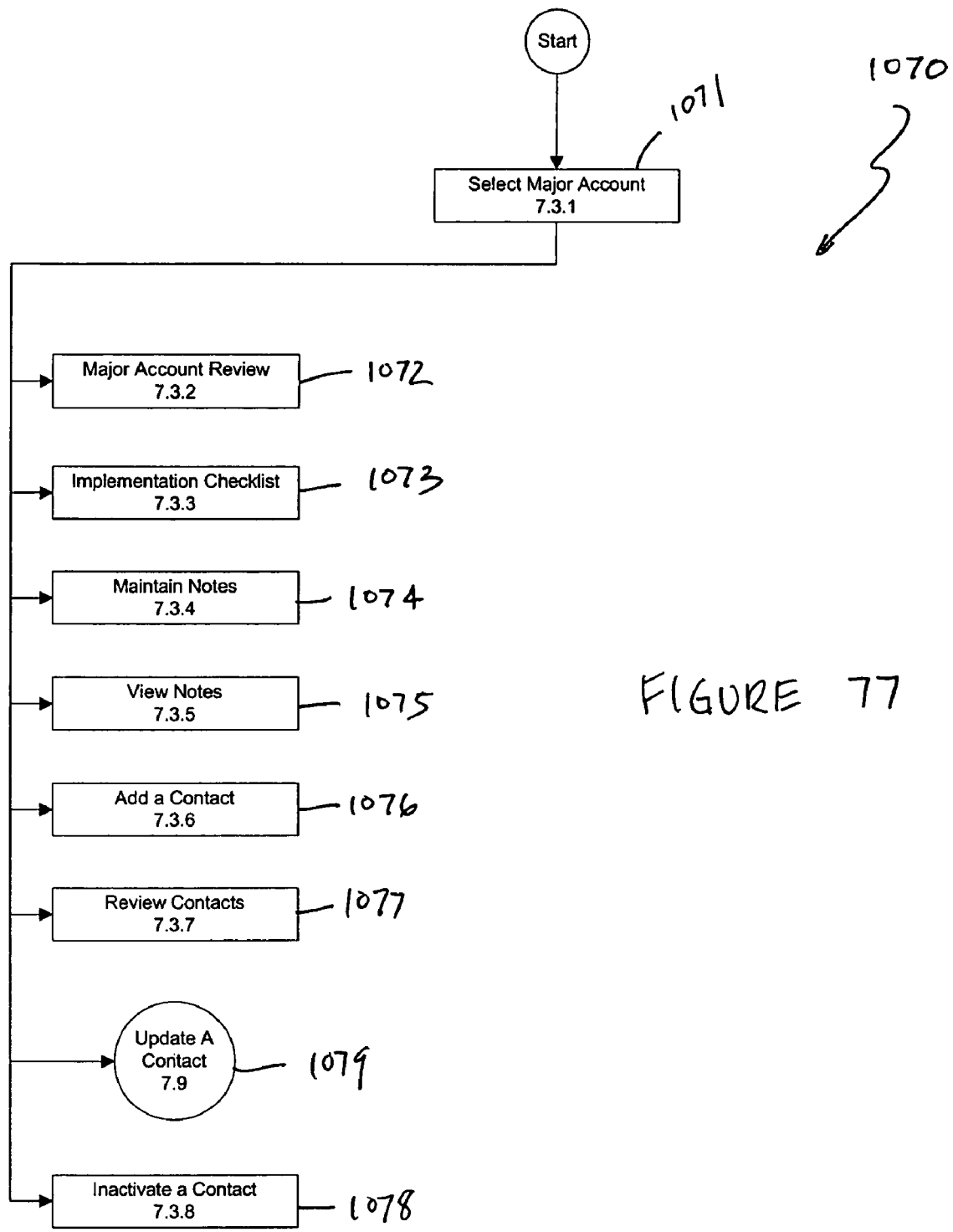
FIG. 77 is a flow diagram showing the major accounts process.

FIG. 77 is a flow chart showing the major accounts process 1070. Using this process, the CSL user may take various actions with regard to 'major accounts' (e.g., physicians, hospitals, etc.), such as, review major account (steps 1071, 1072), view the account implementation checklist (steps 1071, 1073), add or edit notes for a major account (steps 1071, 1074), view notes (steps 1071, 1075), add a contact (steps 1071, 1076), review contacts (steps 1071, 1077), invalidate a contact (steps 1071, 1078), and/or update a contact (steps 1071, 1079). If the CSL user chooses to 'update a contact' the process proceeds to a contact update process 1180 (See FIG. 83).

Figure 78:
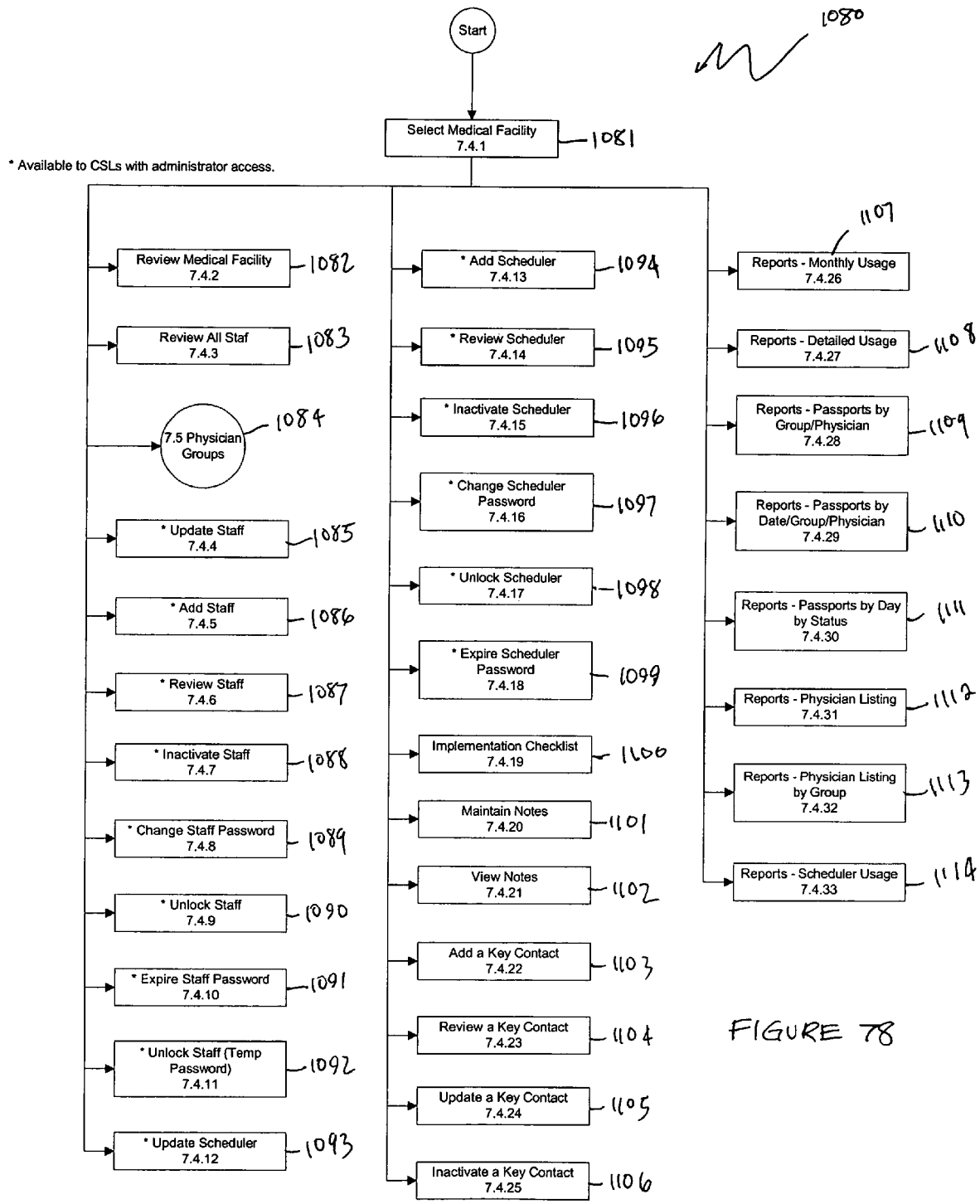
FIG. 78 is a flow diagram showing the medical facilities process.

FIG. 78 is a flow chart showing the medical facilities process 1080. Using this process, the CSL user may take various actions with regard to the medical facilities, such as review a facility (steps 1081, 1082), review all facility staff (steps 1081, 1083), view physician groups for a facility (steps 1081, 1084), update staff (steps 1081, 1085), add staff (steps 1081, 1086), review staff (steps 1081, 1087), inactivate staff (steps 1081, 1088), change staff passwords (steps 1081, 1089), unlock staff locked out of the system (steps 1081, 1090), make a staff password expire (steps 1081, 1091), unlock staff temporary password (steps 1081, 1092), update a scheduler's information (steps 1081, 1093), add a scheduler (steps 1081, 1094), review a scheduler (steps 1081, 1095), inactivate a scheduler (steps 1081, 1096), change a scheduler's password (steps 1081, 1097), unlock a scheduler who has been locked out of the system (steps 1081, 1098), make a scheduler password expire (steps 1081, 1099), unlock a scheduler temporary password (steps 1081, 1100), add or edit notes for a facility (steps 1081, 1101), view notes (steps 1081, 1102), add a key contact (steps 1081, 1103), review a key contact (steps 1081, 1104), update a key contact (steps 1081, 1105), and/or invalidate a key contact (steps 1081, 1106). The CSL user may also generate various reports for each facility, including, a facility monthly usage report (1081, 1107), a facility "detailed" usage report (1081, 1108), a "passports by group/physician" report (1081, 1109), a "passports by date/group/physician" report (1081, 1110), a "passports by day by status" report (1081, 1111), a "physician" report (1081, 1112), a "physician by group" report (1081, 1113), and/or a "scheduler usage" report (1081, 1114).

Figure 79:
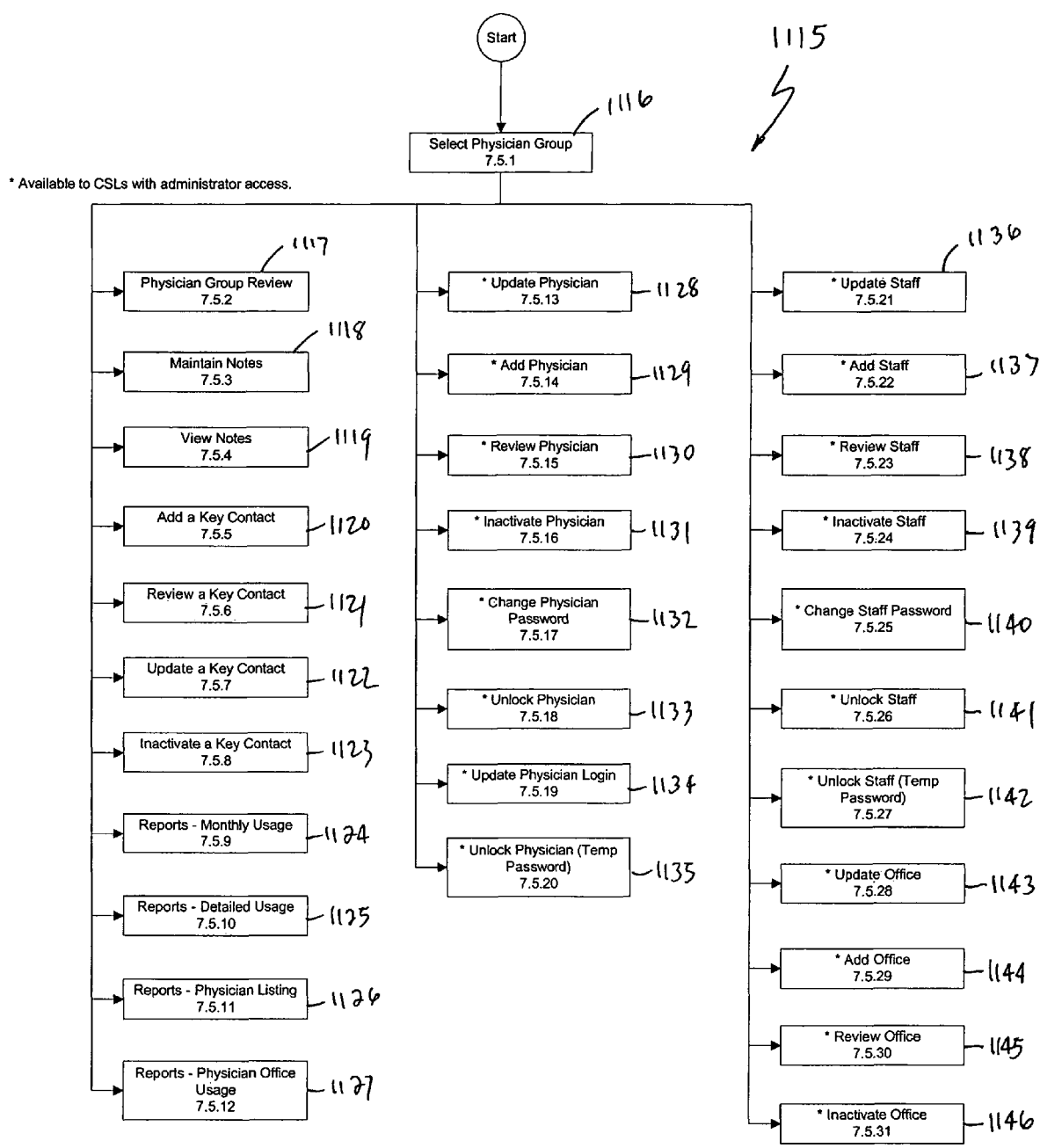
FIG. 79 is a flow diagram showing the physician groups process.

FIG. 79 is a flow chart showing the physician groups process 1115. Using this process, the CSL user may take various actions with regard to the physicians and physicians groups, such as review a physician group (steps 1116, 1117), maintain notes (steps 1116, 1118), view notes (steps 1116, 1119), add a contact (steps 1116, 1120), review a contact (steps 1116, 1121), update a contact (steps 1116, 1122), inactivate a contact (steps 1116, 1123), generate a "monthly usage" report (steps 1116, 1124), generate a "detailed usage" report (steps 1116, 1125), generate a "physician listing" report (steps 1116, 1126), generate a "physician office usage" report (steps 1116, 1127), update a physician's information (steps 1116, 1128), add a physician (steps 1116, 1129), review a physician (steps 1116, 1130), inactivate a physician (steps 1116, 1131), change a physician password (steps 1116, 1132), unlock a physician (steps 1116, 1133), update a physician login (steps 1116, 1134), unlock a physician temporary password (steps 1116, 1135), update staff information (steps 1116, 1136), add staff (steps 1116, 1137), review staff (steps 1116, 1138), inactivate staff (steps 1116, 1139), change staff password (steps 1116, 1140), unlock staff (steps 1116, 1141), unlock staff temporary password (steps 1116, 1142), update office information (steps 1116, 1143), add office (steps 1116, 1144), review office (steps 1116, 1145), and/or inactivate office (steps 1116, 1146).

Figure 80:
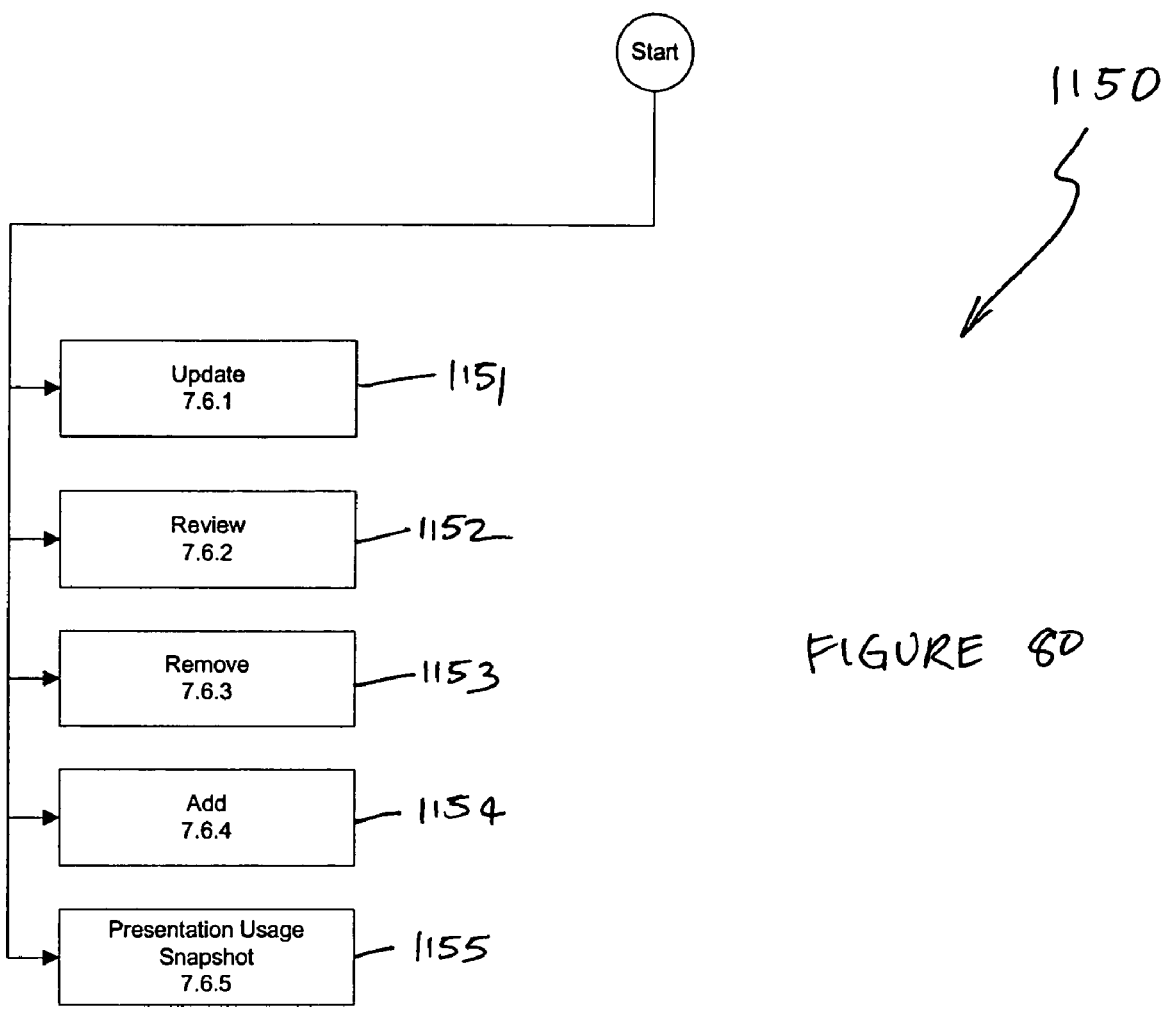
FIG. 80 is a flow diagram showing the sales demonstrations process.

FIG. 80 is a flow chart showing the sales demonstrations process 1150. Using this process, the CSL user may take various actions with regard to sales demonstrators, such as, update a sales demonstrator's information (e.g., name, phone, etc.) (step 1151), review a sales demonstrator's information (step 1152), remove a sales demonstrator's information (step 1153), add a sales demonstrator's information (step 1154), and/or view a sales demonstrator's contacts (step 1155).

Figure 81:
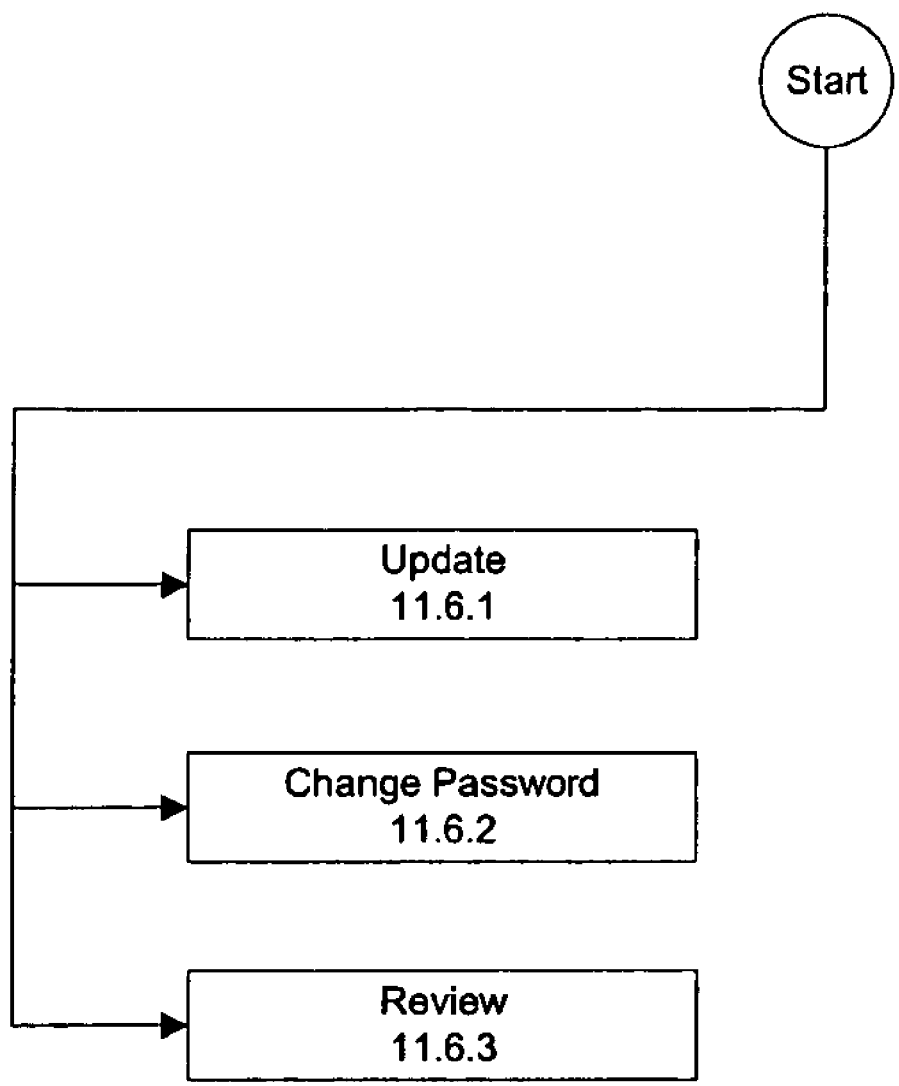
FIG. 81 is a flow diagram showing the personal information process.

FIG. 81 is a flow chart showing the personal information process 1160. Using this process, the CSL user to update his o her personal information (e.g., name, phone, etc.). For example, the CSL user may update his or her personal information (step 1161), and/or change his or her password (step 1162). The CSL user is also given the opportunity to review the information before submitting (step 1163).

Figure 82:
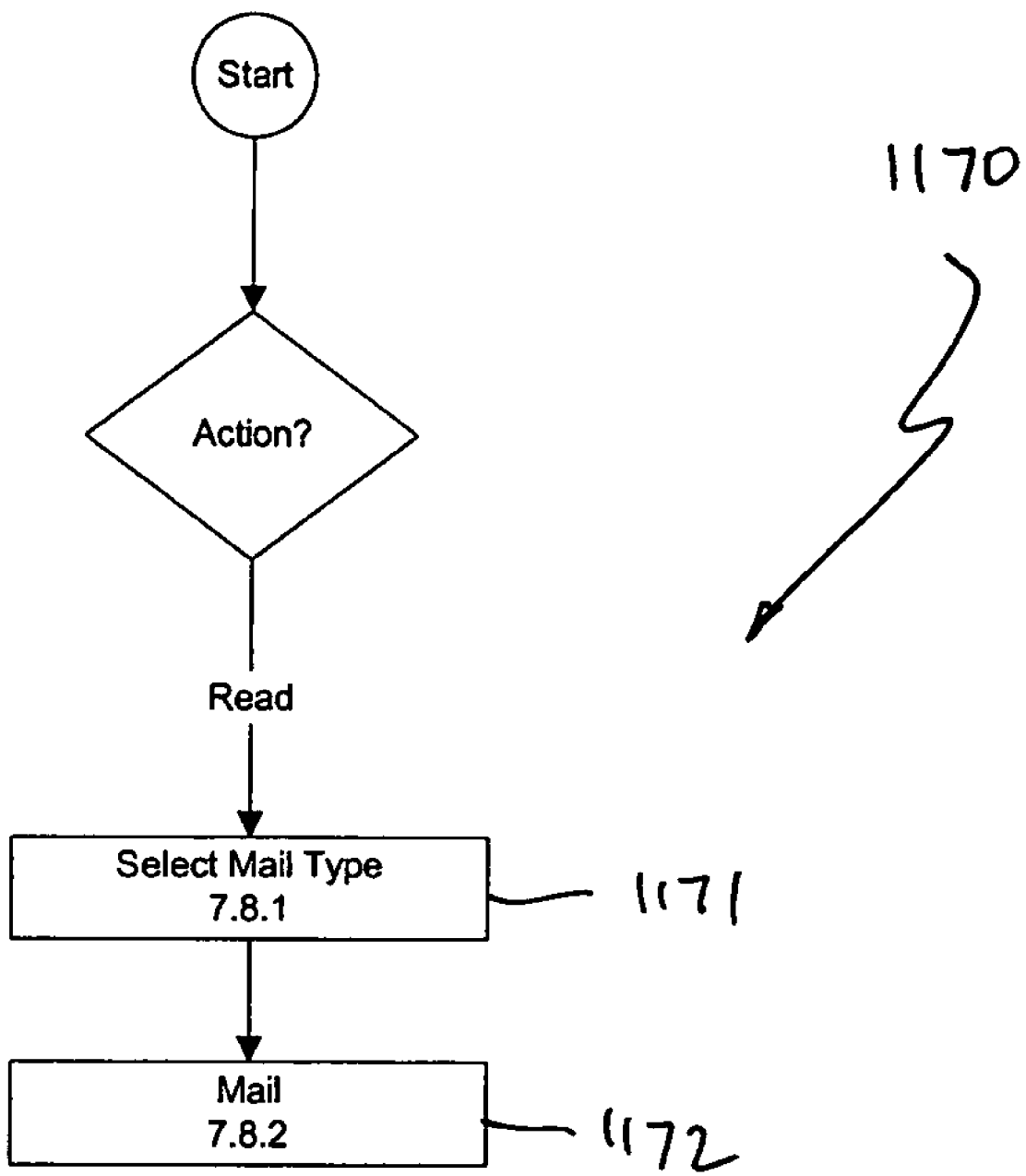
FIG. 82 is a flow diagram showing the mail process.

FIG. 82 is a flow chart showing the mail process 1170. Using this process, the CSL user may view electronic mail messages (steps 1171, 1172).

Figure 83:
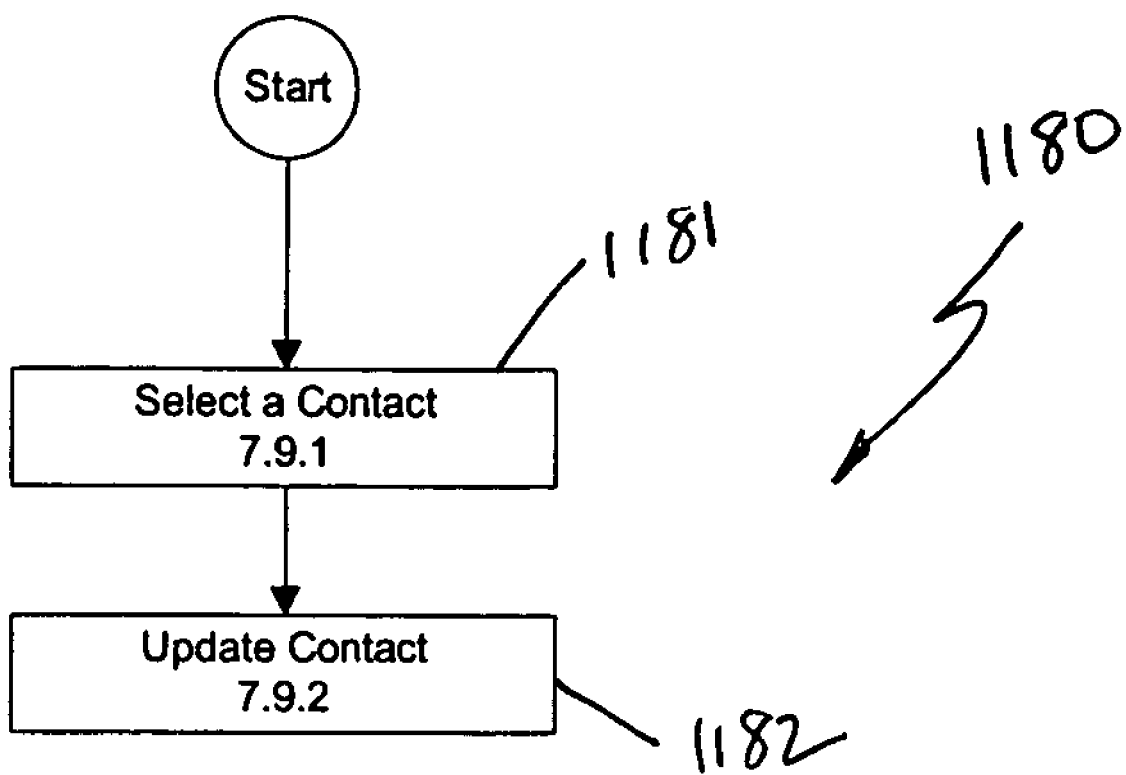
FIG. 83 is a flow diagram showing the update contact process.

FIG. 83 is a flow chart showing the update contact process 1180. Using this process, the CSL user may view update information on any contact (steps 1181, 1182).

The following listing further explains some of the items shown in FIGS. 74-83:

7.0.1 Login Page—Main access point for One Medical Passport customer service liaison's to log in.

7.2.1 Physician—Physician Listing—Report displays listing physicians by Medical Passport ID, physician name, office, and physician group.

7.2.2 Medical Facility—Total Usage—Report displays listing of usage for a specified year. Data displayed is number of visits by physician office, by medical facility, total visits, running total by day, average daily usage, and run rate by date for each month.

7.2.3 Medical Facility—Detail for a Month—Report displays a listing of Medical Passports by date, type of Medical Passport, procedure, physician, Medical Passport ID, and scheduled date by specified date and medical facility.

7.3.1 Select Major Account—Allows selection of a major account.

7.3.2 Major Account Review—Allows the CSL to review the name, address, email, Web site, and comments for a major account.

7.3.3 Implementation Checklist—Displays steps that the CSL should follow for implementation at a medical facility.

7.3.4 Maintain Notes—Allows the CSL to add notes to the specified major account.

7.3.5 View Notes—Allows the CSL to review any notes for the specified major account.

7.3.6 Add a Contact—Allows the CSL to add a new contact for the major account. Information collected is name, position, phone, and email.

7.3.7 Review Contacts—Displays a list of CSL contacts by name, position, phone, and email address.

7.3.8 Inactivate a Contact—Allows the CSL to remove a contact for a major account.

7.4.1 Select Medical Facility—Allows selection of a medical facility.

7.4.2 Review Medical Facility—Displays the facility ID, name, address, phone, medical facility configuration parameters, report configuration parameters, and a sample report.

7.4.3 Review All Staff—Displays a list of the medical facility staff by position.

7.4.4 Update Staff—Allows the CSL to update a specified physician office staff member's name, specialty, suffix, primary medical facility, secondary medical facility, offices associated with, and email.

7.4.5 Add Staff—Allows the CSL to add a new physician office staff member by specifying name, specialty, suffix, primary medical facility, secondary medical facility, offices associated with, email, username, password, and codeword information.

7.4.6 Review Staff—Allows the CSL to review a specified physician office staff member's Physician ID, name, specialty, suffix, primary medical facility, secondary medical facility, offices associated with, email, username, password, and codeword information.

7.4.7 Inactivate Staff—Allows the CSL to remove a physician office staff member from One Medical Passport 7.4.8 Change Staff Password—Allows the CSL to change a physician office staff member's password.

7.4.9 Unlock Staff—Allows the CSL to unlock a physician office staff member whose account has been locked because of 5 invalid login attempts.

7.4.10 Expire Staff Password—Allows the CSL to force the staff member to change their password the next time they log in.

7.4.11 Unlock Staff (Temp Password)—Allows the CSL to reset the password for a physician office staff member that was created but hasn't entered One Medical Passport within 30 days.

7.4.12 Update Scheduler—Allows the CSL to update a specified scheduler's name, phone, email, username, and codeword information.

7.4.13 Add Scheduler—Allows the CSL to add a new scheduler by specifying name, phone, email, username, and codeword information.

7.4.14 Review Scheduler—Allows the CSL to review a specified scheduler's name, phone, email, username, and codeword information.

7.4.15 Inactivate Scheduler—Allows the CSL to remove a scheduler from One Medical Passport.

7.4.16 Change Scheduler Password—Allows the CSL to change a scheduler's password.

7.4.17 Unlock Scheduler—Allows the CSL to unlock a scheduler whose account has been locked because of 5 invalid login attempts.

7.4.18 Expire Scheduler Password—Allows the CSL to force a scheduler to change their password the next time they log into One Medical Passport.

7.4.19 Implementation Checklist—Displays steps that the CSL should follow for implementation at a medical facility.

7.4.20 Maintain Notes—Allows the CSL to add, edit or delete notes to the specified medical facility.

7.4.21 View Notes—Allows the CSL to review any notes for the specified medical facility.

7.4.22 Add a Key Contact—Allows the CSL to add a new contact for the medical facility. Information collected is name, position, phone, and email.

7.4.23 Review a Key Contact—Displays a list of CSL contacts by name, position, phone, and email address.

7.4.24 Update a Key Contact—Allows the CSL to update a specified contact for the medical facility. Information includes name, position, phone, and email.

7.4.25 Inactivate a Key Contact—Allows the CSL to remove a contact for a medical facility.

7.4.26 Reports—Monthly Usage—Displays the count of Medical Passports by month for a specified year and the medical facility.

7.4.27 Reports—Detailed Usage—Displays the count of Medical Passports by date and patient for a specified date range and the medical facility.

7.4.28 Reports—Passports by Group/Physician—Displays a count of instant Medical Passports, patient Medical Passports, and total Medical Passports by group and physician for the medical facility.

7.4.29 Reports—Passports by Date/Group/Physician—Displays a count of instant Medical Passports, patient Medical Passports, and total Medical Passports by year, month, group and physician for the medical facility.

7.4.30 Reports—Passports by Day by Status—Displays the date of procedure, patient name, doctor, and status of Medical Passport for a specified date range and the medical facility.

7.4.31 Reports—Physician Listing—Displays a listing of physicians by Medical Passport ID, physician name, office, and physician group for the medical facility.

7.4.32 Reports—Physician Listing by Group—Displays a listing of physicians by Medical Passport ID, physician name, office, and physician group by physician group for the medical facility.

7.4.33 Reports—Scheduler Usage—Displays a listing of schedulers and their last login date for a specified date range and the medical facility.

7.5.1 Select Physician Group—Allows selection of a physician group.

7.5.2 Physician Group Review—Displays a list of physicians, staff, and offices for the physician group.

7.5.3 Maintain Notes—Allows the CSL to add, edit or delete notes to the specified physician group.

7.5.4 View Notes—Allows the CSL to review any notes for the specified physician group.

7.5.5 Add a Key Contact—Allows the CSL to add a new contact for the physician group. Information collected is name, position, phone, and email.

7.5.6 Review a Key Contact—Displays a list of CSL contacts by name, position, phone, and email address.

7.5.7 Update a Key Contact—Allows the CSL to update a specified contact for the physician group. Information includes name, position, phone, and email.

7.5.8 Inactivate a Key Contact—Allows the CSL to remove a contact for a physician group.

7.5.9 Reports—Monthly Usage—Displays the count of Medical Passports by month for a specified year and the physician group.

7.5.10 Reports—Detailed Usage—Displays the count of Medical Passports by date and patient for a specified date range and the physician group.

7.5.11 Reports—Physician Listing—Displays a listing Medical Passport IDs, physician name, and office for the physician group.

7.5.12 Reports—Physician Office Usage—Displays a listing of physicians and staff for the physician office by their login date/time.

7.5.13 Update Physician—Allows the CSL to update a specified physician's name, specialty, suffix, primary medical facility, secondary medical facility, offices associated with, and email.

7.5.14 Add Physician—Allows the CSL to add a new physician by specifying name, specialty, suffix, primary medical facility, secondary medical facility, offices associated with, email, username, password, and codeword information.

7.5.15 Review Physician—Allows the CSL to review a specified physician's physician ID, name, specialty, suffix, primary medical facility, secondary medical facility, offices associated with, email, username, password, and codeword information.

7.5.16 Inactivate Physician—Allows the CSL to remove a physician from One Medical Passport 7.5.17 Change Physician Password—Allows the CSL to change a physician's password.

7.5.18 Unlock Physician—Allows the CSL to unlock a physician whose account has been locked because of 5 invalid login attempts.

7.5.19 Update Physician Login—Allows the CSL to update the specified physician's username and codeword information 7.5.20 Unlock Physician (Temp Password)—Allows the CSL to reset the password for a physician that was created but hasn't entered One Medical Passport within 30 days.

7.5.21 Update Staff—Allows the CSL to update a specified physician office staff member's name, specialty, suffix, primary medical facility, secondary medical facility, offices associated with, and email.

7.5.22 Add Staff—Allows the CSL to add a new physician office staff member by specifying name, specialty, suffix, primary medical facility, secondary medical facility, offices associated with, email, username, password, and codeword information.

7.5.23 Review Staff—Allows the CSL to review a specified physician office staff member's Physician ID, name, specialty, suffix, primary medical facility, secondary medical facility, offices associated with, email, username, password, and codeword information.

7.5.24 Inactivate Staff—Allows the CSL to remove a physician office staff member from One Medical Passport 7.5.25 Change Staff Password—Allows the CSL to change a physician office staff member's password.

7.5.26 Unlock Staff—Allows the CSL to unlock a physician office staff member whose account has been locked because of 5 invalid login attempts.

7.5.27 Unlock Staff (Temp Password)—Allows the CSL to reset the password for a physician office staff member that was created but hasn't entered One Medical Passport within 30 days.

7.5.28 Update Office—Allows the CSL to update a specified office's address, phone, fax, physicians to associate with, and email.

7.5.29 Add Office—Allows the CSL to add a specified office's address, phone, fax, physicians to associate with, and email.

7.5.30 Review Office—Allows the CSL to review a specified office's Office ID, address, phone, fax, physicians to associate with, and email.

7.5.31 Inactivate Office—Allows the CSL to remove an office from One Medical Passport.

7.6.1 Update—Allows the CSL to update the username, password, name, position, department, medical facility, address, phone, email, contact method, and access level for a specified sales demonstration user.

7.6.2 Review—Allows the CSL to review the username, password, name, position, department, medical facility, address, phone, email, contact method, access level, times used, and date created for a specified sales demonstration user.

7.6.3 Remove—Allows the CSL to remove a sales demonstration user based on their username.

7.6.4 Add—Allows the CSL to add a sales demonstration user by specifying the username, password, name, position, department, medical facility, address, phone, email, contact method, and access level for the specified sales demonstration user.

7.6.5 Presentation Usage Snapshot—Allows the CSL to view sales demonstration contacts by name, facility, date last used, total hits, and date created.

7.7.1 Update—Allows the CSL to update their name, position, phone, email, and username.

7.7.2 Change Password—Permits the CSL to change their password.

7.7.3 Review—Allows the CSL to review name, position, phone, email, and username.

7.8.1 Select Mail Type—Allows the CSL to view unread, on hold, or reviewed mail messages.

7.8.2 Mail—Displays messages for the specified mail type.

7.9.1 Select a Contact—Allows selection of a specified major account's contact.

7.9.2 Update Contact—Allows the CSL to add the name, position, phone, and email for a contact for the specified major account.

Anesthesiologist Login

Figure 84:
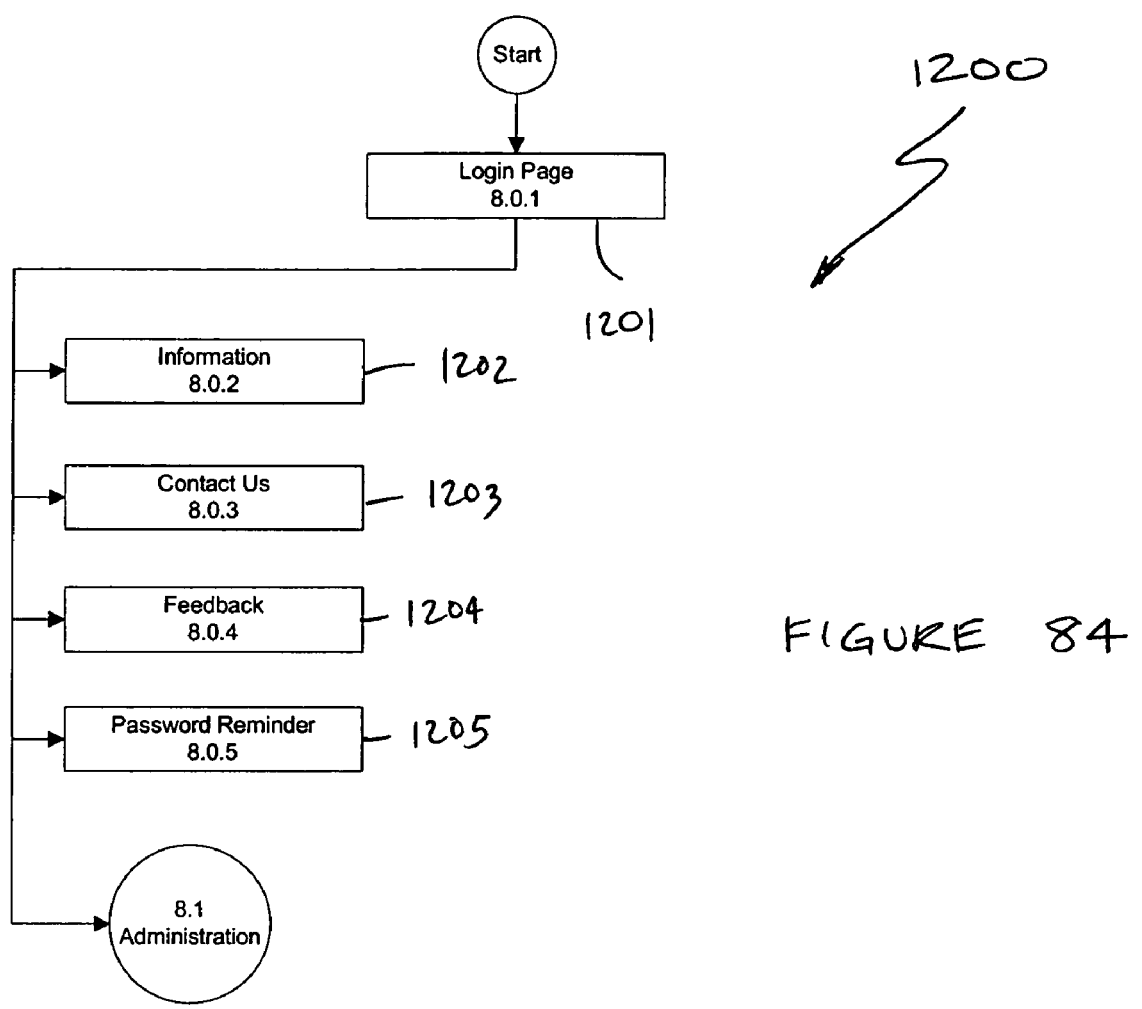
FIG. 84 is a flow diagram showing the anesthesiologist login process.
Figure 103:
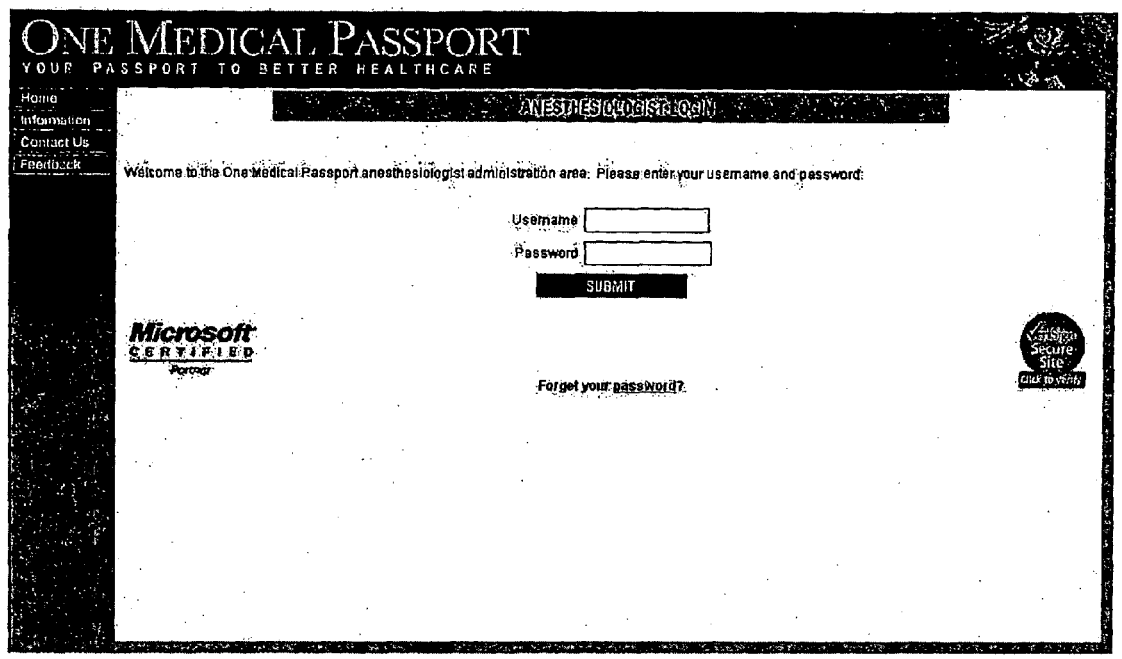
FIG. 103 shows an anesthesiologist login page.

FIG. 84 is a flow chart showing the anesthesiologist login process 1200 which is initiated when the user selects to login as an 'anesthesiologist' from the homepage 2000 (step 108 in FIG. 2). The anesthesiologist login process 1200 begins with the anesthesiologist user selecting to login from an anesthesiologist login page 2700 (step 1201; FIG. 103). The anesthesiologist login page 2700 also provides access to an information page (step 1202), a contact information page (step 1203), a feedback page (step 1204), and a password reminder page (step 1205). If the anesthesiologist selects to login, the process proceeds to an anesthesiologist administration process 1210 (See FIG. 85).

Figure 85:
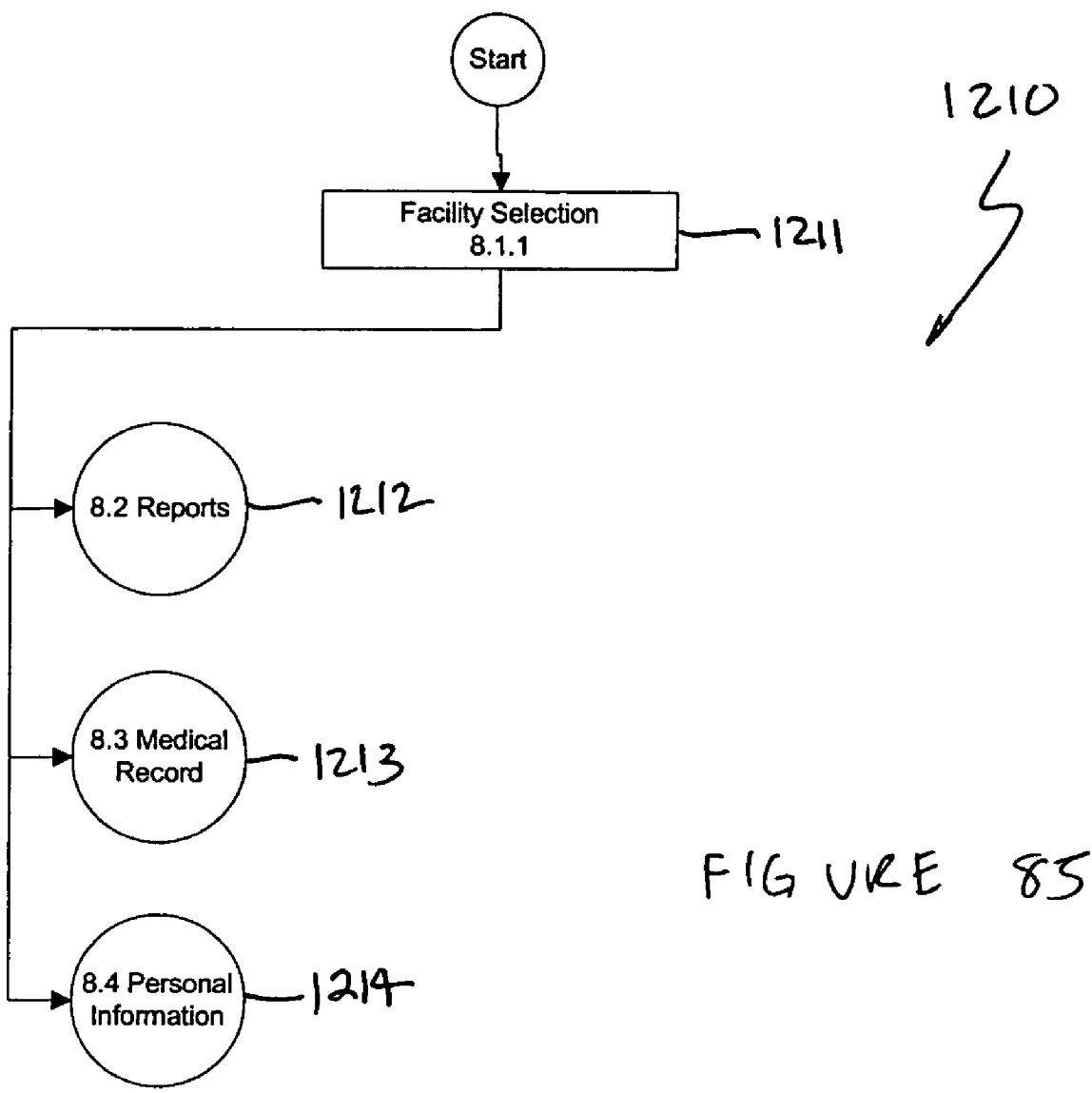
FIG. 85 is a flow chart showing the anesthesiologist administration process.

FIG. 85 is a flow chart showing the anesthesiologist administration process 1210 which is initiated when the user selects to login as an 'anesthesiologist' from the anesthesiologist login page 2700. At this point the anesthesiologist user may select a facility (step 1211), and proceed to one of a reports process 1220 (step 1212), a medical records process 1230 (step 1213), or a personal information process 140 (step 1214).

Figure 86:
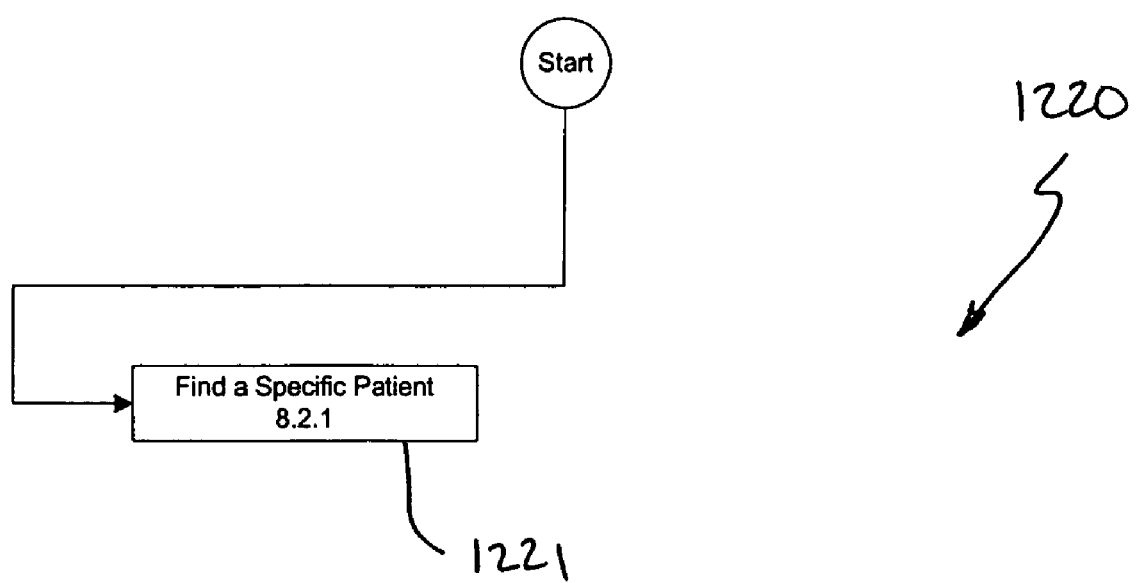
FIG. 86 is a flow diagram showing the reports process.

FIG. 86 is a flow chart showing the reports process 1220. Using this process the anesthesiologist can view all Medical Passports (patient medical records) for a particular medical facility (step 1221).

Figure 87:
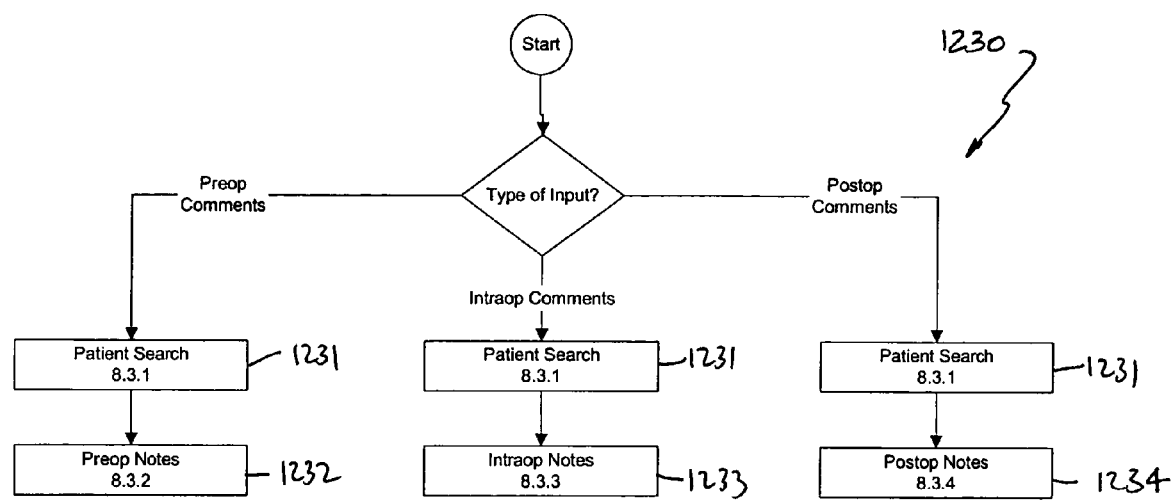
FIG. 87 is a flow diagram showing the medical records process.

FIG. 87 is a flow chart showing the medical records process 1230. Using this process the anesthesiologist can add notes and comments to particular Medical Passports. Initially the anesthesiologist locates the Medical Passport for a particular patient (step 1231). Then, the anesthesiologist may add/edit pre-op comments (step 1232), add/edit intra-op comments (step 1233), and/or add/edit post-op comments (step 1234).

Figure 88:
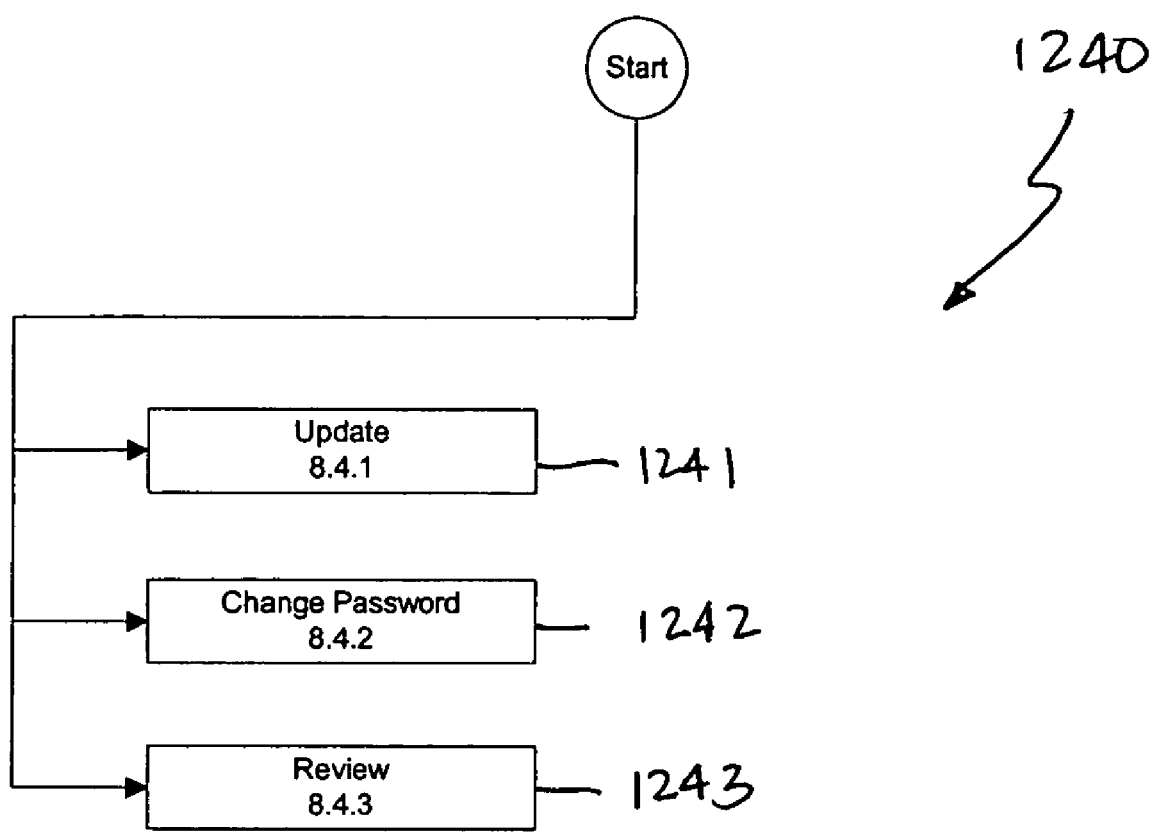
FIG. 88 is a flow diagram showing the personal information process.

FIG. 88 is a flow chart showing the personal information process 1240. Using this process the anesthesiologist may update his or her personal information (e.g., name, address, telephone, etc.). In particular, the anesthesiologist may update his/her personal information (step 1241), change his/her password (1242), and/or review his/her personal information (1243).

The following listing further explains some of the items shown in FIGS. 84-88:
8.0.1 Login Page—Main access point for anesthesiologists to log in.
8.0.2 Information—Main link to the Medical Web Technologies' corporate Web site.
8.0.3 Contact Us—Allows anesthesiologists to send an email to One Medical Passport support.
8.0.4 Feedback—Allows anesthesiologists to provide feedback about the site to One Medical Passport staff.
8.0.5 Password Reminder—Automated password reminder for anesthesiologists. Based on the email address, username, and a codeword the password is reset and emailed to the anesthesiologist.
8.1.1 Facility Selection—Allows the anesthesiologist to select the medical facility from a list of medical facilities they are associated with.
8.2.1 Find a Specific Patient—Displays a list of Medical Passports for the medical facility based on last name and date of birth.
8.3.1 Patient Search—Displays a list of patients with a Medical Passport for the medical facility based on the specified last name and date of birth.
8.3.2 Pre-op Notes—Allows the anesthesiologist to add pre-op notes for the patient and procedure specified.
8.3.3 Intra-op Notes—Allows the anesthesiologist to add intra-op notes for the patient and procedure specified.
8.3.4 Post-op Notes—Allows the anesthesiologist to add post-op notes for the patient and procedure specified.
8.4.1 Update—Allows the anesthesiologist to update their name, phone, email, facilities associated with, username, and codeword information.
8.4.2 Change Password—Permits the anesthesiologist to change their password.
8.4.3 Review—Allows the anesthesiologist to review their name, phone, email, facilities associated with, username, and codeword information.

Post-Op Quality Assurance (QA) Login

Figure 89:
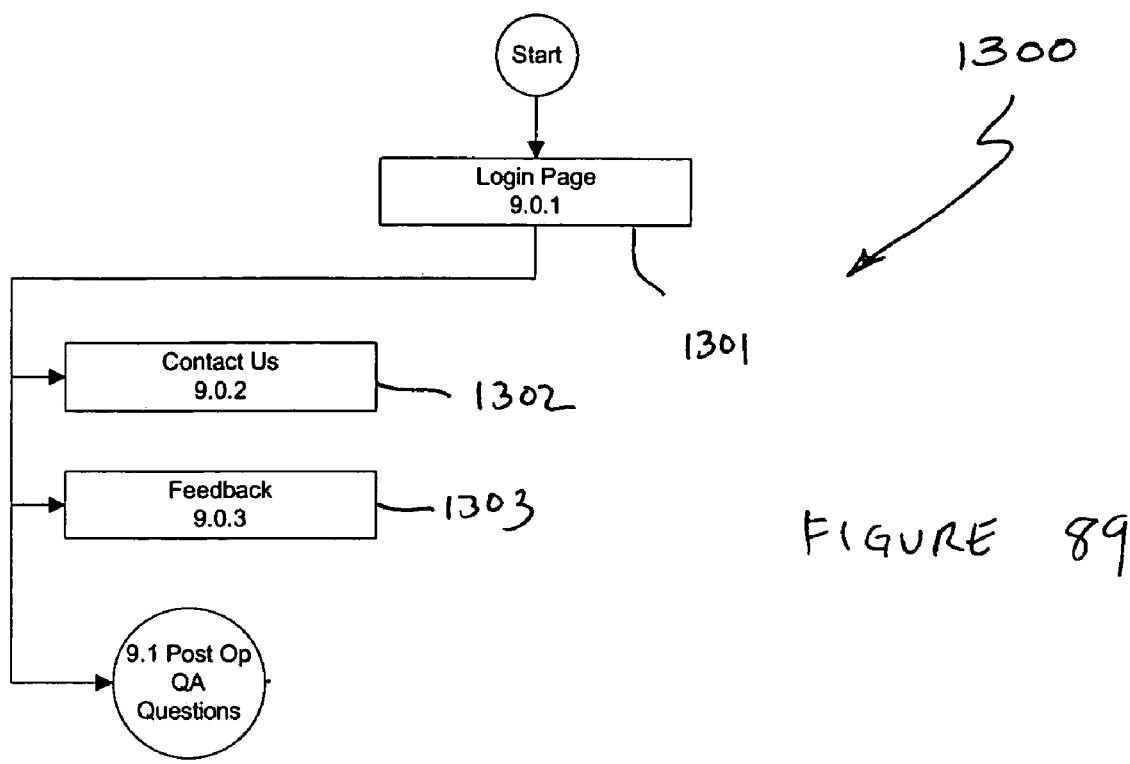
FIG. 89 is a flow diagram showing the post-op QA login process.

FIG. 89 is a flow chart showing the post-op QA login process 1300 which is initiated when the user selects to login as a post-operative patient from the homepage 2000 (step 109 in FIG. 2). The post-op QA login process 1300 begins with the post-op patient user selecting to login from a post-op patient login page 2800 (step 1301; not shown). The post-op patient login page 2800 also provides access to a contact information page (step 1302), and a feedback page (step 1303). If the post-op patient selects to login, the process proceeds to a post-op questions process 1310 (See FIG. 90).

Figure 90:
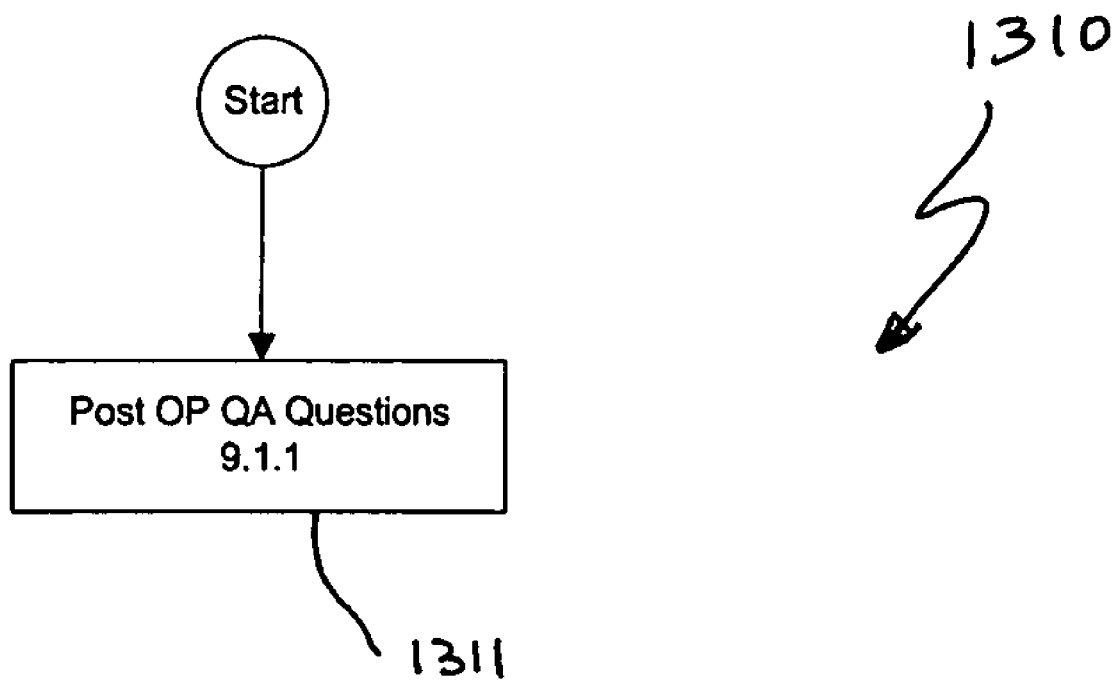
FIG. 90 is a flow diagram showing the post-op questions process.

FIG. 90 is a flow chart showing the post-op questions process 1310. When the post-op patient selects this process they are presented with a series of questions to answer which relate to their overall operative experience (step 1311).

The following listing further explains some of the items shown in FIGS. 89-90:
9.0.1 Login Page.—Main access point for patient to log in to submit a post OP QA survey. After a patient completes a postoperative type of Medical Passport they will receive an email with a computer generated password to log in with. The patient also needs to enter their email address with the password.
9.0.2 Contact Us—Allows patients to send an email to One Medical Passport support.
9.0.3 Feedback—Allows patients to provide feedback about the site to One Medical Passport staff.
9.1 Post Op QA Questions
9.1.1 Post OP QA Questions—Displays a list of QA questions for the patient to complete.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention.

What is claimed is:

1. A method for collecting, organizing, storing, sharing and distributing a patient's medical history information over a network comprising the steps of:

establishing and presenting to a patient representative a medical visit-type questionnaire, the patient representative being any of a medical patient, the medical patient's guardian, and the medical patient's personal representative;

the patient representative selecting a visit type in response to the visit-type questionnaire, said visit type comprising at least one of a medical facility and a physician, a physician only, and a personal use only selection;

generating a structured basic medical history information summary for the patient via:
establishing a plurality of questionnaire sub-sets and an initial series of questions;
presenting to the patient representative the initial series of questions and collecting responses thereto; and successively presenting to the patient representative one or more of the questionnaire sub-sets and collecting responses thereto, wherein a subsequently presented questionnaire subset is selected and presented to the patient representative based on one or more responses to a previously presented questionnaire subset;

storing the basic medical history information summary in a computer database coupled to said network;

receiving a selection from the patient representative of a physician only identifier or a medical facility identifier, said identifier designating a specific physician only or specific medical facility personnel as authorized to access a physician only/medical facility copy of the patient's medical information;

determining, by a processor, at least one medical specialty specific questionnaire to present to the patient representative, wherein the medical specialty specific questionnaire is determined based on said visit type selection and said identifier selection;

generating the physician only/medical facility copy of the patient's medical information, wherein said physician only/medical facility copy includes the patient's structured basic medical history information summary and medical specialty specific information collected in response to the at least one medical specialty specific questionnaire, and storing the physician only/medical facility copy in a computer database coupled to said network;

receiving a request to access said physician only/medical facility copy via the network from the designated physician only or the designated medical facility personnel;

responsive to receiving said request to access said physician only/medical facility copy, automatically modifying said patient representative's access to said physician only/medical facility copy, wherein said patient representative is subsequently not permitted to edit the physician only/medical facility copy; and receiving modifications to medical information contained in the physician only/medical facility copy from the designated physician or designated medical facility personnel, wherein the patient representative selectively updates the patient's structured basic medical history information summary based on said modifications and submits the updated structured basic medical history information summary to at least one of a different physician and different medical facility personnel.

2. The method of claim 1, wherein each of the questionnaire sub-sets includes one or more mandatory questions that must be answered before advancing to subsequent questions, subsequent questionnaire sub-sets, and optional questions.

3. The method of claim 1, wherein the identifier comprises: a unique code corresponding to at least one of said physician only and medical facility personnel.

4. The method of claim 3, wherein a first portion of the unique code identifies the physician only.

5. The method of claim 4, wherein a second portion of said unique code identifies a specific office location the physician only.

6. The method of claim 5, further comprising disseminating the basic medical history information summary according to information provided in the unique code.

7. The method of claim 1, wherein the medical facility personnel includes at least one of an administrator, a nurse, a pharmacist, a medical staff-person, and a healthcare worker.

8. The method of claim 1, further comprising generating one or more medical records from the physician only/medical facility copy; and establishing pre-defined levels of access to the one or more medical records or to the medical information used to generate said medical records commensurate with the particular profession of the physician or of the medical facility personnel.

9. The method of claim 8, wherein at least one of the pre-defined access levels permits at least one of physician only and medical facility personnel to add notes to the one or more medical records, wherein the type and contents of the added notes are related to said pre-defined access level, the method further comprising: adding notes to the one or more records; storing the medical records in the computer database; and storing the medical information forming the basis of the one or more medical records in the computer database.

10. The method of claim 8, wherein the generating one or more medical records step comprises automatically pre-populating each new medical record with information previously gathered and included in the physician only/medical facility copy.

11. The method of claim 1, further comprising: charging at least one or the designated physician only and medical facility a fee for accessing the physician only/medical facility copy.

12. The method of claim 1, further comprising:
tracking access to said basic medical history information summary over said network.

13. The method of claim 1, further comprising: the patient representative requesting a previously submitted username or password; the processor transmitting the username or password to the patient representative, if the patient representative answers a challenge question correctly; and accessing the computer database using the previously submitted username and password.

14. The method of claim 1, further comprising granting access to the basic medical history information summary to at least one of the physician only and medical facility personnel from a communication device associated with a computer network, said access being granted by the patient representative from a communication device associated with the network.

15. The method of claim 14, further comprising:
accessing and viewing the patient's basic medical history information from any communication device associated with the network;
providing additional specialty specific medical information relating to a medical specialty area; and
generating a specialty specific medical information summary that includes at least a portion of the patient's basic medical history information summary and the information relating to the specialty area, wherein information common to the basic medical history information summary and the specialty specific medical information summary is automatically inserted into the specialty specific medical information summary.

16. A computer system comprising:
at least one server computer comprising a processor; and
at least one client computer coupled to the at least one server computer through a network;
wherein the at least one server computer includes at least one program stored thereon that when run, causes the server computer to perform the following steps:
establishing and presenting to a patient representative a medical visit-type questionnaire, the patient representative being any of a medical patient, the medical patient's guardian, and the medical patient's personal representative;
receiving from the patient representative a visit type selection in response to the visit-type questionnaire, said visit type comprising at least one of a medical facility and a physician, a physician only, and a personal use only selection;

generating a structured basic medical history information summary for the patient via:

establishing a plurality of questionnaire sub-sets and an initial series of questions;

presenting to the patient representative the initial series of questions and collecting responses thereto; and successively presenting to the patient representative one or more of the questionnaire sub-sets and collecting responses thereto, wherein a subsequently presented questionnaire subset is selected and presented to the patient representative based on one or more responses to a previously presented questionnaire subset;

storing the basic medical history information summary in a computer database coupled to said network;

receiving a selection from the patient representative of a physician only identifier or a medical facility identifier, said identifier designating a specific physician only or specific medical facility personnel as authorized to access a physician only/medical facility copy of the patient's medical information;

determining at least one medical specialty specific questionnaire to present to the patient representative, wherein the medical specialty specific questionnaire is determined based on said visit type selection and said identifier selection;

generating the physician only/medical facility copy of the patient's medical information, wherein said physician only/medical facility copy includes the patient's structured basic medical history information summary and medical specialty specific information collected in response to the at least one medical specialty specific questionnaire, and storing the physician only/medical facility copy in a computer database coupled to said network;

receiving a request to access said physician only/medical facility copy via the network from the designated physician only or the designated medical facility personnel;

responsive to receiving said request to access said physician only/medical facility copy, automatically modifying said patient representative's access to said physician only/medical facility copy, wherein said patient representative is subsequently not permitted to edit the physician only/medical facility copy;

presenting to the patient representative modifications to medical information contained in the physician only/medical facility copy from the designated physician or designated medical facility personnel; and in response to instructions received from the patient representative, selectively updating the patient's structured basic medical history information summary based on said modifications, and submitting the updated structured basic medical history information summary to at least one of a different physician and different medical facility personnel.

17. The computer system of claim 16 wherein said at least one program is further configured to enable the server computer to: receive and process modifications to the stored basic medical history information summary from any communication device associated with the network.

18. The computer system of claim 16, wherein the at least one client computer comprises code that when executed causes said at least one client computer to generate the one or more medical records by automatically pre-populating each new medical record with information previously gathered and included in the physician only/medical facility copy.

19. A non-transitory computer readable storage medium having embodied therein a computer program for processing by a machine, the computer program comprising:

a first code segment for establishing and presenting to a patient representative a medical visit-type questionnaire, the patient representative being any of a medical patient, the medical patient's guardian, and the medical patient's personal representative;

a second code segment for receiving from the patient representative a visit type selection in response to the visit-type questionnaire, said visit type comprising at least one of a medical facility and a physician, a physician only, and a personal use only selection;

a third code segment for generating a structured basic medical history information summary for the patient via:

establishing a plurality of questionnaire sub-sets and an initial series of questions;

presenting to the patient representative the initial series of questions and collecting responses thereto; and successively presenting to the patient representative one or more of the questionnaire sub-sets and collecting responses thereto, wherein a subsequently presented questionnaire subset is selected and presented to the patient representative based on one or more responses to a previously presented questionnaire subset;

a forth code segment for storing the basic medical history information summary in a computer database coupled to said network;

a fifth code segment for receiving a selection from the patient representative of a physician only identifier or a medical facility identifier, said identifier designating a specific physician only or specific medical facility personnel as authorized to access a physician only/medical facility copy of the patient's medical information;

a sixth code segment for determining at least one medical specialty specific questionnaire to present to the patient representative, wherein the medical specialty specific questionnaire is determined based on said visit type selection and said identifier selection;

a seventh code segment for generating the physician only/medical facility copy of the patient's medical information, wherein said physician only/medical facility copy includes the patient's structured basic medical history information summary and medical specialty specific information collected in response to the at least one medical specialty specific questionnaire, and storing the physician only/medical facility copy in a computer database coupled to said network;

an eighth code segment for receiving a request to access said physician only/medical facility copy via the network from the designated physician only or the designated medical facility personnel;

a ninth code segment for automatically modifying said patient representative's access to said physician only/medical facility copy in response to receiving said request to access said physician only/medical facility copy, wherein said patient representative is subsequently not permitted to edit the physician only/medical facility copy;

a tenth code segment for presenting to the patient representative modifications to medical information contained in the physician only/medical facility copy from the designated physician or designated medical facility personnel; and an eleventh code segment for selectively updating the patient's structured basic medical history information summary based on said modifications in response to instructions received from the patient representative, and for submitting the updated structured basic medical history information summary to at least one of a different physician and different medical facility personnel.

20. The computer readable medium of claim 19, wherein the computer program a twelfth code segment for receiving and processing modification instructions to the stored basic medical history information summary from any communication devices associated with the network.

21. The computer readable medium of claim 19, wherein the fourth code segment is configured to generate the one or more medical records by automatically pre-populating each new medical record with the information previously gathered and included in the medical professional/facility copy.

* * * * *

UNITED STATES PATENT AND TRADEMARK OFFICE
CERTIFICATE OF CORRECTION

| | | |
|---|---|---|
| PATENT NO. | : 7,865,373 B2 | Page 1 of 1 |
| APPLICATION NO. | : 10/686172 | |
| DATED | : January 4, 2011 | |
| INVENTOR(S) | : Punzak et al. | |

It is certified that error appears in the above-identified patent and that said Letters Patent is hereby corrected as shown below:

<u>In Column 50</u>

At line 5, Claim 21, please delete the following:

"21. The computer readable medium of claim 19, wherein the fourth code segment is configured to generate the one or more medical records by automatically pre-populating each new medical record with the information previously gathered and included in the medical professional/facility copy."

and replace it with the following:

--21. The computer readable medium of claim 19 further comprising a thirteenth code segment for generating one or more medical records by automatically pre-populating each new medical record with the information previously gathered and included in the physician only/medical facility copy.--

Signed and Sealed this
Fourteenth Day of June, 2011

David J. Kappos
*Director of the United States Patent and Trademark Office*